United States Patent
He et al.

(10) Patent No.: US 8,354,421 B2
(45) Date of Patent: Jan. 15, 2013

(54) HIV REVERSE TRANSCRIPTASE INHIBITORS

(75) Inventors: Gong-Xin He, Cupertino, CA (US); Choung U. Kim, San Carlos, CA (US); Michael L. Mitchell, Hayward, CA (US); Lianhong Xu, Palo Alto, CA (US)

(73) Assignee: Korea Research Insitute of Chemical Technology, Daejeon (KR)

( * ) Notice: Subject to any disclaimer, the term of this patent is extended or adjusted under 35 U.S.C. 154(b) by 1149 days.

(21) Appl. No.: 12/215,264

(22) Filed: Jun. 26, 2008

(65) Prior Publication Data

US 2009/0075939 A1 Mar. 19, 2009

Related U.S. Application Data

(60) Provisional application No. 60/937,756, filed on Jun. 29, 2007, provisional application No. 60/959,695, filed on Jul. 16, 2007.

(51) Int. Cl.
- *A61K 31/505* (2006.01)
- *C07F 9/09* (2006.01)
- *C07D 239/08* (2006.01)

(52) U.S. Cl. .................. 514/274; 544/243; 544/311
(58) Field of Classification Search .......... 514/274; 544/243, 311
See application file for complete search history.

(56) References Cited

U.S. PATENT DOCUMENTS

| | | | |
|---|---|---|---|
| 4,518,685 A | 5/1985 | Yagihara et al. | |
| 4,656,209 A | 4/1987 | Wehner et al. | |
| 5,112,835 A | 5/1992 | Miyasaka et al. | |
| 5,162,326 A | 11/1992 | Naka et al. | |
| 5,188,928 A | 2/1993 | Karino et al. | |
| 5,219,869 A | 6/1993 | Shiokawa et al. | |
| 5,227,284 A | 7/1993 | Matushita et al. | |
| 5,266,453 A | 11/1993 | Matushita et al. | |
| 5,318,972 A | 6/1994 | Miyasaka et al. | |
| 5,461,060 A | 10/1995 | Miyasaka et al. | |
| 5,604,209 A | 2/1997 | Ubasawa et al. | |
| 5,643,744 A | 7/1997 | Nitta et al. | |
| 5,747,500 A | 5/1998 | Son et al. | |
| 5,859,100 A | 1/1999 | Wehner et al. | |
| 5,889,013 A | 3/1999 | Kim et al. | |
| 5,922,727 A | 7/1999 | Cho et al. | |
| 5,998,411 A | 12/1999 | Vig et al. | |
| 6,136,815 A | 10/2000 | Son et al. | |
| 6,174,941 B1 | 1/2001 | Wehner et al. | |
| 6,174,998 B1 | 1/2001 | Muhlegger et al. | |
| 6,177,437 B1 | 1/2001 | Wright | |
| 6,372,725 B1 | 4/2002 | Zilch et al. | |
| 6,713,486 B1 | 3/2004 | Son et al. | |
| 6,911,450 B1 | 6/2005 | Tronchet | |
| 7,250,421 B2 | 7/2007 | Nair et al. | |
| 2003/0114445 A1* | 6/2003 | Zhi et al. ............ | 514/227.8 |
| 2005/0215568 A1 | 9/2005 | Howell et al. | |
| 2005/0239054 A1 | 10/2005 | Arimilli et al. | |
| 2006/0223834 A1 | 10/2006 | Nair et al. | |
| 2008/0070920 A1 | 3/2008 | Guo et al. | |
| 2011/0076276 A1 | 3/2011 | Guo et al. | |

FOREIGN PATENT DOCUMENTS

| | | |
|---|---|---|
| CN | 101016265 | 8/2007 |
| FR | 2779721 | 12/1999 |
| FR | 2779722 | 12/1999 |
| JP | 3264579 | 11/1991 |
| JP | 05289238 | 11/1993 |
| JP | 06135943 | 5/1994 |
| JP | 08003143 | 1/1996 |
| JP | 09020792 | 1/1997 |
| JP | 10130244 | 5/1998 |
| JP | 10130245 | 5/1998 |
| JP | 10168068 | 6/1998 |
| JP | 11102047 | 4/1999 |
| JP | 2001114767 | 4/2001 |
| JP | 2002284686 | 10/2002 |
| JP | 2005212143 | 8/2005 |
| MX | PA03011298 | 6/2005 |
| WO | WO-8910701 | 11/1989 |
| WO | WO-9200964 | 1/1992 |
| WO | WO-9302044 | 2/1993 |
| WO | WO-9316091 | 8/1993 |
| WO | WO-9316092 | 8/1993 |
| WO | WO-9833505 | 8/1998 |
| WO | WO-0061563 | 10/2000 |
| WO | WO 0061564 | 10/2000 |
| WO | WO-0123363 | 4/2001 |
| WO | WO-0179203 | 10/2001 |
| WO | WO-0183459 | 11/2001 |
| WO | WO-03029226 | 4/2003 |
| WO | WO-03057677 | 7/2003 |
| WO | WO-03064511 | 8/2003 |
| WO | WO-03091264 | 11/2003 |
| WO | WO-2005026184 | 3/2005 |
| WO | WO-2006070292 | 7/2006 |
| WO | WO-2006089221 | 8/2006 |
| WO | WO-2007104834 | 9/2007 |
| WO | WO-2007106450 | 9/2007 |

\* cited by examiner

*Primary Examiner* — James O Wilson
*Assistant Examiner* — Ebenezer O Sackey
(74) *Attorney, Agent, or Firm* — Edwards Wildman Palmer LLP

(57) ABSTRACT

The invention is related to compounds of Formula (I):

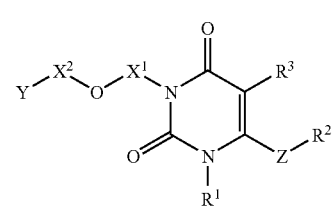

or a pharmaceutically acceptable salt, solvate, ester, and/or phosphonate thereof, compositions containing such compounds, and therapeutic methods that include the administration of such compounds.

14 Claims, No Drawings

HIV REVERSE TRANSCRIPTASE INHIBITORS

CROSS-REFERENCE TO RELATED APPLICATION

The present application claims the benefit of U.S. Provisional Application No. 60/959,695, filed Jul. 16, 2007, and U.S. Provisional Application No. 60/937,756, filed Jun. 29, 2007, both of which are herein incorporated by reference in their entirety for all purposes.

FIELD OF THE INVENTION

This invention relates to novel HIV reverse transcriptase (RT) inhibitors, pharmaceutical compositions thereof, processes for making the novel HIV reverse transcriptase, and methods for inhibiting and treating an HIV infection.

BACKGROUND OF THE INVENTION

In recent years, inhibitors of HIV reverse transcriptase (RT) have become an important class of therapeutic agents for inhibition and treatment of HIV infection in humans. Compounds that inhibit the enzymatic functions of HIV reverse transcriptase inhibit replication of HIV in infected cells. Such compounds are useful in the prevention or treatment of HIV infection in humans, as demonstrated by known RT inhibitors such as zidovudine, didanosine, zalcitabine, stavudine, lamivudine, emtricitabine, abacavir, tenofovir, nevirapine, delavirdine and efavirenz, the main drugs thus far approved for use in the treatment of AIDS.

As with any antiviral therapy, use of RT inhibitors in the treatment of AIDS eventually leads to a virus that is less sensitive to the given drug. Resistance (reduced sensitivity) to these drugs is the result of mutations that occur in the reverse transcriptase segment of the pol gene. Several mutant strains of HIV have been characterized, and resistance to known therapeutic agents is believed to be due to mutations in the RT gene. Thus, to be effective, new HIV RT inhibitors must be effective not only against wild-type strains of HIV, but must also demonstrate efficacy against the newly emerging mutant strains that are resistant to the commercially available RT inhibitors. Accordingly, there continues to be a need for new HIV RT inhibitors, for example, those targeting the HIV RT in both wild type and mutant strains of HIV.

SUMMARY OF THE INVENTION

Accordingly, in one embodiment, the present application provides novel HIV RT inhibitor compounds of Formula (I):

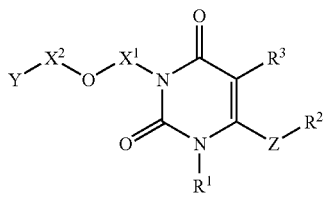

I or a pharmaceutically acceptable tautomer, salt, solvate, and/or ester thereof, wherein:

$R^1$ and $R^3$ are each independently H, alkyl, substituted alkyl, alkenyl, substituted alkenyl, alkynyl, substituted alkynyl, carbocyclyl, substituted carbocyclyl, aryl, substituted aryl, heteroaryl, substituted heteroaryl, heterocyclyl, or substituted heterocyclyl, arylalkyl, substituted arylalkyl, heteroarylalkyl; or substituted heteroarylalkyl;

$R^2$ is carbocyclyl, substituted carbocyclyl, aryl, substituted aryl, heteroaryl, substituted heteroaryl, heterocyclyl, or substituted heterocyclyl;

$X^1$ is alkylene, substituted alkylene, alkenylene, substituted alkenylene, alkynylene, substituted alkynylene, carbocyclylene, substituted carbocyclylene, heterocyclylene, or substituted heterocyclylene;

$X^2$ is a covalent bond, alkylene, or substituted alkylene;

Z is $-CH_2-$, $-C(O)-$, $-S-$, $-S(O)-$, $S(O)_2$, $-NR^3-$, $-NR^3-C(O)-$, or $-O-$;

Y is selected from a group consisting of:

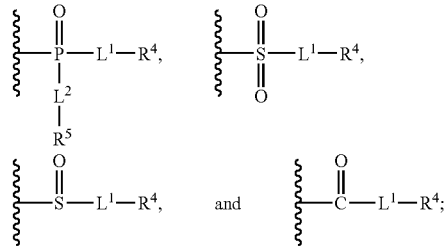

$L^1$ and $L^2$ are each independently a covalent bond, $-O-$, or $-NR^6-$;

$R^4$ and $R^5$ are each independently H, alkyl, substituted alkyl, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, substituted heterocyclylalkyl, -alkylene-C(O)—O—$R^7$, -(substituted alkylene)-C(O)—O—$R^7$, -alkylene-O—C(O)—O—$R^7$, or -(substituted alkylene)-O—C(O)—O—$R^7$; and $R^6$ and $R^7$ are each independently H, alkyl, substituted alkyl, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, or substituted heterocyclylalkyl; and with the following provisos:
(a) when $L^1$ is a covalent bond, then $R^4$ is not H;
(b) when $L^2$ is a covalent bond, then $R^5$ is not H; and
(c) $L^1$ and $L^2$ are not both covalent bonds.

In another embodiment, the present application provides a pharmaceutical composition comprising a therapeutically effective amount of at least one compound of Formula (I), or a pharmaceutically acceptable salt, solvate, and/or ester thereof; and a pharmaceutically acceptable carrier or excipient.

In another embodiment, the above pharmaceutical composition further comprises at least one additional active agent.

In another embodiment, the present application provides a method of inhibiting an HIV reverse transcriptase in a cell, comprising contacting the cell with an amount of at least one compound of Formula (I), or a pharmaceutically acceptable salt, solvate, and/or ester thereof, sufficient to inhibit the HIV reverse transcriptase in the cell.

In another embodiment, the present application provides a method of inhibiting the replication of a retrovirus comprising contacting said retrovirus with at least one compound of Formula (I), or a pharmaceutically acceptable salt, solvate, and/or ester thereof.

In another embodiment, the present application provides a method of treating an HIV infection in a patient, comprising administering to the patient a therapeutically effective amount of at least one compound of Formula (I).

In another embodiment, the present application provides a method for treating AIDS or AIDS Related Complex (ARC) comprising administering a therapeutically effective amount of at least one compound of Formula (I), or a pharmaceutically acceptable salt, solvate, and/or ester thereof, to a patient in need of such treatment.

In another embodiment, each of the above methods further comprises co-administering at least one additional active agent.

DETAILED DESCRIPTION

Reference will now be made in detail to certain claims of the invention, examples of which are illustrated in the accompanying structures and formulas. While the invention will be described in conjunction with the enumerated claims, it will be understood that they are not intended the invention to those claims. On the contrary, the invention is intended to cover all alternatives, modifications, and equivalents, which may be included within the scope of the present invention as defined by the claims.

All documents cited herein are incorporated by reference in their entirety for all purposes.

Unless stated otherwise, the following terms and phrases as used herein are intended to have the following meanings:

When trade names are used herein, applicants intend to independently include the tradename product and the active pharmaceutical ingredient(s) of the tradename product.

In accordance with a convention used in the art,

is used in structural formulas herein to depict the bond that is the point of attachment of the moiety or substituent to the core or backbone structure.

As used herein, "a compound of the invention" or "a compound of Formula (I)" means a compound of Formula (I) or a pharmaceutically acceptable salt, solvate, or physiologically functional derivative thereof. Similarly, with respect to isolatable intermediates such as for example, compounds of formula (4), the phrase "a compound of formula (number)" means a compound of that formula and pharmaceutically acceptable salts, solvates and physiologically functional derivatives thereof.

"Alkyl" is hydrocarbon containing normal, secondary, tertiary or cyclic carbon atoms. For example, an alkyl group can have 1 to 20 carbon atoms (i.e., $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, (n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or —OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —$CF_3$, —$CHF_2$, —$CFH_2$, —$CH_2CF_3$, and the like.

"Alkenyl" is a hydrocarbon containing normal, secondary, tertiary or cyclic carbon atoms with at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 12 carbon atoms (i.e., $C_2$-$C_{12}$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 12 carbon atoms (i.e., $C_2$-$C_{12}$ alkyne), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—$CH_2$—), 1,1-ethyl (—$CH(CH_3)$—), 1,2-ethyl (—$CH_2CH_2$—), 1,1-propyl (—$CH(CH_2CH_3)$—), 1,2-propyl (—$CH_2CH(CH_3)$—), 1,3-propyl (—$CH_2CH_2CH_2$—), 1,4-butyl (—$CH_2CH_2CH_2CH_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH=CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—CH$_2$C≡C—), and 4-pentynyl (—CH$_2$CH$_2$CH$_2$C≡CH—).

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Typical aryl groups include, but are not limited to, radicals derived from benzene (e.g., phenyl), substituted benzene, naphthalene, anthracene, biphenyl, and the like.

"Arylalkyl" refers to an acyclic alkyl radical in which one of the hydrogen atoms bonded to a carbon atom, typically a terminal or Sp$^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 6 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or Sp$^3$ carbon atom, but also an sp$^2$ carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 6 to 20 carbon atoms, e.g., the alkenyl moiety is 1 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or sp$^3$ carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 6 to 20 carbon atoms, e.g., the alkynyl moiety is 1 to 6 carbon atoms and the aryl moiety is 6 to 14 carbon atoms.

The term "substituted" in reference to alkyl, alkylene, aryl, arylalkyl, heterocyclyl, etc., for example "substituted alkyl", "substituted alkylene", "substituted aryl", "substituted arylalkyl", "substituted heterocyclyl", and "substituted carbocyclyl" means alkyl, alkylene, aryl, arylalkyl, heterocyclyl, carbocyclyl respectively, in which one or more hydrogen atoms are each independently replaced with a non-hydrogen substituent. Typical substituents include, but are not limited to, —X, —R, —O—, =O, —OR, —SR, —S—, —NR$_2$, —N+R$_3$, =NR, —CX$_3$, —CN, —OCN, —SCN, —N=C=O, —NCS, —NO, —NO$_2$, =N$_2$, —N$_3$, —NHC(=O)R, —C(=O)R, —C(=O)NRR—S(=O)$_2$O$^-$, —S(=O)$_2$OH, —S(=O)$_2$R, —OS(=O)$_2$OR, —S(=O)$_2$NR, —S(=O)R, —OP(=O)(OR)$_2$, —N(=O)(OR)$_2$, —N(=O)(O—)$_2$, —N(=O)(OH)$_2$, —N(O)(OR)(O—), —C(=O)R, —C(=O)X, —C(S)R, —C(O)OR, —C(O)O—, —C(S)OR, —C(O)SR, —C(S)SR, —C(O)NRR, —C(S)NRR, —C(=NR)NRR, where each X is independently a halogen: F, Cl, Br, or I; and each R is independently H, alkyl, aryl, arylalkyl, a heterocycle, or a protecting group or prodrug moiety. Alkylene, alkenylene, and alkynylene groups may also be similarly substituted.

The term "prodrug" as used herein refers to any compound that when administered to a biological system generates the drug substance, i.e., active ingredient, as a result of sponta-neous chemical reaction(s), enzyme catalyzed chemical reaction(s), photolysis, and/or metabolic chemical reaction(s). A prodrug is thus a covalently modified analog or latent form of a therapeutically active compound.

One skilled in the art will recognize that substituents and other moieties of the compounds of Formula (I) should be selected in order to provide a compound which is sufficiently stable to provide a pharmaceutically useful compound which can be formulated into an acceptably stable pharmaceutical composition. Compounds of Formula (I) which have such stability are contemplated as falling within the scope of the present invention.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —OCH$_3$, etc.), an amine (e.g., —NHCH$_3$, —N(CH$_3$)$_2$, etc.), or a thioalkyl group (e.g., —SCH$_3$). If a non-terminal carbon atom of the alkyl group which is not attached to the parent molecule is replaced with a heteroatom (e.g., O, N, or S) and the resulting heteroalkyl groups are, respectively, an alkyl ether (e.g., —CH$_2$CHF—O—CH$_3$, etc.), an alkyl amine (e.g., —CH$_2$NHCH$_3$, —CH$_2$N(CH$_3$)$_2$, etc.), or a thioalkyl ether (e.g., —CH—S—CH$_3$). If a terminal carbon atom of the alkyl group is replaced with a heteroatom (e.g., O, N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$CH$_2$—SH). A heteroalkyl group can have, for example, 1 to 20 carbon atoms, 1 to 10 carbon atoms, or 1 to 6 carbon atoms. A C$_1$-C$_6$ heteroalkyl group means a heteroalkyl group having 1 to 6 carbon atoms.

"Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl, and the like.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heterocyclylalkyl" refers to an acyclic alkyl radical in which one of the hydrogen atoms bonded to a carbon atom, typically a terminal or $Sp^3$ carbon atom, is replaced with a heterocyclyl radical (i.e., a heterocyclyl-alkylene-moiety). Typical heterocyclyl alkyl groups include, but are not limited to heterocyclyl-$CH_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclyl alkyl group comprises 6 to 20 carbon atoms, e.g., the alkyl portion of the arylalkyl group is 1 to 6 carbon atoms and the heterocyclyl moiety is 5 to 14 carbon atoms. Examples of heterocyclylalkyls include by way of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, etc., 6-membered sulfur, oxygen, and/or nitrogen containing heterocycles such as piperidinylmethyl, piperazinylmethyl, morpholinylmethyl, pyridinylmethyl, pyridizylmethyl, pyrimidylmethyl, pyrazinylmethyl, etc.

"Heterocyclylalkenyl" refers to an acyclic alkenyl radical in which one of the hydrogen atoms bonded to a carbon atom, typically a terminal or $Sp^3$ carbon atom, but also a $Sp^2$ carbon atom, is replaced with a heterocyclyl radical (i.e., a heterocyclyl-alkenylene-moiety). The heterocyclyl portion of the heterocyclyl alkenyl group includes any of the heterocyclyl groups described herein, including those described in *Principles of Modern Heterocyclic Chemistry*, and the alkenyl portion of the heterocyclyl alkenyl group includes any of the alkenyl groups disclosed herein. One skilled in the art will also understand that the heterocyclyl group can be attached to the alkenyl portion of the heterocyclyl alkenyl by means of a carbon-carbon bond or a carbon-heteroatom bond, with the proviso that the resulting group is chemically stable. The heterocyclyl alkenyl group comprises 6 to 20 carbon atoms, e.g., the alkenyl portion of the heterocyclyl alkenyl group is 1 to 6 carbon atoms and the heterocyclyl moiety is 5 to 14 carbon atoms.

"Heterocyclylalkynyl" refers to an acyclic alkynyl radical in which one of the hydrogen atoms bonded to a carbon atom, typically a terminal or $sp^3$ carbon atom, but also an sp carbon atom, is replaced with a heterocyclyl radical (i.e., a heterocyclyl-alkynylene-moiety). The heterocyclyl portion of the heterocyclyl alkynyl group includes any of the heterocyclyl groups described herein, including those described in *Principles of Modern Heterocyclic Chemistry*, and the alkynyl portion of the heterocyclyl alkynyl group includes any of the alkynyl groups disclosed herein. One skilled in the art will also understand that the heterocyclyl group can be attached to the alkynyl portion of the heterocyclyl alkynyl by means of a carbon-carbon bond or a carbon-heteroatom bond, with the proviso that the resulting group is chemically stable. The heterocyclyl alkynyl group comprises 6 to 20 carbon atoms, e.g., the alkynyl portion of the heterocyclyl alkynyl group is 1 to 6 carbon atoms and the heterocyclyl moiety is 5 to 14 carbon atoms.

"Heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

"Carbocycle" or "carbocyclyl" refers to a saturated, partially unsaturated or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl.

"Arylheteroalkyl" refers to a heteroalkyl as defined herein, in which a hydrogen atom (which may be attached either to a carbon atom or a heteroatom) has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-5-aryl, -alkylene-5-alkylene-aryl, etc. In addition, any of the alkylene moieties in the general formulae above can be further substituted with any of the substituents defined or exemplified herein.

"Heteroarylalkyl" refers to an alkyl group, as defined herein, in which a hydrogen atom has been replaced with a heteroaryl group as defined herein. Non-limiting examples of heteroaryl alkyl include —CH$_2$-pyridinyl, —CH$_2$-pyrrolyl, —CH$_2$-oxazolyl, —CH$_2$-indolyl, —CH$_2$-isoindolyl, —CH$_2$-purinyl, —CH$_2$-furanyl, —CH$_2$-thienyl, —CH$_2$-benzofuranyl, —CH$_2$-benzothiophenyl, —CH$_2$-carbazolyl, —CH$_2$-imidazolyl, —CH$_2$-thiazolyl, —CH$_2$-isoxazolyl, —CH$_2$-pyrazolyl, —CH$_2$-isothiazolyl, —CH$_2$-quinolyl, —CH$_2$-isoquinolyl, —CH$_2$-pyridazyl, —CH$_2$-pyrimidyl, —CH$_2$-pyrazyl, —CH(CH$_3$)-pyridinyl, —CH(CH$_3$)-pyrrolyl, —CH(CH$_3$)-oxazolyl, —CH(CH$_3$)-indolyl, —CH(CH$_3$)-isoindolyl, —CH(CH$_3$)-purinyl, —CH(CH$_3$)-furanyl, —CH(CH$_3$)-thienyl, —CH(CH$_3$)-benzofuranyl, —CH(CH$_3$)-benzothiophenyl, —CH(CH$_3$)-carbazolyl, —CH(CH$_3$)-imidazolyl, —CH(CH$_3$)-thiazolyl, —CH(CH$_3$)-isoxazolyl, —CH(CH$_3$)-pyrazolyl, —CH(CH$_3$)-isothiazolyl, —CH(CH$_3$)-quinolyl, —CH(CH$_3$)-isoquinolyl, —CH(CH$_3$)-pyridazyl, —CH(CH$_3$)-pyrimidyl, —CH(CH$_3$)-pyrazyl, etc.

The terms "phosphonate" and "phosphonate group" mean a functional group or moiety within a molecule that comprises at least one phosphorus-carbon bond, and at least one phosphorus-oxygen double bond. The phosphorus atom is further substituted with oxygen, sulfur, and nitrogen substituents. As defined herein, "phosphonate" and "phosphonate group" include molecules with phosphonic acid, phosphonic monoester, phosphonic diester, phosphonamidate, phosphondiamidate, and phosphonthioate functional groups.

"Linker" or "link" refers to a chemical moiety comprising a covalent bond or a chain or group of atoms that covalently attaches a phosphonate or phosphinate group to a drug. Linkers which include moieties such as: repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide.

"Optionally substituted" refers to a particular moiety of the compound of Formula (I) (e.g., an optionally substituted aryl group) refers to a moiety having 0, 1, 2, or more substituents.

"Ester thereof" means any ester of a compound in which any of the —COOH functions of the molecule is replaced by a —COOR function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. The term "ester thereof" includes but is not limited to pharmaceutically acceptable esters thereof.

"Salt thereof" means any acid and/or base addition salt of a compound according to the invention; preferably a pharmaceutically acceptable salt thereof.

"Pharmaceutically acceptable salt" means a salt of a compound which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. Where applicable and compatible with the chemical properties of the compounds of Formula (I), the term includes pharmaceutically-acceptable acid addition salts and pharmaceutically-acceptable base addition salts. Lists of suitable salts are found in, e.g., S. M. Birge et al., J. Pharm. Sci., 1977, 66, pp. 1-19.

"Treatment" or "treating" means the administration of a compound or composition according to the present invention to alleviate or eliminate symptoms of the HIV disease and/or to reduce viral load in a patient. The term "treatment" or "treating" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectible levels in the blood, and the administration of a compound or composition according to the present invention to prevent perinatal transmission of HIV from mother to baby, by administration to the mother before giving birth and to the child within the first days of life.

"Chiral" refers to molecules which have the property of non-superimposability of the mirror image partner, while the term "achiral" refers to molecules which are superimposable on their mirror image partner.

"Stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. N. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether-nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene and Peter G. M. Wuts (John Wiley & Sons, Inc., New York, 1999, ISBN 0-471-16019-9) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-Forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no anti-infective activity of their own.

Compounds of Formula (I)

In one embodiment, the present application provides compounds according to Formula (I), as described herein.

In another embodiment of the compounds of Formula (I), $R^1$ is H, alkyl, substituted alkyl, alkenyl, substituted alkenyl, alkynyl, or substituted alkynyl.

In another embodiment of the compounds of Formula (I), $R^1$ is H or alkyl.

In another embodiment of the compounds of Formula (I), $R^3$ is H, alkyl, substituted alkyl, alkenyl, substituted alkenyl, alkynyl, or substituted alkynyl.

In another embodiment of the compounds of Formula (I), $R^3$ is H or alkyl.

In another embodiment of the compounds of Formula (I), $R^1$ and $R^3$ are each independently H, alkyl, substituted alkyl, alkenyl, substituted alkenyl, alkynyl, or substituted alkynyl.

In another embodiment of the compounds of Formula (I), $R^1$ and $R^3$ are each independently alkyl or substituted alkyl.

In another embodiment of the compounds of Formula (I), $R^2$ is aryl, substituted aryl, heteroaryl, or substituted heteroaryl.

In another embodiment of the compounds of Formula (I), $R^2$ is phenyl or substituted phenyl.

In another embodiment of the compounds of Formula (I), $R^2$ is substituted phenyl having one or more substituents selected from the group consisting of alkyl, alkenyl, alkynyl, halo, cyano, nitro, hydroxyl, amino, alkoxy, N-alkyl amino, N,N-dialkyl amino, and combinations thereof.

In another embodiment of the compounds of Formula (I), $X^1$ is alkylene or substituted alkylene.

In another embodiment of the compounds of Formula (I), $X^1$ is —CH$_2$— or —CH$_2$CH$_2$—.

In another embodiment of the compounds of Formula (I), $X^2$ is a covalent bond.

In another embodiment of the compounds of Formula (I), $X^2$ is alkylene or substituted alkylene.

In another embodiment of the compounds of Formula (I), Y is

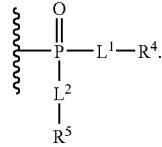

In another embodiment of the compounds of Formula (I), $L^1$ and $L^2$ are each independently —O— or —NR$^6$—.

In another embodiment of the compounds of Formula (I), —X$^1$O—X$^2$—Y is —CH$_2$—O—P(O)(OH)$_2$.

In another embodiment of the compounds of Formula (I), $L^1$ is a covalent bond; and $L^2$ is —O— or —NR$^6$—.

In another embodiment of the compounds of Formula (I), Y is

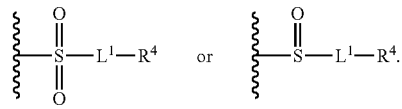

In another embodiment of the compounds of Formula (I), $L^1$ is —O— or —NR$^6$—;

In another embodiment of the compounds of Formula (I), Y is

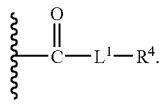

In another embodiment of the compounds of Formula (I), $L^1$ is a covalent bond.

In another embodiment of the compounds of Formula (I), $-X^1-O-X^2-Y$ is $-CH_2-O-C(O)CH_3$.

In another embodiment of the compounds of Formula (I), $R^1$ and $R^3$ are each independently H, alkyl, substituted alkyl, alkenyl, substituted alkenyl, alkynyl, or substituted alkynyl; $R^2$ is aryl, substituted aryl, heteroaryl, or substituted heteroaryl; $X^1$ is alkylene or substituted alkylene; $X^2$ is a covalent bond; Y is

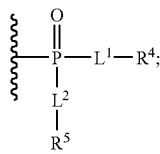

$L^1$ and $L^2$ are each independently $-O-$ or $-NR^6-$; and $R^4$ and $R^5$ are each independently H, alkyl, or substituted alkyl.

In another embodiment of the compounds of Formula (I), $R^1$ and $R^3$ are each independently H, alkyl, substituted alkyl, alkenyl, substituted alkenyl, alkynyl, or substituted alkynyl; $R^2$ is aryl, substituted aryl, heteroaryl, or substituted heteroaryl; $X^1$ is alkylene or substituted alkylene; $X^2$ is a covalent bond; Y is

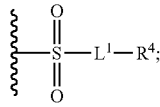

$L^1$ is $-O-$ or $-NR^6-$; and $R^4$ is H, alkyl, or substituted alkyl.

In another embodiment of the compounds of Formula (I), $R^1$ and $R^3$ are each independently H, alkyl, substituted alkyl, alkenyl, substituted alkenyl, alkynyl, or substituted alkynyl; $R^2$ is aryl, substituted aryl, heteroaryl, or substituted heteroaryl; $X^1$ is alkylene or substituted alkylene; $X^2$ is a covalent bond; Y is

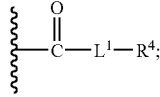

$L^1$ is a covalent bond; and $R^4$ is alkyl or substituted alkyl.

In another embodiment, the compounds of the compounds of Formula (I) include, but are not limited to:

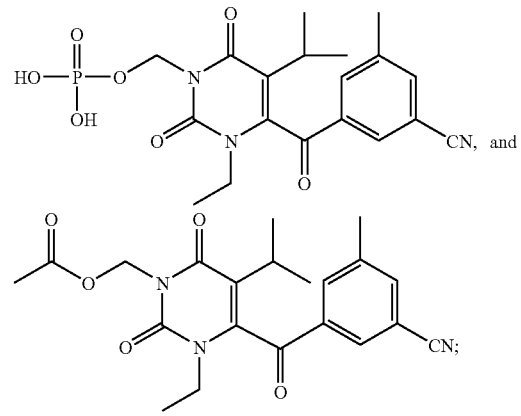

or a pharmaceutically acceptable tautomer, salt, solvate, and/or ester thereof.

In another embodiment of the compounds of Formula (I), $R^1$ and $R^3$ are each independently H, alkyl, substituted alkyl, alkenyl, substituted alkenyl, alkynyl, or substituted alkynyl; $R^2$ is aryl, substituted aryl, heteroaryl, or substituted heteroaryl; $X^1$ is alkylene or substituted alkylene; $X^2$ is a covalent bond; Y is

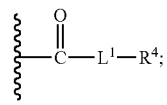

$L^1$ is a covalent bond; and $R^4$ is substituted alkyl.

In another embodiment of the compounds of Formula (I), $R^1$ and $R^3$ are each independently H, alkyl, substituted alkyl, alkenyl, substituted alkenyl, alkynyl, or substituted alkynyl; $R^2$ is aryl, substituted aryl, heteroaryl, or substituted heteroaryl; $X^1$ is alkylene or substituted alkylene; $X^2$ is a covalent bond; Y is

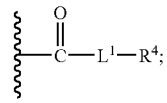

$L^1$ is a covalent bond; and $R^4$ is aminoalkyl.

In another embodiment, the compounds of the compounds of Formula (I) include, but are not limited to:

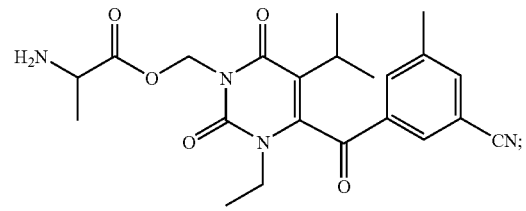 [SMILES: CCn1c(C(=O)c2cc(C)cc(C#N)c2)c(C(C)C)c(=O)n(COC(=O)C(C)N)c1=O]

or a pharmaceutically acceptable tautomer, salt, solvate, and/or ester thereof.

In another embodiment of the compounds of Formula (I), $R^1$ and $R^3$ are each independently H, alkyl, substituted alkyl, alkenyl, substituted alkenyl, alkynyl, or substituted alkynyl; $R^2$ is aryl, substituted aryl, heteroaryl, or substituted heteroaryl; $X^1$ is alkylene or substituted alkylene; $X^2$ is a covalent bond; Y is

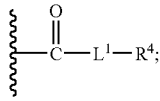

$L^1$ is a covalent bond; and $R^4$ is substituted or unsubstituted heterocyclylalkyl.

In another embodiment of the compounds of Formula (I), $R^1$ and $R^3$ are each independently H, alkyl, substituted alkyl, alkenyl, substituted alkenyl, alkynyl, or substituted alkynyl; $R^2$ is aryl, substituted aryl, heteroaryl, or substituted heteroaryl; $X^1$ is alkylene or substituted alkylene; $X^2$ is a covalent bond; Y is

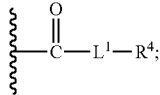

$L^1$ is a covalent bond; and $R^4$ is substituted or unsubstituted heterocycloalkylalkyl.

In another embodiment of the compounds of Formula (I), $R^1$ and $R^3$ are each independently H, alkyl, substituted alkyl, alkenyl, substituted alkenyl, alkynyl, or substituted alkynyl; $R^2$ is aryl, substituted aryl, heteroaryl, or substituted heteroaryl; $X^1$ is alkylene or substituted alkylene; $X^2$ is a covalent bond; Y is

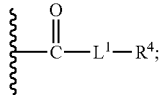

$L^1$ is a covalent bond; and $R^4$ is substituted or unsubstituted morpholinylalkyl.

In another embodiment, the compounds of the compounds of Formula (I) include, but are not limited to:

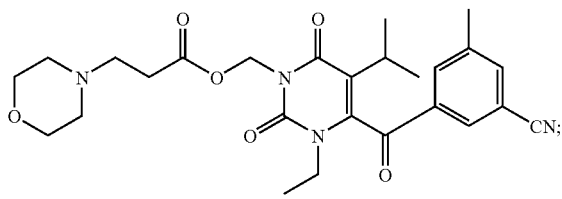 [SMILES: CCn1c(C(=O)c2cc(C)cc(C#N)c2)c(C(C)C)c(=O)n(COC(=O)CCN2CCOCC2)c1=O]

or a pharmaceutically acceptable tautomer, salt, solvate, and/or ester thereof.

In another embodiment of the compounds of Formula (I), $R^1$ and $R^3$ are each independently H, alkyl, substituted alkyl, alkenyl, substituted alkenyl, alkynyl, or substituted alkynyl; $R^2$ is aryl, substituted aryl, heteroaryl, or substituted heteroaryl; $X^1$ is alkylene or substituted alkylene; $X^2$ is a covalent bond; Y is

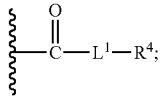

$L^1$ is —; and $R^4$ is substituted or unsubstituted alkyl.

In another embodiment, the compounds of the compounds of Formula (I) include, but are not limited to:

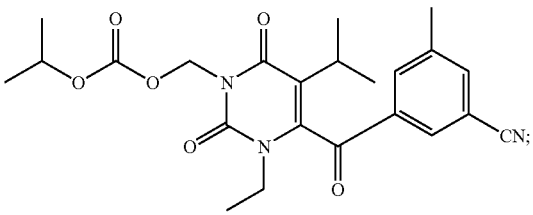 [SMILES: CCn1c(C(=O)c2cc(C)cc(C#N)c2)c(C(C)C)c(=O)n(COC(=O)OC(C)C)c1=O]

or a pharmaceutically acceptable tautomer, salt, solvate, and/or ester thereof.

In another embodiment of the compounds of Formula (I), $R^4$ is alkyl, substituted alkyl, heterocyclylalkyl, or substituted heterocyclylalkyl.

In another embodiment of the compounds of Formula (I), $-X^1-O-X^2-Y$ is $-CH_2-O-C(O)-CH_3$, $-CH_2-O-C(O)-(CH_2)_2-N(CH_2CH_2)_2O$, or $-CH_2-O-C(O)-CH(NH_2)-CH_3$.

In another embodiment of the compounds of Formula (I), $L^1$ is $-O-$.

In another embodiment of the compounds of Formula (I), $R^4$ is alkyl or substituted alkyl.

In another embodiment of the compounds of Formula (I), $R^1$ and $R^3$ are each independently H, alkyl, substituted alkyl, alkenyl, substituted alkenyl, alkynyl, or substituted alkynyl; $R^2$ is aryl, substituted aryl, heteroaryl, or substituted heteroaryl; $X^1$ is alkylene or substituted alkylene; $X^2$ is a covalent bond; Y is

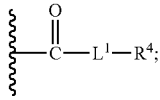

$L^1$ is a covalent bond; and $R^4$ is alkyl, substituted alkyl, heterocyclylalkyl, or substituted heterocyclylalkyl.

In another embodiment of the compounds of Formula (I), $R^1$ and $R^3$ are each independently H, alkyl, substituted alkyl, alkenyl, substituted alkenyl, alkynyl, or substituted alkynyl; $R^2$ is aryl, substituted aryl, heteroaryl, or substituted heteroaryl; $X^1$ is alkylene or substituted alkylene; $X^2$ is a covalent bond; Y is

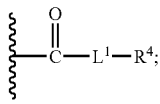

$L^1$ is $-O-$; and $R^4$ is alkyl or substituted alkyl.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the Handbook of Pharmaceutical Excipients (1986), herein incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations of the invention, both for veterinary and for human use, comprise at least one active ingredient, as defined above, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.), herein incorporated by reference in its entirety. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl n-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth herein, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 Mg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 μm (including particle sizes in a range between 0.1 and 500 μm in increments such as 0.5 μm, 1 μm, 30 μm, 35 μm, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of infections as described herein.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

The effective dose of an active ingredient depends at least on the nature of the condition being treated, toxicity, whether the compound is being used prophylactically (lower doses) or against an active disease or condition, the method of delivery, and the pharmaceutical formulation, and will be determined by the clinician using conventional dose escalation studies. The effective dose can be expected to be from about 0.0001 to about 100 mg/kg body weight per day. Typically, an effective dose ranges from about 0.01 to about 10 mg/kg body weight per day. More typically, an effective dose ranges from about 0.01 to about 5 mg/kg body weight per day. Even more typically, an effective dose ranges from about 0.05 to about 0.5 mg/kg body weight per day. For example, the daily candidate dose for an adult human of approximately 70 kg body weight will range from 1 mg to 1000 mg, or between 5 mg and 500 mg, and may take the form of single or multiple doses.

In another embodiment, the present application provides a pharmaceutical composition comprising a therapeutically effective amount of at least one compound of Formula (I), or a pharmaceutically acceptable salt, solvate, and/or ester thereof, and a pharmaceutically acceptable carrier.

In another embodiment, the present application provides a pharmaceutical composition comprising a therapeutically effective amount of at least one compound of Formula (I), or a pharmaceutically acceptable salt, solvate, and/or ester thereof, in combination with at least one additional active therapeutic agent and a pharmaceutically acceptable carrier.

In another embodiment, the present application provides a pharmaceutical composition comprising a therapeutically effective amount of a compound of Formula (I), and one or more additional active agents selected from the group consisting of HIV protease inhibitors, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, G6PD and NADH-oxidase inhibitors, CCR5 inhibitors, CCR8 inhibitors, entry inhibitors, RNase H inhibitors, maturation inhibitors, pharmacokinetic enhancers, and other drugs for treating HIV, and mixtures thereof.

In another embodiment, the present application provides a pharmaceutical composition comprising a therapeutically effective amount of a compound of Formula (I), and at least one another active agent selected from the group consisting of: 1) HIV protease inhibitors, e.g., amprenavir (Agenerase), atazanavir (Reyataz), fosamprenavir (Lexiva), indinavir (Crixivan), lopinavir, ritonavir (norvir), nelfinavir (Viracept), saquinavir (Invirase), tipranavir (Aptivus), brecanavir, darunavir (Prezista), TMC-126, TMC-114, mozenavir (DMP-450), JE-2147 (AG1776), L-756423, RO0334649, KNI-272, DPC-681, DPC-684, DG17, GS-8374, MK-8122 (PPL-100), DG35, and AG 1859, SPI-256, TMC 52390, PL-337, SM-322377, SM-309515, GRL-02031, CRS-074, CRS-075, KB-98, and A-790742; 2) HIV non-nucleoside inhibitors of reverse transcriptase, e.g., capravirine, emivirine, delaviridine (Rescriptor), efavirenz (Sustiva), nevirapine (Viramune), (+)-calanolide A, calanolide B, etravirine (Intelence), GW5634, DPC-083, DPC-961, DPC-963, MIV-150, MIV-160, MIV-170, dapivirine (TMC-120), rilpivirine (TMC-278), BILR 355 BS, VRX 840773, UK-453061, and RDEA806, RDEA 427, RDEA 640, IDX 899, ANX-201 (Thiovir), R-1206, LOC-dd, IQP-0410 (SJ-3366), YM-215389, YM-228855, CMX-052, and CMX-182; 3) HIV nucleoside inhibitors of reverse transcriptase, e.g., zidovudine (Retrovir), emtricitabine (Emtriva), didanosine (Videx), stavudine (Zerit), zalcitabine (Hivid), lamivudine (Epivir), abacavir (Ziagen), amdoxovir, elvucitabine (ACH 126443), alovudine (MIV-310), MIV-210, racivir (racemic FTC, PSI-5004), D-d4FC, phosphazide, fozivudine tidoxil, apricitibine (AVX754, SPD-754), GS-7340, KP-1461, AVX756, OBP-601, dioxolane thymine, TMC-254072, INK-20, PPI-801, PPI-802, MIV-410, 4'-Ed4T, B-108, and fosalvudine tidoxil (HDP 99.0003); 4) HIV nucleotide inhibitors of reverse transcriptase, e.g., tenofovir disoproxil fumarate (Viread), and adefovir dipivoxil; 5) HIV integrase inhibitors, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, raltegravir (Isentress, MK-0518), elvitegravir (GS-9137), BMS-538158, GSK364735C, BMS-707035, MK-2048, GSK-349572 (S-349572), GSK-265744 (S-265744), GSK-247303 (S-247303), S-1360 (GW810871), 1,5-DCQA, INH-001, INT-349, V-165, RIN-25, BFX-1001, BFX-1002, BFX-1003, RSC-1838, BCH-33040, and BA 011; 6) gp41 inhibitors, e.g., enfuvirtide (Fuzeon), sifuvirtide, MPI-451936, FB006M, A-329029, and TRI-1144; 7) CXCR4 inhibitors, e.g., AMD-070, KRH-3955 (CS-3955), AMD-9370, AMD-3451, RPI-MN, MSX-122, and POL-2438; 8) entry inhibitors, e.g., SP01A, PA-161, SPC3, TNX-355, DES6, SP-10, SP-03, CT-319, and CT-326; 9) gp120 inhibitors, e.g., BMS-488043 and its prodrugs, BlockAide/CR, KPC-2, and MNLP62; 10) G6PD and NADH-oxidase inhibitors, e.g., immunitin; 11) CCR5 inhibitors, e.g., aplaviroc, nifeviroc, vicriviroc (SCH-417690), maraviroc (Selzentry), PRO-140, PRO-542, INCB15050, INCB9471, PF-232798, SCH-532706, GSK-706769, TAK-652, TAK-220, ESN-196, RO-1752, ZM-688523, AMD-887, YM-370749, NIBR-1282, SCH-350634, ZM-688523, and CCR5mAb004; 12) CCR8 inhibitors, e.g., ZK-756326; 13) RNase H inhibitors, e.g., ODN-93, and ODN-112; 14) maturation inhibitors, e.g., bevirimat (PA- 457), PA-040, MPC-9055 (vicecon, MPI-49839), ACH-100703, ACH-100706; 15) pharmacokinetic enhancers, e.g., BAS-100, SPI-452, PF-419-4477, TMC-41629, and roxythromycin; 16) other drugs for treating HIV, e.g., REP 9, SP-01A, TNX-355, DES6, ODN-93, ODN-112, VGV-1, Ampligen, HRG214, Cytolin, VGX-410, VGX-820, KD-247, AMZ 0026, CYT 99007, A-221 HIV, HPH-116, DEBIO-025, BAY 50-4798, MDX010 (ipilimumab), PBS119, BIT-225, UBT-8147, ITI-367, AFX-400, BL-1050, GRN-139951, GRN-140665, AX-38679, RGB-340638, PPI-367, and ALG 889; and any combinations or mixtures of the above.

In another embodiment, the present application provides a combination pharmaceutical agent comprising: a first pharmaceutical composition comprising a compound of Formula (I), or a pharmaceutically acceptable salt, solvate, and/or ester thereof; and a second pharmaceutical composition comprising at least one additional active agent selected from the group consisting of HIV protease inhibitors, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, G6PD and NADH-oxidase inhibitors, CCR5 inhibitors, CCR8 inhibitors, entry inhibitors, RNase H inhibitors, maturation inhibitors, pharmacokinetic enhancers, and other drugs for treating HIV, and mixtures thereof.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

In one embodiment, the compounds of Formula (I) can be administered alone, e.g., without other active therapeutic in ingredients or agents. In another embodiment, the compounds of Formula (I) are used in combination with one or more active therapeutic ingredients or agents. Preferably, the other active therapeutic ingredients or agents are HIV protease inhibiting compounds, HIV protease inhibitors, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, G6PD and NADH-oxidase inhibitors, CCR5 inhibitors, CCR8 inhibitors, entry inhibitors, RNase H inhibitors, maturation inhibitors, pharmacokinetic enhancers, other drugs for treating HIV, and mixtures thereof.

Combinations of the compounds of Formula (I) are typically selected based on the condition to be treated, cross-reactivities of ingredients and pharmaco-properties of the combination. For example, when treating an infection (e.g., HIV or HCV), the compositions of the invention are combined with anti-infective agents (such as those described herein).

More specifically, one or more compounds of the present invention may be combined with one or more compounds selected from the group consisting of:

1) HIV protease inhibitors, e.g., amprenavir (Agenerase), atazanavir (Reyataz), fosamprenavir (Lexiva), indinavir (Crixivan), lopinavir, ritonavir (norvir), nelfinavir (Viracept), saquinavir (Invirase), tipranavir (Aptivus), brecanavir, darunavir (Prezista), TMC-126, TMC-114, mozenavir (DMP-450), JE-2147 (AG1776), L-756423, RO0334649, KNI-272, DPC-681, DPC-684, DG17, GS-8374, MK-8122 (PPL-100), DG35, and AG 1859, SPI-256, TMC 52390, PL-337, SM-322377, SM-309515, GRL-02031, CRS-074, CRS-075, KB-98, and A-790742;

2) HIV non-nucleoside inhibitors of reverse transcriptase, e.g., capravirine, emivirine, delaviridine (Rescriptor), efavirenz (Sustiva), nevirapine (Viramune), (+)-calanolide A, calanolide B, etravirine (Intelence), GW5634, DPC-083, DPC-961, DPC-963, MIV-150, MIV-160, MIV-170, dapivirine (TMC-120), rilpivirine (TMC-278), BILR 355 BS, VRX 840773, UK-453061, and RDEA806, RDEA 427, RDEA 640, IDX 899, ANX-201 (Thiovir), R-1206, LOC-dd, IQP-0410 (SJ-3366), YM-215389, YM-228855, CMX-052, and CMX-182;

3) HIV nucleoside inhibitors of reverse transcriptase, e.g., zidovudine (Retrovir), emtricitabine (Emtriva), didanosine (Videx), stavudine (Zerit), zalcitabine (Hivid), lamivudine (Epivir), abacavir (Ziagen), amdoxovir, elvucitabine (ACH 126443), alovudine (MIV-310), MIV-210, racivir (racemic FTC, PSI-5004), D-d4FC, phosphazide, fozivudine tidoxil, apricitibine (AVX754, SPD-754), GS-7340, KP-1461, AVX756, OBP-601, dioxolane thymine, TMC-254072, INK-20, PPI-801, PPI-802, MIV-410, 4'-Ed4T, B-108, and fosalvudine tidoxil (HDP 99.0003);

4) HIV nucleotide inhibitors of reverse transcriptase, e.g., tenofovir disoproxil fumarate (Viread), and adefovir dipivoxil;

5) HIV integrase inhibitors, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, raltegravir (Isentress, MK-0518), elvitegravir (GS-9137), BMS-538158, GSK364735C, BMS-707035, MK-2048, GSK-349572 (S-349572), GSK-265744 (S-265744), GSK-247303 (S-247303), S-1360 (GW810871), 1,5-DCQA, INH-001, INT-349, V-165, RIN-25, BFX-1001, BFX-1002, BFX-1003, RSC-1838, BCH-33040, and BA 011;

6) gp41 inhibitors, e.g., enfuvirtide (Fuzeon), sifuvirtide, MPI-451936, FB006M, A-329029, and TRI-1144;

7) CXCR4 inhibitors, e.g., AMD-070, KRH-3955 (CS-3955), AMD-9370, AMD-3451, RPI-MN, MSX-122, and POL-2438;

8) entry inhibitors, e.g., SP01A, PA-161, SPC3, TNX-355, DES6, SP-10, SP-03, CT-319, and CT-326;

9) gp120 inhibitors, e.g., BMS-488043 and its prodrugs, BlockAide/CR, KPC-2, and MNLP62;

10) G6PD and NADH-oxidase inhibitors, e.g., immunitin;

11) CCR5 inhibitors, e.g., aplaviroc, nifeviroc, vicriviroc (SCH-417690), maraviroc (Selzentry), PRO-140, PRO-542, INCB15050, INCB9471, PF-232798, SCH-532706, GSK-706769, TAK-652, TAK-220, ESN-196, RO-1752, ZM-688523, AMD-887, YM-370749, NIBR-1282, SCH-350634, ZM-688523, and CCR5 mAb004;

12) CCR8 inhibitors, e.g., ZK-756326;

13) RNase H inhibitors, e.g., ODN-93, and ODN-112;

14) maturation inhibitors, e.g., bevirimat (PA-457), PA-040, MPC-9055 (vicecon, MPI-49839), ACH-100703, ACH-100706;

15) pharmacokinetic enhancers, e.g., BAS-100, SPI-452, PF-419-4477, TMC-41629, and roxythromycin; and 160 other drugs for treating HIV, e.g., REP 9, SP-01A, TNX-355, DES6, ODN-93, ODN-112, VGV-1, Ampligen, HRG214, Cytolin, VGX-410, VGX-820, KD-247, AMZ 0026, CYT 99007, A-221 HIV, HPH-116, DEBIO-025, BAY 50-4798, MDX010 (ipilimumab), PBS119, BIT-225, UBT-8147, ITI-367, AFX-400, BL-1050, GRN-139951, GRN-140665, AX-38679, RGB-340638, PPI-367, and ALG 889.

It is also possible to combine any compound of the invention with one or more other active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

In another embodiment, the present invention provides a method for inhibiting HIV RT comprising administering a therapeutically effective amount of at least one compound of Formula (I), or a pharmaceutically acceptable salt, solvate, or ester thereof, to a patient in need of such treatment.

In another embodiment, the present invention provides a method for treating or preventing a HIV infection comprising: administering a therapeutically effective amount of at least one compound of Formula (I), or a pharmaceutically acceptable salt, solvate, and/or ester thereof, to a patient in need of such treatment.

In another embodiment, the present invention provides a method, further comprising co-administering a therapeutic amount of at least one additional active agent selected from the group consisting of HIV protease inhibitors, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, G6PD and NADH-oxidase inhibitors, CCR5 inhibitors, CCR8 inhibitors, entry inhibitors, RNase H inhibitors, maturation inhibitors, pharmacokinetic enhancers, other drugs for treating HIV, and mixtures thereof.

In another embodiment, the present invention provides a method for treating AIDS or AIDS Related Complex (ARC) comprising administering at least one therapeutically effective amount of a compound of Formula (I), or a pharmaceutically acceptable salt, solvate, and/or ester thereof, to a patient in need of such treatment.

In another embodiment, the present invention provides a method of co-administering a therapeutic amount of at least one compound of Formula (I) and at least one additional active agent selected from the group consisting of HIV protease inhibitors, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, G6PD and NADH-oxidase inhibitors, CCR5 inhibitors, CCR8 inhibitors, entry inhibitors, RNase H inhibitors, maturation inhibitors, pharmacokinetic enhancers, other drugs for treating HIV, and mixtures thereof.

In another embodiment, the present invention provides a method of inhibiting the replication of a retrovirus comprising contacting said retrovirus with at least one compound of Formula (I), or a pharmaceutically acceptable salt, solvate, and/or ester thereof.

In another embodiment, the present invention provides a method of inhibiting the replication of a retrovirus comprising contacting the retrovirus with a compound of Formula (I) and at least one additional active agent selected from the group consisting of HIV protease inhibitors, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, G6PD and NADH-oxidase inhibitors, CCR5 inhibitors, CCR8 inhibitors, entry inhibitors, RNase H inhibitors, maturation inhibitors, pharmacokinetic enhancers, other drugs for treating HIV, and mixtures thereof.

In another embodiment, the present application provides for the use of a compound of Formula (I) for the preparation of a medicament for treating or preventing an HIV infection in a patient.

In another embodiment, the present application provides for the use of a compound of Formula (I) for the preparation of a medicament for treating AIDS or AIDS Related Complex (ARC) in a patient.

In another embodiment, the present application provides for the use of a compound of Formula (I) for the preparation of a medicament for inhibiting the replication of a retrovirus in a patient.

In still yet another embodiment, the compounds of Formula I are named below in tabular format (Table 8) as compounds of general Formula II:

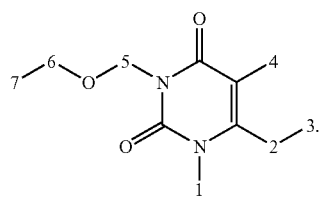

Formula II

Tables 1-7, respectively, show the structures of the "1", "2", "3", "4", "5" "6". and "7" moieties. Each substituent "1", "2", "3", "4", "5", "6", and "7" in Tables 1-7 is represented by a "code" comprising a number and a letter. Each structure of a compound of Formula II can be designated in tabular form by combining the "code" representing each structural moiety using the following syntax: 1.2.3.4.5.6.7. Thus, for example, 1a.2a.3a.4a.5a.6a.7a represents the following structure:

TABLE 1

"1" Structures

| Code | "1" Structures |
|---|---|
| 1a | —CH$_2$CH$_3$ |
| 1b | —CH$_2$CH$_2$CH$_3$ |
| 1c | (cyclopropyl-CH$_2$-C(O)NH$_2$ group) |
| 1d | —CH$_2$CH(CH$_3$)$_2$ |

TABLE 2

"2" Structures

| Code | "2" Structures |
|---|---|
| 2a | —C(O)— |
| 2b | —O— |
| 2c | —NH— |
| 2d | —S— |
| 2e | —CH$_2$— |

TABLE 3

"3" Structures

| Code | "3" Structures |
|---|---|
| 3a | (3,5-disubstituted benzene: methyl, CN) |
| 3b | (3,5-disubstituted benzene with methyl and vinyl-CN) |
| 3c | (3,5-dimethyl benzene) |
| 3d | (3,5-disubstituted benzene: Cl, CN) |
| 3e | (3,5-disubstituted benzene: Cl, CH$_2$CN) |

TABLE 4

"4" Structures

| Code | "4" Structures |
|---|---|
| 4a | —CH(CH$_3$)$_2$ |
| 4b | —CH$_2$CH$_3$ |
| 4c | —C(CH$_3$)$_3$ |
| 4d | —C(CH$_3$)$_2$OH |
| 4e | —CH(CH$_3$)CH$_2$OH |

TABLE 5

"5" Structures

| Code | "5" Structures |
|---|---|
| 5a | —CH$_2$— |
| 5b | —CH(CH$_3$)— |
| 5c | —C(CH$_3$)$_2$— |

TABLE 5-continued

"5" Structures

| Code | "5" Structures |
|---|---|
| 5d | 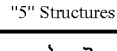 |
| 5e | —CH=CH— |

TABLE 6

"6" Structures

| Code | "6" Structures |
|---|---|
| 6a | covalent bond |
| 6b | —CH$_2$— |
| 6c | —CH(CH$_3$)— |
| 6d | —C(CH$_3$)$_2$— |
| 6e | 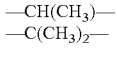 |

TABLE 7

"7" Structures

| Code | "7" Structures |
|---|---|
| 7a | —P(=O)(OH)$_2$ |
| 7b | —C(O)—O—CH(CH$_3$)$_2$ |
| 7c | —C(O)—CH$_3$ |
| 7d | ![morpholine ketone structure] |
| 7e | ![keto acid structure] |

TABLE 8

List of Compounds of Formula (II)

1a.2a.3a.4a.5a.6a, 1a.2a.3a.4a.5a.6b, 1a.2a.3a.4a.5a.6c, 1a.2a.3a.4a.5a.6d,
1a.2a.3a.4a.5a.6e, 1a.2a.3a.4a.5b.6a, 1a.2a.3a.4a.5b.6b, 1a.2a.3a.4a.5b.6c,
1a.2a.3a.4a.5b.6d, 1a.2a.3a.4a.5b.6e, 1a.2a.3a.4a.5c.6a, 1a.2a.3a.4a.5c.6b,
1a.2a.3a.4a.5c.6c, 1a.2a.3a.4a.5c.6d, 1a.2a.3a.4a.5c.6e, 1a.2a.3a.4a.5d.6a,
1a.2a.3a.4a.5d.6b, 1a.2a.3a.4a.5d.6c, 1a.2a.3a.4a.5d.6d, 1a.2a.3a.4a.5d.6e,
1a.2a.3a.4a.5e.6a, 1a.2a.3a.4a.5e.6b, 1a.2a.3a.4a.5e.6c, 1a.2a.3a.4a.5e.6d,
1a.2a.3a.4a.5e.6e, 1a.2a.3a.4b.5a.6a, 1a.2a.3a.4b.5a.6b, 1a.2a.3a.4b.5a.6c,
1a.2a.3a.4b.5a.6d, 1a.2a.3a.4b.5a.6e, 1a.2a.3a.4b.5b.6a, 1a.2a.3a.4b.5b.6b,
1a.2a.3a.4b.5b.6c, 1a.2a.3a.4b.5b.6d, 1a.2a.3a.4b.5b.6e, 1a.2a.3a.4b.5c.6a,
1a.2a.3a.4b.5c.6b, 1a.2a.3a.4b.5c.6c, 1a.2a.3a.4b.5c.6d, 1a.2a.3a.4b.5c.6e,
1a.2a.3a.4b.5d.6a, 1a.2a.3a.4b.5d.6b, 1a.2a.3a.4b.5d.6c, 1a.2a.3a.4b.5d.6d,
1a.2a.3a.4b.5d.6e, 1a.2a.3a.4b.5e.6a, 1a.2a.3a.4b.5e.6b, 1a.2a.3a.4b.5e.6c,
1a.2a.3a.4b.5e.6d, 1a.2a.3a.4b.5e.6e, 1a.2a.3a.4c.5a.6a, 1a.2a.3a.4c.5a.6b,
1a.2a.3a.4c.5a.6c, 1a.2a.3a.4c.5a.6d, 1a.2a.3a.4c.5a.6e, 1a.2a.3a.4c.5b.6a,
1a.2a.3a.4c.5b.6b, 1a.2a.3a.4c.5b.6c, 1a.2a.3a.4c.5b.6d, 1a.2a.3a.4c.5b.6e,
1a.2a.3a.4c.5c.6a, 1a.2a.3a.4c.5c.6b, 1a.2a.3a.4c.5c.6c, 1a.2a.3a.4c.5c.6d,
1a.2a.3a.4c.5c.6e, 1a.2a.3a.4c.5d.6a, 1a.2a.3a.4c.5d.6b, 1a.2a.3a.4c.5d.6c,
1a.2a.3a.4c.5d.6d, 1a.2a.3a.4c.5d.6e, 1a.2a.3a.4c.5e.6a, 1a.2a.3a.4c.5e.6b,
1a.2a.3a.4c.5e.6c, 1a.2a.3a.4c.5e.6d, 1a.2a.3a.4c.5e.6e, 1a.2a.3a.4c.5a.6a,
1a.2a.3a.4d.5a.6b, 1a.2a.3a.4d.5a.6c, 1a.2a.3a.4d.5a.6d, 1a.2a.3a.4d.5a.6e,
1a.2a.3a.4d.5b.6a, 1a.2a.3a.4d.5b.6b, 1a.2a.3a.4d.5b.6c, 1a.2a.3a.4d.5b.6d,
1a.2a.3a.4d.5b.6e, 1a.2a.3a.4d.5c.6a, 1a.2a.3a.4d.5c.6b, 1a.2a.3a.4d.5c.6c,
1a.2a.3a.4d.5c.6d, 1a.2a.3a.4d.5c.6e, 1a.2a.3a.4d.5d.6a, 1a.2a.3a.4d.5d.6b,
1a.2a.3a.4d.5d.6c, 1a.2a.3a.4d.5d.6d, 1a.2a.3a.4d.5d.6e, 1a.2a.3a.4d.5e.6a,
1a.2a.3a.4d.5e.6b, 1a.2a.3a.4d.5e.6c, 1a.2a.3a.4d.5e.6d, 1a.2a.3a.4d.5e.6e,
1a.2a.3a.4e.5a.6a, 1a.2a.3a.4e.5a.6b, 1a.2a.3a.4e.5a.6c, 1a.2a.3a.4e.5a.6d,
1a.2a.3a.4e.5a.6e, 1a.2a.3a.4e.5b.6a, 1a.2a.3a.4e.5b.6b, 1a.2a.3a.4e.5b.6c,
1a.2a.3a.4e.5b.6d, 1a.2a.3a.4e.5b.6e, 1a.2a.3a.4e.5c.6a, 1a.2a.3a.4e.5c.6b,
1a.2a.3a.4e.5c.6c, 1a.2a.3a.4e.5c.6d, 1a.2a.3a.4e.5c.6e, 1a.2a.3a.4e.5d.6a,
1a.2a.3a.4e.5d.6b, 1a.2a.3a.4e.5d.6c, 1a.2a.3a.4e.5d.6d, 1a.2a.3a.4e.5d.6e,
1a.2a.3a.4e.5e.6a, 1a.2a.3a.4e.5e.6b, 1a.2a.3a.4e.5e.6c, 1a.2a.3a.4e.5e.6d,
1a.2a.3a.4e.5e.6e, 1a.2a.3b.4a.5a.6a, 1a.2a.3b.4a.5a.6b, 1a.2a.3b.4a.5a.6c,
1a.2a.3b.4a.5a.6d, 1a.2a.3b.4a.5a.6e, 1a.2a.3b.4a.5b.6a, 1a.2a.3b.4a.5b.6b,
1a.2a.3b.4a.5b.6c, 1a.2a.3b.4a.5b.6d, 1a.2a.3b.4a.5b.6e, 1a.2a.3b.4a.5c.6a,
1a.2a.3b.4a.5c.6b, 1a.2a.3b.4a.5c.6c, 1a.2a.3b.4a.5c.6d, 1a.2a.3b.4a.5c.6e,
1a.2a.3b.4a.5d.6a, 1a.2a.3b.4a.5d.6b, 1a.2a.3b.4a.5d.6c, 1a.2a.3b.4a.5d.6d,
1a.2a.3b.4a.5d.6e, 1a.2a.3b.4a.5e.6a, 1a.2a.3b.4a.5e.6b, 1a.2a.3b.4a.5e.6c,
1a.2a.3b.4a.5e.6d, 1a.2a.3b.4a.5e.6e, 1a.2a.3b.4b.5a.6a, 1a.2a.3b.4b.5a.6b,
1a.2a.3b.4b.5a.6c, 1a.2a.3b.4b.5a.6d, 1a.2a.3b.4b.5a.6e, 1a.2a.3b.4b.5b.6a,
1a.2a.3b.4b.5b.6b, 1a.2a.3b.4b.5b.6c, 1a.2a.3b.4b.5b.6d, 1a.2a.3b.4b.5b.6e,
1a.2a.3b.4b.5c.6a, 1a.2a.3b.4b.5c.6b, 1a.2a.3b.4b.5c.6c, 1a.2a.3b.4b.5c.6d,
1a.2a.3b.4b.5c.6e, 1a.2a.3b.4b.5d.6a, 1a.2a.3b.4b.5d.6b, 1a.2a.3b.4b.5d.6c,

TABLE 8-continued

List of Compounds of Formula (II)

1a.2a.3b.4b.5d.6d, 1a.2a.3b.4b.5d.6e, 1a.2a.3b.4b.5e.6a, 1a.2a.3b.4b.5e.6b,
1a.2a.3b.4b.5e.6c, 1a.2a.3b.4b.5e.6d, 1a.2a.3b.4b.5e.6e, 1a.2a.3b.4c.5a.6a,
1a.2a.3b.4c.5a.6b, 1a.2a.3b.4c.5a.6c, 1a.2a.3b.4c.5a.6d, 1a.2a.3b.4c.5a.6e,
1a.2a.3b.4c.5b.6a, 1a.2a.3b.4c.5b.6b, 1a.2a.3b.4c.5b.6c, 1a.2a.3b.4c.5b.6d,
1a.2a.3b.4c.5b.6e, 1a.2a.3b.4c.5c.6a, 1a.2a.3b.4c.5c.6b, 1a.2a.3b.4c.5c.6c,
1a.2a.3b.4c.5c.6d, 1a.2a.3b.4c.5c.6e, 1a.2a.3b.4c.5d.6a, 1a.2a.3b.4c.5d.6b,
1a.2a.3b.4c.5d.6c, 1a.2a.3b.4c.5d.6d, 1a.2a.3b.4c.5d.6e, 1a.2a.3b.4c.5e.6a,
1a.2a.3b.4c.5e.6b, 1a.2a.3b.4c.5e.6c, 1a.2a.3b.4c.5e.6d, 1a.2a.3b.4c.5e.6e,
1a.2a.3b.4d.5a.6a, 1a.2a.3b.4d.5a.6b, 1a.2a.3b.4d.5a.6c, 1a.2a.3b.4d.5a.6d,
1a.2a.3b.4d.5a.6e, 1a.2a.3b.4d.5b.6a, 1a.2a.3b.4d.5b.6b, 1a.2a.3b.4d.5b.6c,
1a.2a.3b.4d.5b.6d, 1a.2a.3b.4d.5b.6e, 1a.2a.3b.4d.5c.6a, 1a.2a.3b.4d.5c.6b,
1a.2a.3b.4d.5c.6c, 1a.2a.3b.4d.5c.6d, 1a.2a.3b.4d.5c.6e, 1a.2a.3b.4d.5d.6a,
1a.2a.3b.4d.5d.6b, 1a.2a.3b.4d.5d.6c, 1a.2a.3b.4d.5d.6d, 1a.2a.3b.4d.5d.6e,
1a.2a.3b.4d.5e.6a, 1a.2a.3b.4d.5e.6b, 1a.2a.3b.4d.5e.6c, 1a.2a.3b.4d.5e.6d,
1a.2a.3b.4d.5e.6e, 1a.2a.3b.4e.5a.6a, 1a.2a.3b.4e.5a.6b, 1a.2a.3b.4e.5a.6c,
1a.2a.3b.4e.5a.6d, 1a.2a.3b.4e.5a.6e, 1a.2a.3b.4e.5b.6a, 1a.2a.3b.4e.5b.6b,
1a.2a.3b.4e.5b.6c, 1a.2a.3b.4e.5b.6d, 1a.2a.3b.4e.5b.6e, 1a.2a.3b.4e.5c.6a,
1a.2a.3b.4e.5c.6b, 1a.2a.3b.4e.5c.6c, 1a.2a.3b.4e.5c.6d, 1a.2a.3b.4e.5c.6e,
1a.2a.3b.4e.5d.6a, 1a.2a.3b.4e.5d.6b, 1a.2a.3b.4e.5d.6c, 1a.2a.3b.4e.5d.6d,
1a.2a.3b.4e.5d.6e, 1a.2a.3b.4e.5e.6a, 1a.2a.3b.4e.5e.6b, 1a.2a.3b.4e.5e.6c,
1a.2a.3b.4e.5e.6d, 1a.2a.3b.4e.5e.6e, 1a.2a.3c.4a.5a.6a, 1a.2a.3c.4a.5a.6b,
1a.2a.3c.4a.5a.6c, 1a.2a.3c.4a.5a.6d, 1a.2a.3c.4a.5a.6e, 1a.2a.3c.4a.5b.6a,
1a.2a.3c.4a.5b.6b, 1a.2a.3c.4a.5b.6c, 1a.2a.3c.4a.5b.6d, 1a.2a.3c.4a.5b.6e,
1a.2a.3c.4a.5c.6a, 1a.2a.3c.4a.5c.6b, 1a.2a.3c.4a.5c.6c, 1a.2a.3c.4a.5c.6d,
1a.2a.3c.4a.5c.6e, 1a.2a.3c.4a.5d.6a, 1a.2a.3c.4a.5d.6b, 1a.2a.3c.4a.5d.6c,
1a.2a.3c.4a.5d.6d, 1a.2a.3c.4a.5d.6e, 1a.2a.3c.4a.5e.6a, 1a.2a.3c.4a.5e.6b,
1a.2a.3c.4a.5e.6c, 1a.2a.3c.4a.5e.6d, 1a.2a.3c.4a.5e.6e, 1a.2a.3c.4b.5a.6a,
1a.2a.3c.4b.5a.6b, 1a.2a.3c.4b.5a.6c, 1a.2a.3c.4b.5a.6d, 1a.2a.3c.4b.5a.6e,
1a.2a.3c.4b.5b.6a, 1a.2a.3c.4b.5b.6b, 1a.2a.3c.4b.5b.6c, 1a.2a.3c.4b.5b.6d,
1a.2a.3c.4b.5b.6e, 1a.2a.3c.4b.5c.6a, 1a.2a.3c.4b.5c.6b, 1a.2a.3c.4b.5c.6c,
1a.2a.3c.4b.5c.6d, 1a.2a.3c.4b.5c.6e, 1a.2a.3c.4b.5d.6a, 1a.2a.3c.4b.5d.6b,
1a.2a.3c.4b.5d.6c, 1a.2a.3c.4b.5d.6d, 1a.2a.3c.4b.5d.6e, 1a.2a.3c.4b.5e.6a,
1a.2a.3c.4b.5e.6b, 1a.2a.3c.4b.5e.6c, 1a.2a.3c.4b.5e.6d, 1a.2a.3c.4b.5e.6e,
1a.2a.3c.4c.5a.6a, 1a.2a.3c.4c.5a.6b, 1a.2a.3c.4c.5a.6c, 1a.2a.3c.4c.5a.6d,
1a.2a.3c.4c.5a.6e, 1a.2a.3c.4c.5b.6a, 1a.2a.3c.4c.5b.6b, 1a.2a.3c.4c.5b.6c,
1a.2a.3c.4c.5b.6d, 1a.2a.3c.4c.5b.6e, 1a.2a.3c.4c.5c.6a, 1a.2a.3c.4c.5c.6b,
1a.2a.3c.4c.5c.6c, 1a.2a.3c.4c.5c.6d, 1a.2a.3c.4c.5c.6e, 1a.2a.3c.4c.5d.6a,
1a.2a.3c.4c.5d.6b, 1a.2a.3c.4c.5d.6c, 1a.2a.3c.4c.5d.6d, 1a.2a.3c.4c.5d.6e,
1a.2a.3c.4c.5e.6a, 1a.2a.3c.4c.5e.6b, 1a.2a.3c.4c.5e.6c, 1a.2a.3c.4c.5e.6d,
1a.2a.3c.4c.5e.6e, 1a.2a.3c.4d.5a.6a, 1a.2a.3c.4d.5a.6b, 1a.2a.3c.4d.5a.6c,
1a.2a.3c.4d.5a.6d, 1a.2a.3c.4d.5a.6e, 1a.2a.3c.4d.5b.6a, 1a.2a.3c.4d.5b.6b,
1a.2a.3c.4d.5b.6c, 1a.2a.3c.4d.5b.6d, 1a.2a.3c.4d.5b.6e, 1a.2a.3c.4d.5c.6a,
1a.2a.3c.4d.5c.6b, 1a.2a.3c.4d.5c.6c, 1a.2a.3c.4d.5c.6d, 1a.2a.3c.4d.5c.6e,
1a.2a.3c.4d.5d.6a, 1a.2a.3c.4d.5d.6b, 1a.2a.3c.4d.5d.6c, 1a.2a.3c.4d.5d.6d,
1a.2a.3c.4d.5d.6e, 1a.2a.3c.4d.5e.6a, 1a.2a.3c.4d.5e.6b, 1a.2a.3c.4d.5e.6c,
1a.2a.3c.4d.5e.6d, 1a.2a.3c.4d.5e.6e, 1a.2a.3c.4e.5a.6a, 1a.2a.3c.4e.5a.6b,
1a.2a.3c.4e.5a.6c, 1a.2a.3c.4e.5a.6d, 1a.2a.3c.4e.5a.6e, 1a.2a.3c.4e.5b.6a,
1a.2a.3c.4e.5b.6b, 1a.2a.3c.4e.5b.6c, 1a.2a.3c.4e.5b.6d, 1a.2a.3c.4e.5b.6e,
1a.2a.3c.4e.5c.6a, 1a.2a.3c.4e.5c.6b, 1a.2a.3c.4e.5c.6c, 1a.2a.3c.4e.5c.6d,
1a.2a.3c.4e.5c.6e, 1a.2a.3c.4e.5d.6a, 1a.2a.3c.4e.5d.6b, 1a.2a.3c.4e.5d.6c,
1a.2a.3c.4e.5d.6d, 1a.2a.3c.4e.5d.6e, 1a.2a.3c.4e.5e.6a, 1a.2a.3c.4e.5e.6b,
1a.2a.3c.4e.5e.6c, 1a.2a.3c.4e.5e.6d, 1a.2a.3c.4e.5e.6e, 1a.2a.3d.4a.5a.6a,
1a.2a.3d.4a.5a.6b, 1a.2a.3d.4a.5a.6c, 1a.2a.3d.4a.5a.6d, 1a.2a.3d.4a.5a.6e,
1a.2a.3d.4a.5b.6a, 1a.2a.3d.4a.5b.6b, 1a.2a.3d.4a.5b.6c, 1a.2a.3d.4a.5b.6d,
1a.2a.3d.4a.5b.6e, 1a.2a.3d.4a.5c.6a, 1a.2a.3d.4a.5c.6b, 1a.2a.3d.4a.5c.6c,
1a.2a.3d.4a.5c.6d, 1a.2a.3d.4a.5c.6e, 1a.2a.3d.4a.5d.6a, 1a.2a.3d.4a.5d.6b,
1a.2a.3d.4a.5d.6c, 1a.2a.3d.4a.5d.6d, 1a.2a.3d.4a.5d.6e, 1a.2a.3d.4a.5e.6a,
1a.2a.3d.4a.5e.6b, 1a.2a.3d.4a.5e.6c, 1a.2a.3d.4a.5e.6d, 1a.2a.3d.4a.5e.6e,
1a.2a.3d.4b.5a.6a, 1a.2a.3d.4b.5a.6b, 1a.2a.3d.4b.5a.6c, 1a.2a.3d.4b.5a.6d,
1a.2a.3d.4b.5a.6e, 1a.2a.3d.4b.5b.6a, 1a.2a.3d.4b.5b.6b, 1a.2a.3d.4b.5b.6c,
1a.2a.3d.4b.5b.6d, 1a.2a.3d.4b.5b.6e, 1a.2a.3d.4b.5c.6a, 1a.2a.3d.4b.5c.6b,
1a.2a.3d.4b.5c.6c, 1a.2a.3d.4b.5c.6d, 1a.2a.3d.4b.5c.6e, 1a.2a.3d.4b.5d.6a,
1a.2a.3d.4b.5d.6b, 1a.2a.3d.4b.5d.6c, 1a.2a.3d.4b.5d.6d, 1a.2a.3d.4b.5d.6e,
1a.2a.3d.4b.5e.6a, 1a.2a.3d.4b.5e.6b, 1a.2a.3d.4b.5e.6c, 1a.2a.3d.4b.5e.6d,
1a.2a.3d.4b.5e.6e, 1a.2a.3d.4c.5a.6a, 1a.2a.3d.4c.5a.6b, 1a.2a.3d.4c.5a.6c,
1a.2a.3d.4c.5a.6d, 1a.2a.3d.4c.5a.6e, 1a.2a.3d.4c.5b.6a, 1a.2a.3d.4c.5b.6b,
1a.2a.3d.4c.5b.6c, 1a.2a.3d.4c.5b.6d, 1a.2a.3d.4c.5b.6e, 1a.2a.3d.4c.5c.6a,
1a.2a.3d.4c.5c.6b, 1a.2a.3d.4c.5c.6c, 1a.2a.3d.4c.5c.6d, 1a.2a.3d.4c.5c.6e,
1a.2a.3d.4c.5d.6a, 1a.2a.3d.4c.5d.6b, 1a.2a.3d.4c.5d.6c, 1a.2a.3d.4c.5d.6d,
1a.2a.3d.4c.5d.6e, 1a.2a.3d.4c.5e.6a, 1a.2a.3d.4c.5e.6b, 1a.2a.3d.4c.5e.6c,
1a.2a.3d.4c.5e.6d, 1a.2a.3d.4c.5e.6e, 1a.2a.3d.4d.5a.6a, 1a.2a.3d.4d.5a.6b,
1a.2a.3d.4d.5a.6c, 1a.2a.3d.4d.5a.6d, 1a.2a.3d.4d.5a.6e, 1a.2a.3d.4d.5b.6a,
1a.2a.3d.4d.5b.6b, 1a.2a.3d.4d.5b.6c, 1a.2a.3d.4d.5b.6d, 1a.2a.3d.4d.5b.6e,
1a.2a.3d.4d.5c.6a, 1a.2a.3d.4d.5c.6b, 1a.2a.3d.4d.5c.6c, 1a.2a.3d.4d.5c.6d,
1a.2a.3d.4d.5c.6e, 1a.2a.3d.4d.5d.6a, 1a.2a.3d.4d.5d.6b, 1a.2a.3d.4d.5d.6c,
1a.2a.3d.4d.5d.6d, 1a.2a.3d.4d.5d.6e, 1a.2a.3d.4d.5e.6a, 1a.2a.3d.4d.5e.6b,
1a.2a.3d.4d.5e.6c, 1a.2a.3d.4d.5e.6d, 1a.2a.3d.4d.5e.6e, 1a.2a.3d.4e.5a.6a,
1a.2a.3d.4e.5a.6b, 1a.2a.3d.4e.5a.6c, 1a.2a.3d.4e.5a.6d, 1a.2a.3d.4e.5a.6e,

TABLE 8-continued

List of Compounds of Formula (II)

1a.2a.3d.4e.5b.6a, 1a.2a.3d.4e.5b.6b, 1a.2a.3d.4e.5b.6c, 1a.2a.3d.4e.5b.6d,
1a.2a.3d.4e.5b.6e, 1a.2a.3d.4e.5c.6a, 1a.2a.3d.4e.5c.6b, 1a.2a.3d.4e.5c.6c,
1a.2a.3d.4e.5c.6d, 1a.2a.3d.4e.5c.6e, 1a.2a.3d.4e.5d.6a, 1a.2a.3d.4e.5d.6b,
1a.2a.3d.4e.5d.6c, 1a.2a.3d.4e.5d.6d, 1a.2a.3d.4e.5d.6e, 1a.2a.3d.4e.5e.6a,
1a.2a.3d.4e.5e.6b, 1a.2a.3d.4e.5e.6c, 1a.2a.3d.4e.5e.6d, 1a.2a.3d.4e.5e.6e,
1a.2a.3e.4a.5a.6a, 1a.2a.3e.4a.5a.6b, 1a.2a.3e.4a.5a.6c, 1a.2a.3e.4a.5a.6d,
1a.2a.3e.4a.5a.6e, 1a.2a.3e.4a.5b.6a, 1a.2a.3e.4a.5b.6b, 1a.2a.3e.4a.5b.6c,
1a.2a.3e.4a.5b.6d, 1a.2a.3e.4a.5b.6e, 1a.2a.3e.4a.5c.6a, 1a.2a.3e.4a.5c.6b,
1a.2a.3e.4a.5c.6c, 1a.2a.3e.4a.5c.6d, 1a.2a.3e.4a.5c.6e, 1a.2a.3e.4a.5d.6a,
1a.2a.3e.4a.5d.6b, 1a.2a.3e.4a.5d.6c, 1a.2a.3e.4a.5d.6d, 1a.2a.3e.4a.5d.6e,
1a.2a.3e.4a.5e.6a, 1a.2a.3e.4a.5e.6b, 1a.2a.3e.4a.5e.6c, 1a.2a.3e.4a.5e.6d,
1a.2a.3e.4a.5e.6e, 1a.2a.3e.4b.5a.6a, 1a.2a.3e.4b.5a.6b, 1a.2a.3e.4b.5a.6c,
1a.2a.3e.4b.5a.6d, 1a.2a.3e.4b.5a.6e, 1a.2a.3e.4b.5b.6a, 1a.2a.3e.4b.5b.6b,
1a.2a.3e.4b.5b.6c, 1a.2a.3e.4b.5b.6d, 1a.2a.3e.4b.5b.6e, 1a.2a.3e.4b.5c.6a,
1a.2a.3e.4b.5c.6b, 1a.2a.3e.4b.5c.6c, 1a.2a.3e.4b.5c.6d, 1a.2a.3e.4b.5c.6e,
1a.2a.3e.4b.5d.6a, 1a.2a.3e.4b.5d.6b, 1a.2a.3e.4b.5d.6c, 1a.2a.3e.4b.5d.6d,
1a.2a.3e.4b.5d.6e, 1a.2a.3e.4b.5e.6a, 1a.2a.3e.4b.5e.6b, 1a.2a.3e.4b.5e.6c,
1a.2a.3e.4b.5e.6d, 1a.2a.3e.4b.5e.6e, 1a.2a.3e.4c.5a.6a, 1a.2a.3e.4c.5a.6b,
1a.2a.3e.4c.5a.6c, 1a.2a.3e.4c.5a.6d, 1a.2a.3e.4c.5a.6e, 1a.2a.3e.4c.5b.6a,
1a.2a.3e.4c.5b.6b, 1a.2a.3e.4c.5b.6c, 1a.2a.3e.4c.5b.6d, 1a.2a.3e.4c.5b.6e,
1a.2a.3e.4c.5c.6a, 1a.2a.3e.4c.5c.6b, 1a.2a.3e.4c.5c.6c, 1a.2a.3e.4c.5c.6d,
1a.2a.3e.4c.5c.6e, 1a.2a.3e.4c.5d.6a, 1a.2a.3e.4c.5d.6b, 1a.2a.3e.4c.5d.6c,
1a.2a.3e.4c.5d.6d, 1a.2a.3e.4c.5d.6e, 1a.2a.3e.4c.5e.6a, 1a.2a.3e.4c.5e.6b,
1a.2a.3e.4c.5e.6c, 1a.2a.3e.4c.5e.6d, 1a.2a.3e.4c.5e.6e, 1a.2a.3e.4d.5a.6a,
1a.2a.3e.4d.5a.6b, 1a.2a.3e.4d.5a.6c, 1a.2a.3e.4d.5a.6d, 1a.2a.3e.4d.5a.6e,
1a.2a.3e.4d.5b.6a, 1a.2a.3e.4d.5b.6b, 1a.2a.3e.4d.5b.6c, 1a.2a.3e.4d.5b.6d,
1a.2a.3e.4d.5b.6e, 1a.2a.3e.4d.5c.6a, 1a.2a.3e.4d.5c.6b, 1a.2a.3e.4d.5c.6c,
1a.2a.3e.4d.5c.6d, 1a.2a.3e.4d.5c.6e, 1a.2a.3e.4d.5d.6a, 1a.2a.3e.4d.5d.6b,
1a.2a.3e.4d.5d.6c, 1a.2a.3e.4d.5d.6d, 1a.2a.3e.4d.5d.6e, 1a.2a.3e.4d.5e.6a,
1a.2a.3e.4d.5e.6b, 1a.2a.3e.4d.5e.6c, 1a.2a.3e.4d.5e.6d, 1a.2a.3e.4d.5e.6e,
1a.2a.3e.4e.5a.6a, 1a.2a.3e.4e.5a.6b, 1a.2a.3e.4e.5a.6c, 1a.2a.3e.4e.5a.6d,
1a.2a.3e.4e.5a.6e, 1a.2a.3e.4e.5b.6a, 1a.2a.3e.4e.5b.6b, 1a.2a.3e.4e.5b.6c,
1a.2a.3e.4e.5b.6d, 1a.2a.3e.4e.5b.6e, 1a.2a.3e.4e.5c.6a, 1a.2a.3e.4e.5c.6b,
1a.2a.3e.4e.5c.6c, 1a.2a.3e.4e.5c.6d, 1a.2a.3e.4e.5c.6e, 1a.2a.3e.4e.5d.6a,
1a.2a.3e.4e.5d.6b, 1a.2a.3e.4e.5d.6c, 1a.2a.3e.4e.5d.6d, 1a.2a.3e.4e.5d.6e,
1a.2a.3e.4e.5e.6a, 1a.2a.3e.4e.5e.6b, 1a.2a.3e.4e.5e.6c, 1a.2a.3e.4e.5e.6d,
1a.2a.3e.4e.5e.6e, 1a.2b.3a.4a.5a.6a, 1a.2b.3a.4a.5a.6b, 1a.2b.3a.4a.5a.6c,
1a.2b.3a.4a.5a.6d, 1a.2b.3a.4a.5a.6e, 1a.2b.3a.4a.5b.6a, 1a.2b.3a.4a.5b.6b,
1a.2b.3a.4a.5b.6c, 1a.2b.3a.4a.5b.6d, 1a.2b.3a.4a.5b.6e, 1a.2b.3a.4a.5c.6a,
1a.2b.3a.4a.5c.6b, 1a.2b.3a.4a.5c.6c, 1a.2b.3a.4a.5c.6d, 1a.2b.3a.4a.5c.6e,
1a.2b.3a.4a.5d.6a, 1a.2b.3a.4a.5d.6b, 1a.2b.3a.4a.5d.6c, 1a.2b.3a.4a.5d.6d,
1a.2b.3a.4a.5d.6e, 1a.2b.3a.4a.5e.6a, 1a.2b.3a.4a.5e.6b, 1a.2b.3a.4a.5e.6c,
1a.2b.3a.4a.5e.6d, 1a.2b.3a.4a.5e.6e, 1a.2b.3a.4b.5a.6a, 1a.2b.3a.4b.5a.6b,
1a.2b.3a.4b.5a.6c, 1a.2b.3a.4b.5a.6d, 1a.2b.3a.4b.5a.6e, 1a.2b.3a.4b.5b.6a,
1a.2b.3a.4b.5b.6b, 1a.2b.3a.4b.5b.6c, 1a.2b.3a.4b.5b.6d, 1a.2b.3a.4b.5b.6e,
1a.2b.3a.4b.5c.6a, 1a.2b.3a.4b.5c.6b, 1a.2b.3a.4b.5c.6c, 1a.2b.3a.4b.5c.6d,
1a.2b.3a.4b.5c.6e, 1a.2b.3a.4b.5d.6a, 1a.2b.3a.4b.5d.6b, 1a.2b.3a.4b.5d.6c,
1a.2b.3a.4b.5d.6d, 1a.2b.3a.4b.5d.6e, 1a.2b.3a.4b.5e.6a, 1a.2b.3a.4b.5e.6b,
1a.2b.3a.4b.5e.6c, 1a.2b.3a.4b.5e.6d, 1a.2b.3a.4b.5e.6e, 1a.2b.3a.4c.5a.6a,
1a.2b.3a.4c.5a.6b, 1a.2b.3a.4c.5a.6c, 1a.2b.3a.4c.5a.6d, 1a.2b.3a.4c.5a.6e,
1a.2b.3a.4c.5b.6a, 1a.2b.3a.4c.5b.6b, 1a.2b.3a.4c.5b.6c, 1a.2b.3a.4c.5b.6d,
1a.2b.3a.4c.5b.6e, 1a.2b.3a.4c.5c.6a, 1a.2b.3a.4c.5c.6b, 1a.2b.3a.4c.5c.6c,
1a.2b.3a.4c.5c.6d, 1a.2b.3a.4c.5c.6e, 1a.2b.3a.4c.5d.6a, 1a.2b.3a.4c.5d.6b,
1a.2b.3a.4c.5d.6c, 1a.2b.3a.4c.5d.6d, 1a.2b.3a.4c.5d.6e, 1a.2b.3a.4c.5e.6a,
1a.2b.3a.4c.5e.6b, 1a.2b.3a.4c.5e.6c, 1a.2b.3a.4c.5e.6d, 1a.2b.3a.4c.5e.6e,
1a.2b.3a.4d.5a.6a, 1a.2b.3a.4d.5a.6b, 1a.2b.3a.4d.5a.6c, 1a.2b.3a.4d.5a.6d,
1a.2b.3a.4d.5a.6e, 1a.2b.3a.4d.5b.6a, 1a.2b.3a.4d.5b.6b, 1a.2b.3a.4d.5b.6c,
1a.2b.3a.4d.5b.6d, 1a.2b.3a.4d.5b.6e, 1a.2b.3a.4d.5c.6a, 1a.2b.3a.4d.5c.6b,
1a.2b.3a.4d.5c.6c, 1a.2b.3a.4d.5c.6d, 1a.2b.3a.4d.5c.6e, 1a.2b.3a.4d.5d.6a,
1a.2b.3a.4d.5d.6b, 1a.2b.3a.4d.5d.6c, 1a.2b.3a.4d.5d.6d, 1a.2b.3a.4d.5d.6e,
1a.2b.3a.4d.5e.6a, 1a.2b.3a.4d.5e.6b, 1a.2b.3a.4d.5e.6c, 1a.2b.3a.4d.5e.6d,
1a.2b.3a.4d.5e.6e, 1a.2b.3a.4e.5a.6a, 1a.2b.3a.4e.5a.6b, 1a.2b.3a.4e.5a.6c,
1a.2b.3a.4e.5a.6d, 1a.2b.3a.4e.5a.6e, 1a.2b.3a.4e.5b.6a, 1a.2b.3a.4e.5b.6b,
1a.2b.3a.4e.5b.6c, 1a.2b.3a.4e.5b.6d, 1a.2b.3a.4e.5b.6e, 1a.2b.3a.4e.5c.6a,
1a.2b.3a.4e.5c.6b, 1a.2b.3a.4e.5c.6c, 1a.2b.3a.4e.5c.6d, 1a.2b.3a.4e.5c.6e,
1a.2b.3a.4e.5d.6a, 1a.2b.3a.4e.5d.6b, 1a.2b.3a.4e.5d.6c, 1a.2b.3a.4e.5d.6d,
1a.2b.3a.4e.5d.6e, 1a.2b.3a.4e.5e.6a, 1a.2b.3a.4e.5e.6b, 1a.2b.3a.4e.5e.6c,
1a.2b.3a.4e.5e.6d, 1a.2b.3a.4e.5e.6e, 1a.2b.3b.4a.5a.6a, 1a.2b.3b.4a.5a.6b,
1a.2b.3b.4a.5a.6c, 1a.2b.3b.4a.5a.6d, 1a.2b.3b.4a.5a.6e, 1a.2b.3b.4a.5b.6a,
1a.2b.3b.4a.5b.6b, 1a.2b.3b.4a.5b.6c, 1a.2b.3b.4a.5b.6d, 1a.2b.3b.4a.5b.6e,
1a.2b.3b.4a.5c.6a, 1a.2b.3b.4a.5c.6b, 1a.2b.3b.4a.5c.6c, 1a.2b.3b.4a.5c.6d,
1a.2b.3b.4a.5c.6e, 1a.2b.3b.4a.5d.6a, 1a.2b.3b.4a.5d.6b, 1a.2b.3b.4a.5d.6c,
1a.2b.3b.4a.5d.6d, 1a.2b.3b.4a.5d.6e, 1a.2b.3b.4a.5e.6a, 1a.2b.3b.4a.5e.6b,
1a.2b.3b.4a.5e.6c, 1a.2b.3b.4a.5e.6d, 1a.2b.3b.4a.5e.6e, 1a.2b.3b.4b.5a.6a,
1a.2b.3b.4b.5a.6b, 1a.2b.3b.4b.5a.6c, 1a.2b.3b.4b.5a.6d, 1a.2b.3b.4b.5a.6e,
1a.2b.3b.4b.5b.6a, 1a.2b.3b.4b.5b.6b, 1a.2b.3b.4b.5b.6c, 1a.2b.3b.4b.5b.6d,
1a.2b.3b.4b.5b.6e, 1a.2b.3b.4b.5c.6a, 1a.2b.3b.4b.5c.6b, 1a.2b.3b.4b.5c.6c,
1a.2b.3b.4b.5c.6d, 1a.2b.3b.4b.5c.6e, 1a.2b.3b.4b.5d.6a, 1a.2b.3b.4b.5d.6b,

TABLE 8-continued

List of Compounds of Formula (II)

1a.2b.3b.4b.5d.6c, 1a.2b.3b.4b.5d.6d, 1a.2b.3b.4b.5d.6e, 1a.2b.3b.4b.5e.6a,
1a.2b.3b.4b.5e.6b, 1a.2b.3b.4b.5e.6c, 1a.2b.3b.4b.5e.6d, 1a.2b.3b.4b.5e.6e,
1a.2b.3b.4c.5a.6a, 1a.2b.3b.4c.5a.6b, 1a.2b.3b.4c.5a.6c, 1a.2b.3b.4c.5a.6d,
1a.2b.3b.4c.5a.6e, 1a.2b.3b.4c.5b.6a, 1a.2b.3b.4c.5b.6b, 1a.2b.3b.4c.5b.6c,
1a.2b.3b.4c.5b.6d, 1a.2b.3b.4c.5b.6e, 1a.2b.3b.4c.5c.6a, 1a.2b.3b.4c.5c.6b,
1a.2b.3b.4c.5c.6c, 1a.2b.3b.4c.5c.6d, 1a.2b.3b.4c.5c.6e, 1a.2b.3b.4c.5d.6a,
1a.2b.3b.4c.5d.6b, 1a.2b.3b.4c.5d.6c, 1a.2b.3b.4c.5d.6d, 1a.2b.3b.4c.5d.6e,
1a.2b.3b.4c.5e.6a, 1a.2b.3b.4c.5e.6b, 1a.2b.3b.4c.5e.6c, 1a.2b.3b.4c.5e.6d,
1a.2b.3b.4c.5e.6e, 1a.2b.3b.4d.5a.6a, 1a.2b.3b.4d.5a.6b, 1a.2b.3b.4d.5a.6c,
1a.2b.3b.4d.5a.6d, 1a.2b.3b.4d.5a.6e, 1a.2b.3b.4d.5b.6a, 1a.2b.3b.4d.5b.6b,
1a.2b.3b.4d.5b.6c, 1a.2b.3b.4d.5b.6d, 1a.2b.3b.4d.5b.6e, 1a.2b.3b.4d.5c.6a,
1a.2b.3b.4d.5c.6b, 1a.2b.3b.4d.5c.6c, 1a.2b.3b.4d.5c.6d, 1a.2b.3b.4d.5c.6e,
1a.2b.3b.4d.5d.6a, 1a.2b.3b.4d.5d.6b, 1a.2b.3b.4d.5d.6c, 1a.2b.3b.4d.5d.6d,
1a.2b.3b.4d.5d.6e, 1a.2b.3b.4d.5e.6a, 1a.2b.3b.4d.5e.6b, 1a.2b.3b.4d.5e.6c,
1a.2b.3b.4d.5e.6d, 1a.2b.3b.4d.5e.6e, 1a.2b.3b.4e.5a.6a, 1a.2b.3b.4e.5a.6b,
1a.2b.3b.4e.5a.6c, 1a.2b.3b.4e.5a.6d, 1a.2b.3b.4e.5a.6e, 1a.2b.3b.4e.5b.6a,
1a.2b.3b.4e.5b.6b, 1a.2b.3b.4e.5b.6c, 1a.2b.3b.4e.5b.6d, 1a.2b.3b.4e.5b.6e,
1a.2b.3b.4e.5c.6a, 1a.2b.3b.4e.5c.6b, 1a.2b.3b.4e.5c.6c, 1a.2b.3b.4e.5c.6d,
1a.2b.3b.4e.5c.6e, 1a.2b.3b.4e.5d.6a, 1a.2b.3b.4e.5d.6b, 1a.2b.3b.4e.5d.6c,
1a.2b.3b.4e.5d.6d, 1a.2b.3b.4e.5d.6e, 1a.2b.3b.4e.5e.6a, 1a.2b.3b.4e.5e.6b,
1a.2b.3b.4e.5e.6c, 1a.2b.3b.4e.5e.6d, 1a.2b.3b.4e.5e.6e, 1a.2b.3c.4a.5a.6a,
1a.2b.3c.4a.5a.6b, 1a.2b.3c.4a.5a.6c, 1a.2b.3c.4a.5a.6d, 1a.2b.3c.4a.5a.6e,
1a.2b.3c.4a.5b.6a, 1a.2b.3c.4a.5b.6b, 1a.2b.3c.4a.5b.6c, 1a.2b.3c.4a.5b.6d,
1a.2b.3c.4a.5b.6e, 1a.2b.3c.4a.5c.6a, 1a.2b.3c.4a.5c.6b, 1a.2b.3c.4a.5c.6c,
1a.2b.3c.4a.5c.6d, 1a.2b.3c.4a.5c.6e, 1a.2b.3c.4a.5d.6a, 1a.2b.3c.4a.5d.6b,
1a.2b.3c.4a.5d.6c, 1a.2b.3c.4a.5d.6d, 1a.2b.3c.4a.5d.6e, 1a.2b.3c.4a.5e.6a,
1a.2b.3c.4a.5e.6b, 1a.2b.3c.4a.5e.6c, 1a.2b.3c.4a.5e.6d, 1a.2b.3c.4a.5e.6e,
1a.2b.3c.4b.5a.6a, 1a.2b.3c.4b.5a.6b, 1a.2b.3c.4b.5a.6c, 1a.2b.3c.4b.5a.6d,
1a.2b.3c.4b.5a.6e, 1a.2b.3c.4b.5b.6a, 1a.2b.3c.4b.5b.6b, 1a.2b.3c.4b.5b.6c,
1a.2b.3c.4b.5b.6d, 1a.2b.3c.4b.5b.6e, 1a.2b.3c.4b.5c.6a, 1a.2b.3c.4b.5c.6b,
1a.2b.3c.4b.5c.6c, 1a.2b.3c.4b.5c.6d, 1a.2b.3c.4b.5c.6e, 1a.2b.3c.4b.5d.6a,
1a.2b.3c.4b.5d.6b, 1a.2b.3c.4b.5d.6c, 1a.2b.3c.4b.5d.6d, 1a.2b.3c.4b.5d.6e,
1a.2b.3c.4b.5e.6a, 1a.2b.3c.4b.5e.6b, 1a.2b.3c.4b.5e.6c, 1a.2b.3c.4b.5e.6d,
1a.2b.3c.4b.5e.6e, 1a.2b.3c.4c.5a.6a, 1a.2b.3c.4c.5a.6b, 1a.2b.3c.4c.5a.6c,
1a.2b.3c.4c.5a.6d, 1a.2b.3c.4c.5a.6e, 1a.2b.3c.4c.5b.6a, 1a.2b.3c.4c.5b.6b,
1a.2b.3c.4c.5b.6c, 1a.2b.3c.4c.5b.6d, 1a.2b.3c.4c.5b.6e, 1a.2b.3c.4c.5c.6a,
1a.2b.3c.4c.5c.6b, 1a.2b.3c.4c.5c.6c, 1a.2b.3c.4c.5c.6d, 1a.2b.3c.4c.5c.6e,
1a.2b.3c.4c.5d.6a, 1a.2b.3c.4c.5d.6b, 1a.2b.3c.4c.5d.6c, 1a.2b.3c.4c.5d.6d,
1a.2b.3c.4c.5d.6e, 1a.2b.3c.4c.5e.6a, 1a.2b.3c.4c.5e.6b, 1a.2b.3c.4c.5e.6c,
1a.2b.3c.4c.5e.6d, 1a.2b.3c.4c.5e.6e, 1a.2b.3c.4d.5a.6a, 1a.2b.3c.4d.5a.6b,
1a.2b.3c.4d.5a.6c, 1a.2b.3c.4d.5a.6d, 1a.2b.3c.4d.5a.6e, 1a.2b.3c.4d.5b.6a,
1a.2b.3c.4d.5b.6b, 1a.2b.3c.4d.5b.6c, 1a.2b.3c.4d.5b.6d, 1a.2b.3c.4d.5b.6e,
1a.2b.3c.4d.5c.6a, 1a.2b.3c.4d.5c.6b, 1a.2b.3c.4d.5c.6c, 1a.2b.3c.4d.5c.6d,
1a.2b.3c.4d.5c.6e, 1a.2b.3c.4d.5d.6a, 1a.2b.3c.4d.5d.6b, 1a.2b.3c.4d.5d.6c,
1a.2b.3c.4d.5d.6d, 1a.2b.3c.4d.5d.6e, 1a.2b.3c.4d.5e.6a, 1a.2b.3c.4d.5e.6b,
1a.2b.3c.4d.5e.6c, 1a.2b.3c.4d.5e.6d, 1a.2b.3c.4d.5e.6e, 1a.2b.3c.4e.5a.6a,
1a.2b.3c.4e.5a.6b, 1a.2b.3c.4e.5a.6c, 1a.2b.3c.4e.5a.6d, 1a.2b.3c.4e.5a.6e,
1a.2b.3c.4e.5b.6a, 1a.2b.3c.4e.5b.6b, 1a.2b.3c.4e.5b.6c, 1a.2b.3c.4e.5b.6d,
1a.2b.3c.4e.5b.6e, 1a.2b.3c.4e.5c.6a, 1a.2b.3c.4e.5c.6b, 1a.2b.3c.4e.5c.6c,
1a.2b.3c.4e.5c.6d, 1a.2b.3c.4e.5c.6e, 1a.2b.3c.4e.5d.6a, 1a.2b.3c.4e.5d.6b,
1a.2b.3c.4e.5d.6c, 1a.2b.3c.4e.5d.6d, 1a.2b.3c.4e.5d.6e, 1a.2b.3c.4e.5e.6a,
1a.2b.3c.4e.5e.6b, 1a.2b.3c.4e.5e.6c, 1a.2b.3c.4e.5e.6d, 1a.2b.3c.4e.5e.6e,
1a.2b.3d.4a.5a.6a, 1a.2b.3d.4a.5a.6b, 1a.2b.3d.4a.5a.6c, 1a.2b.3d.4a.5a.6d,
1a.2b.3d.4a.5a.6e, 1a.2b.3d.4a.5b.6a, 1a.2b.3d.4a.5b.6b, 1a.2b.3d.4a.5b.6c,
1a.2b.3d.4a.5b.6d, 1a.2b.3d.4a.5b.6e, 1a.2b.3d.4a.5c.6a, 1a.2b.3d.4a.5c.6b,
1a.2b.3d.4a.5c.6c, 1a.2b.3d.4a.5c.6d, 1a.2b.3d.4a.5c.6e, 1a.2b.3d.4a.5d.6a,
1a.2b.3d.4a.5d.6b, 1a.2b.3d.4a.5d.6c, 1a.2b.3d.4a.5d.6d, 1a.2b.3d.4a.5d.6e,
1a.2b.3d.4a.5e.6a, 1a.2b.3d.4a.5e.6b, 1a.2b.3d.4a.5e.6c, 1a.2b.3d.4a.5e.6d,
1a.2b.3d.4a.5e.6e, 1a.2b.3d.4b.5a.6a, 1a.2b.3d.4b.5a.6b, 1a.2b.3d.4b.5a.6c,
1a.2b.3d.4b.5a.6d, 1a.2b.3d.4b.5a.6e, 1a.2b.3d.4b.5b.6a, 1a.2b.3d.4b.5b.6b,
1a.2b.3d.4b.5b.6c, 1a.2b.3d.4b.5b.6d, 1a.2b.3d.4b.5b.6e, 1a.2b.3d.4b.5c.6a,
1a.2b.3d.4b.5c.6b, 1a.2b.3d.4b.5c.6c, 1a.2b.3d.4b.5c.6d, 1a.2b.3d.4b.5c.6e,
1a.2b.3d.4b.5d.6a, 1a.2b.3d.4b.5d.6b, 1a.2b.3d.4b.5d.6c, 1a.2b.3d.4b.5d.6d,
1a.2b.3d.4b.5d.6e, 1a.2b.3d.4b.5e.6a, 1a.2b.3d.4b.5e.6b, 1a.2b.3d.4b.5e.6c,
1a.2b.3d.4b.5e.6d, 1a.2b.3d.4b.5e.6e, 1a.2b.3d.4c.5a.6a, 1a.2b.3d.4c.5a.6b,
1a.2b.3d.4c.5a.6c, 1a.2b.3d.4c.5a.6d, 1a.2b.3d.4c.5a.6e, 1a.2b.3d.4c.5b.6a,
1a.2b.3d.4c.5b.6b, 1a.2b.3d.4c.5b.6c, 1a.2b.3d.4c.5b.6d, 1a.2b.3d.4c.5b.6e,
1a.2b.3d.4c.5c.6a, 1a.2b.3d.4c.5c.6b, 1a.2b.3d.4c.5c.6c, 1a.2b.3d.4c.5c.6d,
1a.2b.3d.4c.5c.6e, 1a.2b.3d.4c.5d.6a, 1a.2b.3d.4c.5d.6b, 1a.2b.3d.4c.5d.6c,
1a.2b.3d.4c.5d.6d, 1a.2b.3d.4c.5d.6e, 1a.2b.3d.4c.5e.6a, 1a.2b.3d.4c.5e.6b,
1a.2b.3d.4c.5e.6c, 1a.2b.3d.4c.5e.6d, 1a.2b.3d.4c.5e.6e, 1a.2b.3d.4d.5a.6a,
1a.2b.3d.4d.5a.6b, 1a.2b.3d.4d.5a.6c, 1a.2b.3d.4d.5a.6d, 1a.2b.3d.4d.5a.6e,
1a.2b.3d.4d.5b.6a, 1a.2b.3d.4d.5b.6b, 1a.2b.3d.4d.5b.6c, 1a.2b.3d.4d.5b.6d,
1a.2b.3d.4d.5b.6e, 1a.2b.3d.4d.5c.6a, 1a.2b.3d.4d.5c.6b, 1a.2b.3d.4d.5c.6c,
1a.2b.3d.4d.5c.6d, 1a.2b.3d.4d.5c.6e, 1a.2b.3d.4d.5d.6a, 1a.2b.3d.4d.5d.6b,
1a.2b.3d.4d.5d.6c, 1a.2b.3d.4d.5d.6d, 1a.2b.3d.4d.5d.6e, 1a.2b.3d.4d.5e.6a,
1a.2b.3d.4d.5e.6b, 1a.2b.3d.4d.5e.6c, 1a.2b.3d.4d.5e.6d, 1a.2b.3d.4d.5e.6e,
1a.2b.3d.4e.5a.6a, 1a.2b.3d.4e.5a.6b, 1a.2b.3d.4e.5a.6c, 1a.2b.3d.4e.5a.6d,

TABLE 8-continued

List of Compounds of Formula (II)

1a.2b.3d.4e.5a.6e, 1a.2b.3d.4e.5b.6a, 1a.2b.3d.4e.5b.6b, 1a.2b.3d.4e.5b.6c,
1a.2b.3d.4e.5b.6d, 1a.2b.3d.4e.5b.6e, 1a.2b.3d.4e.5c.6a, 1a.2b.3d.4e.5c.6b,
1a.2b.3d.4e.5c.6c, 1a.2b.3d.4e.5c.6d, 1a.2b.3d.4e.5c.6e, 1a.2b.3d.4e.5d.6a,
1a.2b.3d.4e.5d.6b, 1a.2b.3d.4e.5d.6c, 1a.2b.3d.4e.5d.6d, 1a.2b.3d.4e.5d.6e,
1a.2b.3d.4e.5e.6a, 1a.2b.3d.4e.5e.6b, 1a.2b.3d.4e.5e.6c, 1a.2b.3d.4e.5e.6d,
1a.2b.3d.4e.5e.6e, 1a.2b.3e.4a.5a.6a, 1a.2b.3e.4a.5a.6b, 1a.2b.3e.4a.5a.6c,
1a.2b.3e.4a.5a.6d, 1a.2b.3e.4a.5a.6e, 1a.2b.3e.4a.5b.6a, 1a.2b.3e.4a.5b.6b,
1a.2b.3e.4a.5b.6c, 1a.2b.3e.4a.5b.6d, 1a.2b.3e.4a.5b.6e, 1a.2b.3e.4a.5c.6a,
1a.2b.3e.4a.5c.6b, 1a.2b.3e.4a.5c.6c, 1a.2b.3e.4a.5c.6d, 1a.2b.3e.4a.5c.6e,
1a.2b.3e.4a.5d.6a, 1a.2b.3e.4a.5d.6b, 1a.2b.3e.4a.5d.6c, 1a.2b.3e.4a.5d.6d,
1a.2b.3e.4a.5d.6e, 1a.2b.3e.4a.5e.6a, 1a.2b.3e.4a.5e.6b, 1a.2b.3e.4a.5e.6c,
1a.2b.3e.4a.5e.6d, 1a.2b.3e.4a.5e.6e, 1a.2b.3e.4b.5a.6a, 1a.2b.3e.4b.5a.6b,
1a.2b.3e.4b.5a.6c, 1a.2b.3e.4b.5a.6d, 1a.2b.3e.4b.5a.6e, 1a.2b.3e.4b.5b.6a,
1a.2b.3e.4b.5b.6b, 1a.2b.3e.4b.5b.6c, 1a.2b.3e.4b.5b.6d, 1a.2b.3e.4b.5b.6e,
1a.2b.3e.4b.5c.6a, 1a.2b.3e.4b.5c.6b, 1a.2b.3e.4b.5c.6c, 1a.2b.3e.4b.5c.6d,
1a.2b.3e.4b.5c.6e, 1a.2b.3e.4b.5d.6a, 1a.2b.3e.4b.5d.6b, 1a.2b.3e.4b.5d.6c,
1a.2b.3e.4b.5d.6d, 1a.2b.3e.4b.5d.6e, 1a.2b.3e.4b.5e.6a, 1a.2b.3e.4b.5e.6b,
1a.2b.3e.4b.5e.6c, 1a.2b.3e.4b.5e.6d, 1a.2b.3e.4b.5e.6e, 1a.2b.3e.4c.5a.6a,
1a.2b.3e.4c.5a.6b, 1a.2b.3e.4c.5a.6c, 1a.2b.3e.4c.5a.6d, 1a.2b.3e.4c.5a.6e,
1a.2b.3e.4c.5b.6a, 1a.2b.3e.4c.5b.6b, 1a.2b.3e.4c.5b.6c, 1a.2b.3e.4c.5b.6d,
1a.2b.3e.4c.5b.6e, 1a.2b.3e.4c.5c.6a, 1a.2b.3e.4c.5c.6b, 1a.2b.3e.4c.5c.6c,
1a.2b.3e.4c.5c.6d, 1a.2b.3e.4c.5c.6e, 1a.2b.3e.4c.5d.6a, 1a.2b.3e.4c.5c.6b,
1a.2b.3e.4c.5d.6c, 1a.2b.3e.4c.5d.6d, 1a.2b.3e.4c.5d.6e, 1a.2b.3e.4c.5e.6a,
1a.2b.3e.4c.5e.6b, 1a.2b.3e.4c.5e.6c, 1a.2b.3e.4c.5e.6d, 1a.2b.3e.4c.5e.6e,
1a.2b.3e.4d.5a.6a, 1a.2b.3e.4d.5a.6b, 1a.2b.3e.4d.5a.6c, 1a.2b.3e.4d.5a.6d,
1a.2b.3e.4d.5a.6e, 1a.2b.3e.4d.5b.6a, 1a.2b.3e.4d.5b.6b, 1a.2b.3e.4d.5b.6c,
1a.2b.3e.4d.5b.6d, 1a.2b.3e.4d.5b.6e, 1a.2b.3e.4d.5c.6a, 1a.2b.3e.4d.5c.6b,
1a.2b.3e.4d.5c.6c, 1a.2b.3e.4d.5c.6d, 1a.2b.3e.4d.5c.6e, 1a.2b.3e.4d.5d.6a,
1a.2b.3e.4d.5d.6b, 1a.2b.3e.4d.5d.6c, 1a.2b.3e.4d.5d.6d, 1a.2b.3e.4d.5d.6e,
1a.2b.3e.4d.5e.6a, 1a.2b.3e.4d.5e.6b, 1a.2b.3e.4d.5e.6c, 1a.2b.3e.4d.5e.6d,
1a.2b.3e.4d.5e.6e, 1a.2b.3e.4e.5a.6a, 1a.2b.3e.4e.5a.6b, 1a.2b.3e.4e.5a.6c,
1a.2b.3e.4e.5a.6d, 1a.2b.3e.4e.5a.6e, 1a.2b.3e.4e.5b.6a, 1a.2b.3e.4e.5b.6b,
1a.2b.3e.4e.5b.6c, 1a.2b.3e.4e.5b.6d, 1a.2b.3e.4e.5b.6e, 1a.2b.3e.4e.5c.6a,
1a.2b.3e.4e.5c.6b, 1a.2b.3e.4e.5c.6c, 1a.2b.3e.4e.5c.6d, 1a.2b.3e.4e.5c.6e,
1a.2b.3e.4e.5d.6a, 1a.2b.3e.4e.5d.6b, 1a.2b.3e.4e.5d.6c, 1a.2b.3e.4e.5d.6d,
1a.2b.3e.4e.5d.6e, 1a.2b.3e.4e.5e.6a, 1a.2b.3e.4e.5e.6b, 1a.2b.3e.4e.5e.6c,
1a.2b.3e.4e.5e.6d, 1a.2b.3e.4e.5e.6e, 1a.2c.3a.4a.5a.6a, 1a.2c.3a.4a.5a.6b,
1a.2c.3a.4a.5a.6c, 1a.2c.3a.4a.5a.6d, 1a.2c.3a.4a.5a.6e, 1a.2c.3a.4a.5b.6a,
1a.2c.3a.4a.5b.6b, 1a.2c.3a.4a.5b.6c, 1a.2c.3a.4a.5b.6d, 1a.2c.3a.4a.5b.6e,
1a.2c.3a.4a.5c.6a, 1a.2c.3a.4a.5c.6b, 1a.2c.3a.4a.5c.6c, 1a.2c.3a.4a.5c.6d,
1a.2c.3a.4a.5c.6e, 1a.2c.3a.4a.5d.6a, 1a.2c.3a.4a.5d.6b, 1a.2c.3a.4a.5d.6c,
1a.2c.3a.4a.5d.6d, 1a.2c.3a.4a.5d.6e, 1a.2c.3a.4a.5e.6a, 1a.2c.3a.4a.5e.6b,
1a.2c.3a.4a.5e.6c, 1a.2c.3a.4a.5e.6d, 1a.2c.3a.4a.5e.6e, 1a.2c.3a.4b.5a.6a,
1a.2c.3a.4b.5a.6b, 1a.2c.3a.4b.5a.6c, 1a.2c.3a.4b.5a.6d, 1a.2c.3a.4b.5a.6e,
1a.2c.3a.4b.5b.6a, 1a.2c.3a.4b.5b.6b, 1a.2c.3a.4b.5b.6c, 1a.2c.3a.4b.5b.6d,
1a.2c.3a.4b.5b.6e, 1a.2c.3a.4b.5c.6a, 1a.2c.3a.4b.5c.6b, 1a.2c.3a.4b.5c.6c,
1a.2c.3a.4b.5c.6d, 1a.2c.3a.4b.5c.6e, 1a.2c.3a.4b.5d.6a, 1a.2c.3a.4b.5d.6b,
1a.2c.3a.4b.5d.6c, 1a.2c.3a.4b.5d.6d, 1a.2c.3a.4b.5d.6e, 1a.2c.3a.4b.5e.6a,
1a.2c.3a.4b.5e.6b, 1a.2c.3a.4b.5e.6c, 1a.2c.3a.4b.5e.6d, 1a.2c.3a.4b.5e.6e,
1a.2c.3a.4c.5a.6a, 1a.2c.3a.4c.5a.6b, 1a.2c.3a.4c.5a.6c, 1a.2c.3a.4c.5a.6d,
1a.2c.3a.4c.5a.6e, 1a.2c.3a.4c.5b.6a, 1a.2c.3a.4c.5b.6b, 1a.2c.3a.4c.5b.6c,
1a.2c.3a.4c.5b.6d, 1a.2c.3a.4c.5b.6e, 1a.2c.3a.4c.5c.6a, 1a.2c.3a.4c.5c.6b,
1a.2c.3a.4c.5c.6c, 1a.2c.3a.4c.5c.6d, 1a.2c.3a.4c.5c.6e, 1a.2c.3a.4c.5d.6a,
1a.2c.3a.4c.5d.6b, 1a.2c.3a.4c.5d.6c, 1a.2c.3a.4c.5d.6d, 1a.2c.3a.4c.5d.6e,
1a.2c.3a.4c.5e.6a, 1a.2c.3a.4c.5e.6b, 1a.2c.3a.4c.5e.6c, 1a.2c.3a.4c.5e.6d,
1a.2c.3a.4c.5e.6e, 1a.2c.3a.4d.5a.6a, 1a.2c.3a.4d.5a.6b, 1a.2c.3a.4d.5a.6c,
1a.2c.3a.4d.5a.6d, 1a.2c.3a.4d.5a.6e, 1a.2c.3a.4d.5b.6a, 1a.2c.3a.4d.5b.6b,
1a.2c.3a.4d.5b.6c, 1a.2c.3a.4d.5b.6d, 1a.2c.3a.4d.5b.6e, 1a.2c.3a.4d.5c.6a,
1a.2c.3a.4d.5c.6b, 1a.2c.3a.4d.5c.6c, 1a.2c.3a.4d.5c.6d, 1a.2c.3a.4d.5c.6e,
1a.2c.3a.4d.5d.6a, 1a.2c.3a.4d.5d.6b, 1a.2c.3a.4d.5d.6c, 1a.2c.3a.4d.5d.6d,
1a.2c.3a.4d.5d.6e, 1a.2c.3a.4d.5e.6a, 1a.2c.3a.4d.5e.6b, 1a.2c.3a.4d.5e.6c,
1a.2c.3a.4d.5e.6d, 1a.2c.3a.4d.5e.6e, 1a.2c.3a.4e.5a.6a, 1a.2c.3a.4e.5a.6b,
1a.2c.3a.4e.5a.6c, 1a.2c.3a.4e.5a.6d, 1a.2c.3a.4e.5a.6e, 1a.2c.3a.4e.5b.6a,
1a.2c.3a.4e.5b.6b, 1a.2c.3a.4e.5b.6c, 1a.2c.3a.4e.5b.6d, 1a.2c.3a.4e.5b.6e,
1a.2c.3a.4e.5c.6a, 1a.2c.3a.4e.5c.6b, 1a.2c.3a.4e.5c.6c, 1a.2c.3a.4e.5c.6d,
1a.2c.3a.4e.5c.6e, 1a.2c.3a.4e.5d.6a, 1a.2c.3a.4e.5d.6b, 1a.2c.3a.4e.5d.6c,
1a.2c.3a.4e.5d.6d, 1a.2c.3a.4e.5d.6e, 1a.2c.3a.4e.5e.6a, 1a.2c.3a.4e.5e.6b,
1a.2c.3a.4e.5e.6c, 1a.2c.3a.4e.5e.6d, 1a.2c.3a.4e.5e.6e, 1a.2c.3b.4a.5a.6a,
1a.2c.3b.4a.5a.6b, 1a.2c.3b.4a.5a.6c, 1a.2c.3b.4a.5a.6d, 1a.2c.3b.4a.5a.6e,
1a.2c.3b.4a.5b.6a, 1a.2c.3b.4a.5b.6b, 1a.2c.3b.4a.5b.6c, 1a.2c.3b.4a.5b.6d,
1a.2c.3b.4a.5b.6e, 1a.2c.3b.4a.5c.6a, 1a.2c.3b.4a.5c.6b, 1a.2c.3b.4a.5c.6c,
1a.2c.3b.4a.5c.6d, 1a.2c.3b.4a.5c.6e, 1a.2c.3b.4a.5d.6a, 1a.2c.3b.4a.5d.6b,
1a.2c.3b.4a.5d.6c, 1a.2c.3b.4a.5d.6d, 1a.2c.3b.4a.5d.6e, 1a.2c.3b.4a.5e.6a,
1a.2c.3b.4a.5e.6b, 1a.2c.3b.4a.5e.6c, 1a.2c.3b.4a.5e.6d, 1a.2c.3b.4a.5e.6e,
1a.2c.3b.4b.5a.6a, 1a.2c.3b.4b.5a.6b, 1a.2c.3b.4b.5a.6c, 1a.2c.3b.4b.5a.6d,
1a.2c.3b.4b.5a.6e, 1a.2c.3b.4b.5b.6a, 1a.2c.3b.4b.5b.6b, 1a.2c.3b.4b.5b.6c,
1a.2c.3b.4b.5b.6d, 1a.2c.3b.4b.5b.6e, 1a.2c.3b.4b.5c.6a, 1a.2c.3b.4b.5c.6b,
1a.2c.3b.4b.5c.6c, 1a.2c.3b.4b.5c.6d, 1a.2c.3b.4b.5c.6e, 1a.2c.3b.4b.5d.6a,

TABLE 8-continued

List of Compounds of Formula (II)

1a.2c.3b.4b.5d.6b, 1a.2c.3b.4b.5d.6c, 1a.2c.3b.4b.5d.6d, 1a.2c.3b.4b.5d.6e,
1a.2c.3b.4b.5e.6a, 1a.2c.3b.4b.5e.6b, 1a.2c.3b.4b.5e.6c, 1a.2c.3b.4b.5e.6d,
1a.2c.3b.4b.5e.6e, 1a.2c.3b.4c.5a.6a, 1a.2c.3b.4c.5a.6b, 1a.2c.3b.4c.5a.6c,
1a.2c.3b.4c.5a.6d, 1a.2c.3b.4c.5a.6e, 1a.2c.3b.4c.5b.6a, 1a.2c.3b.4c.5b.6b,
1a.2c.3b.4c.5b.6c, 1a.2c.3b.4c.5b.6d, 1a.2c.3b.4c.5b.6e, 1a.2c.3b.4c.5c.6a,
1a.2c.3b.4c.5c.6b, 1a.2c.3b.4c.5c.6c, 1a.2c.3b.4c.5c.6d, 1a.2c.3b.4c.5c.6e,
1a.2c.3b.4c.5d.6a, 1a.2c.3b.4c.5d.6b, 1a.2c.3b.4c.5d.6c, 1a.2c.3b.4c.5d.6d,
1a.2c.3b.4c.5d.6e, 1a.2c.3b.4c.5e.6a, 1a.2c.3b.4c.5e.6b, 1a.2c.3b.4c.5e.6c,
1a.2c.3b.4c.5e.6d, 1a.2c.3b.4c.5e.6e, 1a.2c.3b.4d.5a.6a, 1a.2c.3b.4d.5a.6b,
1a.2c.3b.4d.5a.6c, 1a.2c.3b.4d.5a.6d, 1a.2c.3b.4d.5a.6e, 1a.2c.3b.4d.5b.6a,
1a.2c.3b.4d.5b.6b, 1a.2c.3b.4d.5b.6c, 1a.2c.3b.4d.5b.6d, 1a.2c.3b.4d.5b.6e,
1a.2c.3b.4d.5c.6a, 1a.2c.3b.4d.5c.6b, 1a.2c.3b.4d.5c.6c, 1a.2c.3b.4d.5c.6d,
1a.2c.3b.4d.5c.6e, 1a.2c.3b.4d.5d.6a, 1a.2c.3b.4d.5d.6b, 1a.2c.3b.4d.5d.6c,
1a.2c.3b.4d.5d.6d, 1a.2c.3b.4d.5d.6e, 1a.2c.3b.4d.5e.6a, 1a.2c.3b.4d.5e.6b,
1a.2c.3b.4d.5e.6c, 1a.2c.3b.4d.5e.6d, 1a.2c.3b.4d.5e.6e, 1a.2c.3b.4e.5a.6a,
1a.2c.3b.4e.5a.6b, 1a.2c.3b.4e.5a.6c, 1a.2c.3b.4e.5a.6d, 1a.2c.3b.4e.5a.6e,
1a.2c.3b.4e.5b.6a, 1a.2c.3b.4e.5b.6b, 1a.2c.3b.4e.5b.6c, 1a.2c.3b.4e.5b.6d,
1a.2c.3b.4e.5b.6e, 1a.2c.3b.4e.5c.6a, 1a.2c.3b.4e.5c.6b, 1a.2c.3b.4e.5c.6c,
1a.2c.3b.4e.5c.6d, 1a.2c.3b.4e.5c.6e, 1a.2c.3b.4e.5d.6a, 1a.2c.3b.4e.5d.6b,
1a.2c.3b.4e.5d.6c, 1a.2c.3b.4e.5d.6d, 1a.2c.3b.4e.5d.6e, 1a.2c.3b.4e.5e.6a,
1a.2c.3b.4e.5e.6b, 1a.2c.3b.4e.5e.6c, 1a.2c.3b.4e.5e.6d, 1a.2c.3b.4e.5e.6e,
1a.2c.3c.4a.5a.6a, 1a.2c.3c.4a.5a.6b, 1a.2c.3c.4a.5a.6c, 1a.2c.3c.4a.5a.6d,
1a.2c.3c.4a.5a.6e, 1a.2c.3c.4a.5b.6a, 1a.2c.3c.4a.5b.6b, 1a.2c.3c.4a.5b.6c,
1a.2c.3c.4a.5b.6d, 1a.2c.3c.4a.5b.6e, 1a.2c.3c.4a.5c.6a, 1a.2c.3c.4a.5c.6b,
1a.2c.3c.4a.5c.6c, 1a.2c.3c.4a.5c.6d, 1a.2c.3c.4a.5c.6e, 1a.2c.3c.4a.5d.6a,
1a.2c.3c.4a.5d.6b, 1a.2c.3c.4a.5d.6c, 1a.2c.3c.4a.5d.6d, 1a.2c.3c.4a.5d.6e,
1a.2c.3c.4a.5e.6a, 1a.2c.3c.4a.5e.6b, 1a.2c.3c.4a.5e.6c, 1a.2c.3c.4a.5e.6d,
1a.2c.3c.4a.5e.6e, 1a.2c.3c.4b.5a.6a, 1a.2c.3c.4b.5a.6b, 1a.2c.3c.4b.5a.6c,
1a.2c.3c.4b.5a.6d, 1a.2c.3c.4b.5a.6e, 1a.2c.3c.4b.5b.6a, 1a.2c.3c.4b.5b.6b,
1a.2c.3c.4b.5b.6c, 1a.2c.3c.4b.5b.6d, 1a.2c.3c.4b.5b.6e, 1a.2c.3c.4b.5c.6a,
1a.2c.3c.4b.5c.6b, 1a.2c.3c.4b.5c.6c, 1a.2c.3c.4b.5c.6d, 1a.2c.3c.4b.5c.6e,
1a.2c.3c.4b.5d.6a, 1a.2c.3c.4b.5d.6b, 1a.2c.3c.4b.5d.6c, 1a.2c.3c.4b.5d.6d,
1a.2c.3c.4b.5d.6e, 1a.2c.3c.4b.5e.6a, 1a.2c.3c.4b.5e.6b, 1a.2c.3c.4b.5e.6c,
1a.2c.3c.4b.5e.6d, 1a.2c.3c.4b.5e.6e, 1a.2c.3c.4c.5a.6a, 1a.2c.3c.4c.5a.6b,
1a.2c.3c.4c.5a.6c, 1a.2c.3c.4c.5a.6d, 1a.2c.3c.4c.5a.6e, 1a.2c.3c.4c.5b.6a,
1a.2c.3c.4c.5b.6b, 1a.2c.3c.4c.5b.6c, 1a.2c.3c.4c.5b.6d, 1a.2c.3c.4c.5b.6e,
1a.2c.3c.4c.5c.6a, 1a.2c.3c.4c.5c.6b, 1a.2c.3c.4c.5c.6c, 1a.2c.3c.4c.5c.6d,
1a.2c.3c.4c.5c.6e, 1a.2c.3c.4c.5d.6a, 1a.2c.3c.4c.5d.6b, 1a.2c.3c.4c.5d.6c,
1a.2c.3c.4c.5d.6d, 1a.2c.3c.4c.5d.6e, 1a.2c.3c.4c.5e.6a, 1a.2c.3c.4c.5e.6b,
1a.2c.3c.4c.5e.6c, 1a.2c.3c.4c.5e.6d, 1a.2c.3c.4c.5e.6e, 1a.2c.3c.4d.5a.6a,
1a.2c.3c.4d.5a.6b, 1a.2c.3c.4d.5a.6c, 1a.2c.3c.4d.5a.6d, 1a.2c.3c.4d.5a.6e,
1a.2c.3c.4d.5b.6a, 1a.2c.3c.4d.5b.6b, 1a.2c.3c.4d.5b.6c, 1a.2c.3c.4d.5b.6d,
1a.2c.3c.4d.5b.6e, 1a.2c.3c.4d.5c.6a, 1a.2c.3c.4d.5c.6b, 1a.2c.3c.4d.5c.6c,
1a.2c.3c.4d.5c.6d, 1a.2c.3c.4d.5c.6e, 1a.2c.3c.4d.5d.6a, 1a.2c.3c.4d.5d.6b,
1a.2c.3c.4d.5d.6c, 1a.2c.3c.4d.5d.6d, 1a.2c.3c.4d.5d.6e, 1a.2c.3c.4d.5e.6a,
1a.2c.3c.4d.5e.6b, 1a.2c.3c.4d.5e.6c, 1a.2c.3c.4d.5e.6d, 1a.2c.3c.4d.5e.6e,
1a.2c.3c.4e.5a.6a, 1a.2c.3c.4e.5a.6b, 1a.2c.3c.4e.5a.6c, 1a.2c.3c.4e.5a.6d,
1a.2c.3c.4e.5a.6e, 1a.2c.3c.4e.5b.6a, 1a.2c.3c.4e.5b.6b, 1a.2c.3c.4e.5b.6c,
1a.2c.3c.4e.5b.6d, 1a.2c.3c.4e.5b.6e, 1a.2c.3c.4e.5c.6a, 1a.2c.3c.4e.5c.6b,
1a.2c.3c.4e.5c.6c, 1a.2c.3c.4e.5c.6d, 1a.2c.3c.4e.5c.6e, 1a.2c.3c.4e.5d.6a,
1a.2c.3c.4e.5d.6b, 1a.2c.3c.4e.5d.6c, 1a.2c.3c.4e.5d.6d, 1a.2c.3c.4e.5d.6e,
1a.2c.3c.4e.5e.6a, 1a.2c.3c.4e.5e.6b, 1a.2c.3c.4e.5e.6c, 1a.2c.3c.4e.5e.6d,
1a.2c.3c.4e.5e.6e, 1a.2c.3d.4a.5a.6a, 1a.2c.3d.4a.5a.6b, 1a.2c.3d.4a.5a.6c,
1a.2c.3d.4a.5a.6d, 1a.2c.3d.4a.5a.6e, 1a.2c.3d.4a.5b.6a, 1a.2c.3d.4a.5b.6b,
1a.2c.3d.4a.5b.6c, 1a.2c.3d.4a.5b.6d, 1a.2c.3d.4a.5b.6e, 1a.2c.3d.4a.5c.6a,
1a.2c.3d.4a.5c.6b, 1a.2c.3d.4a.5c.6c, 1a.2c.3d.4a.5c.6d, 1a.2c.3d.4a.5c.6e,
1a.2c.3d.4a.5d.6a, 1a.2c.3d.4a.5d.6b, 1a.2c.3d.4a.5d.6c, 1a.2c.3d.4a.5d.6d,
1a.2c.3d.4a.5d.6e, 1a.2c.3d.4a.5e.6a, 1a.2c.3d.4a.5e.6b, 1a.2c.3d.4a.5e.6c,
1a.2c.3d.4a.5e.6d, 1a.2c.3d.4a.5e.6e, 1a.2c.3d.4b.5a.6a, 1a.2c.3d.4b.5a.6b,
1a.2c.3d.4b.5a.6c, 1a.2c.3d.4b.5a.6d, 1a.2c.3d.4b.5a.6e, 1a.2c.3d.4b.5b.6a,
1a.2c.3d.4b.5b.6b, 1a.2c.3d.4b.5b.6c, 1a.2c.3d.4b.5b.6d, 1a.2c.3d.4b.5b.6e,
1a.2c.3d.4b.5c.6a, 1a.2c.3d.4b.5c.6b, 1a.2c.3d.4b.5c.6c, 1a.2c.3d.4b.5c.6d,
1a.2c.3d.4b.5c.6e, 1a.2c.3d.4b.5d.6a, 1a.2c.3d.4b.5d.6b, 1a.2c.3d.4b.5d.6c,
1a.2c.3d.4b.5d.6d, 1a.2c.3d.4b.5d.6e, 1a.2c.3d.4b.5e.6a, 1a.2c.3d.4b.5e.6b,
1a.2c.3d.4b.5e.6c, 1a.2c.3d.4b.5e.6d, 1a.2c.3d.4b.5e.6e, 1a.2c.3d.4c.5a.6a,
1a.2c.3d.4c.5a.6b, 1a.2c.3d.4c.5a.6c, 1a.2c.3d.4c.5a.6d, 1a.2c.3d.4c.5a.6e,
1a.2c.3d.4c.5b.6a, 1a.2c.3d.4c.5b.6b, 1a.2c.3d.4c.5b.6c, 1a.2c.3d.4c.5b.6d,
1a.2c.3d.4c.5b.6e, 1a.2c.3d.4c.5c.6a, 1a.2c.3d.4c.5c.6b, 1a.2c.3d.4c.5c.6c,
1a.2c.3d.4c.5c.6d, 1a.2c.3d.4c.5c.6e, 1a.2c.3d.4c.5d.6a, 1a.2c.3d.4c.5d.6b,
1a.2c.3d.4c.5d.6c, 1a.2c.3d.4c.5d.6d, 1a.2c.3d.4c.5d.6e, 1a.2c.3d.4c.5e.6a,
1a.2c.3d.4c.5e.6b, 1a.2c.3d.4c.5e.6c, 1a.2c.3d.4c.5e.6d, 1a.2c.3d.4c.5e.6e,
1a.2c.3d.4d.5a.6a, 1a.2c.3d.4d.5a.6b, 1a.2c.3d.4d.5a.6c, 1a.2c.3d.4d.5a.6d,
1a.2c.3d.4d.5a.6e, 1a.2c.3d.4d.5b.6a, 1a.2c.3d.4d.5b.6b, 1a.2c.3d.4d.5b.6c,
1a.2c.3d.4d.5b.6d, 1a.2c.3d.4d.5b.6e, 1a.2c.3d.4d.5c.6a, 1a.2c.3d.4d.5c.6b,
1a.2c.3d.4d.5c.6c, 1a.2c.3d.4d.5c.6d, 1a.2c.3d.4d.5c.6e, 1a.2c.3d.4d.5d.6a,
1a.2c.3d.4d.5d.6b, 1a.2c.3d.4d.5d.6c, 1a.2c.3d.4d.5d.6d, 1a.2c.3d.4d.5d.6e,
1a.2c.3d.4d.5e.6a, 1a.2c.3d.4d.5e.6b, 1a.2c.3d.4d.5e.6c, 1a.2c.3d.4d.5e.6d,
1a.2c.3d.4d.5e.6e, 1a.2c.3d.4e.5a.6a, 1a.2c.3d.4e.5a.6b, 1a.2c.3d.4e.5a.6c,

TABLE 8-continued

List of Compounds of Formula (II)

1a.2c.3d.4e.5a.6d, 1a.2c.3d.4e.5a.6e, 1a.2c.3d.4e.5b.6a, 1a.2c.3d.4e.5b.6b,
1a.2c.3d.4e.5b.6c, 1a.2c.3d.4e.5b.6d, 1a.2c.3d.4e.5b.6e, 1a.2c.3d.4e.5c.6a,
1a.2c.3d.4e.5c.6b, 1a.2c.3d.4e.5c.6c, 1a.2c.3d.4e.5c.6d, 1a.2c.3d.4e.5c.6e,
1a.2c.3d.4e.5d.6a, 1a.2c.3d.4e.5d.6b, 1a.2c.3d.4e.5d.6c, 1a.2c.3d.4e.5d.6d,
1a.2c.3d.4e.5d.6e, 1a.2c.3d.4e.5e.6a, 1a.2c.3d.4e.5e.6b, 1a.2c.3d.4e.5e.6c,
1a.2c.3d.4e.5e.6d, 1a.2c.3d.4e.5e.6e, 1a.2c.3e.4a.5a.6a, 1a.2c.3e.4a.5a.6b,
1a.2c.3e.4a.5a.6c, 1a.2c.3e.4a.5a.6d, 1a.2c.3e.4a.5a.6e, 1a.2c.3e.4a.5b.6a,
1a.2c.3e.4a.5b.6b, 1a.2c.3e.4a.5b.6c, 1a.2c.3e.4a.5b.6d, 1a.2c.3e.4a.5b.6e,
1a.2c.3e.4a.5c.6a, 1a.2c.3e.4a.5c.6b, 1a.2c.3e.4a.5c.6c, 1a.2c.3e.4a.5c.6d,
1a.2c.3e.4a.5c.6e, 1a.2c.3e.4a.5d.6a, 1a.2c.3e.4a.5d.6b, 1a.2c.3e.4a.5d.6c,
1a.2c.3e.4a.5d.6d, 1a.2c.3e.4a.5d.6e, 1a.2c.3e.4a.5e.6a, 1a.2c.3e.4a.5e.6b,
1a.2c.3e.4a.5e.6c, 1a.2c.3e.4a.5e.6d, 1a.2c.3e.4a.5e.6e, 1a.2c.3e.4b.5a.6a,
1a.2c.3e.4b.5a.6b, 1a.2c.3e.4b.5a.6c, 1a.2c.3e.4b.5a.6d, 1a.2c.3e.4b.5a.6e,
1a.2c.3e.4b.5b.6a, 1a.2c.3e.4b.5b.6b, 1a.2c.3e.4b.5b.6c, 1a.2c.3e.4b.5b.6d,
1a.2c.3e.4b.5b.6e, 1a.2c.3e.4b.5c.6a, 1a.2c.3e.4b.5c.6b, 1a.2c.3e.4b.5c.6c,
1a.2c.3e.4b.5c.6d, 1a.2c.3e.4b.5c.6e, 1a.2c.3e.4b.5d.6a, 1a.2c.3e.4b.5d.6b,
1a.2c.3e.4b.5d.6c, 1a.2c.3e.4b.5d.6d, 1a.2c.3e.4b.5d.6e, 1a.2c.3e.4b.5e.6a,
1a.2c.3e.4b.5e.6b, 1a.2c.3e.4b.5e.6c, 1a.2c.3e.4b.5e.6d, 1a.2c.3e.4b.5e.6e,
1a.2c.3e.4c.5a.6a, 1a.2c.3e.4c.5a.6b, 1a.2c.3e.4c.5a.6c, 1a.2c.3e.4c.5a.6d,
1a.2c.3e.4c.5a.6e, 1a.2c.3e.4c.5b.6a, 1a.2c.3e.4c.5b.6b, 1a.2c.3e.4c.5b.6c,
1a.2c.3e.4c.5b.6d, 1a.2c.3e.4c.5b.6e, 1a.2c.3e.4c.5c.6a, 1a.2c.3e.4c.5c.6b,
1a.2c.3e.4c.5c.6c, 1a.2c.3e.4c.5c.6d, 1a.2c.3e.4c.5c.6e, 1a.2c.3e.4c.5d.6a,
1a.2c.3e.4c.5d.6b, 1a.2c.3e.4c.5d.6c, 1a.2c.3e.4c.5d.6d, 1a.2c.3e.4c.5d.6e,
1a.2c.3e.4c.5e.6a, 1a.2c.3e.4c.5e.6b, 1a.2c.3e.4c.5e.6c, 1a.2c.3e.4c.5e.6d,
1a.2c.3e.4c.5e.6e, 1a.2c.3e.4d.5a.6a, 1a.2c.3e.4d.5a.6b, 1a.2c.3e.4d.5a.6c,
1a.2c.3e.4d.5a.6d, 1a.2c.3e.4d.5a.6e, 1a.2c.3e.4d.5b.6a, 1a.2c.3e.4d.5b.6b,
1a.2c.3e.4d.5b.6c, 1a.2c.3e.4d.5b.6d, 1a.2c.3e.4d.5b.6e, 1a.2c.3e.4d.5c.6a,
1a.2c.3e.4d.5c.6b, 1a.2c.3e.4d.5c.6c, 1a.2c.3e.4d.5c.6d, 1a.2c.3e.4d.5c.6e,
1a.2c.3e.4d.5d.6a, 1a.2c.3e.4d.5d.6b, 1a.2c.3e.4d.5d.6c, 1a.2c.3e.4d.5d.6d,
1a.2c.3e.4d.5d.6e, 1a.2c.3e.4d.5e.6a, 1a.2c.3e.4d.5e.6b, 1a.2c.3e.4d.5e.6c,
1a.2c.3e.4d.5e.6d, 1a.2c.3e.4d.5e.6e, 1a.2c.3e.4e.5a.6a, 1a.2c.3e.4e.5a.6b,
1a.2c.3e.4e.5a.6c, 1a.2c.3e.4e.5a.6d, 1a.2c.3e.4e.5a.6e, 1a.2c.3e.4e.5b.6a,
1a.2c.3e.4e.5b.6b, 1a.2c.3e.4e.5b.6c, 1a.2c.3e.4e.5b.6d, 1a.2c.3e.4e.5b.6e,
1a.2c.3e.4e.5c.6a, 1a.2c.3e.4e.5c.6b, 1a.2c.3e.4e.5c.6c, 1a.2c.3e.4e.5c.6d,
1a.2c.3e.4e.5c.6e, 1a.2c.3e.4e.5d.6a, 1a.2c.3e.4e.5d.6b, 1a.2c.3e.4e.5d.6c,
1a.2c.3e.4e.5d.6d, 1a.2c.3e.4e.5d.6e, 1a.2c.3e.4e.5e.6a, 1a.2c.3e.4e.5e.6b,
1a.2c.3e.4e.5e.6c, 1a.2c.3e.4e.5e.6d, 1a.2c.3e.4e.5e.6e, 1a.2d.3a.4a.5a.6a,
1a.2d.3a.4a.5a.6b, 1a.2d.3a.4a.5a.6c, 1a.2d.3a.4a.5a.6d, 1a.2d.3a.4a.5a.6e,
1a.2d.3a.4a.5b.6a, 1a.2d.3a.4a.5b.6b, 1a.2d.3a.4a.5b.6c, 1a.2d.3a.4a.5b.6d,
1a.2d.3a.4a.5b.6e, 1a.2d.3a.4a.5c.6a, 1a.2d.3a.4a.5c.6b, 1a.2d.3a.4a.5c.6c,
1a.2d.3a.4a.5c.6d, 1a.2d.3a.4a.5c.6e, 1a.2d.3a.4a.5d.6a, 1a.2d.3a.4a.5d.6b,
1a.2d.3a.4a.5d.6c, 1a.2d.3a.4a.5d.6d, 1a.2d.3a.4a.5d.6e, 1a.2d.3a.4a.5e.6a,
1a.2d.3a.4a.5e.6b, 1a.2d.3a.4a.5e.6c, 1a.2d.3a.4a.5e.6d, 1a.2d.3a.4a.5e.6e,
1a.2d.3a.4b.5a.6a, 1a.2d.3a.4b.5a.6b, 1a.2d.3a.4b.5a.6c, 1a.2d.3a.4b.5a.6d,
1a.2d.3a.4b.5a.6e, 1a.2d.3a.4b.5b.6a, 1a.2d.3a.4b.5b.6b, 1a.2d.3a.4b.5b.6c,
1a.2d.3a.4b.5b.6d, 1a.2d.3a.4b.5b.6e, 1a.2d.3a.4b.5c.6a, 1a.2d.3a.4b.5c.6b,
1a.2d.3a.4b.5c.6c, 1a.2d.3a.4b.5c.6d, 1a.2d.3a.4b.5c.6e, 1a.2d.3a.4b.5d.6a,
1a.2d.3a.4b.5d.6b, 1a.2d.3a.4b.5d.6c, 1a.2d.3a.4b.5d.6d, 1a.2d.3a.4b.5d.6e,
1a.2d.3a.4b.5e.6a, 1a.2d.3a.4b.5e.6b, 1a.2d.3a.4b.5e.6c, 1a.2d.3a.4b.5e.6d,
1a.2d.3a.4b.5e.6e, 1a.2d.3a.4c.5a.6a, 1a.2d.3a.4c.5a.6b, 1a.2d.3a.4c.5a.6c,
1a.2d.3a.4c.5a.6d, 1a.2d.3a.4c.5a.6e, 1a.2d.3a.4c.5b.6a, 1a.2d.3a.4c.5b.6b,
1a.2d.3a.4c.5b.6c, 1a.2d.3a.4c.5b.6d, 1a.2d.3a.4c.5b.6e, 1a.2d.3a.4c.5c.6a,
1a.2d.3a.4c.5c.6b, 1a.2d.3a.4c.5c.6c, 1a.2d.3a.4c.5c.6d, 1a.2d.3a.4c.5c.6e,
1a.2d.3a.4c.5d.6a, 1a.2d.3a.4c.5d.6b, 1a.2d.3a.4c.5d.6c, 1a.2d.3a.4c.5d.6d,
1a.2d.3a.4c.5d.6e, 1a.2d.3a.4c.5e.6a, 1a.2d.3a.4c.5e.6b, 1a.2d.3a.4c.5e.6c,
1a.2d.3a.4c.5e.6d, 1a.2d.3a.4c.5e.6e, 1a.2d.3a.4d.5a.6a, 1a.2d.3a.4d.5a.6b,
1a.2d.3a.4d.5a.6c, 1a.2d.3a.4d.5a.6d, 1a.2d.3a.4d.5a.6e, 1a.2d.3a.4d.5b.6a,
1a.2d.3a.4d.5b.6b, 1a.2d.3a.4d.5b.6c, 1a.2d.3a.4d.5b.6d, 1a.2d.3a.4d.5b.6e,
1a.2d.3a.4d.5c.6a, 1a.2d.3a.4d.5c.6b, 1a.2d.3a.4d.5c.6c, 1a.2d.3a.4d.5c.6d,
1a.2d.3a.4d.5c.6e, 1a.2d.3a.4d.5d.6a, 1a.2d.3a.4d.5d.6b, 1a.2d.3a.4d.5d.6c,
1a.2d.3a.4d.5d.6d, 1a.2d.3a.4d.5d.6e, 1a.2d.3a.4d.5e.6a, 1a.2d.3a.4d.5e.6b,
1a.2d.3a.4d.5e.6c, 1a.2d.3a.4d.5e.6d, 1a.2d.3a.4d.5e.6e, 1a.2d.3a.4e.5a.6a,
1a.2d.3a.4e.5a.6b, 1a.2d.3a.4e.5a.6c, 1a.2d.3a.4e.5a.6d, 1a.2d.3a.4e.5a.6e,
1a.2d.3a.4e.5b.6a, 1a.2d.3a.4e.5b.6b, 1a.2d.3a.4e.5b.6c, 1a.2d.3a.4e.5b.6d,
1a.2d.3a.4e.5b.6e, 1a.2d.3a.4e.5c.6a, 1a.2d.3a.4e.5c.6b, 1a.2d.3a.4e.5c.6c,
1a.2d.3a.4e.5c.6d, 1a.2d.3a.4e.5c.6e, 1a.2d.3a.4e.5d.6a, 1a.2d.3a.4e.5d.6b,
1a.2d.3a.4e.5d.6c, 1a.2d.3a.4e.5d.6d, 1a.2d.3a.4e.5d.6e, 1a.2d.3a.4e.5e.6a,
1a.2d.3a.4e.5e.6b, 1a.2d.3a.4e.5e.6c, 1a.2d.3a.4e.5e.6d, 1a.2d.3a.4e.5e.6e,
1a.2d.3b.4a.5a.6a, 1a.2d.3b.4a.5a.6b, 1a.2d.3b.4a.5a.6c, 1a.2d.3b.4a.5a.6d,
1a.2d.3b.4a.5a.6e, 1a.2d.3b.4a.5b.6a, 1a.2d.3b.4a.5b.6b, 1a.2d.3b.4a.5b.6c,
1a.2d.3b.4a.5b.6d, 1a.2d.3b.4a.5b.6e, 1a.2d.3b.4a.5c.6a, 1a.2d.3b.4a.5c.6b,
1a.2d.3b.4a.5c.6c, 1a.2d.3b.4a.5c.6d, 1a.2d.3b.4a.5c.6e, 1a.2d.3b.4a.5d.6a,
1a.2d.3b.4a.5d.6b, 1a.2d.3b.4a.5d.6c, 1a.2d.3b.4a.5d.6d, 1a.2d.3b.4a.5d.6e,
1a.2d.3b.4a.5e.6a, 1a.2d.3b.4a.5e.6b, 1a.2d.3b.4a.5e.6c, 1a.2d.3b.4a.5e.6d,
1a.2d.3b.4a.5e.6e, 1a.2d.3b.4b.5a.6a, 1a.2d.3b.4b.5a.6b, 1a.2d.3b.4b.5a.6c,
1a.2d.3b.4b.5a.6d, 1a.2d.3b.4b.5a.6e, 1a.2d.3b.4b.5b.6a, 1a.2d.3b.4b.5b.6b,
1a.2d.3b.4b.5b.6c, 1a.2d.3b.4b.5b.6d, 1a.2d.3b.4b.5b.6e, 1a.2d.3b.4b.5c.6a,
1a.2d.3b.4b.5c.6b, 1a.2d.3b.4b.5c.6c, 1a.2d.3b.4b.5c.6d, 1a.2d.3b.4b.5c.6e,

TABLE 8-continued

List of Compounds of Formula (II)

1a.2d.3b.4b.5d.6a, 1a.2d.3b.4b.5d.6b, 1a.2d.3b.4b.5d.6c, 1a.2d.3b.4b.5d.6d,
1a.2d.3b.4b.5d.6e, 1a.2d.3b.4b.5e.6a, 1a.2d.3b.4b.5e.6b, 1a.2d.3b.4b.5e.6c,
1a.2d.3b.4b.5e.6d, 1a.2d.3b.4b.5e.6e, 1a.2d.3b.4c.5a.6a, 1a.2d.3b.4c.5a.6b,
1a.2d.3b.4c.5a.6c, 1a.2d.3b.4c.5a.6d, 1a.2d.3b.4c.5a.6e, 1a.2d.3b.4c.5b.6a,
1a.2d.3b.4c.5b.6b, 1a.2d.3b.4c.5b.6c, 1a.2d.3b.4c.5b.6d, 1a.2d.3b.4c.5b.6e,
1a.2d.3b.4c.5c.6a, 1a.2d.3b.4c.5c.6b, 1a.2d.3b.4c.5c.6c, 1a.2d.3b.4c.5c.6d,
1a.2d.3b.4c.5c.6e, 1a.2d.3b.4c.5d.6a, 1a.2d.3b.4c.5d.6b, 1a.2d.3b.4c.5d.6c,
1a.2d.3b.4c.5d.6d, 1a.2d.3b.4c.5d.6e, 1a.2d.3b.4c.5e.6a, 1a.2d.3b.4c.5e.6b,
1a.2d.3b.4c.5e.6c, 1a.2d.3b.4c.5e.6d, 1a.2d.3b.4c.5e.6e, 1a.2d.3b.4d.5a.6a,
1a.2d.3b.4d.5a.6b, 1a.2d.3b.4d.5a.6c, 1a.2d.3b.4d.5a.6d, 1a.2d.3b.4d.5a.6e,
1a.2d.3b.4d.5b.6a, 1a.2d.3b.4d.5b.6b, 1a.2d.3b.4d.5b.6c, 1a.2d.3b.4d.5b.6d,
1a.2d.3b.4d.5b.6e, 1a.2d.3b.4d.5c.6a, 1a.2d.3b.4d.5c.6b, 1a.2d.3b.4d.5c.6c,
1a.2d.3b.4d.5c.6d, 1a.2d.3b.4d.5c.6e, 1a.2d.3b.4d.5d.6a, 1a.2d.3b.4d.5d.6b,
1a.2d.3b.4d.5d.6c, 1a.2d.3b.4d.5d.6d, 1a.2d.3b.4d.5d.6e, 1a.2d.3b.4d.5e.6a,
1a.2d.3b.4d.5e.6b, 1a.2d.3b.4d.5e.6c, 1a.2d.3b.4d.5e.6d, 1a.2d.3b.4d.5e.6e,
1a.2d.3b.4e.5a.6a, 1a.2d.3b.4e.5a.6b, 1a.2d.3b.4e.5a.6c, 1a.2d.3b.4e.5a.6d,
1a.2d.3b.4e.5a.6e, 1a.2d.3b.4e.5b.6a, 1a.2d.3b.4e.5b.6b, 1a.2d.3b.4e.5b.6c,
1a.2d.3b.4e.5b.6d, 1a.2d.3b.4e.5b.6e, 1a.2d.3b.4e.5c.6a, 1a.2d.3b.4e.5c.6b,
1a.2d.3b.4e.5c.6c, 1a.2d.3b.4e.5c.6d, 1a.2d.3b.4e.5c.6e, 1a.2d.3b.4e.5d.6a,
1a.2d.3b.4e.5d.6b, 1a.2d.3b.4e.5d.6c, 1a.2d.3b.4e.5d.6d, 1a.2d.3b.4e.5d.6e,
1a.2d.3b.4e.5e.6a, 1a.2d.3b.4e.5e.6b, 1a.2d.3b.4e.5e.6c, 1a.2d.3b.4e.5e.6d,
1a.2d.3b.4e.5e.6e, 1a.2d.3c.4a.5a.6a, 1a.2d.3c.4a.5a.6b, 1a.2d.3c.4a.5a.6c,
1a.2d.3c.4a.5a.6d, 1a.2d.3c.4a.5a.6e, 1a.2d.3c.4a.5b.6a, 1a.2d.3c.4a.5b.6b,
1a.2d.3c.4a.5b.6c, 1a.2d.3c.4a.5b.6d, 1a.2d.3c.4a.5b.6e, 1a.2d.3c.4a.5c.6a,
1a.2d.3c.4a.5c.6b, 1a.2d.3c.4a.5c.6c, 1a.2d.3c.4a.5c.6d, 1a.2d.3c.4a.5c.6e,
1a.2d.3c.4a.5d.6a, 1a.2d.3c.4a.5d.6b, 1a.2d.3c.4a.5d.6c, 1a.2d.3c.4a.5d.6d,
1a.2d.3c.4a.5d.6e, 1a.2d.3c.4a.5e.6a, 1a.2d.3c.4a.5e.6b, 1a.2d.3c.4a.5e.6c,
1a.2d.3c.4a.5e.6d, 1a.2d.3c.4a.5e.6e, 1a.2d.3c.4b.5a.6a, 1a.2d.3c.4b.5a.6b,
1a.2d.3c.4b.5a.6c, 1a.2d.3c.4b.5a.6d, 1a.2d.3c.4b.5a.6e, 1a.2d.3c.4b.5b.6a,
1a.2d.3c.4b.5b.6b, 1a.2d.3c.4b.5b.6c, 1a.2d.3c.4b.5b.6d, 1a.2d.3c.4b.5b.6e,
1a.2d.3c.4b.5c.6a, 1a.2d.3c.4b.5c.6b, 1a.2d.3c.4b.5c.6c, 1a.2d.3c.4b.5c.6d,
1a.2d.3c.4b.5c.6e, 1a.2d.3c.4b.5d.6a, 1a.2d.3c.4b.5d.6b, 1a.2d.3c.4b.5d.6c,
1a.2d.3c.4b.5d.6d, 1a.2d.3c.4b.5d.6e, 1a.2d.3c.4b.5e.6a, 1a.2d.3c.4b.5e.6b,
1a.2d.3c.4b.5e.6c, 1a.2d.3c.4b.5e.6d, 1a.2d.3c.4b.5e.6e, 1a.2d.3c.4c.5a.6a,
1a.2d.3c.4c.5a.6b, 1a.2d.3c.4c.5a.6c, 1a.2d.3c.4c.5a.6d, 1a.2d.3c.4c.5a.6e,
1a.2d.3c.4c.5b.6a, 1a.2d.3c.4c.5b.6b, 1a.2d.3c.4c.5b.6c, 1a.2d.3c.4c.5b.6d,
1a.2d.3c.4c.5b.6e, 1a.2d.3c.4c.5c.6a, 1a.2d.3c.4c.5c.6b, 1a.2d.3c.4c.5c.6c,
1a.2d.3c.4c.5c.6d, 1a.2d.3c.4c.5c.6e, 1a.2d.3c.4c.5d.6a, 1a.2d.3c.4c.5d.6b,
1a.2d.3c.4c.5d.6c, 1a.2d.3c.4c.5d.6d, 1a.2d.3c.4c.5d.6e, 1a.2d.3c.4c.5e.6a,
1a.2d.3c.4c.5e.6b, 1a.2d.3c.4c.5e.6c, 1a.2d.3c.4c.5e.6d, 1a.2d.3c.4c.5e.6e,
1a.2d.3c.4d.5a.6a, 1a.2d.3c.4d.5a.6b, 1a.2d.3c.4d.5a.6c, 1a.2d.3c.4d.5a.6d,
1a.2d.3c.4d.5a.6e, 1a.2d.3c.4d.5b.6a, 1a.2d.3c.4d.5b.6b, 1a.2d.3c.4d.5b.6c,
1a.2d.3c.4d.5b.6d, 1a.2d.3c.4d.5b.6e, 1a.2d.3c.4d.5c.6a, 1a.2d.3c.4d.5c.6b,
1a.2d.3c.4d.5c.6c, 1a.2d.3c.4d.5c.6d, 1a.2d.3c.4d.5c.6e, 1a.2d.3c.4d.5d.6a,
1a.2d.3c.4d.5d.6b, 1a.2d.3c.4d.5d.6c, 1a.2d.3c.4d.5d.6d, 1a.2d.3c.4d.5d.6e,
1a.2d.3c.4d.5e.6a, 1a.2d.3c.4d.5e.6b, 1a.2d.3c.4d.5e.6c, 1a.2d.3c.4d.5e.6d,
1a.2d.3c.4d.5e.6e, 1a.2d.3c.4e.5a.6a, 1a.2d.3c.4e.5a.6b, 1a.2d.3c.4e.5a.6c,
1a.2d.3c.4e.5a.6d, 1a.2d.3c.4e.5a.6e, 1a.2d.3c.4e.5b.6a, 1a.2d.3c.4e.5b.6b,
1a.2d.3c.4e.5b.6c, 1a.2d.3c.4e.5b.6d, 1a.2d.3c.4e.5b.6e, 1a.2d.3c.4e.5c.6a,
1a.2d.3c.4e.5c.6b, 1a.2d.3c.4e.5c.6c, 1a.2d.3c.4e.5c.6d, 1a.2d.3c.4e.5c.6e,
1a.2d.3c.4e.5d.6a, 1a.2d.3c.4e.5d.6b, 1a.2d.3c.4e.5d.6c, 1a.2d.3c.4e.5d.6d,
1a.2d.3c.4e.5d.6e, 1a.2d.3c.4e.5e.6a, 1a.2d.3c.4e.5e.6b, 1a.2d.3c.4e.5e.6c,
1a.2d.3c.4e.5e.6d, 1a.2d.3c.4e.5e.6e, 1a.2d.3d.4a.5a.6a, 1a.2d.3d.4a.5a.6b,
1a.2d.3d.4a.5a.6c, 1a.2d.3d.4a.5a.6d, 1a.2d.3d.4a.5a.6e, 1a.2d.3d.4a.5b.6a,
1a.2d.3d.4a.5b.6b, 1a.2d.3d.4a.5b.6c, 1a.2d.3d.4a.5b.6d, 1a.2d.3d.4a.5b.6e,
1a.2d.3d.4a.5c.6a, 1a.2d.3d.4a.5c.6b, 1a.2d.3d.4a.5c.6c, 1a.2d.3d.4a.5c.6d,
1a.2d.3d.4a.5c.6e, 1a.2d.3d.4a.5d.6a, 1a.2d.3d.4a.5d.6b, 1a.2d.3d.4a.5d.6c,
1a.2d.3d.4a.5d.6d, 1a.2d.3d.4a.5d.6e, 1a.2d.3d.4a.5e.6a, 1a.2d.3d.4a.5e.6b,
1a.2d.3d.4a.5e.6c, 1a.2d.3d.4a.5e.6d, 1a.2d.3d.4a.5e.6e, 1a.2d.3d.4b.5a.6a,
1a.2d.3d.4b.5a.6b, 1a.2d.3d.4b.5a.6c, 1a.2d.3d.4b.5a.6d, 1a.2d.3d.4b.5a.6e,
1a.2d.3d.4b.5b.6a, 1a.2d.3d.4b.5b.6b, 1a.2d.3d.4b.5b.6c, 1a.2d.3d.4b.5b.6d,
1a.2d.3d.4b.5b.6e, 1a.2d.3d.4b.5c.6a, 1a.2d.3d.4b.5c.6b, 1a.2d.3d.4b.5c.6c,
1a.2d.3d.4b.5c.6d, 1a.2d.3d.4b.5c.6e, 1a.2d.3d.4b.5d.6a, 1a.2d.3d.4b.5d.6b,
1a.2d.3d.4b.5d.6c, 1a.2d.3d.4b.5d.6d, 1a.2d.3d.4b.5d.6e, 1a.2d.3d.4b.5e.6a,
1a.2d.3d.4b.5e.6b, 1a.2d.3d.4b.5e.6c, 1a.2d.3d.4b.5e.6d, 1a.2d.3d.4b.5e.6e,
1a.2d.3d.4c.5a.6a, 1a.2d.3d.4c.5a.6b, 1a.2d.3d.4c.5a.6c, 1a.2d.3d.4c.5a.6d,
1a.2d.3d.4c.5a.6e, 1a.2d.3d.4c.5b.6a, 1a.2d.3d.4c.5b.6b, 1a.2d.3d.4c.5b.6c,
1a.2d.3d.4c.5b.6d, 1a.2d.3d.4c.5b.6e, 1a.2d.3d.4c.5c.6a, 1a.2d.3d.4c.5c.6b,
1a.2d.3d.4c.5c.6c, 1a.2d.3d.4c.5c.6d, 1a.2d.3d.4c.5c.6e, 1a.2d.3d.4c.5d.6a,
1a.2d.3d.4c.5d.6b, 1a.2d.3d.4c.5d.6c, 1a.2d.3d.4c.5d.6d, 1a.2d.3d.4c.5d.6e,
1a.2d.3d.4c.5e.6a, 1a.2d.3d.4c.5e.6b, 1a.2d.3d.4c.5e.6c, 1a.2d.3d.4c.5e.6d,
1a.2d.3d.4c.5e.6e, 1a.2d.3d.4d.5a.6a, 1a.2d.3d.4d.5a.6b, 1a.2d.3d.4d.5a.6c,
1a.2d.3d.4d.5a.6d, 1a.2d.3d.4d.5a.6e, 1a.2d.3d.4d.5b.6a, 1a.2d.3d.4d.5b.6b,
1a.2d.3d.4d.5b.6c, 1a.2d.3d.4d.5b.6d, 1a.2d.3d.4d.5b.6e, 1a.2d.3d.4d.5c.6a,
1a.2d.3d.4d.5c.6b, 1a.2d.3d.4d.5c.6c, 1a.2d.3d.4d.5c.6d, 1a.2d.3d.4d.5c.6e,
1a.2d.3d.4d.5d.6a, 1a.2d.3d.4d.5d.6b, 1a.2d.3d.4d.5d.6c, 1a.2d.3d.4d.5d.6d,
1a.2d.3d.4d.5d.6e, 1a.2d.3d.4d.5e.6a, 1a.2d.3d.4d.5e.6b, 1a.2d.3d.4d.5e.6c,
1a.2d.3d.4d.5e.6d, 1a.2d.3d.4d.5e.6e, 1a.2d.3d.4e.5a.6a, 1a.2d.3d.4e.5a.6b,

TABLE 8-continued

List of Compounds of Formula (II)

1a.2d.3d.4e.5a.6c, 1a.2d.3d.4e.5a.6d, 1a.2d.3d.4e.5a.6e, 1a.2d.3d.4e.5b.6a,
1a.2d.3d.4e.5b.6b, 1a.2d.3d.4e.5b.6c, 1a.2d.3d.4e.5b.6d, 1a.2d.3d.4e.5b.6e,
1a.2d.3d.4e.5c.6a, 1a.2d.3d.4e.5c.6b, 1a.2d.3d.4e.5c.6c, 1a.2d.3d.4e.5c.6d,
1a.2d.3d.4e.5c.6e, 1a.2d.3d.4e.5d.6a, 1a.2d.3d.4e.5d.6b, 1a.2d.3d.4e.5d.6c,
1a.2d.3d.4e.5d.6d, 1a.2d.3d.4e.5d.6e, 1a.2d.3d.4e.5e.6a, 1a.2d.3d.4e.5e.6b,
1a.2d.3d.4e.5e.6c, 1a.2d.3d.4e.5e.6d, 1a.2d.3d.4e.5e.6e, 1a.2d.3e.4a.5a.6a,
1a.2d.3e.4a.5a.6b, 1a.2d.3e.4a.5a.6c, 1a.2d.3e.4a.5a.6d, 1a.2d.3e.4a.5a.6e,
1a.2d.3e.4a.5b.6a, 1a.2d.3e.4a.5b.6b, 1a.2d.3e.4a.5b.6c, 1a.2d.3e.4a.5b.6d,
1a.2d.3e.4a.5b.6e, 1a.2d.3e.4a.5c.6a, 1a.2d.3e.4a.5c.6b, 1a.2d.3e.4a.5c.6c,
1a.2d.3e.4a.5c.6d, 1a.2d.3e.4a.5c.6e, 1a.2d.3e.4a.5d.6a, 1a.2d.3e.4a.5d.6b,
1a.2d.3e.4a.5d.6c, 1a.2d.3e.4a.5d.6d, 1a.2d.3e.4a.5d.6e, 1a.2d.3e.4a.5e.6a,
1a.2d.3e.4a.5e.6b, 1a.2d.3e.4a.5e.6c, 1a.2d.3e.4a.5e.6d, 1a.2d.3e.4a.5e.6e,
1a.2d.3e.4b.5a.6a, 1a.2d.3e.4b.5a.6b, 1a.2d.3e.4b.5a.6c, 1a.2d.3e.4b.5a.6d,
1a.2d.3e.4b.5a.6e, 1a.2d.3e.4b.5b.6a, 1a.2d.3e.4b.5b.6b, 1a.2d.3e.4b.5b.6c,
1a.2d.3e.4b.5b.6d, 1a.2d.3e.4b.5b.6e, 1a.2d.3e.4b.5c.6a, 1a.2d.3e.4b.5c.6b,
1a.2d.3e.4b.5c.6c, 1a.2d.3e.4b.5c.6d, 1a.2d.3e.4b.5c.6e, 1a.2d.3e.4b.5d.6a,
1a.2d.3e.4b.5d.6b, 1a.2d.3e.4b.5d.6c, 1a.2d.3e.4b.5d.6d, 1a.2d.3e.4b.5d.6e,
1a.2d.3e.4b.5e.6a, 1a.2d.3e.4b.5e.6b, 1a.2d.3e.4b.5e.6c, 1a.2d.3e.4b.5e.6d,
1a.2d.3e.4b.5e.6e, 1a.2d.3e.4c.5a.6a, 1a.2d.3e.4c.5a.6b, 1a.2d.3e.4c.5a.6c,
1a.2d.3e.4c.5a.6d, 1a.2d.3e.4c.5a.6e, 1a.2d.3e.4c.5b.6a, 1a.2d.3e.4c.5b.6b,
1a.2d.3e.4c.5b.6c, 1a.2d.3e.4c.5b.6d, 1a.2d.3e.4c.5b.6e, 1a.2d.3e.4c.5c.6a,
1a.2d.3e.4c.5c.6b, 1a.2d.3e.4c.5c.6c, 1a.2d.3e.4c.5c.6d, 1a.2d.3e.4c.5c.6e,
1a.2d.3e.4c.5d.6a, 1a.2d.3e.4c.5d.6b, 1a.2d.3e.4c.5d.6c, 1a.2d.3e.4c.5d.6d,
1a.2d.3e.4c.5d.6e, 1a.2d.3e.4c.5e.6a, 1a.2d.3e.4c.5e.6b, 1a.2d.3e.4c.5e.6c,
1a.2d.3e.4c.5e.6d, 1a.2d.3e.4c.5e.6e, 1a.2d.3e.4d.5a.6a, 1a.2d.3e.4d.5a.6b,
1a.2d.3e.4d.5a.6c, 1a.2d.3e.4d.5a.6d, 1a.2d.3e.4d.5a.6e, 1a.2d.3e.4d.5b.6a,
1a.2d.3e.4d.5b.6b, 1a.2d.3e.4d.5b.6c, 1a.2d.3e.4d.5b.6d, 1a.2d.3e.4d.5b.6e,
1a.2d.3e.4d.5c.6a, 1a.2d.3e.4d.5c.6b, 1a.2d.3e.4d.5c.6c, 1a.2d.3e.4d.5c.6d,
1a.2d.3e.4d.5c.6e, 1a.2d.3e.4d.5d.6a, 1a.2d.3e.4d.5d.6b, 1a.2d.3e.4d.5d.6c,
1a.2d.3e.4d.5d.6d, 1a.2d.3e.4d.5d.6e, 1a.2d.3e.4d.5e.6a, 1a.2d.3e.4d.5e.6b,
1a.2d.3e.4d.5e.6c, 1a.2d.3e.4d.5e.6d, 1a.2d.3e.4d.5e.6e, 1a.2d.3e.4e.5a.6a,
1a.2d.3e.4e.5a.6b, 1a.2d.3e.4e.5a.6c, 1a.2d.3e.4e.5a.6d, 1a.2d.3e.4e.5a.6e,
1a.2d.3e.4e.5b.6a, 1a.2d.3e.4e.5b.6b, 1a.2d.3e.4e.5b.6c, 1a.2d.3e.4e.5b.6d,
1a.2d.3e.4e.5b.6e, 1a.2d.3e.4e.5c.6a, 1a.2d.3e.4e.5c.6b, 1a.2d.3e.4e.5c.6c,
1a.2d.3e.4e.5c.6d, 1a.2d.3e.4e.5c.6e, 1a.2d.3e.4e.5d.6a, 1a.2d.3e.4e.5d.6b,
1a.2d.3e.4e.5d.6c, 1a.2d.3e.4e.5d.6d, 1a.2d.3e.4e.5d.6e, 1a.2d.3e.4e.5e.6a,
1a.2d.3e.4e.5e.6b, 1a.2d.3e.4e.5e.6c, 1a.2d.3e.4e.5e.6d, 1a.2d.3e.4e.5e.6e,
1a.2e.3a.4a.5a.6a, 1a.2e.3a.4a.5a.6b, 1a.2e.3a.4a.5a.6c, 1a.2e.3a.4a.5a.6d,
1a.2e.3a.4a.5a.6e, 1a.2e.3a.4a.5b.6a, 1a.2e.3a.4a.5b.6b, 1a.2e.3a.4a.5b.6c,
1a.2e.3a.4a.5b.6d, 1a.2e.3a.4a.5b.6e, 1a.2e.3a.4a.5c.6a, 1a.2e.3a.4a.5c.6b,
1a.2e.3a.4a.5c.6c, 1a.2e.3a.4a.5c.6d, 1a.2e.3a.4a.5c.6e, 1a.2e.3a.4a.5d.6a,
1a.2e.3a.4a.5d.6b, 1a.2e.3a.4a.5d.6c, 1a.2e.3a.4a.5d.6d, 1a.2e.3a.4a.5d.6e,
1a.2e.3a.4a.5e.6a, 1a.2e.3a.4a.5e.6b, 1a.2e.3a.4a.5e.6c, 1a.2e.3a.4a.5e.6d,
1a.2e.3a.4a.5e.6e, 1a.2e.3a.4b.5a.6a, 1a.2e.3a.4b.5a.6b, 1a.2e.3a.4b.5a.6c,
1a.2e.3a.4b.5a.6d, 1a.2e.3a.4b.5a.6e, 1a.2e.3a.4b.5b.6a, 1a.2e.3a.4b.5b.6b,
1a.2e.3a.4b.5b.6c, 1a.2e.3a.4b.5b.6d, 1a.2e.3a.4b.5b.6e, 1a.2e.3a.4b.5c.6a,
1a.2e.3a.4b.5c.6b, 1a.2e.3a.4b.5c.6c, 1a.2e.3a.4b.5c.6d, 1a.2e.3a.4b.5c.6e,
1a.2e.3a.4b.5d.6a, 1a.2e.3a.4b.5d.6b, 1a.2e.3a.4b.5d.6c, 1a.2e.3a.4b.5d.6d,
1a.2e.3a.4b.5d.6e, 1a.2e.3a.4b.5e.6a, 1a.2e.3a.4b.5e.6b, 1a.2e.3a.4b.5e.6c,
1a.2e.3a.4b.5e.6d, 1a.2e.3a.4b.5e.6e, 1a.2e.3a.4c.5a.6a, 1a.2e.3a.4c.5a.6b,
1a.2e.3a.4c.5a.6c, 1a.2e.3a.4c.5a.6d, 1a.2e.3a.4c.5a.6e, 1a.2e.3a.4c.5b.6a,
1a.2e.3a.4c.5b.6b, 1a.2e.3a.4c.5b.6c, 1a.2e.3a.4c.5b.6d, 1a.2e.3a.4c.5b.6e,
1a.2e.3a.4c.5c.6a, 1a.2e.3a.4c.5c.6b, 1a.2e.3a.4c.5c.6c, 1a.2e.3a.4c.5c.6d,
1a.2e.3a.4c.5c.6e, 1a.2e.3a.4c.5d.6a, 1a.2e.3a.4c.5d.6b, 1a.2e.3a.4c.5d.6c,
1a.2e.3a.4c.5d.6d, 1a.2e.3a.4c.5d.6e, 1a.2e.3a.4c.5e.6a, 1a.2e.3a.4c.5e.6b,
1a.2e.3a.4c.5e.6c, 1a.2e.3a.4c.5e.6d, 1a.2e.3a.4c.5e.6e, 1a.2e.3a.4d.5a.6a,
1a.2e.3a.4d.5a.6b, 1a.2e.3a.4d.5a.6c, 1a.2e.3a.4d.5a.6d, 1a.2e.3a.4d.5a.6e,
1a.2e.3a.4d.5b.6a, 1a.2e.3a.4d.5b.6b, 1a.2e.3a.4d.5b.6c, 1a.2e.3a.4d.5b.6d,
1a.2e.3a.4d.5b.6e, 1a.2e.3a.4d.5c.6a, 1a.2e.3a.4d.5c.6b, 1a.2e.3a.4d.5c.6c,
1a.2e.3a.4d.5c.6d, 1a.2e.3a.4d.5c.6e, 1a.2e.3a.4d.5d.6a, 1a.2e.3a.4d.5d.6b,
1a.2e.3a.4d.5d.6c, 1a.2e.3a.4d.5d.6d, 1a.2e.3a.4d.5d.6e, 1a.2e.3a.4d.5e.6a,
1a.2e.3a.4d.5e.6b, 1a.2e.3a.4d.5e.6c, 1a.2e.3a.4d.5e.6d, 1a.2e.3a.4d.5e.6e,
1a.2e.3a.4e.5a.6a, 1a.2e.3a.4e.5a.6b, 1a.2e.3a.4e.5a.6c, 1a.2e.3a.4e.5a.6d,
1a.2e.3a.4e.5a.6e, 1a.2e.3a.4e.5b.6a, 1a.2e.3a.4e.5b.6b, 1a.2e.3a.4e.5b.6c,
1a.2e.3a.4e.5b.6d, 1a.2e.3a.4e.5b.6e, 1a.2e.3a.4e.5c.6a, 1a.2e.3a.4e.5c.6b,
1a.2e.3a.4e.5c.6c, 1a.2e.3a.4e.5c.6d, 1a.2e.3a.4e.5c.6e, 1a.2e.3a.4e.5d.6a,
1a.2e.3a.4e.5d.6b, 1a.2e.3a.4e.5d.6c, 1a.2e.3a.4e.5d.6d, 1a.2e.3a.4e.5d.6e,
1a.2e.3a.4e.5e.6a, 1a.2e.3a.4e.5e.6b, 1a.2e.3a.4e.5e.6c, 1a.2e.3a.4e.5e.6d,
1a.2e.3a.4e.5e.6e, 1a.2e.3b.4a.5a.6a, 1a.2e.3b.4a.5a.6b, 1a.2e.3b.4a.5a.6c,
1a.2e.3b.4a.5a.6d, 1a.2e.3b.4a.5a.6e, 1a.2e.3b.4a.5b.6a, 1a.2e.3b.4a.5b.6b,
1a.2e.3b.4a.5b.6c, 1a.2e.3b.4a.5b.6d, 1a.2e.3b.4a.5b.6e, 1a.2e.3b.4a.5c.6a,
1a.2e.3b.4a.5c.6b, 1a.2e.3b.4a.5c.6c, 1a.2e.3b.4a.5c.6d, 1a.2e.3b.4a.5c.6e,
1a.2e.3b.4a.5d.6a, 1a.2e.3b.4a.5d.6b, 1a.2e.3b.4a.5d.6c, 1a.2e.3b.4a.5d.6d,
1a.2e.3b.4a.5d.6e, 1a.2e.3b.4a.5e.6a, 1a.2e.3b.4a.5e.6b, 1a.2e.3b.4a.5e.6c,
1a.2e.3b.4a.5e.6d, 1a.2e.3b.4a.5e.6e, 1a.2e.3b.4b.5a.6a, 1a.2e.3b.4b.5a.6b,
1a.2e.3b.4b.5a.6c, 1a.2e.3b.4b.5a.6d, 1a.2e.3b.4b.5a.6e, 1a.2e.3b.4b.5b.6a,
1a.2e.3b.4b.5b.6b, 1a.2e.3b.4b.5b.6c, 1a.2e.3b.4b.5b.6d, 1a.2e.3b.4b.5b.6e,
1a.2e.3b.4b.5c.6a, 1a.2e.3b.4b.5c.6b, 1a.2e.3b.4b.5c.6c, 1a.2e.3b.4b.5c.6d,

TABLE 8-continued

List of Compounds of Formula (II)

1a.2e.3b.4b.5c.6e, 1a.2e.3b.4b.5d.6a, 1a.2e.3b.4b.5d.6b, 1a.2e.3b.4b.5d.6c,
1a.2e.3b.4b.5d.6d, 1a.2e.3b.4b.5d.6e, 1a.2e.3b.4b.5e.6a, 1a.2e.3b.4b.5e.6b,
1a.2e.3b.4b.5e.6c, 1a.2e.3b.4b.5e.6d, 1a.2e.3b.4b.5e.6e, 1a.2e.3b.4c.5a.6a,
1a.2e.3b.4c.5a.6b, 1a.2e.3b.4c.5a.6c, 1a.2e.3b.4c.5a.6d, 1a.2e.3b.4c.5a.6e,
1a.2e.3b.4c.5b.6a, 1a.2e.3b.4c.5b.6b, 1a.2e.3b.4c.5b.6c, 1a.2e.3b.4c.5b.6d,
1a.2e.3b.4c.5b.6e, 1a.2e.3b.4c.5c.6a, 1a.2e.3b.4c.5c.6b, 1a.2e.3b.4c.5c.6c,
1a.2e.3b.4c.5c.6d, 1a.2e.3b.4c.5c.6e, 1a.2e.3b.4c.5d.6a, 1a.2e.3b.4c.5d.6b,
1a.2e.3b.4c.5d.6c, 1a.2e.3b.4c.5d.6d, 1a.2e.3b.4c.5d.6e, 1a.2e.3b.4c.5e.6a,
1a.2e.3b.4c.5e.6b, 1a.2e.3b.4c.5e.6c, 1a.2e.3b.4c.5e.6d, 1a.2e.3b.4c.5e.6e,
1a.2e.3b.4d.5a.6a, 1a.2e.3b.4d.5a.6b, 1a.2e.3b.4d.5a.6c, 1a.2e.3b.4d.5a.6d,
1a.2e.3b.4d.5a.6e, 1a.2e.3b.4d.5b.6a, 1a.2e.3b.4d.5b.6b, 1a.2e.3b.4d.5b.6c,
1a.2e.3b.4d.5b.6d, 1a.2e.3b.4d.5b.6e, 1a.2e.3b.4d.5c.6a, 1a.2e.3b.4d.5c.6b,
1a.2e.3b.4d.5c.6c, 1a.2e.3b.4d.5c.6d, 1a.2e.3b.4d.5c.6e, 1a.2e.3b.4d.5d.6a,
1a.2e.3b.4d.5d.6b, 1a.2e.3b.4d.5d.6c, 1a.2e.3b.4d.5d.6d, 1a.2e.3b.4d.5d.6e,
1a.2e.3b.4d.5e.6a, 1a.2e.3b.4d.5e.6b, 1a.2e.3b.4d.5e.6c, 1a.2e.3b.4d.5e.6d,
1a.2e.3b.4d.5e.6e, 1a.2e.3b.4e.5a.6a, 1a.2e.3b.4e.5a.6b, 1a.2e.3b.4e.5a.6c,
1a.2e.3b.4e.5a.6d, 1a.2e.3b.4e.5a.6e, 1a.2e.3b.4e.5b.6a, 1a.2e.3b.4e.5b.6b,
1a.2e.3b.4e.5b.6c, 1a.2e.3b.4e.5b.6d, 1a.2e.3b.4e.5b.6e, 1a.2e.3b.4e.5c.6a,
1a.2e.3b.4e.5c.6b, 1a.2e.3b.4e.5c.6c, 1a.2e.3b.4e.5c.6d, 1a.2e.3b.4e.5c.6e,
1a.2e.3b.4e.5d.6a, 1a.2e.3b.4e.5d.6b, 1a.2e.3b.4e.5d.6c, 1a.2e.3b.4e.5d.6d,
1a.2e.3b.4e.5d.6e, 1a.2e.3b.4e.5e.6a, 1a.2e.3b.4e.5e.6b, 1a.2e.3b.4e.5e.6c,
1a.2e.3b.4e.5e.6d, 1a.2e.3b.4e.5e.6e, 1a.2e.3c.4a.5a.6a, 1a.2e.3c.4a.5a.6b,
1a.2e.3c.4a.5a.6c, 1a.2e.3c.4a.5a.6d, 1a.2e.3c.4a.5a.6e, 1a.2e.3c.4a.5b.6a,
1a.2e.3c.4a.5b.6b, 1a.2e.3c.4a.5b.6c, 1a.2e.3c.4a.5b.6d, 1a.2e.3c.4a.5b.6e,
1a.2e.3c.4a.5c.6a, 1a.2e.3c.4a.5c.6b, 1a.2e.3c.4a.5c.6c, 1a.2e.3c.4a.5c.6d,
1a.2e.3c.4a.5c.6e, 1a.2e.3c.4a.5d.6a, 1a.2e.3c.4a.5d.6b, 1a.2e.3c.4a.5d.6c,
1a.2e.3c.4a.5d.6d, 1a.2e.3c.4a.5d.6e, 1a.2e.3c.4a.5e.6a, 1a.2e.3c.4a.5e.6b,
1a.2e.3c.4a.5e.6c, 1a.2e.3c.4a.5e.6d, 1a.2e.3c.4a.5e.6e, 1a.2e.3c.4b.5a.6a,
1a.2e.3c.4b.5a.6b, 1a.2e.3c.4b.5a.6c, 1a.2e.3c.4b.5a.6d, 1a.2e.3c.4b.5a.6e,
1a.2e.3c.4b.5b.6a, 1a.2e.3c.4b.5b.6b, 1a.2e.3c.4b.5b.6c, 1a.2e.3c.4b.5b.6d,
1a.2e.3c.4b.5b.6e, 1a.2e.3c.4b.5c.6a, 1a.2e.3c.4b.5c.6b, 1a.2e.3c.4b.5c.6c,
1a.2e.3c.4b.5c.6d, 1a.2e.3c.4b.5c.6e, 1a.2e.3c.4b.5d.6a, 1a.2e.3c.4b.5d.6b,
1a.2e.3c.4b.5d.6c, 1a.2e.3c.4b.5d.6d, 1a.2e.3c.4b.5d.6e, 1a.2e.3c.4b.5e.6a,
1a.2e.3c.4b.5e.6b, 1a.2e.3c.4b.5e.6c, 1a.2e.3c.4b.5e.6d, 1a.2e.3c.4b.5e.6e,
1a.2e.3c.4c.5a.6a, 1a.2e.3c.4c.5a.6b, 1a.2e.3c.4c.5a.6c, 1a.2e.3c.4c.5a.6d,
1a.2e.3c.4c.5a.6e, 1a.2e.3c.4c.5b.6a, 1a.2e.3c.4c.5b.6b, 1a.2e.3c.4c.5b.6c,
1a.2e.3c.4c.5b.6d, 1a.2e.3c.4c.5b.6e, 1a.2e.3c.4c.5c.6a, 1a.2e.3c.4c.5c.6b,
1a.2e.3c.4c.5c.6c, 1a.2e.3c.4c.5c.6d, 1a.2e.3c.4c.5c.6e, 1a.2e.3c.4c.5d.6a,
1a.2e.3c.4c.5d.6b, 1a.2e.3c.4c.5d.6c, 1a.2e.3c.4c.5d.6d, 1a.2e.3c.4c.5d.6e,
1a.2e.3c.4c.5e.6a, 1a.2e.3c.4c.5e.6b, 1a.2e.3c.4c.5e.6c, 1a.2e.3c.4c.5e.6d,
1a.2e.3c.4c.5e.6e, 1a.2e.3c.4d.5a.6a, 1a.2e.3c.4d.5a.6b, 1a.2e.3c.4d.5a.6c,
1a.2e.3c.4d.5a.6d, 1a.2e.3c.4d.5a.6e, 1a.2e.3c.4d.5b.6a, 1a.2e.3c.4d.5b.6b,
1a.2e.3c.4d.5b.6c, 1a.2e.3c.4d.5b.6d, 1a.2e.3c.4d.5b.6e, 1a.2e.3c.4d.5c.6a,
1a.2e.3c.4d.5c.6b, 1a.2e.3c.4d.5c.6c, 1a.2e.3c.4d.5c.6d, 1a.2e.3c.4d.5c.6e,
1a.2e.3c.4d.5d.6a, 1a.2e.3c.4d.5d.6b, 1a.2e.3c.4d.5d.6c, 1a.2e.3c.4d.5d.6d,
1a.2e.3c.4d.5d.6e, 1a.2e.3c.4d.5e.6a, 1a.2e.3c.4d.5e.6b, 1a.2e.3c.4d.5e.6c,
1a.2e.3c.4d.5e.6d, 1a.2e.3c.4d.5e.6e, 1a.2e.3c.4e.5a.6a, 1a.2e.3c.4e.5a.6b,
1a.2e.3c.4e.5a.6c, 1a.2e.3c.4e.5a.6d, 1a.2e.3c.4e.5a.6e, 1a.2e.3c.4e.5b.6a,
1a.2e.3c.4e.5b.6b, 1a.2e.3c.4e.5b.6c, 1a.2e.3c.4e.5b.6d, 1a.2e.3c.4e.5b.6e,
1a.2e.3c.4e.5c.6a, 1a.2e.3c.4e.5c.6b, 1a.2e.3c.4e.5c.6c, 1a.2e.3c.4e.5c.6d,
1a.2e.3c.4e.5c.6e, 1a.2e.3c.4e.5d.6a, 1a.2e.3c.4e.5d.6b, 1a.2e.3c.4e.5d.6c,
1a.2e.3c.4e.5d.6d, 1a.2e.3c.4e.5d.6e, 1a.2e.3c.4e.5e.6a, 1a.2e.3c.4e.5e.6b,
1a.2e.3c.4e.5e.6c, 1a.2e.3c.4e.5e.6d, 1a.2e.3c.4e.5e.6e, 1a.2e.3d.4a.5a.6a,
1a.2e.3d.4a.5a.6b, 1a.2e.3d.4a.5a.6c, 1a.2e.3d.4a.5a.6d, 1a.2e.3d.4a.5a.6e,
1a.2e.3d.4a.5b.6a, 1a.2e.3d.4a.5b.6b, 1a.2e.3d.4a.5b.6c, 1a.2e.3d.4a.5b.6d,
1a.2e.3d.4a.5b.6e, 1a.2e.3d.4a.5c.6a, 1a.2e.3d.4a.5c.6b, 1a.2e.3d.4a.5c.6c,
1a.2e.3d.4a.5c.6d, 1a.2e.3d.4a.5c.6e, 1a.2e.3d.4a.5d.6a, 1a.2e.3d.4a.5d.6b,
1a.2e.3d.4a.5d.6c, 1a.2e.3d.4a.5d.6d, 1a.2e.3d.4a.5d.6e, 1a.2e.3d.4a.5e.6a,
1a.2e.3d.4a.5e.6b, 1a.2e.3d.4a.5e.6c, 1a.2e.3d.4a.5e.6d, 1a.2e.3d.4a.5e.6e,
1a.2e.3d.4b.5a.6a, 1a.2e.3d.4b.5a.6b, 1a.2e.3d.4b.5a.6c, 1a.2e.3d.4b.5a.6d,
1a.2e.3d.4b.5a.6e, 1a.2e.3d.4b.5b.6a, 1a.2e.3d.4b.5b.6b, 1a.2e.3d.4b.5b.6c,
1a.2e.3d.4b.5b.6d, 1a.2e.3d.4b.5b.6e, 1a.2e.3d.4b.5c.6a, 1a.2e.3d.4b.5c.6b,
1a.2e.3d.4b.5c.6c, 1a.2e.3d.4b.5c.6d, 1a.2e.3d.4b.5c.6e, 1a.2e.3d.4b.5d.6a,
1a.2e.3d.4b.5d.6b, 1a.2e.3d.4b.5d.6c, 1a.2e.3d.4b.5d.6d, 1a.2e.3d.4b.5d.6e,
1a.2e.3d.4b.5e.6a, 1a.2e.3d.4b.5e.6b, 1a.2e.3d.4b.5e.6c, 1a.2e.3d.4b.5e.6d,
1a.2e.3d.4b.5e.6e, 1a.2e.3d.4c.5a.6a, 1a.2e.3d.4c.5a.6b, 1a.2e.3d.4c.5a.6c,
1a.2e.3d.4c.5a.6d, 1a.2e.3d.4c.5a.6e, 1a.2e.3d.4c.5b.6a, 1a.2e.3d.4c.5b.6b,
1a.2e.3d.4c.5b.6c, 1a.2e.3d.4c.5b.6d, 1a.2e.3d.4c.5b.6e, 1a.2e.3d.4c.5c.6a,
1a.2e.3d.4c.5c.6b, 1a.2e.3d.4c.5c.6c, 1a.2e.3d.4c.5c.6d, 1a.2e.3d.4c.5c.6e,
1a.2e.3d.4c.5d.6a, 1a.2e.3d.4c.5d.6b, 1a.2e.3d.4c.5d.6c, 1a.2e.3d.4c.5d.6d,
1a.2e.3d.4c.5d.6e, 1a.2e.3d.4c.5e.6a, 1a.2e.3d.4c.5e.6b, 1a.2e.3d.4c.5e.6c,
1a.2e.3d.4c.5e.6d, 1a.2e.3d.4c.5e.6e, 1a.2e.3d.4d.5a.6a, 1a.2e.3d.4d.5a.6b,
1a.2e.3d.4d.5a.6c, 1a.2e.3d.4d.5a.6d, 1a.2e.3d.4d.5a.6e, 1a.2e.3d.4d.5b.6a,
1a.2e.3d.4d.5b.6b, 1a.2e.3d.4d.5b.6c, 1a.2e.3d.4d.5b.6d, 1a.2e.3d.4d.5b.6e,
1a.2e.3d.4d.5c.6a, 1a.2e.3d.4d.5c.6b, 1a.2e.3d.4d.5c.6c, 1a.2e.3d.4d.5c.6d,
1a.2e.3d.4d.5c.6e, 1a.2e.3d.4d.5d.6a, 1a.2e.3d.4d.5d.6b, 1a.2e.3d.4d.5d.6c,
1a.2e.3d.4d.5d.6d, 1a.2e.3d.4d.5d.6e, 1a.2e.3d.4d.5e.6a, 1a.2e.3d.4d.5e.6b,
1a.2e.3d.4d.5e.6c, 1a.2e.3d.4d.5e.6d, 1a.2e.3d.4d.5e.6e, 1a.2e.3d.4e.5a.6a,

TABLE 8-continued

List of Compounds of Formula (II)

1a.2e.3d.4e.5a.6b, 1a.2e.3d.4e.5a.6c, 1a.2e.3d.4e.5a.6d, 1a.2e.3d.4e.5a.6e,
1a.2e.3d.4e.5b.6a, 1a.2e.3d.4e.5b.6b, 1a.2e.3d.4e.5b.6c, 1a.2e.3d.4e.5b.6d,
1a.2e.3d.4e.5b.6e, 1a.2e.3d.4e.5c.6a, 1a.2e.3d.4e.5c.6b, 1a.2e.3d.4e.5c.6c,
1a.2e.3d.4e.5c.6d, 1a.2e.3d.4e.5c.6e, 1a.2e.3d.4e.5d.6a, 1a.2e.3d.4e.5d.6b,
1a.2e.3d.4e.5d.6c, 1a.2e.3d.4e.5d.6d, 1a.2e.3d.4e.5d.6e, 1a.2e.3d.4e.5e.6a,
1a.2e.3d.4e.5e.6b, 1a.2e.3d.4e.5e.6c, 1a.2e.3d.4e.5e.6d, 1a.2e.3d.4e.5e.6e,
1a.2e.3e.4a.5a.6a, 1a.2e.3e.4a.5a.6b, 1a.2e.3e.4a.5a.6c, 1a.2e.3e.4a.5a.6d,
1a.2e.3e.4a.5a.6e, 1a.2e.3e.4a.5b.6a, 1a.2e.3e.4a.5b.6b, 1a.2e.3e.4a.5b.6c,
1a.2e.3e.4a.5b.6d, 1a.2e.3e.4a.5b.6e, 1a.2e.3e.4a.5c.6a, 1a.2e.3e.4a.5c.6b,
1a.2e.3e.4a.5c.6c, 1a.2e.3e.4a.5c.6d, 1a.2e.3e.4a.5c.6e, 1a.2e.3e.4a.5d.6a,
1a.2e.3e.4a.5d.6b, 1a.2e.3e.4a.5d.6c, 1a.2e.3e.4a.5d.6d, 1a.2e.3e.4a.5d.6e,
1a.2e.3e.4a.5e.6a, 1a.2e.3e.4a.5e.6b, 1a.2e.3e.4a.5e.6c, 1a.2e.3e.4a.5e.6d,
1a.2e.3e.4a.5e.6e, 1a.2e.3e.4b.5a.6a, 1a.2e.3e.4b.5a.6b, 1a.2e.3e.4b.5a.6c,
1a.2e.3e.4b.5a.6d, 1a.2e.3e.4b.5a.6e, 1a.2e.3e.4b.5b.6a, 1a.2e.3e.4b.5b.6b,
1a.2e.3e.4b.5b.6c, 1a.2e.3e.4b.5b.6d, 1a.2e.3e.4b.5b.6e, 1a.2e.3e.4b.5c.6a,
1a.2e.3e.4b.5c.6b, 1a.2e.3e.4b.5c.6c, 1a.2e.3e.4b.5c.6d, 1a.2e.3e.4b.5c.6e,
1a.2e.3e.4b.5d.6a, 1a.2e.3e.4b.5d.6b, 1a.2e.3e.4b.5d.6c, 1a.2e.3e.4b.5d.6d,
1a.2e.3e.4b.5d.6e, 1a.2e.3e.4b.5e.6a, 1a.2e.3e.4b.5e.6b, 1a.2e.3e.4b.5e.6c,
1a.2e.3e.4b.5e.6d, 1a.2e.3e.4b.5e.6e, 1a.2e.3e.4c.5a.6a, 1a.2e.3e.4c.5a.6b,
1a.2e.3e.4c.5a.6c, 1a.2e.3e.4c.5a.6d, 1a.2e.3e.4c.5a.6e, 1a.2e.3e.4c.5b.6a,
1a.2e.3e.4c.5b.6b, 1a.2e.3e.4c.5b.6c, 1a.2e.3e.4c.5b.6d, 1a.2e.3e.4c.5b.6e,
1a.2e.3e.4c.5c.6a, 1a.2e.3e.4c.5c.6b, 1a.2e.3e.4c.5c.6c, 1a.2e.3e.4c.5c.6d,
1a.2e.3e.4c.5c.6e, 1a.2e.3e.4c.5d.6a, 1a.2e.3e.4c.5d.6b, 1a.2e.3e.4c.5d.6c,
1a.2e.3e.4c.5d.6d, 1a.2e.3e.4c.5d.6e, 1a.2e.3e.4c.5e.6a, 1a.2e.3e.4c.5e.6b,
1a.2e.3e.4c.5e.6c, 1a.2e.3e.4c.5e.6d, 1a.2e.3e.4c.5e.6e, 1a.2e.3e.4d.5a.6a,
1a.2e.3e.4d.5a.6b, 1a.2e.3e.4d.5a.6c, 1a.2e.3e.4d.5a.6d, 1a.2e.3e.4d.5a.6e,
1a.2e.3e.4d.5b.6a, 1a.2e.3e.4d.5b.6b, 1a.2e.3e.4d.5b.6c, 1a.2e.3e.4d.5b.6d,
1a.2e.3e.4d.5b.6e, 1a.2e.3e.4d.5c.6a, 1a.2e.3e.4d.5c.6b, 1a.2e.3e.4d.5c.6c,
1a.2e.3e.4d.5c.6d, 1a.2e.3e.4d.5c.6e, 1a.2e.3e.4d.5d.6a, 1a.2e.3e.4d.5d.6b,
1a.2e.3e.4d.5d.6c, 1a.2e.3e.4d.5d.6d, 1a.2e.3e.4d.5d.6e, 1a.2e.3e.4d.5e.6a,
1a.2e.3e.4d.5e.6b, 1a.2e.3e.4d.5e.6c, 1a.2e.3e.4d.5e.6d, 1a.2e.3e.4d.5e.6e,
1a.2e.3e.4e.5a.6a, 1a.2e.3e.4e.5a.6b, 1a.2e.3e.4e.5a.6c, 1a.2e.3e.4e.5a.6d,
1a.2e.3e.4e.5a.6e, 1a.2e.3e.4e.5b.6a, 1a.2e.3e.4e.5b.6b, 1a.2e.3e.4e.5b.6c,
1a.2e.3e.4e.5b.6d, 1a.2e.3e.4e.5b.6e, 1a.2e.3e.4e.5c.6a, 1a.2e.3e.4e.5c.6b,
1a.2e.3e.4e.5c.6c, 1a.2e.3e.4e.5c.6d, 1a.2e.3e.4e.5c.6e, 1a.2e.3e.4e.5d.6a,
1a.2e.3e.4e.5d.6b, 1a.2e.3e.4e.5d.6c, 1a.2e.3e.4e.5d.6d, 1a.2e.3e.4e.5d.6e,
1a.2e.3e.4e.5e.6a, 1a.2e.3e.4e.5e.6b, 1a.2e.3e.4e.5e.6c, 1a.2e.3e.4e.5e.6d,
1a.2e.3e.4e.5e.6e, 1b.2a.3a.4a.5a.6a, 1b.2a.3a.4a.5a.6b, 1b.2a.3a.4a.5a.6c,
1b.2a.3a.4a.5a.6d, 1b.2a.3a.4a.5a.6e, 1b.2a.3a.4a.5b.6a, 1b.2a.3a.4a.5b.6b,
1b.2a.3a.4a.5b.6c, 1b.2a.3a.4a.5b.6d, 1b.2a.3a.4a.5b.6e, 1b.2a.3a.4a.5c.6a,
1b.2a.3a.4a.5c.6b, 1b.2a.3a.4a.5c.6c, 1b.2a.3a.4a.5c.6d, 1b.2a.3a.4a.5c.6e,
1b.2a.3a.4a.5d.6a, 1b.2a.3a.4a.5d.6b, 1b.2a.3a.4a.5d.6c, 1b.2a.3a.4a.5d.6d,
1b.2a.3a.4a.5d.6e, 1b.2a.3a.4a.5e.6a, 1b.2a.3a.4a.5e.6b, 1b.2a.3a.4a.5e.6c,
1b.2a.3a.4a.5e.6d, 1b.2a.3a.4a.5e.6e, 1b.2a.3a.4b.5a.6a, 1b.2a.3a.4b.5a.6b,
1b.2a.3a.4b.5a.6c, 1b.2a.3a.4b.5a.6d, 1b.2a.3a.4b.5a.6e, 1b.2a.3a.4b.5b.6a,
1b.2a.3a.4b.5b.6b, 1b.2a.3a.4b.5b.6c, 1b.2a.3a.4b.5b.6d, 1b.2a.3a.4b.5b.6e,
1b.2a.3a.4b.5c.6a, 1b.2a.3a.4b.5c.6b, 1b.2a.3a.4b.5c.6c, 1b.2a.3a.4b.5c.6d,
1b.2a.3a.4b.5c.6e, 1b.2a.3a.4b.5d.6a, 1b.2a.3a.4b.5d.6b, 1b.2a.3a.4b.5d.6c,
1b.2a.3a.4b.5d.6d, 1b.2a.3a.4b.5d.6e, 1b.2a.3a.4b.5e.6a, 1b.2a.3a.4b.5e.6b,
1b.2a.3a.4b.5e.6c, 1b.2a.3a.4b.5e.6d, 1b.2a.3a.4b.5e.6e, 1b.2a.3a.4c.5a.6a,
1b.2a.3a.4c.5a.6b, 1b.2a.3a.4c.5a.6c, 1b.2a.3a.4c.5a.6d, 1b.2a.3a.4c.5a.6e,
1b.2a.3a.4c.5b.6a, 1b.2a.3a.4c.5b.6b, 1b.2a.3a.4c.5b.6c, 1b.2a.3a.4c.5b.6d,
1b.2a.3a.4c.5b.6e, 1b.2a.3a.4c.5c.6a, 1b.2a.3a.4c.5c.6b, 1b.2a.3a.4c.5c.6c,
1b.2a.3a.4c.5c.6d, 1b.2a.3a.4c.5c.6e, 1b.2a.3a.4c.5d.6a, 1b.2a.3a.4c.5d.6b,
1b.2a.3a.4c.5d.6c, 1b.2a.3a.4c.5d.6d, 1b.2a.3a.4c.5d.6e, 1b.2a.3a.4c.5e.6a,
1b.2a.3a.4c.5e.6b, 1b.2a.3a.4c.5e.6c, 1b.2a.3a.4c.5e.6d, 1b.2a.3a.4c.5e.6e,
1b.2a.3a.4d.5a.6a, 1b.2a.3a.4d.5a.6b, 1b.2a.3a.4d.5a.6c, 1b.2a.3a.4d.5a.6d,
1b.2a.3a.4d.5a.6e, 1b.2a.3a.4d.5b.6a, 1b.2a.3a.4d.5b.6b, 1b.2a.3a.4d.5b.6c,
1b.2a.3a.4d.5b.6d, 1b.2a.3a.4d.5b.6e, 1b.2a.3a.4d.5c.6a, 1b.2a.3a.4d.5c.6b,
1b.2a.3a.4d.5c.6c, 1b.2a.3a.4d.5c.6d, 1b.2a.3a.4d.5c.6e, 1b.2a.3a.4d.5d.6a,
1b.2a.3a.4d.5d.6b, 1b.2a.3a.4d.5d.6c, 1b.2a.3a.4d.5d.6d, 1b.2a.3a.4d.5d.6e,
1b.2a.3a.4d.5e.6a, 1b.2a.3a.4d.5e.6b, 1b.2a.3a.4d.5e.6c, 1b.2a.3a.4d.5e.6d,
1b.2a.3a.4d.5e.6e, 1b.2a.3a.4e.5a.6a, 1b.2a.3a.4e.5a.6b, 1b.2a.3a.4e.5a.6c,
1b.2a.3a.4e.5a.6d, 1b.2a.3a.4e.5a.6e, 1b.2a.3a.4e.5b.6a, 1b.2a.3a.4e.5b.6b,
1b.2a.3a.4e.5b.6c, 1b.2a.3a.4e.5b.6d, 1b.2a.3a.4e.5b.6e, 1b.2a.3a.4e.5c.6a,
1b.2a.3a.4e.5c.6b, 1b.2a.3a.4e.5c.6c, 1b.2a.3a.4e.5c.6d, 1b.2a.3a.4e.5c.6e,
1b.2a.3a.4e.5d.6a, 1b.2a.3a.4e.5d.6b, 1b.2a.3a.4e.5d.6c, 1b.2a.3a.4e.5d.6d,
1b.2a.3a.4e.5d.6e, 1b.2a.3a.4e.5e.6a, 1b.2a.3a.4e.5e.6b, 1b.2a.3a.4e.5e.6c,
1b.2a.3a.4e.5e.6d, 1b.2a.3a.4e.5e.6e, 1b.2a.3b.4a.5a.6a, 1b.2a.3b.4a.5a.6b,
1b.2a.3b.4a.5a.6c, 1b.2a.3b.4a.5a.6d, 1b.2a.3b.4a.5a.6e, 1b.2a.3b.4a.5b.6a,
1b.2a.3b.4a.5b.6b, 1b.2a.3b.4a.5b.6c, 1b.2a.3b.4a.5b.6d, 1b.2a.3b.4a.5b.6e,
1b.2a.3b.4a.5c.6a, 1b.2a.3b.4a.5c.6b, 1b.2a.3b.4a.5c.6c, 1b.2a.3b.4a.5c.6d,
1b.2a.3b.4a.5c.6e, 1b.2a.3b.4a.5d.6a, 1b.2a.3b.4a.5d.6b, 1b.2a.3b.4a.5d.6c,
1b.2a.3b.4a.5d.6d, 1b.2a.3b.4a.5d.6e, 1b.2a.3b.4a.5e.6a, 1b.2a.3b.4a.5e.6b,
1b.2a.3b.4a.5e.6c, 1b.2a.3b.4a.5e.6d, 1b.2a.3b.4a.5e.6e, 1b.2a.3b.4b.5a.6a,
1b.2a.3b.4b.5a.6b, 1b.2a.3b.4b.5a.6c, 1b.2a.3b.4b.5a.6d, 1b.2a.3b.4b.5a.6e,
1b.2a.3b.4b.5b.6a, 1b.2a.3b.4b.5b.6b, 1b.2a.3b.4b.5b.6c, 1b.2a.3b.4b.5b.6d,
1b.2a.3b.4b.5b.6e, 1b.2a.3b.4b.5c.6a, 1b.2a.3b.4b.5c.6b, 1b.2a.3b.4b.5c.6c,

TABLE 8-continued

List of Compounds of Formula (II)

1b.2a.3b.4b.5c.6d, 1b.2a.3b.4b.5c.6e, 1b.2a.3b.4b.5d.6a, 1b.2a.3b.4b.5d.6b,
1b.2a.3b.4b.5d.6c, 1b.2a.3b.4b.5d.6d, 1b.2a.3b.4b.5d.6e, 1b.2a.3b.4b.5e.6a,
1b.2a.3b.4b.5e.6b, 1b.2a.3b.4b.5e.6c, 1b.2a.3b.4b.5e.6d, 1b.2a.3b.4b.5e.6e,
1b.2a.3b.4c.5a.6a, 1b.2a.3b.4c.5a.6b, 1b.2a.3b.4c.5a.6c, 1b.2a.3b.4c.5a.6d,
1b.2a.3b.4c.5a.6e, 1b.2a.3b.4c.5b.6a, 1b.2a.3b.4c.5b.6b, 1b.2a.3b.4c.5b.6c,
1b.2a.3b.4c.5b.6d, 1b.2a.3b.4c.5b.6e, 1b.2a.3b.4c.5c.6a, 1b.2a.3b.4c.5c.6b,
1b.2a.3b.4c.5c.6c, 1b.2a.3b.4c.5c.6d, 1b.2a.3b.4c.5c.6e, 1b.2a.3b.4c.5d.6a,
1b.2a.3b.4c.5d.6b, 1b.2a.3b.4c.5d.6c, 1b.2a.3b.4c.5d.6d, 1b.2a.3b.4c.5d.6e,
1b.2a.3b.4c.5e.6a, 1b.2a.3b.4c.5e.6b, 1b.2a.3b.4c.5e.6c, 1b.2a.3b.4c.5e.6d,
1b.2a.3b.4c.5e.6e, 1b.2a.3b.4d.5a.6a, 1b.2a.3b.4d.5a.6b, 1b.2a.3b.4d.5a.6c,
1b.2a.3b.4d.5a.6d, 1b.2a.3b.4d.5a.6e, 1b.2a.3b.4d.5b.6a, 1b.2a.3b.4d.5b.6b,
1b.2a.3b.4d.5b.6c, 1b.2a.3b.4d.5b.6d, 1b.2a.3b.4d.5b.6e, 1b.2a.3b.4d.5c.6a,
1b.2a.3b.4d.5c.6b, 1b.2a.3b.4d.5c.6c, 1b.2a.3b.4d.5c.6d, 1b.2a.3b.4d.5c.6e,
1b.2a.3b.4d.5d.6a, 1b.2a.3b.4d.5d.6b, 1b.2a.3b.4d.5d.6c, 1b.2a.3b.4d.5d.6d,
1b.2a.3b.4d.5d.6e, 1b.2a.3b.4d.5e.6a, 1b.2a.3b.4d.5e.6b, 1b.2a.3b.4d.5e.6c,
1b.2a.3b.4d.5e.6d, 1b.2a.3b.4d.5e.6e, 1b.2a.3b.4e.5a.6a, 1b.2a.3b.4e.5a.6b,
1b.2a.3b.4e.5a.6c, 1b.2a.3b.4e.5a.6d, 1b.2a.3b.4e.5a.6e, 1b.2a.3b.4e.5b.6a,
1b.2a.3b.4e.5b.6b, 1b.2a.3b.4e.5b.6c, 1b.2a.3b.4e.5b.6d, 1b.2a.3b.4e.5b.6e,
1b.2a.3b.4e.5c.6a, 1b.2a.3b.4e.5c.6b, 1b.2a.3b.4e.5c.6c, 1b.2a.3b.4e.5c.6d,
1b.2a.3b.4e.5c.6e, 1b.2a.3b.4e.5d.6a, 1b.2a.3b.4e.5d.6b, 1b.2a.3b.4e.5d.6c,
1b.2a.3b.4e.5d.6d, 1b.2a.3b.4e.5d.6e, 1b.2a.3b.4e.5e.6a, 1b.2a.3b.4e.5e.6b,
1b.2a.3b.4e.5e.6c, 1b.2a.3b.4e.5e.6d, 1b.2a.3b.4e.5e.6e, 1b.2a.3c.4a.5a.6a,
1b.2a.3c.4a.5a.6b, 1b.2a.3c.4a.5a.6c, 1b.2a.3c.4a.5a.6d, 1b.2a.3c.4a.5a.6e,
1b.2a.3c.4a.5b.6a, 1b.2a.3c.4a.5b.6b, 1b.2a.3c.4a.5b.6c, 1b.2a.3c.4a.5b.6d,
1b.2a.3c.4a.5b.6e, 1b.2a.3c.4a.5c.6a, 1b.2a.3c.4a.5c.6b, 1b.2a.3c.4a.5c.6c,
1b.2a.3c.4a.5c.6d, 1b.2a.3c.4a.5c.6e, 1b.2a.3c.4a.5d.6a, 1b.2a.3c.4a.5d.6b,
1b.2a.3c.4a.5d.6c, 1b.2a.3c.4a.5d.6d, 1b.2a.3c.4a.5d.6e, 1b.2a.3c.4a.5e.6a,
1b.2a.3c.4a.5e.6b, 1b.2a.3c.4a.5e.6c, 1b.2a.3c.4a.5e.6d, 1b.2a.3c.4a.5e.6e,
1b.2a.3c.4b.5a.6a, 1b.2a.3c.4b.5a.6b, 1b.2a.3c.4b.5a.6c, 1b.2a.3c.4b.5a.6d,
1b.2a.3c.4b.5a.6e, 1b.2a.3c.4b.5b.6a, 1b.2a.3c.4b.5b.6b, 1b.2a.3c.4b.5b.6c,
1b.2a.3c.4b.5b.6d, 1b.2a.3c.4b.5b.6e, 1b.2a.3c.4b.5c.6a, 1b.2a.3c.4b.5c.6b,
1b.2a.3c.4b.5c.6c, 1b.2a.3c.4b.5c.6d, 1b.2a.3c.4b.5c.6e, 1b.2a.3c.4b.5d.6a,
1b.2a.3c.4b.5d.6b, 1b.2a.3c.4b.5d.6c, 1b.2a.3c.4b.5d.6d, 1b.2a.3c.4b.5d.6e,
1b.2a.3c.4b.5e.6a, 1b.2a.3c.4b.5e.6b, 1b.2a.3c.4b.5e.6c, 1b.2a.3c.4b.5e.6d,
1b.2a.3c.4b.5e.6e, 1b.2a.3c.4c.5a.6a, 1b.2a.3c.4c.5a.6b, 1b.2a.3c.4c.5a.6c,
1b.2a.3c.4c.5a.6d, 1b.2a.3c.4c.5a.6e, 1b.2a.3c.4c.5b.6a, 1b.2a.3c.4c.5b.6b,
1b.2a.3c.4c.5b.6c, 1b.2a.3c.4c.5b.6d, 1b.2a.3c.4c.5b.6e, 1b.2a.3c.4c.5c.6a,
1b.2a.3c.4c.5c.6b, 1b.2a.3c.4c.5c.6c, 1b.2a.3c.4c.5c.6d, 1b.2a.3c.4c.5c.6e,
1b.2a.3c.4c.5d.6a, 1b.2a.3c.4c.5d.6b, 1b.2a.3c.4c.5d.6c, 1b.2a.3c.4c.5d.6d,
1b.2a.3c.4c.5d.6e, 1b.2a.3c.4c.5e.6a, 1b.2a.3c.4c.5e.6b, 1b.2a.3c.4c.5e.6c,
1b.2a.3c.4c.5e.6d, 1b.2a.3c.4c.5e.6e, 1b.2a.3c.4d.5a.6a, 1b.2a.3c.4d.5a.6b,
1b.2a.3c.4d.5a.6c, 1b.2a.3c.4d.5a.6d, 1b.2a.3c.4d.5a.6e, 1b.2a.3c.4d.5b.6a,
1b.2a.3c.4d.5b.6b, 1b.2a.3c.4d.5b.6c, 1b.2a.3c.4d.5b.6d, 1b.2a.3c.4d.5b.6e,
1b.2a.3c.4d.5c.6a, 1b.2a.3c.4d.5c.6b, 1b.2a.3c.4d.5c.6c, 1b.2a.3c.4d.5c.6d,
1b.2a.3c.4d.5c.6e, 1b.2a.3c.4d.5d.6a, 1b.2a.3c.4d.5d.6b, 1b.2a.3c.4d.5d.6c,
1b.2a.3c.4d.5d.6d, 1b.2a.3c.4d.5d.6e, 1b.2a.3c.4d.5e.6a, 1b.2a.3c.4d.5e.6b,
1b.2a.3c.4d.5e.6c, 1b.2a.3c.4d.5e.6d, 1b.2a.3c.4d.5e.6e, 1b.2a.3c.4e.5a.6a,
1b.2a.3c.4e.5a.6b, 1b.2a.3c.4e.5a.6c, 1b.2a.3c.4e.5a.6d, 1b.2a.3c.4e.5a.6e,
1b.2a.3c.4e.5b.6a, 1b.2a.3c.4e.5b.6b, 1b.2a.3c.4e.5b.6c, 1b.2a.3c.4e.5b.6d,
1b.2a.3c.4e.5b.6e, 1b.2a.3c.4e.5c.6a, 1b.2a.3c.4e.5c.6b, 1b.2a.3c.4e.5c.6c,
1b.2a.3c.4e.5c.6d, 1b.2a.3c.4e.5c.6e, 1b.2a.3c.4e.5d.6a, 1b.2a.3c.4e.5d.6b,
1b.2a.3c.4e.5d.6c, 1b.2a.3c.4e.5d.6d, 1b.2a.3c.4e.5d.6e, 1b.2a.3c.4e.5e.6a,
1b.2a.3c.4e.5e.6b, 1b.2a.3c.4e.5e.6c, 1b.2a.3c.4e.5e.6d, 1b.2a.3c.4e.5e.6e,
1b.2a.3d.4a.5a.6a, 1b.2a.3d.4a.5a.6b, 1b.2a.3d.4a.5a.6c, 1b.2a.3d.4a.5a.6d,
1b.2a.3d.4a.5a.6e, 1b.2a.3d.4a.5b.6a, 1b.2a.3d.4a.5b.6b, 1b.2a.3d.4a.5b.6c,
1b.2a.3d.4a.5b.6d, 1b.2a.3d.4a.5b.6e, 1b.2a.3d.4a.5c.6a, 1b.2a.3d.4a.5c.6b,
1b.2a.3d.4a.5c.6c, 1b.2a.3d.4a.5c.6d, 1b.2a.3d.4a.5c.6e, 1b.2a.3d.4a.5d.6a,
1b.2a.3d.4a.5d.6b, 1b.2a.3d.4a.5d.6c, 1b.2a.3d.4a.5d.6d, 1b.2a.3d.4a.5d.6e,
1b.2a.3d.4a.5e.6a, 1b.2a.3d.4a.5e.6b, 1b.2a.3d.4a.5e.6c, 1b.2a.3d.4a.5e.6d,
1b.2a.3d.4a.5e.6e, 1b.2a.3d.4b.5a.6a, 1b.2a.3d.4b.5a.6b, 1b.2a.3d.4b.5a.6c,
1b.2a.3d.4b.5a.6d, 1b.2a.3d.4b.5a.6e, 1b.2a.3d.4b.5b.6a, 1b.2a.3d.4b.5b.6b,
1b.2a.3d.4b.5b.6c, 1b.2a.3d.4b.5b.6d, 1b.2a.3d.4b.5b.6e, 1b.2a.3d.4b.5c.6a,
1b.2a.3d.4b.5c.6b, 1b.2a.3d.4b.5c.6c, 1b.2a.3d.4b.5c.6d, 1b.2a.3d.4b.5c.6e,
1b.2a.3d.4b.5d.6a, 1b.2a.3d.4b.5d.6b, 1b.2a.3d.4b.5d.6c, 1b.2a.3d.4b.5d.6d,
1b.2a.3d.4b.5d.6e, 1b.2a.3d.4b.5e.6a, 1b.2a.3d.4b.5e.6b, 1b.2a.3d.4b.5e.6c,
1b.2a.3d.4b.5e.6d, 1b.2a.3d.4b.5e.6e, 1b.2a.3d.4c.5a.6a, 1b.2a.3d.4c.5a.6b,
1b.2a.3d.4c.5a.6c, 1b.2a.3d.4c.5a.6d, 1b.2a.3d.4c.5a.6e, 1b.2a.3d.4c.5b.6a,
1b.2a.3d.4c.5b.6b, 1b.2a.3d.4c.5b.6c, 1b.2a.3d.4c.5b.6d, 1b.2a.3d.4c.5b.6e,
1b.2a.3d.4c.5c.6a, 1b.2a.3d.4c.5c.6b, 1b.2a.3d.4c.5c.6c, 1b.2a.3d.4c.5c.6d,
1b.2a.3d.4c.5c.6e, 1b.2a.3d.4c.5d.6a, 1b.2a.3d.4c.5d.6b, 1b.2a.3d.4c.5d.6c,
1b.2a.3d.4c.5d.6d, 1b.2a.3d.4c.5d.6e, 1b.2a.3d.4c.5e.6a, 1b.2a.3d.4c.5e.6b,
1b.2a.3d.4c.5e.6c, 1b.2a.3d.4c.5e.6d, 1b.2a.3d.4c.5e.6e, 1b.2a.3d.4d.5a.6a,
1b.2a.3d.4d.5a.6b, 1b.2a.3d.4d.5a.6c, 1b.2a.3d.4d.5a.6d, 1b.2a.3d.4d.5a.6e,
1b.2a.3d.4d.5b.6a, 1b.2a.3d.4d.5b.6b, 1b.2a.3d.4d.5b.6c, 1b.2a.3d.4d.5b.6d,
1b.2a.3d.4d.5b.6e, 1b.2a.3d.4d.5c.6a, 1b.2a.3d.4d.5c.6b, 1b.2a.3d.4d.5c.6c,
1b.2a.3d.4d.5c.6d, 1b.2a.3d.4d.5c.6e, 1b.2a.3d.4d.5d.6a, 1b.2a.3d.4d.5d.6b,
1b.2a.3d.4d.5d.6c, 1b.2a.3d.4d.5d.6d, 1b.2a.3d.4d.5d.6e, 1b.2a.3d.4d.5e.6a,
1b.2a.3d.4d.5e.6b, 1b.2a.3d.4d.5e.6c, 1b.2a.3d.4d.5e.6d, 1b.2a.3d.4d.5e.6e,

TABLE 8-continued

List of Compounds of Formula (II)

1b.2a.3d.4e.5a.6a, 1b.2a.3d.4e.5a.6b, 1b.2a.3d.4e.5a.6c, 1b.2a.3d.4e.5a.6d,
1b.2a.3d.4e.5a.6e, 1b.2a.3d.4e.5b.6a, 1b.2a.3d.4e.5b.6b, 1b.2a.3d.4e.5b.6c,
1b.2a.3d.4e.5b.6d, 1b.2a.3d.4e.5b.6e, 1b.2a.3d.4e.5c.6a, 1b.2a.3d.4e.5c.6b,
1b.2a.3d.4e.5c.6c, 1b.2a.3d.4e.5c.6d, 1b.2a.3d.4e.5c.6e, 1b.2a.3d.4e.5d.6a,
1b.2a.3d.4e.5d.6b, 1b.2a.3d.4e.5d.6c, 1b.2a.3d.4e.5d.6d, 1b.2a.3d.4e.5d.6e,
1b.2a.3d.4e.5e.6a, 1b.2a.3d.4e.5e.6b, 1b.2a.3d.4e.5e.6c, 1b.2a.3d.4e.5e.6d,
1b.2a.3d.4e.5e.6e, 1b.2a.3e.4a.5a.6a, 1b.2a.3e.4a.5a.6b, 1b.2a.3e.4a.5a.6c,
1b.2a.3e.4a.5a.6d, 1b.2a.3e.4a.5a.6e, 1b.2a.3e.4a.5b.6a, 1b.2a.3e.4a.5b.6b,
1b.2a.3e.4a.5b.6c, 1b.2a.3e.4a.5b.6d, 1b.2a.3e.4a.5b.6e, 1b.2a.3e.4a.5c.6a,
1b.2a.3e.4a.5c.6b, 1b.2a.3e.4a.5c.6c, 1b.2a.3e.4a.5c.6d, 1b.2a.3e.4a.5c.6e,
1b.2a.3e.4a.5d.6a, 1b.2a.3e.4a.5d.6b, 1b.2a.3e.4a.5d.6c, 1b.2a.3e.4a.5d.6d,
1b.2a.3e.4a.5d.6e, 1b.2a.3e.4a.5e.6a, 1b.2a.3e.4a.5e.6b, 1b.2a.3e.4a.5e.6c,
1b.2a.3e.4a.5e.6d, 1b.2a.3e.4a.5e.6e, 1b.2a.3e.4b.5a.6a, 1b.2a.3e.4b.5a.6b,
1b.2a.3e.4b.5a.6c, 1b.2a.3e.4b.5a.6d, 1b.2a.3e.4b.5a.6e, 1b.2a.3e.4b.5b.6a,
1b.2a.3e.4b.5b.6b, 1b.2a.3e.4b.5b.6c, 1b.2a.3e.4b.5b.6d, 1b.2a.3e.4b.5b.6e,
1b.2a.3e.4b.5c.6a, 1b.2a.3e.4b.5c.6b, 1b.2a.3e.4b.5c.6c, 1b.2a.3e.4b.5c.6d,
1b.2a.3e.4b.5c.6e, 1b.2a.3e.4b.5d.6a, 1b.2a.3e.4b.5d.6b, 1b.2a.3e.4b.5d.6c,
1b.2a.3e.4b.5d.6d, 1b.2a.3e.4b.5d.6e, 1b.2a.3e.4b.5e.6a, 1b.2a.3e.4b.5e.6b,
1b.2a.3e.4b.5e.6c, 1b.2a.3e.4b.5e.6d, 1b.2a.3e.4b.5e.6e, 1b.2a.3e.4c.5a.6a,
1b.2a.3e.4c.5a.6b, 1b.2a.3e.4c.5a.6c, 1b.2a.3e.4c.5a.6d, 1b.2a.3e.4c.5a.6e,
1b.2a.3e.4c.5b.6a, 1b.2a.3e.4c.5b.6b, 1b.2a.3e.4c.5b.6c, 1b.2a.3e.4c.5b.6d,
1b.2a.3e.4c.5b.6e, 1b.2a.3e.4c.5c.6a, 1b.2a.3e.4c.5c.6b, 1b.2a.3e.4c.5c.6c,
1b.2a.3e.4c.5c.6d, 1b.2a.3e.4c.5c.6e, 1b.2a.3e.4c.5d.6a, 1b.2a.3e.4c.5d.6b,
1b.2a.3e.4c.5d.6c, 1b.2a.3e.4c.5d.6d, 1b.2a.3e.4c.5d.6e, 1b.2a.3e.4c.5e.6a,
1b.2a.3e.4c.5e.6b, 1b.2a.3e.4c.5e.6c, 1b.2a.3e.4c.5e.6d, 1b.2a.3e.4c.5e.6e,
1b.2a.3e.4d.5a.6a, 1b.2a.3e.4d.5a.6b, 1b.2a.3e.4d.5a.6c, 1b.2a.3e.4d.5a.6d,
1b.2a.3e.4d.5a.6e, 1b.2a.3e.4d.5b.6a, 1b.2a.3e.4d.5b.6b, 1b.2a.3e.4d.5b.6c,
1b.2a.3e.4d.5b.6d, 1b.2a.3e.4d.5b.6e, 1b.2a.3e.4d.5c.6a, 1b.2a.3e.4d.5c.6b,
1b.2a.3e.4d.5c.6c, 1b.2a.3e.4d.5c.6d, 1b.2a.3e.4d.5c.6e, 1b.2a.3e.4d.5d.6a,
1b.2a.3e.4d.5d.6b, 1b.2a.3e.4d.5d.6c, 1b.2a.3e.4d.5d.6d, 1b.2a.3e.4d.5d.6e,
1b.2a.3e.4d.5e.6a, 1b.2a.3e.4d.5e.6b, 1b.2a.3e.4d.5e.6c, 1b.2a.3e.4d.5e.6d,
1b.2a.3e.4d.5e.6e, 1b.2a.3e.4e.5a.6a, 1b.2a.3e.4e.5a.6b, 1b.2a.3e.4e.5a.6c,
1b.2a.3e.4e.5a.6d, 1b.2a.3e.4e.5a.6e, 1b.2a.3e.4e.5b.6a, 1b.2a.3e.4e.5b.6b,
1b.2a.3e.4e.5b.6c, 1b.2a.3e.4e.5b.6d, 1b.2a.3e.4e.5b.6e, 1b.2a.3e.4e.5c.6a,
1b.2a.3e.4e.5c.6b, 1b.2a.3e.4e.5c.6c, 1b.2a.3e.4e.5c.6d, 1b.2a.3e.4e.5c.6e,
1b.2a.3e.4e.5d.6a, 1b.2a.3e.4e.5d.6b, 1b.2a.3e.4e.5d.6c, 1b.2a.3e.4e.5d.6d,
1b.2a.3e.4e.5d.6e, 1b.2a.3e.4e.5e.6a, 1b.2a.3e.4e.5e.6b, 1b.2a.3e.4e.5e.6c,
1b.2a.3e.4e.5e.6d, 1b.2a.3e.4e.5e.6e, 1b.2b.3a.4a.5a.6a, 1b.2b.3a.4a.5a.6b,
1b.2b.3a.4a.5a.6c, 1b.2b.3a.4a.5a.6d, 1b.2b.3a.4a.5a.6e, 1b.2b.3a.4a.5b.6a,
1b.2b.3a.4a.5b.6b, 1b.2b.3a.4a.5b.6c, 1b.2b.3a.4a.5b.6d, 1b.2b.3a.4a.5b.6e,
1b.2b.3a.4a.5c.6a, 1b.2b.3a.4a.5c.6b, 1b.2b.3a.4a.5c.6c, 1b.2b.3a.4a.5c.6d,
1b.2b.3a.4a.5c.6e, 1b.2b.3a.4a.5d.6a, 1b.2b.3a.4a.5d.6b, 1b.2b.3a.4a.5d.6c,
1b.2b.3a.4a.5d.6d, 1b.2b.3a.4a.5d.6e, 1b.2b.3a.4a.5e.6a, 1b.2b.3a.4a.5e.6b,
1b.2b.3a.4a.5e.6c, 1b.2b.3a.4a.5e.6d, 1b.2b.3a.4a.5e.6e, 1b.2b.3a.4b.5a.6a,
1b.2b.3a.4b.5a.6b, 1b.2b.3a.4b.5a.6c, 1b.2b.3a.4b.5a.6d, 1b.2b.3a.4b.5a.6e,
1b.2b.3a.4b.5b.6a, 1b.2b.3a.4b.5b.6b, 1b.2b.3a.4b.5b.6c, 1b.2b.3a.4b.5b.6d,
1b.2b.3a.4b.5b.6e, 1b.2b.3a.4b.5c.6a, 1b.2b.3a.4b.5c.6b, 1b.2b.3a.4b.5c.6c,
1b.2b.3a.4b.5c.6d, 1b.2b.3a.4b.5c.6e, 1b.2b.3a.4b.5d.6a, 1b.2b.3a.4b.5d.6b,
1b.2b.3a.4b.5d.6c, 1b.2b.3a.4b.5d.6d, 1b.2b.3a.4b.5d.6e, 1b.2b.3a.4b.5e.6a,
1b.2b.3a.4b.5e.6b, 1b.2b.3a.4b.5e.6c, 1b.2b.3a.4b.5e.6d, 1b.2b.3a.4b.5e.6e,
1b.2b.3a.4c.5a.6a, 1b.2b.3a.4c.5a.6b, 1b.2b.3a.4c.5a.6c, 1b.2b.3a.4c.5a.6d,
1b.2b.3a.4c.5a.6e, 1b.2b.3a.4c.5b.6a, 1b.2b.3a.4c.5b.6b, 1b.2b.3a.4c.5b.6c,
1b.2b.3a.4c.5b.6d, 1b.2b.3a.4c.5b.6e, 1b.2b.3a.4c.5c.6a, 1b.2b.3a.4c.5c.6b,
1b.2b.3a.4c.5c.6c, 1b.2b.3a.4c.5c.6d, 1b.2b.3a.4c.5c.6e, 1b.2b.3a.4c.5d.6a,
1b.2b.3a.4c.5d.6b, 1b.2b.3a.4c.5d.6c, 1b.2b.3a.4c.5d.6d, 1b.2b.3a.4c.5d.6e,
1b.2b.3a.4c.5e.6a, 1b.2b.3a.4c.5e.6b, 1b.2b.3a.4c.5e.6c, 1b.2b.3a.4c.5e.6d,
1b.2b.3a.4c.5e.6e, 1b.2b.3a.4d.5a.6a, 1b.2b.3a.4d.5a.6b, 1b.2b.3a.4d.5a.6c,
1b.2b.3a.4d.5a.6d, 1b.2b.3a.4d.5a.6e, 1b.2b.3a.4d.5b.6a, 1b.2b.3a.4d.5b.6b,
1b.2b.3a.4d.5b.6c, 1b.2b.3a.4d.5b.6d, 1b.2b.3a.4d.5b.6e, 1b.2b.3a.4d.5c.6a,
1b.2b.3a.4d.5c.6b, 1b.2b.3a.4d.5c.6c, 1b.2b.3a.4d.5c.6d, 1b.2b.3a.4d.5c.6e,
1b.2b.3a.4d.5d.6a, 1b.2b.3a.4d.5d.6b, 1b.2b.3a.4d.5d.6c, 1b.2b.3a.4d.5d.6d,
1b.2b.3a.4d.5d.6e, 1b.2b.3a.4d.5e.6a, 1b.2b.3a.4d.5e.6b, 1b.2b.3a.4d.5e.6c,
1b.2b.3a.4d.5e.6d, 1b.2b.3a.4d.5e.6e, 1b.2b.3a.4e.5a.6a, 1b.2b.3a.4e.5a.6b,
1b.2b.3a.4e.5a.6c, 1b.2b.3a.4e.5a.6d, 1b.2b.3a.4e.5a.6e, 1b.2b.3a.4e.5b.6a,
1b.2b.3a.4e.5b.6b, 1b.2b.3a.4e.5b.6c, 1b.2b.3a.4e.5b.6d, 1b.2b.3a.4e.5b.6e,
1b.2b.3a.4e.5c.6a, 1b.2b.3a.4e.5c.6b, 1b.2b.3a.4e.5c.6c, 1b.2b.3a.4e.5c.6d,
1b.2b.3a.4e.5c.6e, 1b.2b.3a.4e.5d.6a, 1b.2b.3a.4e.5d.6b, 1b.2b.3a.4e.5d.6c,
1b.2b.3a.4e.5d.6d, 1b.2b.3a.4e.5d.6e, 1b.2b.3a.4e.5e.6a, 1b.2b.3a.4e.5e.6b,
1b.2b.3a.4e.5e.6c, 1b.2b.3a.4e.5e.6d, 1b.2b.3a.4e.5e.6e, 1b.2b.3b.4a.5a.6a,
1b.2b.3b.4a.5a.6b, 1b.2b.3b.4a.5a.6c, 1b.2b.3b.4a.5a.6d, 1b.2b.3b.4a.5a.6e,
1b.2b.3b.4a.5b.6a, 1b.2b.3b.4a.5b.6b, 1b.2b.3b.4a.5b.6c, 1b.2b.3b.4a.5b.6d,
1b.2b.3b.4a.5b.6e, 1b.2b.3b.4a.5c.6a, 1b.2b.3b.4a.5c.6b, 1b.2b.3b.4a.5c.6c,
1b.2b.3b.4a.5c.6d, 1b.2b.3b.4a.5c.6e, 1b.2b.3b.4a.5d.6a, 1b.2b.3b.4a.5d.6b,
1b.2b.3b.4a.5d.6c, 1b.2b.3b.4a.5d.6d, 1b.2b.3b.4a.5d.6e, 1b.2b.3b.4a.5e.6a,
1b.2b.3b.4a.5e.6b, 1b.2b.3b.4a.5e.6c, 1b.2b.3b.4a.5e.6d, 1b.2b.3b.4a.5e.6e,
1b.2b.3b.4b.5a.6a, 1b.2b.3b.4b.5a.6b, 1b.2b.3b.4b.5a.6c, 1b.2b.3b.4b.5a.6d,
1b.2b.3b.4b.5a.6e, 1b.2b.3b.4b.5b.6a, 1b.2b.3b.4b.5b.6b, 1b.2b.3b.4b.5b.6c,
1b.2b.3b.4b.5b.6d, 1b.2b.3b.4b.5b.6e, 1b.2b.3b.4b.5c.6a, 1b.2b.3b.4b.5c.6b,

TABLE 8-continued

List of Compounds of Formula (II)

1b.2b.3b.4b.5c.6c, 1b.2b.3b.4b.5c.6d, 1b.2b.3b.4b.5c.6e, 1b.2b.3b.4b.5d.6a,
1b.2b.3b.4b.5d.6b, 1b.2b.3b.4b.5d.6c, 1b.2b.3b.4b.5d.6d, 1b.2b.3b.4b.5d.6e,
1b.2b.3b.4b.5e.6a, 1b.2b.3b.4b.5e.6b, 1b.2b.3b.4b.5e.6c, 1b.2b.3b.4b.5e.6d,
1b.2b.3b.4b.5e.6e, 1b.2b.3b.4c.5a.6a, 1b.2b.3b.4c.5a.6b, 1b.2b.3b.4c.5a.6c,
1b.2b.3b.4c.5a.6d, 1b.2b.3b.4c.5a.6e, 1b.2b.3b.4c.5b.6a, 1b.2b.3b.4c.5b.6b,
1b.2b.3b.4c.5b.6c, 1b.2b.3b.4c.5b.6d, 1b.2b.3b.4c.5b.6e, 1b.2b.3b.4c.5c.6a,
1b.2b.3b.4c.5c.6b, 1b.2b.3b.4c.5c.6c, 1b.2b.3b.4c.5c.6d, 1b.2b.3b.4c.5c.6e,
1b.2b.3b.4c.5d.6a, 1b.2b.3b.4c.5d.6b, 1b.2b.3b.4c.5d.6c, 1b.2b.3b.4c.5d.6d,
1b.2b.3b.4c.5d.6e, 1b.2b.3b.4c.5e.6a, 1b.2b.3b.4c.5e.6b, 1b.2b.3b.4c.5e.6c,
1b.2b.3b.4c.5e.6d, 1b.2b.3b.4c.5e.6e, 1b.2b.3b.4d.5a.6a, 1b.2b.3b.4d.5a.6b,
1b.2b.3b.4d.5a.6c, 1b.2b.3b.4d.5a.6d, 1b.2b.3b.4d.5a.4e, 1b.2b.3b.4d.5b.6a,
1b.2b.3b.4d.5b.6b, 1b.2b.3b.4d.5b.6c, 1b.2b.3b.4d.5b.6d, 1b.2b.3b.4d.5b.6e,
1b.2b.3b.4d.5c.6a, 1b.2b.3b.4d.5c.6b, 1b.2b.3b.4d.5c.6c, 1b.2b.3b.4d.5c.6d,
1b.2b.3b.4d.5c.6e, 1b.2b.3b.4d.5d.6a, 1b.2b.3b.4d.5d.6b, 1b.2b.3b.4d.5d.6c,
1b.2b.3b.4d.5d.6d, 1b.2b.3b.4d.5d.6e, 1b.2b.3b.4d.5e.6a, 1b.2b.3b.4d.5e.6b,
1b.2b.3b.4d.5e.6c, 1b.2b.3b.4d.5e.6d, 1b.2b.3b.4d.5e.6e, 1b.2b.3b.4e.5a.6a,
1b.2b.3b.4e.5a.6b, 1b.2b.3b.4e.5a.6c, 1b.2b.3b.4e.5a.6d, 1b.2b.3b.4e.5a.6e,
1b.2b.3b.4e.5b.6a, 1b.2b.3b.4e.5b.6b, 1b.2b.3b.4e.5b.6c, 1b.2b.3b.4e.5b.6d,
1b.2b.3b.4e.5b.6e, 1b.2b.3b.4e.5c.6a, 1b.2b.3b.4e.5c.6b, 1b.2b.3b.4e.5c.6c,
1b.2b.3b.4e.5c.6d, 1b.2b.3b.4e.5c.6e, 1b.2b.3b.4e.5d.6a, 1b.2b.3b.4e.5d.6b,
1b.2b.3b.4e.5d.6c, 1b.2b.3b.4e.5d.6d, 1b.2b.3b.4e.5d.6e, 1b.2b.3b.4e.5e.6a,
1b.2b.3b.4e.5e.6b, 1b.2b.3b.4e.5e.6c, 1b.2b.3b.4e.5e.6d, 1b.2b.3b.4e.5e.6e,
1b.2b.3c.4a.5a.6a, 1b.2b.3c.4a.5a.6b, 1b.2b.3c.4a.5a.6c, 1b.2b.3c.4a.5a.6d,
1b.2b.3c.4a.5a.6e, 1b.2b.3c.4a.5b.6a, 1b.2b.3c.4a.5b.6b, 1b.2b.3c.4a.5b.6c,
1b.2b.3c.4a.5b.6d, 1b.2b.3c.4a.5b.6e, 1b.2b.3c.4a.5c.6a, 1b.2b.3c.4a.5c.6b,
1b.2b.3c.4a.5c.6c, 1b.2b.3c.4a.5c.6d, 1b.2b.3c.4a.5c.6e, 1b.2b.3c.4a.5d.6a,
1b.2b.3c.4a.5d.6b, 1b.2b.3c.4a.5d.6c, 1b.2b.3c.4a.5d.6d, 1b.2b.3c.4a.5d.6e,
1b.2b.3c.4a.5e.6a, 1b.2b.3c.4a.5e.6b, 1b.2b.3c.4a.5e.6c, 1b.2b.3c.4a.5e.6d,
1b.2b.3c.4a.5e.6e, 1b.2b.3c.4b.5a.6a, 1b.2b.3c.4b.5a.6b, 1b.2b.3c.4b.5a.6c,
1b.2b.3c.4b.5a.6d, 1b.2b.3c.4b.5a.6e, 1b.2b.3c.4b.5b.6a, 1b.2b.3c.4b.5b.6b,
1b.2b.3c.4b.5b.6c, 1b.2b.3c.4b.5b.6d, 1b.2b.3c.4b.5b.6e, 1b.2b.3c.4b.5c.6a,
1b.2b.3c.4b.5c.6b, 1b.2b.3c.4b.5c.6c, 1b.2b.3c.4b.5c.6d, 1b.2b.3c.4b.5c.6e,
1b.2b.3c.4b.5d.6a, 1b.2b.3c.4b.5d.6b, 1b.2b.3c.4b.5d.6c, 1b.2b.3c.4b.5d.6d,
1b.2b.3c.4b.5d.6e, 1b.2b.3c.4b.5e.6a, 1b.2b.3c.4b.5e.6b, 1b.2b.3c.4b.5e.6c,
1b.2b.3c.4b.5e.6d, 1b.2b.3c.4b.5e.6e, 1b.2b.3c.4c.5a.6a, 1b.2b.3c.4c.5a.6b,
1b.2b.3c.4c.5a.6c, 1b.2b.3c.4c.5a.6d, 1b.2b.3c.4c.5a.6e, 1b.2b.3c.4c.5b.6a,
1b.2b.3c.4c.5b.6b, 1b.2b.3c.4c.5b.6c, 1b.2b.3c.4c.5b.6d, 1b.2b.3c.4c.5b.6e,
1b.2b.3c.4c.5c.6a, 1b.2b.3c.4c.5c.6b, 1b.2b.3c.4c.5c.6c, 1b.2b.3c.4c.5c.6d,
1b.2b.3c.4c.5c.6e, 1b.2b.3c.4c.5d.6a, 1b.2b.3c.4c.5d.6b, 1b.2b.3c.4c.5d.6c,
1b.2b.3c.4c.5d.6d, 1b.2b.3c.4c.5d.6e, 1b.2b.3c.4c.5e.6a, 1b.2b.3c.4c.5e.6b,
1b.2b.3c.4c.5e.6c, 1b.2b.3c.4c.5e.6d, 1b.2b.3c.4c.5e.6e, 1b.2b.3c.4d.5a.6a,
1b.2b.3c.4d.5a.6b, 1b.2b.3c.4d.5a.6c, 1b.2b.3c.4d.5a.6d, 1b.2b.3c.4d.5a.6e,
1b.2b.3c.4d.5b.6a, 1b.2b.3c.4d.5b.6b, 1b.2b.3c.4d.5b.6c, 1b.2b.3c.4d.5b.6d,
1b.2b.3c.4d.5b.6e, 1b.2b.3c.4d.5c.6a, 1b.2b.3c.4d.5c.6b, 1b.2b.3c.4d.5c.6c,
1b.2b.3c.4d.5c.6d, 1b.2b.3c.4d.5c.6e, 1b.2b.3c.4d.5d.6a, 1b.2b.3c.4d.5d.6b,
1b.2b.3c.4d.5d.6c, 1b.2b.3c.4d.5d.6d, 1b.2b.3c.4d.5d.6e, 1b.2b.3c.4d.5e.6a,
1b.2b.3c.4d.5e.6b, 1b.2b.3c.4d.5e.6c, 1b.2b.3c.4d.5e.6d, 1b.2b.3c.4d.5e.6e,
1b.2b.3c.4e.5a.6a, 1b.2b.3c.4e.5a.6b, 1b.2b.3c.4e.5a.6c, 1b.2b.3c.4e.5a.6d,
1b.2b.3c.4e.5a.6e, 1b.2b.3c.4e.5b.6a, 1b.2b.3c.4e.5b.6b, 1b.2b.3c.4e.5b.6c,
1b.2b.3c.4e.5b.6d, 1b.2b.3c.4e.5b.6e, 1b.2b.3c.4e.5c.6a, 1b.2b.3c.4e.5c.6b,
1b.2b.3c.4e.5c.6c, 1b.2b.3c.4e.5c.6d, 1b.2b.3c.4e.5c.6e, 1b.2b.3c.4e.5d.6a,
1b.2b.3c.4e.5d.6b, 1b.2b.3c.4e.5d.6c, 1b.2b.3c.4e.5d.6d, 1b.2b.3c.4e.5d.6e,
1b.2b.3c.4e.5e.6a, 1b.2b.3c.4e.5e.6b, 1b.2b.3c.4e.5e.6c, 1b.2b.3c.4e.5e.6d,
1b.2b.3c.4e.5e.6e, 1b.2b.3d.4a.5a.6a, 1b.2b.3d.4a.5a.6b, 1b.2b.3d.4a.5a.6c,
1b.2b.3d.4a.5a.6d, 1b.2b.3d.4a.5a.6e, 1b.2b.3d.4a.5b.6a, 1b.2b.3d.4a.5b.6b,
1b.2b.3d.4a.5b.6c, 1b.2b.3d.4a.5b.6d, 1b.2b.3d.4a.5b.6e, 1b.2b.3d.4a.5c.6a,
1b.2b.3d.4a.5c.6b, 1b.2b.3d.4a.5c.6c, 1b.2b.3d.4a.5c.6d, 1b.2b.3d.4a.5c.6e,
1b.2b.3d.4a.5d.6a, 1b.2b.3d.4a.5d.6b, 1b.2b.3d.4a.5d.6c, 1b.2b.3d.4a.5d.6d,
1b.2b.3d.4a.5d.6e, 1b.2b.3d.4a.5e.6a, 1b.2b.3d.4a.5e.6b, 1b.2b.3d.4a.5e.6c,
1b.2b.3d.4a.5e.6d, 1b.2b.3d.4a.5e.6e, 1b.2b.3d.4b.5a.6a, 1b.2b.3d.4b.5a.6b,
1b.2b.3d.4b.5a.6c, 1b.2b.3d.4b.5a.6d, 1b.2b.3d.4b.5a.6e, 1b.2b.3d.4b.5b.6a,
1b.2b.3d.4b.5b.6b, 1b.2b.3d.4b.5b.6c, 1b.2b.3d.4b.5b.6d, 1b.2b.3d.4b.5b.6e,
1b.2b.3d.4b.5c.6a, 1b.2b.3d.4b.5c.6b, 1b.2b.3d.4b.5c.6c, 1b.2b.3d.4b.5c.6d,
1b.2b.3d.4b.5c.6e, 1b.2b.3d.4b.5d.6a, 1b.2b.3d.4b.5d.6b, 1b.2b.3d.4b.5d.6c,
1b.2b.3d.4b.5d.6d, 1b.2b.3d.4b.5d.6e, 1b.2b.3d.4b.5e.6a, 1b.2b.3d.4b.5e.6b,
1b.2b.3d.4b.5e.6c, 1b.2b.3d.4b.5e.6d, 1b.2b.3d.4b.5e.6e, 1b.2b.3d.4c.5a.6a,
1b.2b.3d.4c.5a.6b, 1b.2b.3d.4c.5a.6c, 1b.2b.3d.4c.5a.6d, 1b.2b.3d.4c.5a.6e,
1b.2b.3d.4c.5b.6a, 1b.2b.3d.4c.5b.6b, 1b.2b.3d.4c.5b.6c, 1b.2b.3d.4c.5b.6d,
1b.2b.3d.4c.5b.6e, 1b.2b.3d.4c.5c.6a, 1b.2b.3d.4c.5c.6b, 1b.2b.3d.4c.5c.6c,
1b.2b.3d.4c.5c.6d, 1b.2b.3d.4c.5c.6e, 1b.2b.3d.4c.5d.6a, 1b.2b.3d.4c.5d.6b,
1b.2b.3d.4c.5d.6c, 1b.2b.3d.4c.5d.6d, 1b.2b.3d.4c.5d.6e, 1b.2b.3d.4c.5e.6a,
1b.2b.3d.4c.5e.6b, 1b.2b.3d.4c.5e.6c, 1b.2b.3d.4c.5e.6d, 1b.2b.3d.4c.5e.6e,
1b.2b.3d.4d.5a.6a, 1b.2b.3d.4d.5a.6b, 1b.2b.3d.4d.5a.6c, 1b.2b.3d.4d.5a.6d,
1b.2b.3d.4d.5a.6e, 1b.2b.3d.4d.5b.6a, 1b.2b.3d.4d.5b.6b, 1b.2b.3d.4d.5b.6c,
1b.2b.3d.4d.5b.6d, 1b.2b.3d.4d.5b.6e, 1b.2b.3d.4d.5c.6a, 1b.2b.3d.4d.5c.6b,
1b.2b.3d.4d.5c.6c, 1b.2b.3d.4d.5c.6d, 1b.2b.3d.4d.5c.6e, 1b.2b.3d.4d.5d.6a,
1b.2b.3d.4d.5d.6b, 1b.2b.3d.4d.5d.6c, 1b.2b.3d.4d.5d.6d, 1b.2b.3d.4d.5d.6e,
1b.2b.3d.4d.5e.6a, 1b.2b.3d.4d.5e.6b, 1b.2b.3d.4d.5e.6c, 1b.2b.3d.4d.5e.6d,

TABLE 8-continued

List of Compounds of Formula (II)

1b.2b.3d.4d.5e.6e, 1b.2b.3d.4e.5a.6a, 1b.2b.3d.4e.5a.6b, 1b.2b.3d.4e.5a.6c,
1b.2b.3d.4e.5a.6d, 1b.2b.3d.4e.5a.6e, 1b.2b.3d.4e.5b.6a, 1b.2b.3d.4e.5b.6b,
1b.2b.3d.4e.5b.6c, 1b.2b.3d.4e.5b.6d, 1b.2b.3d.4e.5b.6e, 1b.2b.3d.4e.5c.6a,
1b.2b.3d.4e.5c.6b, 1b.2b.3d.4e.5c.6c, 1b.2b.3d.4e.5c.6d, 1b.2b.3d.4e.5c.6e,
1b.2b.3d.4e.5d.6a, 1b.2b.3d.4e.5d.6b, 1b.2b.3d.4e.5d.6c, 1b.2b.3d.4e.5d.6d,
1b.2b.3d.4e.5d.6e, 1b.2b.3d.4e.5e.6a, 1b.2b.3d.4e.5e.6b, 1b.2b.3d.4e.5e.6c,
1b.2b.3d.4e.5e.6d, 1b.2b.3d.4e.5e.6e, 1b.2b.3e.4a.5a.6a, 1b.2b.3e.4a.5a.6b,
1b.2b.3e.4a.5a.6c, 1b.2b.3e.4a.5a.6d, 1b.2b.3e.4a.5a.6e, 1b.2b.3e.4a.5b.6a,
1b.2b.3e.4a.5b.6b, 1b.2b.3e.4a.5b.6c, 1b.2b.3e.4a.5b.6d, 1b.2b.3e.4a.5b.6e,
1b.2b.3e.4a.5c.6a, 1b.2b.3e.4a.5c.6b, 1b.2b.3e.4a.5c.6c, 1b.2b.3e.4a.5c.6d,
1b.2b.3e.4a.5c.6e, 1b.2b.3e.4a.5d.6a, 1b.2b.3e.4a.5d.6b, 1b.2b.3e.4a.5d.6c,
1b.2b.3e.4a.5d.6d, 1b.2b.3e.4a.5d.6e, 1b.2b.3e.4a.5e.6a, 1b.2b.3e.4a.5e.6b,
1b.2b.3e.4a.5e.6c, 1b.2b.3e.4a.5e.6d, 1b.2b.3e.4a.5e.6e, 1b.2b.3e.4b.5a.6a,
1b.2b.3e.4b.5a.6b, 1b.2b.3e.4b.5a.6c, 1b.2b.3e.4b.5a.6d, 1b.2b.3e.4b.5a.6e,
1b.2b.3e.4b.5b.6a, 1b.2b.3e.4b.5b.6b, 1b.2b.3e.4b.5b.6c, 1b.2b.3e.4b.5b.6d,
1b.2b.3e.4b.5b.6e, 1b.2b.3e.4b.5c.6a, 1b.2b.3e.4b.5c.6b, 1b.2b.3e.4b.5c.6c,
1b.2b.3e.4b.5c.6d, 1b.2b.3e.4b.5c.6e, 1b.2b.3e.4b.5d.6a, 1b.2b.3e.4b.5d.6b,
1b.2b.3e.4b.5d.6c, 1b.2b.3e.4b.5d.6d, 1b.2b.3e.4b.5d.6e, 1b.2b.3e.4b.5e.6a,
1b.2b.3e.4b.5e.6b, 1b.2b.3e.4b.5e.6c, 1b.2b.3e.4b.5e.6d, 1b.2b.3e.4b.5e.6e,
1b.2b.3e.4c.5a.6a, 1b.2b.3e.4c.5a.6b, 1b.2b.3e.4c.5a.6c, 1b.2b.3e.4c.5a.6d,
1b.2b.3e.4c.5a.6e, 1b.2b.3e.4c.5b.6a, 1b.2b.3e.4c.5b.6b, 1b.2b.3e.4c.5b.6c,
1b.2b.3e.4c.5b.6d, 1b.2b.3e.4c.5b.6e, 1b.2b.3e.4c.5c.6a, 1b.2b.3e.4c.5c.6b,
1b.2b.3e.4c.5c.6c, 1b.2b.3e.4c.5c.6d, 1b.2b.3e.4c.5c.6e, 1b.2b.3e.4c.5d.6a,
1b.2b.3e.4c.5d.6b, 1b.2b.3e.4c.5d.6c, 1b.2b.3e.4c.5d.6d, 1b.2b.3e.4c.5d.6e,
1b.2b.3e.4c.5e.6a, 1b.2b.3e.4c.5e.6b, 1b.2b.3e.4c.5e.6c, 1b.2b.3e.4c.5e.6d,
1b.2b.3e.4c.5e.6e, 1b.2b.3e.4d.5a.6a, 1b.2b.3e.4d.5a.6b, 1b.2b.3e.4d.5a.6c,
1b.2b.3e.4d.5a.6d, 1b.2b.3e.4d.5a.6e, 1b.2b.3e.4d.5b.6a, 1b.2b.3e.4d.5b.6b,
1b.2b.3e.4d.5b.6c, 1b.2b.3e.4d.5b.6d, 1b.2b.3e.4d.5b.6e, 1b.2b.3e.4d.5c.6a,
1b.2b.3e.4d.5c.6b, 1b.2b.3e.4d.5c.6c, 1b.2b.3e.4d.5c.6d, 1b.2b.3e.4d.5c.6e,
1b.2b.3e.4d.5d.6a, 1b.2b.3e.4d.5d.6b, 1b.2b.3e.4d.5d.6c, 1b.2b.3e.4d.5d.6d,
1b.2b.3e.4d.5d.6e, 1b.2b.3e.4d.5e.6a, 1b.2b.3e.4d.5e.6b, 1b.2b.3e.4d.5e.6c,
1b.2b.3e.4d.5e.6d, 1b.2b.3e.4d.5e.6e, 1b.2b.3e.4e.5a.6a, 1b.2b.3e.4e.5a.6b,
1b.2b.3e.4e.5a.6c, 1b.2b.3e.4e.5a.6d, 1b.2b.3e.4e.5a.6e, 1b.2b.3e.4e.5b.6a,
1b.2b.3e.4e.5b.6b, 1b.2b.3e.4e.5b.6c, 1b.2b.3e.4e.5b.6d, 1b.2b.3e.4e.5b.6e,
1b.2b.3e.4e.5c.6a, 1b.2b.3e.4e.5c.6b, 1b.2b.3e.4e.5c.6c, 1b.2b.3e.4e.5c.6d,
1b.2b.3e.4e.5c.6e, 1b.2b.3e.4e.5d.6a, 1b.2b.3e.4e.5d.6b, 1b.2b.3e.4e.5d.6c,
1b.2b.3e.4e.5d.6d, 1b.2b.3e.4e.5d.6e, 1b.2b.3e.4e.5e.6a, 1b.2b.3e.4e.5e.6b,
1b.2b.3e.4e.5e.6c, 1b.2b.3e.4e.5e.6d, 1b.2b.3e.4e.5e.6e, 1b.2c.3a.4a.5a.6a,
1b.2c.3a.4a.5a.6b, 1b.2c.3a.4a.5a.6c, 1b.2c.3a.4a.5a.6d, 1b.2c.3a.4a.5a.6e,
1b.2c.3a.4a.5b.6a, 1b.2c.3a.4a.5b.6b, 1b.2c.3a.4a.5b.6c, 1b.2c.3a.4a.5b.6d,
1b.2c.3a.4a.5b.6e, 1b.2c.3a.4a.5c.6a, 1b.2c.3a.4a.5c.6b, 1b.2c.3a.4a.5c.6c,
1b.2c.3a.4a.5c.6d, 1b.2c.3a.4a.5c.6e, 1b.2c.3a.4a.5d.6a, 1b.2c.3a.4a.5d.6b,
1b.2c.3a.4a.5d.6c, 1b.2c.3a.4a.5d.6d, 1b.2c.3a.4a.5d.6e, 1b.2c.3a.4a.5e.6a,
1b.2c.3a.4a.5e.6b, 1b.2c.3a.4a.5e.6c, 1b.2c.3a.4a.5e.6d, 1b.2c.3a.4a.5e.6e,
1b.2c.3a.4b.5a.6a, 1b.2c.3a.4b.5a.6b, 1b.2c.3a.4b.5a.6c, 1b.2c.3a.4b.5a.6d,
1b.2c.3a.4b.5a.6e, 1b.2c.3a.4b.5b.6a, 1b.2c.3a.4b.5b.6b, 1b.2c.3a.4b.5b.6c,
1b.2c.3a.4b.5b.6d, 1b.2c.3a.4b.5b.6e, 1b.2c.3a.4b.5c.6a, 1b.2c.3a.4b.5c.6b,
1b.2c.3a.4b.5c.6c, 1b.2c.3a.4b.5c.6d, 1b.2c.3a.4b.5c.6e, 1b.2c.3a.4b.5d.6a,
1b.2c.3a.4b.5d.6b, 1b.2c.3a.4b.5d.6c, 1b.2c.3a.4b.5d.6d, 1b.2c.3a.4b.5d.6e,
1b.2c.3a.4b.5e.6a, 1b.2c.3a.4b.5e.6b, 1b.2c.3a.4b.5e.6c, 1b.2c.3a.4b.5e.6d,
1b.2c.3a.4b.5e.6e, 1b.2c.3a.4c.5a.6a, 1b.2c.3a.4c.5a.6b, 1b.2c.3a.4c.5a.6c,
1b.2c.3a.4c.5a.6d, 1b.2c.3a.4c.5a.6e, 1b.2c.3a.4c.5b.6a, 1b.2c.3a.4c.5b.6b,
1b.2c.3a.4c.5b.6c, 1b.2c.3a.4c.5b.6d, 1b.2c.3a.4c.5b.6e, 1b.2c.3a.4c.5c.6a,
1b.2c.3a.4c.5c.6b, 1b.2c.3a.4c.5c.6c, 1b.2c.3a.4c.5c.6d, 1b.2c.3a.4c.5c.6e,
1b.2c.3a.4c.5d.6a, 1b.2c.3a.4c.5d.6b, 1b.2c.3a.4c.5d.6c, 1b.2c.3a.4c.5d.6d,
1b.2c.3a.4c.5d.6e, 1b.2c.3a.4c.5e.6a, 1b.2c.3a.4c.5e.6b, 1b.2c.3a.4c.5e.6c,
1b.2c.3a.4c.5e.6d, 1b.2c.3a.4c.5e.6e, 1b.2c.3a.4d.5a.6a, 1b.2c.3a.4d.5a.6b,
1b.2c.3a.4d.5a.6c, 1b.2c.3a.4d.5a.6d, 1b.2c.3a.4d.5a.6e, 1b.2c.3a.4d.5b.6a,
1b.2c.3a.4d.5b.6b, 1b.2c.3a.4d.5b.6c, 1b.2c.3a.4d.5b.6d, 1b.2c.3a.4d.5b.6e,
1b.2c.3a.4d.5c.6a, 1b.2c.3a.4d.5c.6b, 1b.2c.3a.4d.5c.6c, 1b.2c.3a.4d.5c.6d,
1b.2c.3a.4d.5c.6e, 1b.2c.3a.4d.5d.6a, 1b.2c.3a.4d.5d.6b, 1b.2c.3a.4d.5d.6c,
1b.2c.3a.4d.5d.6d, 1b.2c.3a.4d.5d.6e, 1b.2c.3a.4d.5e.6a, 1b.2c.3a.4d.5e.6b,
1b.2c.3a.4d.5e.6c, 1b.2c.3a.4d.5e.6d, 1b.2c.3a.4d.5e.6e, 1b.2c.3a.4e.5a.6a,
1b.2c.3a.4e.5a.6b, 1b.2c.3a.4e.5a.6c, 1b.2c.3a.4e.5a.6d, 1b.2c.3a.4e.5a.6e,
1b.2c.3a.4e.5b.6a, 1b.2c.3a.4e.5b.6b, 1b.2c.3a.4e.5b.6c, 1b.2c.3a.4e.5b.6d,
1b.2c.3a.4e.5b.6e, 1b.2c.3a.4e.5c.6a, 1b.2c.3a.4e.5c.6b, 1b.2c.3a.4e.5c.6c,
1b.2c.3a.4e.5c.6d, 1b.2c.3a.4e.5c.6e, 1b.2c.3a.4e.5d.6a, 1b.2c.3a.4e.5d.6b,
1b.2c.3a.4e.5d.6c, 1b.2c.3a.4e.5d.6d, 1b.2c.3a.4e.5d.6e, 1b.2c.3a.4e.5e.6a,
1b.2c.3a.4e.5e.6b, 1b.2c.3a.4e.5e.6c, 1b.2c.3a.4e.5e.6d, 1b.2c.3a.4e.5e.6e,
1b.2c.3b.4a.5a.6a, 1b.2c.3b.4a.5a.6b, 1b.2c.3b.4a.5a.6c, 1b.2c.3b.4a.5a.6d,
1b.2c.3b.4a.5a.6e, 1b.2c.3b.4a.5b.6a, 1b.2c.3b.4a.5b.6b, 1b.2c.3b.4a.5b.6c,
1b.2c.3b.4a.5b.6d, 1b.2c.3b.4a.5b.6e, 1b.2c.3b.4a.5c.6a, 1b.2c.3b.4a.5c.6b,
1b.2c.3b.4a.5c.6c, 1b.2c.3b.4a.5c.6d, 1b.2c.3b.4a.5c.6e, 1b.2c.3b.4a.5d.6a,
1b.2c.3b.4a.5d.6b, 1b.2c.3b.4a.5d.6c, 1b.2c.3b.4a.5d.6d, 1b.2c.3b.4a.5d.6e,
1b.2c.3b.4a.5e.6a, 1b.2c.3b.4a.5e.6b, 1b.2c.3b.4a.5e.6c, 1b.2c.3b.4a.5e.6d,
1b.2c.3b.4a.5e.6e, 1b.2c.3b.4b.5a.6a, 1b.2c.3b.4b.5a.6b, 1b.2c.3b.4b.5a.6c,
1b.2c.3b.4b.5a.6d, 1b.2c.3b.4b.5a.6e, 1b.2c.3b.4b.5b.6a, 1b.2c.3b.4b.5b.6b,
1b.2c.3b.4b.5b.6c, 1b.2c.3b.4b.5b.6d, 1b.2c.3b.4b.5b.6e, 1b.2c.3b.4b.5c.6a,

TABLE 8-continued

List of Compounds of Formula (II)

1b.2c.3b.4b.5c.6b, 1b.2c.3b.4b.5c.6c, 1b.2c.3b.4b.5c.6d, 1b.2c.3b.4b.5c.6e,
1b.2c.3b.4b.5d.6a, 1b.2c.3b.4b.5d.6b, 1b.2c.3b.4b.5d.6c, 1b.2c.3b.4b.5d.6d,
1b.2c.3b.4b.5d.6e, 1b.2c.3b.4b.5e.6a, 1b.2c.3b.4b.5e.6b, 1b.2c.3b.4b.5e.6c,
1b.2c.3b.4b.5e.6d, 1b.2c.3b.4b.5e.6e, 1b.2c.3b.4c.5a.6a, 1b.2c.3b.4c.5a.6b,
1b.2c.3b.4c.5a.6c, 1b.2c.3b.4c.5a.6d, 1b.2c.3b.4c.5a.6e, 1b.2c.3b.4c.5b.6a,
1b.2c.3b.4c.5b.6b, 1b.2c.3b.4c.5b.6c, 1b.2c.3b.4c.5b.6d, 1b.2c.3b.4c.5b.6e,
1b.2c.3b.4c.5c.6a, 1b.2c.3b.4c.5c.6b, 1b.2c.3b.4c.5c.6c, 1b.2c.3b.4c.5c.6d,
1b.2c.3b.4c.5c.6e, 1b.2c.3b.4c.5d.6a, 1b.2c.3b.4c.5d.6b, 1b.2c.3b.4c.5d.6c,
1b.2c.3b.4c.5d.6d, 1b.2c.3b.4c.5d.6e, 1b.2c.3b.4c.5e.6a, 1b.2c.3b.4c.5e.6b,
1b.2c.3b.4c.5e.6c, 1b.2c.3b.4c.5e.6d, 1b.2c.3b.4c.5e.6e, 1b.2c.3b.4d.5a.6a,
1b.2c.3b.4d.5a.6b, 1b.2c.3b.4d.5a.6c, 1b.2c.3b.4d.5a.6d, 1b.2c.3b.4d.5a.6e,
1b.2c.3b.4d.5b.6a, 1b.2c.3b.4d.5b.6b, 1b.2c.3b.4d.5b.6c, 1b.2c.3b.4d.5b.6d,
1b.2c.3b.4d.5b.6e, 1b.2c.3b.4d.5c.6a, 1b.2c.3b.4d.5c.6b, 1b.2c.3b.4d.5c.6c,
1b.2c.3b.4d.5c.6d, 1b.2c.3b.4d.5c.6e, 1b.2c.3b.4d.5d.6a, 1b.2c.3b.4d.5d.6b,
1b.2c.3b.4d.5d.6c, 1b.2c.3b.4d.5d.6d, 1b.2c.3b.4d.5d.6e, 1b.2c.3b.4d.5e.6a,
1b.2c.3b.4d.5e.6b, 1b.2c.3b.4d.5e.6c, 1b.2c.3b.4d.5e.6d, 1b.2c.3b.4d.5e.6e,
1b.2c.3b.4e.5a.6a, 1b.2c.3b.4e.5a.6b, 1b.2c.3b.4e.5a.6c, 1b.2c.3b.4e.5a.6d,
1b.2c.3b.4e.5a.6e, 1b.2c.3b.4e.5b.6a, 1b.2c.3b.4e.5b.6b, 1b.2c.3b.4e.5b.6c,
1b.2c.3b.4e.5b.6d, 1b.2c.3b.4e.5b.6e, 1b.2c.3b.4e.5c.6a, 1b.2c.3b.4e.5c.6b,
1b.2c.3b.4e.5c.6c, 1b.2c.3b.4e.5c.6d, 1b.2c.3b.4e.5c.6e, 1b.2c.3b.4e.5d.6a,
1b.2c.3b.4e.5d.6b, 1b.2c.3b.4e.5d.6c, 1b.2c.3b.4e.5d.6d, 1b.2c.3b.4e.5d.6e,
1b.2c.3b.4e.5e.6a, 1b.2c.3b.4e.5e.6b, 1b.2c.3b.4e.5e.6c, 1b.2c.3b.4e.5e.6d,
1b.2c.3b.4e.5e.6e, 1b.2c.3c.4a.5a.6a, 1b.2c.3c.4a.5a.6b, 1b.2c.3c.4a.5a.6c,
1b.2c.3c.4a.5a.6d, 1b.2c.3c.4a.5a.6e, 1b.2c.3c.4a.5b.6a, 1b.2c.3c.4a.5b.6b,
1b.2c.3c.4a.5b.6c, 1b.2c.3c.4a.5b.6d, 1b.2c.3c.4a.5b.6e, 1b.2c.3c.4a.5c.6a,
1b.2c.3c.4a.5c.6b, 1b.2c.3c.4a.5c.6c, 1b.2c.3c.4a.5c.6d, 1b.2c.3c.4a.5c.6e,
1b.2c.3c.4a.5d.6a, 1b.2c.3c.4a.5d.6b, 1b.2c.3c.4a.5d.6c, 1b.2c.3c.4a.5d.6d,
1b.2c.3c.4a.5d.6e, 1b.2c.3c.4a.5e.6a, 1b.2c.3c.4a.5e.6b, 1b.2c.3c.4a.5e.6c,
1b.2c.3c.4a.5e.6d, 1b.2c.3c.4a.5e.6e, 1b.2c.3c.4b.5a.6a, 1b.2c.3c.4b.5a.6b,
1b.2c.3c.4b.5a.6c, 1b.2c.3c.4b.5a.6d, 1b.2c.3c.4b.5a.6e, 1b.2c.3c.4b.5b.6a,
1b.2c.3c.4b.5b.6b, 1b.2c.3c.4b.5b.6c, 1b.2c.3c.4b.5b.6d, 1b.2c.3c.4b.5b.6e,
1b.2c.3c.4b.5c.6a, 1b.2c.3c.4b.5c.6b, 1b.2c.3c.4b.5c.6c, 1b.2c.3c.4b.5c.6d,
1b.2c.3c.4b.5c.6e, 1b.2c.3c.4b.5d.6a, 1b.2c.3c.4b.5d.6b, 1b.2c.3c.4b.5d.6c,
1b.2c.3c.4b.5d.6d, 1b.2c.3c.4b.5d.6e, 1b.2c.3c.4b.5e.6a, 1b.2c.3c.4b.5e.6b,
1b.2c.3c.4b.5e.6c, 1b.2c.3c.4b.5e.6d, 1b.2c.3c.4b.5e.6e, 1b.2c.3c.4c.5a.6a,
1b.2c.3c.4c.5a.6b, 1b.2c.3c.4c.5a.6c, 1b.2c.3c.4c.5a.6d, 1b.2c.3c.4c.5a.6e,
1b.2c.3c.4c.5b.6a, 1b.2c.3c.4c.5b.6b, 1b.2c.3c.4c.5b.6c, 1b.2c.3c.4c.5b.6d,
1b.2c.3c.4c.5b.6e, 1b.2c.3c.4c.5c.6a, 1b.2c.3c.4c.5c.6b, 1b.2c.3c.4c.5c.6c,
1b.2c.3c.4c.5c.6d, 1b.2c.3c.4c.5c.6e, 1b.2c.3c.4c.5d.6a, 1b.2c.3c.4c.5d.6b,
1b.2c.3c.4c.5d.6c, 1b.2c.3c.4c.5d.6d, 1b.2c.3c.4c.5d.6e, 1b.2c.3c.4c.5e.6a,
1b.2c.3c.4c.5e.6b, 1b.2c.3c.4c.5e.6c, 1b.2c.3c.4c.5e.6d, 1b.2c.3c.4c.5e.6e,
1b.2c.3c.4d.5a.6a, 1b.2c.3c.4d.5a.6b, 1b.2c.3c.4d.5a.6c, 1b.2c.3c.4d.5a.6d,
1b.2c.3c.4d.5a.6e, 1b.2c.3c.4d.5b.6a, 1b.2c.3c.4d.5b.6b, 1b.2c.3c.4d.5b.6c,
1b.2c.3c.4d.5b.6d, 1b.2c.3c.4d.5b.6e, 1b.2c.3c.4d.5c.6a, 1b.2c.3c.4d.5c.6b,
1b.2c.3c.4d.5c.6c, 1b.2c.3c.4d.5c.6d, 1b.2c.3c.4d.5c.6e, 1b.2c.3c.4d.5d.6a,
1b.2c.3c.4d.5d.6b, 1b.2c.3c.4d.5d.6c, 1b.2c.3c.4d.5d.6d, 1b.2c.3c.4d.5d.6e,
1b.2c.3c.4d.5e.6a, 1b.2c.3c.4d.5e.6b, 1b.2c.3c.4d.5e.6c, 1b.2c.3c.4d.5e.6d,
1b.2c.3c.4d.5e.6e, 1b.2c.3c.4e.5a.6a, 1b.2c.3c.4e.5a.6b, 1b.2c.3c.4e.5a.6c,
1b.2c.3c.4e.5a.6d, 1b.2c.3c.4e.5a.6e, 1b.2c.3c.4e.5b.6a, 1b.2c.3c.4e.5b.6b,
1b.2c.3c.4e.5b.6c, 1b.2c.3c.4e.5b.6d, 1b.2c.3c.4e.5b.6e, 1b.2c.3c.4e.5c.6a,
1b.2c.3c.4e.5c.6b, 1b.2c.3c.4e.5c.6c, 1b.2c.3c.4e.5c.6d, 1b.2c.3c.4e.5c.6e,
1b.2c.3c.4e.5d.6a, 1b.2c.3c.4e.5d.6b, 1b.2c.3c.4e.5d.6c, 1b.2c.3c.4e.5d.6d,
1b.2c.3c.4e.5d.6e, 1b.2c.3c.4e.5e.6a, 1b.2c.3c.4e.5e.6b, 1b.2c.3c.4e.5e.6c,
1b.2c.3c.4e.5e.6d, 1b.2c.3c.4e.5e.6e, 1b.2c.3d.4a.5a.6a, 1b.2c.3d.4a.5a.6b,
1b.2c.3d.4a.5a.6c, 1b.2c.3d.4a.5a.6d, 1b.2c.3d.4a.5a.6e, 1b.2c.3d.4a.5b.6a,
1b.2c.3d.4a.5b.6b, 1b.2c.3d.4a.5b.6c, 1b.2c.3d.4a.5b.6d, 1b.2c.3d.4a.5b.6e,
1b.2c.3d.4a.5c.6a, 1b.2c.3d.4a.5c.6b, 1b.2c.3d.4a.5c.6c, 1b.2c.3d.4a.5c.6d,
1b.2c.3d.4a.5c.6e, 1b.2c.3d.4a.5d.6a, 1b.2c.3d.4a.5d.6b, 1b.2c.3d.4a.5d.6c,
1b.2c.3d.4a.5d.6d, 1b.2c.3d.4a.5d.6e, 1b.2c.3d.4a.5e.6a, 1b.2c.3d.4a.5e.6b,
1b.2c.3d.4a.5e.6c, 1b.2c.3d.4a.5e.6d, 1b.2c.3d.4a.5e.6e, 1b.2c.3d.4b.5a.6a,
1b.2c.3d.4b.5a.6b, 1b.2c.3d.4b.5a.6c, 1b.2c.3d.4b.5a.6d, 1b.2c.3d.4b.5a.6e,
1b.2c.3d.4b.5b.6a, 1b.2c.3d.4b.5b.6b, 1b.2c.3d.4b.5b.6c, 1b.2c.3d.4b.5b.6d,
1b.2c.3d.4b.5b.6e, 1b.2c.3d.4b.5c.6a, 1b.2c.3d.4b.5c.6b, 1b.2c.3d.4b.5c.6c,
1b.2c.3d.4b.5c.6d, 1b.2c.3d.4b.5c.6e, 1b.2c.3d.4b.5d.6a, 1b.2c.3d.4b.5d.6b,
1b.2c.3d.4b.5d.6c, 1b.2c.3d.4b.5d.6d, 1b.2c.3d.4b.5d.6e, 1b.2c.3d.4b.5e.6a,
1b.2c.3d.4b.5e.6b, 1b.2c.3d.4b.5e.6c, 1b.2c.3d.4b.5e.6d, 1b.2c.3d.4b.5e.6e,
1b.2c.3d.4c.5a.6a, 1b.2c.3d.4c.5a.6b, 1b.2c.3d.4c.5a.6c, 1b.2c.3d.4c.5a.6d,
1b.2c.3d.4c.5a.6e, 1b.2c.3d.4c.5b.6a, 1b.2c.3d.4c.5b.6b, 1b.2c.3d.4c.5b.6c,
1b.2c.3d.4c.5b.6d, 1b.2c.3d.4c.5b.6e, 1b.2c.3d.4c.5c.6a, 1b.2c.3d.4c.5c.6b,
1b.2c.3d.4c.5c.6c, 1b.2c.3d.4c.5c.6d, 1b.2c.3d.4c.5c.6e, 1b.2c.3d.4c.5d.6a,
1b.2c.3d.4c.5d.6b, 1b.2c.3d.4c.5d.6c, 1b.2c.3d.4c.5d.6d, 1b.2c.3d.4c.5d.6e,
1b.2c.3d.4c.5e.6a, 1b.2c.3d.4c.5e.6b, 1b.2c.3d.4c.5e.6c, 1b.2c.3d.4c.5e.6d,
1b.2c.3d.4c.5e.6e, 1b.2c.3d.4d.5a.6a, 1b.2c.3d.4d.5a.6b, 1b.2c.3d.4d.5a.6c,
1b.2c.3d.4d.5a.6d, 1b.2c.3d.4c.5a.6e, 1b.2c.3d.4d.5b.6a, 1b.2c.3d.4d.5b.6b,
1b.2c.3d.4d.5b.6c, 1b.2c.3d.4d.5b.6d, 1b.2c.3d.4d.5b.6e, 1b.2c.3d.4d.5c.6a,
1b.2c.3d.4d.5c.6b, 1b.2c.3d.4d.5c.6c, 1b.2c.3d.4d.5c.6d, 1b.2c.3d.4d.5c.6e,
1b.2c.3d.4d.5d.6a, 1b.2c.3d.4d.5d.6b, 1b.2c.3d.4d.5d.6c, 1b.2c.3d.4d.5d.6d,
1b.2c.3d.4d.5d.6e, 1b.2c.3d.4d.5e.6a, 1b.2c.3d.4d.5e.6b, 1b.2c.3d.4d.5e.6c,

TABLE 8-continued

List of Compounds of Formula (II)

1b.2c.3d.4d.5e.6d, 1b.2c.3d.4d.5e.6e, 1b.2c.3d.4e.5a.6a, 1b.2c.3d.4e.5a.6b,
1b.2c.3d.4e.5a.6c, 1b.2c.3d.4e.5a.6d, 1b.2c.3d.4e.5a.6e, 1b.2c.3d.4e.5b.6a,
1b.2c.3d.4e.5b.6b, 1b.2c.3d.4e.5b.6c, 1b.2c.3d.4e.5b.6d, 1b.2c.3d.4e.5b.6e,
1b.2c.3d.4e.5c.6a, 1b.2c.3d.4e.5c.6b, 1b.2c.3d.4e.5c.6c, 1b.2c.3d.4e.5c.6d,
1b.2c.3d.4e.5c.6e, 1b.2c.3d.4e.5d.6a, 1b.2c.3d.4e.5d.6b, 1b.2c.3d.4e.5d.6c,
1b.2c.3d.4e.5d.6d, 1b.2c.3d.4e.5d.6e, 1b.2c.3d.4e.5e.6a, 1b.2c.3d.4e.5e.6b,
1b.2c.3d.4e.5e.6c, 1b.2c.3d.4e.5e.6d, 1b.2c.3d.4e.5e.6e, 1b.2c.3e.4a.5a.6a,
1b.2c.3e.4a.5a.6b, 1b.2c.3e.4a.5a.6c, 1b.2c.3e.4a.5a.6d, 1b.2c.3e.4a.5a.6e,
1b.2c.3e.4a.5b.6a, 1b.2c.3e.4a.5b.6b, 1b.2c.3e.4a.5b.6c, 1b.2c.3e.4a.5b.6d,
1b.2c.3e.4a.5b.6e, 1b.2c.3e.4a.5c.6a, 1b.2c.3e.4a.5c.6b, 1b.2c.3e.4a.5c.6c,
1b.2c.3e.4a.5c.6d, 1b.2c.3e.4a.5c.6e, 1b.2c.3e.4a.5d.6a, 1b.2c.3e.4a.5d.6b,
1b.2c.3e.4a.5d.6c, 1b.2c.3e.4a.5d.6d, 1b.2c.3e.4a.5d.6e, 1b.2c.3e.4a.5e.6a,
1b.2c.3e.4a.5e.6b, 1b.2c.3e.4a.5e.6c, 1b.2c.3e.4a.5e.6d, 1b.2c.3e.4a.5e.6e,
1b.2c.3e.4b.5a.6a, 1b.2c.3e.4b.5a.6b, 1b.2c.3e.4b.5a.6c, 1b.2c.3e.4b.5a.6d,
1b.2c.3e.4b.5a.6e, 1b.2c.3e.4b.5b.6a, 1b.2c.3e.4b.5b.6b, 1b.2c.3e.4b.5b.6c,
1b.2c.3e.4b.5b.6d, 1b.2c.3e.4b.5b.6e, 1b.2c.3e.4b.5c.6a, 1b.2c.3e.4b.5c.6b,
1b.2c.3e.4b.5c.6c, 1b.2c.3e.4b.5c.6d, 1b.2c.3e.4b.5c.6e, 1b.2c.3e.4b.5d.6a,
1b.2c.3e.4b.5d.6b, 1b.2c.3e.4b.5d.6c, 1b.2c.3e.4b.5d.6d, 1b.2c.3e.4b.5d.6e,
1b.2c.3e.4b.5e.6a, 1b.2c.3e.4b.5e.6b, 1b.2c.3e.4b.5e.6c, 1b.2c.3e.4b.5e.6d,
1b.2c.3e.4b.5e.6e, 1b.2c.3e.4c.5a.6a, 1b.2c.3e.4c.5a.6b, 1b.2c.3e.4c.5a.6c,
1b.2c.3e.4c.5a.6d, 1b.2c.3e.4c.5a.6e, 1b.2c.3e.4c.5b.6a, 1b.2c.3e.4c.5b.6b,
1b.2c.3e.4c.5b.6c, 1b.2c.3e.4c.5b.6d, 1b.2c.3e.4c.5b.6e, 1b.2c.3e.4c.5c.6a,
1b.2c.3e.4c.5c.6b, 1b.2c.3e.4c.5c.6c, 1b.2c.3e.4c.5c.6d, 1b.2c.3e.4c.5c.6e,
1b.2c.3e.4c.5d.6a, 1b.2c.3e.4c.5d.6b, 1b.2c.3e.4c.5d.6c, 1b.2c.3e.4c.5d.6d,
1b.2c.3e.4c.5d.6e, 1b.2c.3e.4c.5e.6a, 1b.2c.3e.4c.5e.6b, 1b.2c.3e.4c.5e.6c,
1b.2c.3e.4c.5e.6d, 1b.2c.3e.4c.5e.6e, 1b.2c.3e.4d.5a.6a, 1b.2c.3e.4d.5a.6b,
1b.2c.3e.4d.5a.6c, 1b.2c.3e.4d.5a.6d, 1b.2c.3e.4d.5a.6e, 1b.2c.3e.4d.5b.6a,
1b.2c.3e.4d.5b.6b, 1b.2c.3e.4d.5b.6c, 1b.2c.3e.4d.5b.6d, 1b.2c.3e.4d.5b.6e,
1b.2c.3e.4d.5c.6a, 1b.2c.3e.4d.5c.6b, 1b.2c.3e.4d.5c.6c, 1b.2c.3e.4d.5c.6d,
1b.2c.3e.4d.5c.6e, 1b.2c.3e.4d.5d.6a, 1b.2c.3e.4d.5d.6b, 1b.2c.3e.4d.5d.6c,
1b.2c.3e.4d.5d.6d, 1b.2c.3e.4d.5d.6e, 1b.2c.3e.4d.5e.6a, 1b.2c.3e.4d.5e.6b,
1b.2c.3e.4d.5e.6c, 1b.2c.3e.4d.5e.6d, 1b.2c.3e.4d.5e.6e, 1b.2c.3e.4e.5a.6a,
1b.2c.3e.4e.5a.6b, 1b.2c.3e.4e.5a.6c, 1b.2c.3e.4e.5a.6d, 1b.2c.3e.4e.5a.6e,
1b.2c.3e.4e.5b.6a, 1b.2c.3e.4e.5b.6b, 1b.2c.3e.4e.5b.6c, 1b.2c.3e.4e.5b.6d,
1b.2c.3e.4e.5b.6e, 1b.2c.3e.4e.5c.6a, 1b.2c.3e.4e.5c.6b, 1b.2c.3e.4e.5c.6c,
1b.2c.3e.4e.5c.6d, 1b.2c.3e.4e.5c.6e, 1b.2c.3e.4e.5d.6a, 1b.2c.3e.4e.5d.6b,
1b.2c.3e.4e.5d.6c, 1b.2c.3e.4e.5d.6d, 1b.2c.3e.4e.5d.6e, 1b.2c.3e.4e.5e.6a,
1b.2c.3e.4e.5e.6b, 1b.2c.3e.4e.5e.6c, 1b.2c.3e.4e.5e.6d, 1b.2c.3e.4e.5e.6e,
1b.2d.3a.4a.5a.6a, 1b.2d.3a.4a.5a.6b, 1b.2d.3a.4a.5a.6c, 1b.2d.3a.4a.5a.6d,
1b.2d.3a.4a.5a.6e, 1b.2d.3a.4a.5b.6a, 1b.2d.3a.4a.5b.6b, 1b.2d.3a.4a.5b.6c,
1b.2d.3a.4a.5b.6d, 1b.2d.3a.4a.5b.6e, 1b.2d.3a.4a.5c.6a, 1b.2d.3a.4a.5c.6b,
1b.2d.3a.4a.5c.6c, 1b.2d.3a.4a.5c.6d, 1b.2d.3a.4a.5c.6e, 1b.2d.3a.4a.5d.6a,
1b.2d.3a.4a.5d.6b, 1b.2d.3a.4a.5d.6c, 1b.2d.3a.4a.5d.6d, 1b.2d.3a.4a.5d.6e,
1b.2d.3a.4a.5e.6a, 1b.2d.3a.4a.5e.6b, 1b.2d.3a.4a.5e.6c, 1b.2d.3a.4a.5e.6d,
1b.2d.3a.4a.5e.6e, 1b.2d.3a.4b.5a.6a, 1b.2d.3a.4b.5a.6b, 1b.2d.3a.4b.5a.6c,
1b.2d.3a.4b.5a.6d, 1b.2d.3a.4b.5a.6e, 1b.2d.3a.4b.5b.6a, 1b.2d.3a.4b.5b.6b,
1b.2d.3a.4b.5b.6c, 1b.2d.3a.4b.5b.6d, 1b.2d.3a.4b.5b.6e, 1b.2d.3a.4b.5c.6a,
1b.2d.3a.4b.5c.6b, 1b.2d.3a.4b.5c.6c, 1b.2d.3a.4b.5c.6d, 1b.2d.3a.4b.5c.6e,
1b.2d.3a.4b.5d.6a, 1b.2d.3a.4b.5d.6b, 1b.2d.3a.4b.5d.6c, 1b.2d.3a.4b.5d.6d,
1b.2d.3a.4b.5d.6e, 1b.2d.3a.4b.5e.6a, 1b.2d.3a.4b.5e.6b, 1b.2d.3a.4b.5e.6c,
1b.2d.3a.4b.5e.6d, 1b.2d.3a.4b.5e.6e, 1b.2d.3a.4c.5a.6a, 1b.2d.3a.4c.5a.6b,
1b.2d.3a.4c.5a.6c, 1b.2d.3a.4c.5a.6d, 1b.2d.3a.4c.5a.6e, 1b.2d.3a.4c.5b.6a,
1b.2d.3a.4c.5b.6b, 1b.2d.3a.4c.5b.6c, 1b.2d.3a.4c.5b.6d, 1b.2d.3a.4c.5b.6e,
1b.2d.3a.4c.5c.6a, 1b.2d.3a.4c.5c.6b, 1b.2d.3a.4c.5c.6c, 1b.2d.3a.4c.5c.6d,
1b.2d.3a.4c.5c.6e, 1b.2d.3a.4c.5d.6a, 1b.2d.3a.4c.5d.6b, 1b.2d.3a.4c.5d.6c,
1b.2d.3a.4c.5d.6d, 1b.2d.3a.4c.5d.6e, 1b.2d.3a.4c.5e.6a, 1b.2d.3a.4c.5e.6b,
1b.2d.3a.4c.5e.6c, 1b.2d.3a.4c.5e.6d, 1b.2d.3a.4c.5e.6e, 1b.2d.3a.4d.5a.6a,
1b.2d.3a.4d.5a.6b, 1b.2d.3a.4d.5a.6c, 1b.2d.3a.4d.5a.6d, 1b.2d.3a.4d.5a.6e,
1b.2d.3a.4d.5b.6a, 1b.2d.3a.4d.5b.6b, 1b.2d.3a.4d.5b.6c, 1b.2d.3a.4d.5b.6d,
1b.2d.3a.4d.5b.6e, 1b.2d.3a.4d.5c.6a, 1b.2d.3a.4d.5c.6b, 1b.2d.3a.4d.5c.6c,
1b.2d.3a.4d.5c.6d, 1b.2d.3a.4d.5c.6e, 1b.2d.3a.4d.5d.6a, 1b.2d.3a.4d.5d.6b,
1b.2d.3a.4d.5d.6c, 1b.2d.3a.4d.5d.6d, 1b.2d.3a.4d.5d.6e, 1b.2d.3a.4d.5e.6a,
1b.2d.3a.4d.5e.6b, 1b.2d.3a.4d.5e.6c, 1b.2d.3a.4d.5e.6d, 1b.2d.3a.4d.5e.6e,
1b.2d.3a.4e.5a.6a, 1b.2d.3a.4e.5a.6b, 1b.2d.3a.4e.5a.6c, 1b.2d.3a.4e.5a.6d,
1b.2d.3a.4e.5a.6e, 1b.2d.3a.4e.5b.6a, 1b.2d.3a.4e.5b.6b, 1b.2d.3a.4e.5b.6c,
1b.2d.3a.4e.5b.6d, 1b.2d.3a.4e.5b.6e, 1b.2d.3a.4e.5c.6a, 1b.2d.3a.4e.5c.6b,
1b.2d.3a.4e.5c.6c, 1b.2d.3a.4e.5c.6d, 1b.2d.3a.4e.5c.6e, 1b.2d.3a.4e.5d.6a,
1b.2d.3a.4e.5d.6b, 1b.2d.3a.4e.5d.6c, 1b.2d.3a.4e.5d.6d, 1b.2d.3a.4e.5d.6e,
1b.2d.3a.4e.5e.6a, 1b.2d.3a.4e.5e.6b, 1b.2d.3a.4e.5e.6c, 1b.2d.3a.4e.5e.6d,
1b.2d.3a.4e.5e.6e, 1b.2d.3b.4a.5a.6a, 1b.2d.3b.4a.5a.6b, 1b.2d.3b.4a.5a.6c,
1b.2d.3b.4a.5a.6d, 1b.2d.3b.4a.5a.6e, 1b.2d.3b.4a.5b.6a, 1b.2d.3b.4a.5b.6b,
1b.2d.3b.4a.5b.6c, 1b.2d.3b.4a.5b.6d, 1b.2d.3b.4a.5b.6e, 1b.2d.3b.4a.5c.6a,
1b.2d.3b.4a.5c.6b, 1b.2d.3b.4a.5c.6c, 1b.2d.3b.4a.5c.6d, 1b.2d.3b.4a.5c.6e,
1b.2d.3b.4a.5d.6a, 1b.2d.3b.4a.5d.6b, 1b.2d.3b.4a.5d.6c, 1b.2d.3b.4a.5d.6d,
1b.2d.3b.4a.5d.6e, 1b.2d.3b.4a.5e.6a, 1b.2d.3b.4a.5e.6b, 1b.2d.3b.4a.5e.6c,
1b.2d.3b.4a.5e.6d, 1b.2d.3b.4a.5e.6e, 1b.2d.3b.4b.5a.6a, 1b.2d.3b.4b.5a.6b,
1b.2d.3b.4b.5a.6c, 1b.2d.3b.4b.5a.6d, 1b.2d.3b.4b.5a.6e, 1b.2d.3b.4b.5b.6a,
1b.2d.3b.4b.5b.6b, 1b.2d.3b.4b.5b.6c, 1b.2d.3b.4b.5b.6d, 1b.2d.3b.4b.5b.6e,

TABLE 8-continued

List of Compounds of Formula (II)

1b.2d.3b.4b.5c.6a, 1b.2d.3b.4b.5c.6b, 1b.2d.3b.4b.5c.6c, 1b.2d.3b.4b.5c.6d,
1b.2d.3b.4b.5c.6e, 1b.2d.3b.4b.5d.6a, 1b.2d.3b.4b.5d.6b, 1b.2d.3b.4b.5d.6c,
1b.2d.3b.4b.5d.6d, 1b.2d.3b.4b.5d.6e, 1b.2d.3b.4b.5e.6a, 1b.2d.3b.4b.5e.6b,
1b.2d.3b.4b.5e.6c, 1b.2d.3b.4b.5e.6d, 1b.2d.3b.4b.5e.6e, 1b.2d.3b.4c.5a.6a,
1b.2d.3b.4c.5a.6b, 1b.2d.3b.4c.5a.6c, 1b.2d.3b.4c.5a.6d, 1b.2d.3b.4c.5a.6e,
1b.2d.3b.4c.5b.6a, 1b.2d.3b.4c.5b.6b, 1b.2d.3b.4c.5b.6c, 1b.2d.3b.4c.5b.6d,
1b.2d.3b.4c.5b.6e, 1b.2d.3b.4c.5c.6a, 1b.2d.3b.4c.5c.6b, 1b.2d.3b.4c.5c.6c,
1b.2d.3b.4c.5c.6d, 1b.2d.3b.4c.5c.6e, 1b.2d.3b.4c.5d.6a, 1b.2d.3b.4c.5d.6b,
1b.2d.3b.4c.5d.6c, 1b.2d.3b.4c.5d.6d, 1b.2d.3b.4c.5d.6e, 1b.2d.3b.4c.5e.6a,
1b.2d.3b.4c.5e.6b, 1b.2d.3b.4c.5e.6c, 1b.2d.3b.4c.5e.6d, 1b.2d.3b.4c.5e.6e,
1b.2d.3b.4d.5a.6a, 1b.2d.3b.4d.5a.6b, 1b.2d.3b.4d.5a.6c, 1b.2d.3b.4d.5a.6d,
1b.2d.3b.4d.5a.6e, 1b.2d.3b.4d.5b.6a, 1b.2d.3b.4d.5b.6b, 1b.2d.3b.4d.5b.6c,
1b.2d.3b.4d.5b.6d, 1b.2d.3b.4d.5b.6e, 1b.2d.3b.4d.5c.6a, 1b.2d.3b.4d.5c.6b,
1b.2d.3b.4d.5c.6c, 1b.2d.3b.4d.5c.6d, 1b.2d.3b.4d.5c.6e, 1b.2d.3b.4d.5d.6a,
1b.2d.3b.4d.5d.6b, 1b.2d.3b.4d.5d.6c, 1b.2d.3b.4d.5d.6d, 1b.2d.3b.4d.5d.6e,
1b.2d.3b.4d.5e.6a, 1b.2d.3b.4d.5e.6b, 1b.2d.3b.4d.5e.6c, 1b.2d.3b.4d.5e.6d,
1b.2d.3b.4d.5e.6e, 1b.2d.3b.4e.5a.6a, 1b.2d.3b.4e.5a.6b, 1b.2d.3b.4e.5a.6c,
1b.2d.3b.4e.5a.6d, 1b.2d.3b.4e.5a.6e, 1b.2d.3b.4e.5b.6a, 1b.2d.3b.4e.5b.6b,
1b.2d.3b.4e.5b.6c, 1b.2d.3b.4e.5b.6d, 1b.2d.3b.4e.5b.6e, 1b.2d.3b.4e.5c.6a,
1b.2d.3b.4e.5c.6b, 1b.2d.3b.4e.5c.6c, 1b.2d.3b.4e.5c.6d, 1b.2d.3b.4e.5c.6e,
1b.2d.3b.4e.5d.6a, 1b.2d.3b.4e.5d.6b, 1b.2d.3b.4e.5d.6c, 1b.2d.3b.4e.5d.6d,
1b.2d.3b.4e.5d.6e, 1b.2d.3b.4e.5e.6a, 1b.2d.3b.4e.5e.6b, 1b.2d.3b.4e.5e.6c,
1b.2d.3b.4e.5e.6d, 1b.2d.3b.4e.5e.6e, 1b.2d.3c.4a.5a.6a, 1b.2d.3c.4a.5a.6b,
1b.2d.3c.4a.5a.6c, 1b.2d.3c.4a.5a.6d, 1b.2d.3c.4a.5a.6e, 1b.2d.3c.4a.5b.6a,
1b.2d.3c.4a.5b.6b, 1b.2d.3c.4a.5b.6c, 1b.2d.3c.4a.5b.6d, 1b.2d.3c.4a.5b.6e,
1b.2d.3c.4a.5c.6a, 1b.2d.3c.4a.5c.6b, 1b.2d.3c.4a.5c.6c, 1b.2d.3c.4a.5c.6d,
1b.2d.3c.4a.5c.6e, 1b.2d.3c.4a.5d.6a, 1b.2d.3c.4a.5d.6b, 1b.2d.3c.4a.5d.6c,
1b.2d.3c.4a.5d.6d, 1b.2d.3c.4a.5d.6e, 1b.2d.3c.4a.5e.6a, 1b.2d.3c.4a.5e.6b,
1b.2d.3c.4a.5e.6c, 1b.2d.3c.4a.5e.6d, 1b.2d.3c.4a.5e.6e, 1b.2d.3c.4b.5a.6a,
1b.2d.3c.4b.5a.6b, 1b.2d.3c.4b.5a.6c, 1b.2d.3c.4b.5a.6d, 1b.2d.3c.4b.5a.6e,
1b.2d.3c.4b.5b.6a, 1b.2d.3c.4b.5b.6b, 1b.2d.3c.4b.5b.6c, 1b.2d.3c.4b.5b.6d,
1b.2d.3c.4b.5b.6e, 1b.2d.3c.4b.5c.6a, 1b.2d.3c.4b.5c.6b, 1b.2d.3c.4b.5c.6c,
1b.2d.3c.4b.5c.6d, 1b.2d.3c.4b.5c.6e, 1b.2d.3c.4b.5d.6a, 1b.2d.3c.4b.5d.6b,
1b.2d.3c.4b.5d.6c, 1b.2d.3c.4b.5d.6d, 1b.2d.3c.4b.5d.6e, 1b.2d.3c.4b.5e.6a,
1b.2d.3c.4b.5e.6b, 1b.2d.3c.4b.5e.6c, 1b.2d.3c.4b.5e.6d, 1b.2d.3c.4b.5e.6e,
1b.2d.3c.4c.5a.6a, 1b.2d.3c.4c.5a.6b, 1b.2d.3c.4c.5a.6c, 1b.2d.3c.4c.5a.6d,
1b.2d.3c.4c.5a.6e, 1b.2d.3c.4c.5b.6a, 1b.2d.3c.4c.5b.6b, 1b.2d.3c.4c.5b.6c,
1b.2d.3c.4c.5b.6d, 1b.2d.3c.4c.5b.6e, 1b.2d.3c.4c.5c.6a, 1b.2d.3c.4c.5c.6b,
1b.2d.3c.4c.5c.6c, 1b.2d.3c.4c.5c.6d, 1b.2d.3c.4c.5c.6e, 1b.2d.3c.4c.5d.6a,
1b.2d.3c.4c.5d.6b, 1b.2d.3c.4c.5d.6c, 1b.2d.3c.4c.5d.6d, 1b.2d.3c.4c.5d.6e,
1b.2d.3c.4c.5e.6a, 1b.2d.3c.4c.5e.6b, 1b.2d.3c.4c.5e.6c, 1b.2d.3c.4c.5e.6d,
1b.2d.3c.4c.5e.6e, 1b.2d.3c.4d.5a.6a, 1b.2d.3c.4d.5a.6b, 1b.2d.3c.4d.5a.6c,
1b.2d.3c.4d.5a.6d, 1b.2d.3c.4d.5a.6e, 1b.2d.3c.4d.5b.6a, 1b.2d.3c.4d.5b.6b,
1b.2d.3c.4d.5b.6c, 1b.2d.3c.4d.5b.6d, 1b.2d.3c.4d.5b.6e, 1b.2d.3c.4d.5c.6a,
1b.2d.3c.4d.5c.6b, 1b.2d.3c.4d.5c.6c, 1b.2d.3c.4d.5c.6d, 1b.2d.3c.4d.5c.6e,
1b.2d.3c.4d.5d.6a, 1b.2d.3c.4d.5d.6b, 1b.2d.3c.4d.5d.6c, 1b.2d.3c.4d.5d.6d,
1b.2d.3c.4d.5d.6e, 1b.2d.3c.4d.5e.6a, 1b.2d.3c.4d.5e.6b, 1b.2d.3c.4d.5e.6c,
1b.2d.3c.4d.5e.6d, 1b.2d.3c.4d.5e.6e, 1b.2d.3c.4e.5a.6a, 1b.2d.3c.4e.5a.6b,
1b.2d.3c.4e.5a.6c, 1b.2d.3c.4e.5a.6d, 1b.2d.3c.4e.5a.6e, 1b.2d.3c.4e.5b.6a,
1b.2d.3c.4e.5b.6b, 1b.2d.3c.4e.5b.6c, 1b.2d.3c.4e.5b.6d, 1b.2d.3c.4e.5b.6e,
1b.2d.3c.4e.5c.6a, 1b.2d.3c.4e.5c.6b, 1b.2d.3c.4e.5c.6c, 1b.2d.3c.4e.5c.6d,
1b.2d.3c.4e.5c.6e, 1b.2d.3c.4e.5d.6a, 1b.2d.3c.4e.5d.6b, 1b.2d.3c.4e.5d.6c,
1b.2d.3c.4e.5d.6d, 1b.2d.3c.4e.5d.6e, 1b.2d.3c.4e.5e.6a, 1b.2d.3c.4e.5e.6b,
1b.2d.3c.4e.5e.6c, 1b.2d.3c.4e.5e.6d, 1b.2d.3c.4e.5e.6e, 1b.2d.3d.4a.5a.6a,
1b.2d.3d.4a.5a.6b, 1b.2d.3d.4a.5a.6c, 1b.2d.3d.4a.5a.6d, 1b.2d.3d.4a.5a.6e,
1b.2d.3d.4a.5b.6a, 1b.2d.3d.4a.5b.6b, 1b.2d.3d.4a.5b.6c, 1b.2d.3d.4a.5b.6d,
1b.2d.3d.4a.5b.6e, 1b.2d.3d.4a.5c.6a, 1b.2d.3d.4a.5c.6b, 1b.2d.3d.4a.5c.6c,
1b.2d.3d.4a.5c.6d, 1b.2d.3d.4a.5c.6e, 1b.2d.3d.4a.5d.6a, 1b.2d.3d.4a.5d.6b,
1b.2d.3d.4a.5d.6c, 1b.2d.3d.4a.5d.6d, 1b.2d.3d.4a.5d.6e, 1b.2d.3d.4a.5e.6a,
1b.2d.3d.4a.5e.6b, 1b.2d.3d.4a.5e.6c, 1b.2d.3d.4a.5e.6d, 1b.2d.3d.4a.5e.6e,
1b.2d.3d.4b.5a.6a, 1b.2d.3d.4b.5a.6b, 1b.2d.3d.4b.5a.6c, 1b.2d.3d.4b.5a.6d,
1b.2d.3d.4b.5a.6e, 1b.2d.3d.4b.5b.6a, 1b.2d.3d.4b.5b.6b, 1b.2d.3d.4b.5b.6c,
1b.2d.3d.4b.5b.6d, 1b.2d.3d.4b.5b.6e, 1b.2d.3d.4b.5c.6a, 1b.2d.3d.4b.5c.6b,
1b.2d.3d.4b.5c.6c, 1b.2d.3d.4b.5c.6d, 1b.2d.3d.4b.5c.6e, 1b.2d.3d.4b.5d.6a,
1b.2d.3d.4b.5d.6b, 1b.2d.3d.4b.5d.6c, 1b.2d.3d.4b.5d.6d, 1b.2d.3d.4b.5d.6e,
1b.2d.3d.4b.5e.6a, 1b.2d.3d.4b.5e.6b, 1b.2d.3d.4b.5e.6c, 1b.2d.3d.4b.5e.6d,
1b.2d.3d.4b.5e.6e, 1b.2d.3d.4c.5a.6a, 1b.2d.3d.4c.5a.6b, 1b.2d.3d.4c.5a.6c,
1b.2d.3d.4c.5a.6d, 1b.2d.3d.4c.5a.6e, 1b.2d.3d.4c.5b.6a, 1b.2d.3d.4c.5b.6b,
1b.2d.3d.4c.5b.6c, 1b.2d.3d.4c.5b.6d, 1b.2d.3d.4c.5b.6e, 1b.2d.3d.4c.5c.6a,
1b.2d.3d.4c.5c.6b, 1b.2d.3d.4c.5c.6c, 1b.2d.3d.4c.5c.6d, 1b.2d.3d.4c.5c.6e,
1b.2d.3d.4c.5d.6a, 1b.2d.3d.4c.5d.6b, 1b.2d.3d.4c.5d.6c, 1b.2d.3d.4c.5d.6d,
1b.2d.3d.4c.5d.6e, 1b.2d.3d.4c.5e.6a, 1b.2d.3d.4c.5e.6b, 1b.2d.3d.4c.5e.6c,
1b.2d.3d.4c.5e.6d, 1b.2d.3d.4c.5e.6e, 1b.2d.3d.4d.5a.6a, 1b.2d.3d.4d.5a.6b,
1b.2d.3d.4d.5a.6c, 1b.2d.3d.4d.5a.6d, 1b.2d.3d.4d.5a.6e, 1b.2d.3d.4d.5b.6a,
1b.2d.3d.4d.5b.6b, 1b.2d.3d.4d.5b.6c, 1b.2d.3d.4d.5b.6d, 1b.2d.3d.4d.5b.6e,
1b.2d.3d.4d.5c.6a, 1b.2d.3d.4d.5c.6b, 1b.2d.3d.4d.5c.6c, 1b.2d.3d.4d.5c.6d,
1b.2d.3d.4d.5c.6e, 1b.2d.3d.4d.5d.6a, 1b.2d.3d.4d.5d.6b, 1b.2d.3d.4d.5d.6c,
1b.2d.3d.4d.5d.6d, 1b.2d.3d.4d.5d.6e, 1b.2d.3d.4d.5e.6a, 1b.2d.3d.4d.5e.6b,

TABLE 8-continued

List of Compounds of Formula (II)

1b.2d.3d.4d.5e.6c, 1b.2d.3d.4d.5e.6d, 1b.2d.3d.4d.5e.6e, 1b.2d.3d.4e.5a.6a,
1b.2d.3d.4e.5a.6b, 1b.2d.3d.4e.5a.6c, 1b.2d.3d.4e.5a.6d, 1b.2d.3d.4e.5a.6e,
1b.2d.3d.4e.5b.6a, 1b.2d.3d.4e.5b.6b, 1b.2d.3d.4e.5b.6c, 1b.2d.3d.4e.5b.6d,
1b.2d.3d.4e.5b.6e, 1b.2d.3d.4e.5c.6a, 1b.2d.3d.4e.5c.6b, 1b.2d.3d.4e.5c.6c,
1b.2d.3d.4e.5c.6d, 1b.2d.3d.4e.5c.6e, 1b.2d.3d.4e.5d.6a, 1b.2d.3d.4e.5d.6b,
1b.2d.3d.4e.5d.6c, 1b.2d.3d.4e.5d.6d, 1b.2d.3d.4e.5d.6e, 1b.2d.3d.4e.5e.6a,
1b.2d.3d.4e.5e.6b, 1b.2d.3d.4e.5e.6c, 1b.2d.3d.4e.5e.6d, 1b.2d.3d.4e.5e.6e,
1b.2d.3e.4a.5a.6a, 1b.2d.3e.4a.5a.6b, 1b.2d.3e.4a.5a.6c, 1b.2d.3e.4a.5a.6d,
1b.2d.3e.4a.5a.6e, 1b.2d.3e.4a.5b.6a, 1b.2d.3e.4a.5b.6b, 1b.2d.3e.4a.5b.6c,
1b.2d.3e.4a.5b.6d, 1b.2d.3e.4a.5b.6e, 1b.2d.3e.4a.5c.6a, 1b.2d.3e.4a.5c.6b,
1b.2d.3e.4a.5c.6c, 1b.2d.3e.4a.5c.6d, 1b.2d.3e.4a.5c.6e, 1b.2d.3e.4a.5d.6a,
1b.2d.3e.4a.5d.6b, 1b.2d.3e.4a.5d.6c, 1b.2d.3e.4a.5d.6d, 1b.2d.3e.4a.5d.6e,
1b.2d.3e.4a.5e.6a, 1b.2d.3e.4a.5e.6b, 1b.2d.3e.4a.5e.6c, 1b.2d.3e.4a.5e.6d,
1b.2d.3e.4a.5e.6e, 1b.2d.3e.4b.5a.6a, 1b.2d.3e.4b.5a.6b, 1b.2d.3e.4b.5a.6c,
1b.2d.3e.4b.5a.6d, 1b.2d.3e.4b.5a.6e, 1b.2d.3e.4b.5b.6a, 1b.2d.3e.4b.5b.6b,
1b.2d.3e.4b.5b.6c, 1b.2d.3e.4b.5b.6d, 1b.2d.3e.4b.5b.6e, 1b.2d.3e.4b.5c.6a,
1b.2d.3e.4b.5c.6b, 1b.2d.3e.4b.5c.6c, 1b.2d.3e.4b.5c.6d, 1b.2d.3e.4b.5c.6e,
1b.2d.3e.4b.5d.6a, 1b.2d.3e.4b.5d.6b, 1b.2d.3e.4b.5d.6c, 1b.2d.3e.4b.5d.6d,
1b.2d.3e.4b.5d.6e, 1b.2d.3e.4b.5e.6a, 1b.2d.3e.4b.5e.6b, 1b.2d.3e.4b.5e.6c,
1b.2d.3e.4b.5e.6d, 1b.2d.3e.4b.5e.6e, 1b.2d.3e.4c.5a.6a, 1b.2d.3e.4c.5a.6b,
1b.2d.3e.4c.5a.6c, 1b.2d.3e.4c.5a.6d, 1b.2d.3e.4c.5a.6e, 1b.2d.3e.4c.5b.6a,
1b.2d.3e.4c.5b.6b, 1b.2d.3e.4c.5b.6c, 1b.2d.3e.4c.5b.6d, 1b.2d.3e.4c.5b.6e,
1b.2d.3e.4c.5c.6a, 1b.2d.3e.4c.5c.6b, 1b.2d.3e.4c.5c.6c, 1b.2d.3e.4c.5c.6d,
1b.2d.3e.4c.5c.6e, 1b.2d.3e.4c.5d.6a, 1b.2d.3e.4c.5d.6b, 1b.2d.3e.4c.5d.6c,
1b.2d.3e.4c.5d.6d, 1b.2d.3e.4c.5d.6e, 1b.2d.3e.4c.5e.6a, 1b.2d.3e.4c.5e.6b,
1b.2d.3e.4c.5e.6c, 1b.2d.3e.4c.5e.6d, 1b.2d.3e.4c.5e.6e, 1b.2d.3e.4d.5a.6a,
1b.2d.3e.4d.5a.6b, 1b.2d.3e.4d.5a.6c, 1b.2d.3e.4d.5a.6d, 1b.2d.3e.4d.5a.6e,
1b.2d.3e.4d.5b.6a, 1b.2d.3e.4d.5b.6b, 1b.2d.3e.4d.5b.6c, 1b.2d.3e.4d.5b.6d,
1b.2d.3e.4d.5b.6e, 1b.2d.3e.4d.5c.6a, 1b.2d.3e.4d.5c.6b, 1b.2d.3e.4d.5c.6c,
1b.2d.3e.4d.5c.6d, 1b.2d.3e.4d.5c.6e, 1b.2d.3e.4d.5d.6a, 1b.2d.3e.4d.5d.6b,
1b.2d.3e.4d.5d.6c, 1b.2d.3e.4d.5d.6d, 1b.2d.3e.4d.5d.6e, 1b.2d.3e.4d.5e.6a,
1b.2d.3e.4d.5e.6b, 1b.2d.3e.4d.5e.6c, 1b.2d.3e.4d.5e.6d, 1b.2d.3e.4d.5e.6e,
1b.2d.3e.4e.5a.6a, 1b.2d.3e.4e.5a.6b, 1b.2d.3e.4e.5a.6c, 1b.2d.3e.4e.5a.6d,
1b.2d.3e.4e.5a.6e, 1b.2d.3e.4e.5b.6a, 1b.2d.3e.4e.5b.6b, 1b.2d.3e.4e.5b.6c,
1b.2d.3e.4e.5b.6d, 1b.2d.3e.4e.5b.6e, 1b.2d.3e.4e.5c.6a, 1b.2d.3e.4e.5c.6b,
1b.2d.3e.4e.5c.6c, 1b.2d.3e.4e.5c.6d, 1b.2d.3e.4e.5c.6e, 1b.2d.3e.4e.5d.6a,
1b.2d.3e.4e.5d.6b, 1b.2d.3e.4e.5d.6c, 1b.2d.3e.4e.5d.6d, 1b.2d.3e.4e.5d.6e,
1b.2d.3e.4e.5e.6a, 1b.2d.3e.4e.5e.6b, 1b.2d.3e.4e.5e.6c, 1b.2d.3e.4e.5e.6d,
1b.2d.3e.4e.5e.6e, 1b.2e.3a.4a.5a.6a, 1b.2e.3a.4a.5a.6b, 1b.2e.3a.4a.5a.6c,
1b.2e.3a.4a.5a.6d, 1b.2e.3a.4a.5a.6e, 1b.2e.3a.4a.5b.6a, 1b.2e.3a.4a.5b.6b,
1b.2e.3a.4a.5b.6c, 1b.2e.3a.4a.5b.6d, 1b.2e.3a.4a.5b.6e, 1b.2e.3a.4a.5c.6a,
1b.2e.3a.4a.5c.6b, 1b.2e.3a.4a.5c.6c, 1b.2e.3a.4a.5c.6d, 1b.2e.3a.4a.5c.6e,
1b.2e.3a.4a.5d.6a, 1b.2e.3a.4a.5d.6b, 1b.2e.3a.4a.5d.6c, 1b.2e.3a.4a.5d.6d,
1b.2e.3a.4a.5d.6e, 1b.2e.3a.4a.5e.6a, 1b.2e.3a.4a.5e.6b, 1b.2e.3a.4a.5e.6c,
1b.2e.3a.4a.5e.6d, 1b.2e.3a.4a.5e.6e, 1b.2e.3a.4b.5a.6a, 1b.2e.3a.4b.5a.6b,
1b.2e.3a.4b.5a.6c, 1b.2e.3a.4b.5a.6d, 1b.2e.3a.4b.5a.6e, 1b.2e.3a.4b.5b.6a,
1b.2e.3a.4b.5b.6b, 1b.2e.3a.4b.5b.6c, 1b.2e.3a.4b.5b.6d, 1b.2e.3a.4b.5b.6e,
1b.2e.3a.4b.5c.6a, 1b.2e.3a.4b.5c.6b, 1b.2e.3a.4b.5c.6c, 1b.2e.3a.4b.5c.6d,
1b.2e.3a.4b.5c.6e, 1b.2e.3a.4b.5d.6a, 1b.2e.3a.4b.5d.6b, 1b.2e.3a.4b.5d.6c,
1b.2e.3a.4b.5d.6d, 1b.2e.3a.4b.5d.6e, 1b.2e.3a.4b.5e.6a, 1b.2e.3a.4b.5e.6b,
1b.2e.3a.4b.5e.6c, 1b.2e.3a.4b.5e.6d, 1b.2e.3a.4b.5e.6e, 1b.2e.3a.4c.5a.6a,
1b.2e.3a.4c.5a.6b, 1b.2e.3a.4c.5a.6c, 1b.2e.3a.4c.5a.6d, 1b.2e.3a.4c.5a.6e,
1b.2e.3a.4c.5b.6a, 1b.2e.3a.4c.5b.6b, 1b.2e.3a.4c.5b.6c, 1b.2e.3a.4c.5b.6d,
1b.2e.3a.4c.5b.6e, 1b.2e.3a.4c.5c.6a, 1b.2e.3a.4c.5c.6b, 1b.2e.3a.4c.5c.6c,
1b.2e.3a.4c.5c.6d, 1b.2e.3a.4c.5c.6e, 1b.2e.3a.4c.5d.6a, 1b.2e.3a.4c.5d.6b,
1b.2e.3a.4c.5d.6c, 1b.2e.3a.4c.5d.6d, 1b.2e.3a.4c.5d.6e, 1b.2e.3a.4c.5e.6a,
1b.2e.3a.4c.5e.6b, 1b.2e.3a.4c.5e.6c, 1b.2e.3a.4c.5e.6d, 1b.2e.3a.4c.5e.6e,
1b.2e.3a.4d.5a.6a, 1b.2e.3a.4d.5a.6b, 1b.2e.3a.4d.5a.6c, 1b.2e.3a.4d.5a.6d,
1b.2e.3a.4d.5a.6e, 1b.2e.3a.4d.5b.6a, 1b.2e.3a.4d.5b.6b, 1b.2e.3a.4d.5b.6c,
1b.2e.3a.4d.5b.6d, 1b.2e.3a.4d.5b.6e, 1b.2e.3a.4d.5c.6a, 1b.2e.3a.4d.5c.6b,
1b.2e.3a.4d.5c.6c, 1b.2e.3a.4d.5c.6d, 1b.2e.3a.4d.5c.6e, 1b.2e.3a.4d.5d.6a,
1b.2e.3a.4d.5d.6b, 1b.2e.3a.4d.5d.6c, 1b.2e.3a.4d.5d.6d, 1b.2e.3a.4d.5d.6e,
1b.2e.3a.4d.5e.6a, 1b.2e.3a.4d.5e.6b, 1b.2e.3a.4d.5e.6c, 1b.2e.3a.4d.5e.6d,
1b.2e.3a.4d.5e.6e, 1b.2e.3a.4e.5a.6a, 1b.2e.3a.4e.5a.6b, 1b.2e.3a.4e.5a.6c,
1b.2e.3a.4e.5a.6d, 1b.2e.3a.4e.5a.6e, 1b.2e.3a.4e.5b.6a, 1b.2e.3a.4e.5b.6b,
1b.2e.3a.4e.5b.6c, 1b.2e.3a.4e.5b.6d, 1b.2e.3a.4e.5b.6e, 1b.2e.3a.4e.5c.6a,
1b.2e.3a.4e.5c.6b, 1b.2e.3a.4e.5c.6c, 1b.2e.3a.4e.5c.6d, 1b.2e.3a.4e.5c.6e,
1b.2e.3a.4e.5d.6a, 1b.2e.3a.4e.5d.6b, 1b.2e.3a.4e.5d.6c, 1b.2e.3a.4e.5d.6d,
1b.2e.3a.4e.5d.6e, 1b.2e.3a.4e.5e.6a, 1b.2e.3a.4e.5e.6b, 1b.2e.3a.4e.5e.6c,
1b.2e.3a.4e.5e.6d, 1b.2e.3a.4e.5e.6e, 1b.2e.3b.4a.5a.6a, 1b.2e.3b.4a.5a.6b,
1b.2e.3b.4a.5a.6c, 1b.2e.3b.4a.5a.6d, 1b.2e.3b.4a.5a.6e, 1b.2e.3b.4a.5b.6a,
1b.2e.3b.4a.5b.6b, 1b.2e.3b.4a.5b.6c, 1b.2e.3b.4a.5b.6d, 1b.2e.3b.4a.5b.6e,
1b.2e.3b.4a.5c.6a, 1b.2e.3b.4a.5c.6b, 1b.2e.3b.4a.5c.6c, 1b.2e.3b.4a.5c.6d,
1b.2e.3b.4a.5c.6e, 1b.2e.3b.4a.5d.6a, 1b.2e.3b.4a.5d.6b, 1b.2e.3b.4a.5d.6c,
1b.2e.3b.4a.5d.6d, 1b.2e.3b.4a.5d.6e, 1b.2e.3b.4a.5e.6a, 1b.2e.3b.4a.5e.6b,
1b.2e.3b.4a.5e.6c, 1b.2e.3b.4a.5e.6d, 1b.2e.3b.4a.5e.6e, 1b.2e.3b.4b.5a.6a,
1b.2e.3b.4b.5a.6b, 1b.2e.3b.4b.5a.6c, 1b.2e.3b.4b.5a.6d, 1b.2e.3b.4b.5a.6e,
1b.2e.3b.4b.5b.6a, 1b.2e.3b.4b.5b.6b, 1b.2e.3b.4b.5b.6c, 1b.2e.3b.4b.5b.6d,

TABLE 8-continued

List of Compounds of Formula (II)

1b.2e.3b.4b.5b.6e, 1b.2e.3b.4b.5c.6a, 1b.2e.3b.4b.5c.6b, 1b.2e.3b.4b.5c.6c,
1b.2e.3b.4b.5c.6d, 1b.2e.3b.4b.5c.6e, 1b.2e.3b.4b.5d.6a, 1b.2e.3b.4b.5d.6b,
1b.2e.3b.4b.5d.6c, 1b.2e.3b.4b.5d.6d, 1b.2e.3b.4b.5d.6e, 1b.2e.3b.4b.5e.6a,
1b.2e.3b.4b.5e.6b, 1b.2e.3b.4b.5e.6c, 1b.2e.3b.4b.5e.6d, 1b.2e.3b.4b.5e.6e,
1b.2e.3b.4c.5a.6a, 1b.2e.3b.4c.5a.6b, 1b.2e.3b.4c.5a.6c, 1b.2e.3b.4c.5a.6d,
1b.2e.3b.4c.5a.6e, 1b.2e.3b.4c.5b.6a, 1b.2e.3b.4c.5b.6b, 1b.2e.3b.4c.5b.6c,
1b.2e.3b.4c.5b.6d, 1b.2e.3b.4c.5b.6e, 1b.2e.3b.4c.5c.6a, 1b.2e.3b.4c.5c.6b,
1b.2e.3b.4c.5c.6c, 1b.2e.3b.4c.5c.6d, 1b.2e.3b.4c.5c.6e, 1b.2e.3b.4c.5d.6a,
1b.2e.3b.4c.5d.6b, 1b.2e.3b.4c.5d.6c, 1b.2e.3b.4c.5d.6d, 1b.2e.3b.4c.5d.6e,
1b.2e.3b.4c.5e.6a, 1b.2e.3b.4c.5e.6b, 1b.2e.3b.4c.5e.6c, 1b.2e.3b.4c.5e.6d,
1b.2e.3b.4c.5e.6e, 1b.2e.3b.4d.5a.6a, 1b.2e.3b.4d.5a.6b, 1b.2e.3b.4d.5a.6c,
1b.2e.3b.4d.5a.6d, 1b.2e.3b.4d.5a.6e, 1b.2e.3b.4d.5b.6a, 1b.2e.3b.4d.5b.6b,
1b.2e.3b.4d.5b.6c, 1b.2e.3b.4d.5b.6d, 1b.2e.3b.4d.5b.6e, 1b.2e.3b.4d.5c.6a,
1b.2e.3b.4d.5c.6b, 1b.2e.3b.4d.5c.6c, 1b.2e.3b.4d.5c.6d, 1b.2e.3b.4d.5c.6e,
1b.2e.3b.4d.5d.6a, 1b.2e.3b.4d.5d.6b, 1b.2e.3b.4d.5d.6c, 1b.2e.3b.4d.5d.6d,
1b.2e.3b.4d.5d.6e, 1b.2e.3b.4d.5e.6a, 1b.2e.3b.4d.5e.6b, 1b.2e.3b.4d.5e.6c,
1b.2e.3b.4d.5e.6d, 1b.2e.3b.4d.5e.6e, 1b.2e.3b.4e.5a.6a, 1b.2e.3b.4e.5a.6b,
1b.2e.3b.4e.5a.6c, 1b.2e.3b.4e.5a.6d, 1b.2e.3b.4e.5a.6e, 1b.2e.3b.4e.5b.6a,
1b.2e.3b.4e.5b.6b, 1b.2e.3b.4e.5b.6c, 1b.2e.3b.4e.5b.6d, 1b.2e.3b.4e.5b.6e,
1b.2e.3b.4e.5c.6a, 1b.2e.3b.4e.5c.6b, 1b.2e.3b.4e.5c.6c, 1b.2e.3b.4e.5c.6d,
1b.2e.3b.4e.5c.6e, 1b.2e.3b.4e.5d.6a, 1b.2e.3b.4e.5d.6b, 1b.2e.3b.4e.5d.6c,
1b.2e.3b.4e.5d.6d, 1b.2e.3b.4e.5d.6e, 1b.2e.3b.4e.5e.6a, 1b.2e.3b.4e.5e.6b,
1b.2e.3b.4e.5e.6c, 1b.2e.3b.4e.5e.6d, 1b.2e.3b.4e.5e.6e, 1b.2e.3c.4a.5a.6a,
1b.2e.3c.4a.5a.6b, 1b.2e.3c.4a.5a.6c, 1b.2e.3c.4a.5a.6d, 1b.2e.3c.4a.5a.6e,
1b.2e.3c.4a.5b.6a, 1b.2e.3c.4a.5b.6b, 1b.2e.3c.4a.5b.6c, 1b.2e.3c.4a.5b.6d,
1b.2e.3c.4a.5b.6e, 1b.2e.3c.4a.5c.6a, 1b.2e.3c.4a.5c.6b, 1b.2e.3c.4a.5c.6c,
1b.2e.3c.4a.5c.6d, 1b.2e.3c.4a.5c.6e, 1b.2e.3c.4a.5d.6a, 1b.2e.3c.4a.5d.6b,
1b.2e.3c.4a.5d.6c, 1b.2e.3c.4a.5d.6d, 1b.2e.3c.4a.5d.6e, 1b.2e.3c.4a.5e.6a,
1b.2e.3c.4a.5e.6b, 1b.2e.3c.4a.5e.6c, 1b.2e.3c.4a.5e.6d, 1b.2e.3c.4a.5e.6e,
1b.2e.3c.4b.5a.6a, 1b.2e.3c.4b.5a.6b, 1b.2e.3c.4b.5a.6c, 1b.2e.3c.4b.5a.6d,
1b.2e.3c.4b.5a.6e, 1b.2e.3c.4b.5b.6a, 1b.2e.3c.4b.5b.6b, 1b.2e.3c.4b.5b.6c,
1b.2e.3c.4b.5b.6d, 1b.2e.3c.4b.5b.6e, 1b.2e.3c.4b.5c.6a, 1b.2e.3c.4b.5c.6b,
1b.2e.3c.4b.5c.6c, 1b.2e.3c.4b.5c.6d, 1b.2e.3c.4b.5c.6e, 1b.2e.3c.4b.5d.6a,
1b.2e.3c.4b.5d.6b, 1b.2e.3c.4b.5d.6c, 1b.2e.3c.4b.5d.6d, 1b.2e.3c.4b.5d.6e,
1b.2e.3c.4b.5e.6a, 1b.2e.3c.4b.5e.6b, 1b.2e.3c.4b.5e.6c, 1b.2e.3c.4b.5e.6d,
1b.2e.3c.4b.5e.6e, 1b.2e.3c.4c.5a.6a, 1b.2e.3c.4c.5a.6b, 1b.2e.3c.4c.5a.6c,
1b.2e.3c.4c.5a.6d, 1b.2e.3c.4c.5a.6e, 1b.2e.3c.4c.5b.6a, 1b.2e.3c.4c.5b.6b,
1b.2e.3c.4c.5b.6c, 1b.2e.3c.4c.5b.6d, 1b.2e.3c.4c.5b.6e, 1b.2e.3c.4c.5c.6a,
1b.2e.3c.4c.5c.6b, 1b.2e.3c.4c.5c.6c, 1b.2e.3c.4c.5c.6d, 1b.2e.3c.4c.5c.6e,
1b.2e.3c.4c.5d.6a, 1b.2e.3c.4c.5d.6b, 1b.2e.3c.4c.5d.6c, 1b.2e.3c.4c.5d.6d,
1b.2e.3c.4c.5d.6e, 1b.2e.3c.4c.5e.6a, 1b.2e.3c.4c.5e.6b, 1b.2e.3c.4c.5e.6c,
1b.2e.3c.4c.5e.6d, 1b.2e.3c.4c.5e.6e, 1b.2e.3c.4d.5a.6a, 1b.2e.3c.4d.5a.6b,
1b.2e.3c.4d.5a.6c, 1b.2e.3c.4d.5a.6d, 1b.2e.3c.4d.5a.6e, 1b.2e.3c.4d.5b.6a,
1b.2e.3c.4d.5b.6b, 1b.2e.3c.4d.5b.6c, 1b.2e.3c.4d.5b.6d, 1b.2e.3c.4d.5b.6e,
1b.2e.3c.4d.5c.6a, 1b.2e.3c.4d.5c.6b, 1b.2e.3c.4d.5c.6c, 1b.2e.3c.4d.5c.6d,
1b.2e.3c.4d.5c.6e, 1b.2e.3c.4d.5d.6a, 1b.2e.3c.4d.5d.6b, 1b.2e.3c.4d.5d.6c,
1b.2e.3c.4d.5d.6d, 1b.2e.3c.4d.5d.6e, 1b.2e.3c.4d.5e.6a, 1b.2e.3c.4d.5e.6b,
1b.2e.3c.4d.5e.6c, 1b.2e.3c.4d.5e.6d, 1b.2e.3c.4d.5e.6e, 1b.2e.3c.4e.5a.6a,
1b.2e.3c.4e.5a.6b, 1b.2e.3c.4e.5a.6c, 1b.2e.3c.4e.5a.6d, 1b.2e.3c.4e.5a.6e,
1b.2e.3c.4e.5b.6a, 1b.2e.3c.4e.5b.6b, 1b.2e.3c.4e.5b.6c, 1b.2e.3c.4e.5b.6d,
1b.2e.3c.4e.5b.6e, 1b.2e.3c.4e.5c.6a, 1b.2e.3c.4e.5c.6b, 1b.2e.3c.4e.5c.6c,
1b.2e.3c.4e.5c.6d, 1b.2e.3c.4e.5c.6e, 1b.2e.3c.4e.5d.6a, 1b.2e.3c.4e.5d.6b,
1b.2e.3c.4e.5d.6c, 1b.2e.3c.4e.5d.6d, 1b.2e.3c.4e.5d.6e, 1b.2e.3c.4e.5e.6a,
1b.2e.3c.4e.5e.6b, 1b.2e.3c.4e.5e.6c, 1b.2e.3c.4e.5e.6d, 1b.2e.3c.4e.5e.6e,
1b.2e.3d.4a.5a.6a, 1b.2e.3d.4a.5a.6b, 1b.2e.3d.4a.5a.6c, 1b.2e.3d.4a.5a.6d,
1b.2e.3d.4a.5a.6e, 1b.2e.3d.4a.5b.6a, 1b.2e.3d.4a.5b.6b, 1b.2e.3d.4a.5b.6c,
1b.2e.3d.4a.5b.6d, 1b.2e.3d.4a.5b.6e, 1b.2e.3d.4a.5c.6a, 1b.2e.3d.4a.5c.6b,
1b.2e.3d.4a.5c.6c, 1b.2e.3d.4a.5c.6d, 1b.2e.3d.4a.5c.6e, 1b.2e.3d.4a.5d.6a,
1b.2e.3d.4a.5d.6b, 1b.2e.3d.4a.5d.6c, 1b.2e.3d.4a.5d.6d, 1b.2e.3d.4a.5d.6e,
1b.2e.3d.4a.5e.6a, 1b.2e.3d.4a.5e.6b, 1b.2e.3d.4a.5e.6c, 1b.2e.3d.4a.5e.6d,
1b.2e.3d.4a.5e.6e, 1b.2e.3d.4b.5a.6a, 1b.2e.3d.4b.5a.6b, 1b.2e.3d.4b.5a.6c,
1b.2e.3d.4b.5a.6d, 1b.2e.3d.4b.5a.6e, 1b.2e.3d.4b.5b.6a, 1b.2e.3d.4b.5b.6b,
1b.2e.3d.4b.5b.6c, 1b.2e.3d.4b.5b.6d, 1b.2e.3d.4b.5b.6e, 1b.2e.3d.4b.5c.6a,
1b.2e.3d.4b.5c.6b, 1b.2e.3d.4b.5c.6c, 1b.2e.3d.4b.5c.6d, 1b.2e.3d.4b.5c.6e,
1b.2e.3d.4b.5d.6a, 1b.2e.3d.4b.5d.6b, 1b.2e.3d.4b.5d.6c, 1b.2e.3d.4b.5d.6d,
1b.2e.3d.4b.5d.6e, 1b.2e.3d.4b.5e.6a, 1b.2e.3d.4b.5e.6b, 1b.2e.3d.4b.5e.6c,
1b.2e.3d.4b.5e.6d, 1b.2e.3d.4b.5e.6e, 1b.2e.3d.4c.5a.6a, 1b.2e.3d.4c.5a.6b,
1b.2e.3d.4c.5a.6c, 1b.2e.3d.4c.5a.6d, 1b.2e.3d.4c.5a.6e, 1b.2e.3d.4c.5b.6a,
1b.2e.3d.4c.5b.6b, 1b.2e.3d.4c.5b.6c, 1b.2e.3d.4c.5b.6d, 1b.2e.3d.4c.5b.6e,
1b.2e.3d.4c.5c.6a, 1b.2e.3d.4c.5c.6b, 1b.2e.3d.4c.5c.6c, 1b.2e.3d.4c.5c.6d,
1b.2e.3d.4c.5c.6e, 1b.2e.3d.4c.5d.6a, 1b.2e.3d.4c.5d.6b, 1b.2e.3d.4c.5d.6c,
1b.2e.3d.4c.5d.6d, 1b.2e.3d.4c.5d.6e, 1b.2e.3d.4c.5e.6a, 1b.2e.3d.4c.5e.6b,
1b.2e.3d.4c.5e.6c, 1b.2e.3d.4c.5e.6d, 1b.2e.3d.4c.5e.6e, 1b.2e.3d.4d.5a.6a,
1b.2e.3d.4d.5a.6b, 1b.2e.3d.4d.5a.6c, 1b.2e.3d.4d.5a.6d, 1b.2e.3d.4d.5a.6e,
1b.2e.3d.4d.5b.6a, 1b.2e.3d.4d.5b.6b, 1b.2e.3d.4d.5b.6c, 1b.2e.3d.4d.5b.6d,
1b.2e.3d.4d.5b.6e, 1b.2e.3d.4d.5c.6a, 1b.2e.3d.4d.5c.6b, 1b.2e.3d.4d.5c.6c,
1b.2e.3d.4d.5c.6d, 1b.2e.3d.4d.5c.6e, 1b.2e.3d.4d.5d.6a, 1b.2e.3d.4d.5d.6b,
1b.2e.3d.4d.5d.6c, 1b.2e.3d.4d.5d.6d, 1b.2e.3d.4d.5d.6e, 1b.2e.3d.4d.5e.6a,

TABLE 8-continued

List of Compounds of Formula (II)

1b.2e.3d.4d.5e.6b, 1b.2e.3d.4d.5e.6c, 1b.2e.3d.4d.5e.6d, 1b.2e.3d.4d.5e.6e,
1b.2e.3d.4e.5a.6a, 1b.2e.3d.4e.5a.6b, 1b.2e.3d.4e.5a.6c, 1b.2e.3d.4e.5a.6d,
1b.2e.3d.4e.5a.6e, 1b.2e.3d.4e.5b.6a, 1b.2e.3d.4e.5b.6b, 1b.2e.3d.4e.5b.6c,
1b.2e.3d.4e.5b.6d, 1b.2e.3d.4e.5b.6e, 1b.2e.3d.4e.5c.6a, 1b.2e.3d.4e.5c.6b,
1b.2e.3d.4e.5c.6c, 1b.2e.3d.4e.5c.6d, 1b.2e.3d.4e.5c.6e, 1b.2e.3d.4e.5d.6a,
1b.2e.3d.4e.5d.6b, 1b.2e.3d.4e.5d.6c, 1b.2e.3d.4e.5d.6d, 1b.2e.3d.4e.5d.6e,
1b.2e.3d.4e.5e.6a, 1b.2e.3d.4e.5e.6b, 1b.2e.3d.4e.5e.6c, 1b.2e.3d.4e.5e.6d,
1b.2e.3d.4e.5e.6e, 1b.2e.3e.4a.5a.6a, 1b.2e.3e.4a.5a.6b, 1b.2e.3e.4a.5a.6c,
1b.2e.3e.4a.5a.6d, 1b.2e.3e.4a.5a.6e, 1b.2e.3e.4a.5b.6a, 1b.2e.3e.4a.5b.6b,
1b.2e.3e.4a.5b.6c, 1b.2e.3e.4a.5b.6d, 1b.2e.3e.4a.5b.6e, 1b.2e.3e.4a.5c.6a,
1b.2e.3e.4a.5c.6b, 1b.2e.3e.4a.5c.6c, 1b.2e.3e.4a.5c.6d, 1b.2e.3e.4a.5c.6e,
1b.2e.3e.4a.5d.6a, 1b.2e.3e.4a.5d.6b, 1b.2e.3e.4a.5d.6c, 1b.2e.3e.4a.5d.6d,
1b.2e.3e.4a.5d.6e, 1b.2e.3e.4a.5e.6a, 1b.2e.3e.4a.5e.6b, 1b.2e.3e.4a.5e.6c,
1b.2e.3e.4a.5e.6d, 1b.2e.3e.4a.5e.6e, 1b.2e.3e.4b.5a.6a, 1b.2e.3e.4b.5a.6b,
1b.2e.3e.4b.5a.6c, 1b.2e.3e.4b.5a.6d, 1b.2e.3e.4b.5a.6e, 1b.2e.3e.4b.5b.6a,
1b.2e.3e.4b.5b.6b, 1b.2e.3e.4b.5b.6c, 1b.2e.3e.4b.5b.6d, 1b.2e.3e.4b.5b.6e,
1b.2e.3e.4b.5c.6a, 1b.2e.3e.4b.5c.6b, 1b.2e.3e.4b.5c.6c, 1b.2e.3e.4b.5c.6d,
1b.2e.3e.4b.5c.6e, 1b.2e.3e.4b.5d.6a, 1b.2e.3e.4b.5d.6b, 1b.2e.3e.4b.5d.6c,
1b.2e.3e.4b.5d.6d, 1b.2e.3e.4b.5d.6e, 1b.2e.3e.4b.5e.6a, 1b.2e.3e.4b.5e.6b,
1b.2e.3e.4b.5e.6c, 1b.2e.3e.4b.5e.6d, 1b.2e.3e.4b.5e.6e, 1b.2e.3e.4c.5a.6a,
1b.2e.3e.4c.5a.6b, 1b.2e.3e.4c.5a.6c, 1b.2e.3e.4c.5a.6d, 1b.2e.3e.4c.5a.6e,
1b.2e.3e.4c.5b.6a, 1b.2e.3e.4c.5b.6b, 1b.2e.3e.4c.5b.6c, 1b.2e.3e.4c.5b.6d,
1b.2e.3e.4c.5b.6e, 1b.2e.3e.4c.5c.6a, 1b.2e.3e.4c.5c.6b, 1b.2e.3e.4c.5c.6c,
1b.2e.3e.4c.5c.6d, 1b.2e.3e.4c.5c.6e, 1b.2e.3e.4c.5d.6a, 1b.2e.3e.4c.5d.6b,
1b.2e.3e.4c.5d.6c, 1b.2e.3e.4c.5d.6d, 1b.2e.3e.4c.5d.6e, 1b.2e.3e.4c.5e.6a,
1b.2e.3e.4c.5e.6b, 1b.2e.3e.4c.5e.6c, 1b.2e.3e.4c.5e.6d, 1b.2e.3e.4c.5e.6e,
1b.2e.3e.4d.5a.6a, 1b.2e.3e.4d.5a.6b, 1b.2e.3e.4d.5a.6c, 1b.2e.3e.4d.5a.6d,
1b.2e.3e.4d.5a.6e, 1b.2e.3e.4d.5b.6a, 1b.2e.3e.4d.5b.6b, 1b.2e.3e.4d.5b.6c,
1b.2e.3e.4d.5b.6d, 1b.2e.3e.4d.5b.6e, 1b.2e.3e.4d.5c.6a, 1b.2e.3e.4d.5c.6b,
1b.2e.3e.4d.5c.6c, 1b.2e.3e.4d.5c.6d, 1b.2e.3e.4d.5c.6e, 1b.2e.3e.4d.5d.6a,
1b.2e.3e.4d.5d.6b, 1b.2e.3e.4d.5d.6c, 1b.2e.3e.4d.5d.6d, 1b.2e.3e.4d.5d.6e,
1b.2e.3e.4d.5e.6a, 1b.2e.3e.4d.5e.6b, 1b.2e.3e.4d.5e.6c, 1b.2e.3e.4d.5e.6d,
1b.2e.3e.4d.5e.6e, 1b.2e.3e.4e.5a.6a, 1b.2e.3e.4e.5a.6b, 1b.2e.3e.4e.5a.6c,
1b.2e.3e.4e.5a.6d, 1b.2e.3e.4e.5a.6e, 1b.2e.3e.4e.5b.6a, 1b.2e.3e.4e.5b.6b,
1b.2e.3e.4e.5b.6c, 1b.2e.3e.4e.5b.6d, 1b.2e.3e.4e.5b.6e, 1b.2e.3e.4e.5c.6a,
1b.2e.3e.4e.5c.6b, 1b.2e.3e.4e.5c.6c, 1b.2e.3e.4e.5c.6d, 1b.2e.3e.4e.5c.6e,
1b.2e.3e.4e.5d.6a, 1b.2e.3e.4e.5d.6b, 1b.2e.3e.4e.5d.6c, 1b.2e.3e.4e.5d.6d,
1b.2e.3e.4e.5d.6e, 1b.2e.3e.4e.5e.6a, 1b.2e.3e.4e.5e.6b, 1b.2e.3e.4e.5e.6c,
1b.2e.3e.4e.5e.6d, 1b.2e.3e.4e.5e.6e, 1c.2a.3a.4a.5a.6a, 1c.2a.3a.4a.5a.6b,
1c.2a.3a.4a.5a.6c, 1c.2a.3a.4a.5a.6d, 1c.2a.3a.4a.5a.6e, 1c.2a.3a.4a.5b.6a,
1c.2a.3a.4a.5b.6b, 1c.2a.3a.4a.5b.6c, 1c.2a.3a.4a.5b.6d, 1c.2a.3a.4a.5b.6e,
1c.2a.3a.4a.5c.6a, 1c.2a.3a.4a.5c.6b, 1c.2a.3a.4a.5c.6c, 1c.2a.3a.4a.5c.6d,
1c.2a.3a.4a.5c.6e, 1c.2a.3a.4a.5d.6a, 1c.2a.3a.4a.5d.6b, 1c.2a.3a.4a.5d.6c,
1c.2a.3a.4a.5d.6d, 1c.2a.3a.4a.5d.6e, 1c.2a.3a.4a.5e.6a, 1c.2a.3a.4a.5e.6b,
1c.2a.3a.4a.5e.6c, 1c.2a.3a.4a.5e.6d, 1c.2a.3a.4a.5e.6e, 1c.2a.3a.4b.5a.6a,
1c.2a.3a.4b.5a.6b, 1c.2a.3a.4b.5a.6c, 1c.2a.3a.4b.5a.6d, 1c.2a.3a.4b.5a.6e,
1c.2a.3a.4b.5b.6a, 1c.2a.3a.4b.5b.6b, 1c.2a.3a.4b.5b.6c, 1c.2a.3a.4b.5b.6d,
1c.2a.3a.4b.5b.6e, 1c.2a.3a.4b.5c.6a, 1c.2a.3a.4b.5c.6b, 1c.2a.3a.4b.5c.6c,
1c.2a.3a.4b.5c.6d, 1c.2a.3a.4b.5c.6e, 1c.2a.3a.4b.5d.6a, 1c.2a.3a.4b.5d.6b,
1c.2a.3a.4b.5d.6c, 1c.2a.3a.4b.5d.6d, 1c.2a.3a.4b.5d.6e, 1c.2a.3a.4b.5e.6a,
1c.2a.3a.4b.5e.6b, 1c.2a.3a.4b.5e.6c, 1c.2a.3a.4b.5e.6d, 1c.2a.3a.4b.5e.6e,
1c.2a.3a.4c.5a.6a, 1c.2a.3a.4c.5a.6b, 1c.2a.3a.4c.5a.6c, 1c.2a.3a.4c.5a.6d,
1c.2a.3a.4c.5a.6e, 1c.2a.3a.4c.5b.6a, 1c.2a.3a.4c.5b.6b, 1c.2a.3a.4c.5b.6c,
1c.2a.3a.4c.5b.6d, 1c.2a.3a.4c.5b.6e, 1c.2a.3a.4c.5c.6a, 1c.2a.3a.4c.5c.6b,
1c.2a.3a.4c.5c.6c, 1c.2a.3a.4c.5c.6d, 1c.2a.3a.4c.5c.6e, 1c.2a.3a.4c.5d.6a,
1c.2a.3a.4c.5d.6b, 1c.2a.3a.4c.5d.6c, 1c.2a.3a.4c.5d.6d, 1c.2a.3a.4c.5d.6e,
1c.2a.3a.4c.5e.6a, 1c.2a.3a.4c.5e.6b, 1c.2a.3a.4c.5e.6c, 1c.2a.3a.4c.5e.6d,
1c.2a.3a.4c.5e.6e, 1c.2a.3a.4d.5a.6a, 1c.2a.3a.4d.5a.6b, 1c.2a.3a.4d.5a.6c,
1c.2a.3a.4d.5a.6d, 1c.2a.3a.4d.5a.6e, 1c.2a.3a.4d.5b.6a, 1c.2a.3a.4d.5b.6b,
1c.2a.3a.4d.5b.6c, 1c.2a.3a.4d.5b.6d, 1c.2a.3a.4d.5b.6e, 1c.2a.3a.4d.5c.6a,
1c.2a.3a.4d.5c.6b, 1c.2a.3a.4d.5c.6c, 1c.2a.3a.4d.5c.6d, 1c.2a.3a.4d.5c.6e,
1c.2a.3a.4d.5d.6a, 1c.2a.3a.4d.5d.6b, 1c.2a.3a.4d.5d.6c, 1c.2a.3a.4d.5d.6d,
1c.2a.3a.4d.5d.6e, 1c.2a.3a.4d.5e.6a, 1c.2a.3a.4d.5e.6b, 1c.2a.3a.4d.5e.6c,
1c.2a.3a.4d.5e.6d, 1c.2a.3a.4d.5e.6e, 1c.2a.3a.4e.5a.6a, 1c.2a.3a.4e.5a.6b,
1c.2a.3a.4e.5a.6c, 1c.2a.3a.4e.5a.6d, 1c.2a.3a.4e.5a.6e, 1c.2a.3a.4e.5b.6a,
1c.2a.3a.4e.5b.6b, 1c.2a.3a.4e.5b.6c, 1c.2a.3a.4e.5b.6d, 1c.2a.3a.4e.5b.6e,
1c.2a.3a.4e.5c.6a, 1c.2a.3a.4e.5c.6b, 1c.2a.3a.4e.5c.6c, 1c.2a.3a.4e.5c.6d,
1c.2a.3a.4e.5c.6e, 1c.2a.3a.4e.5d.6a, 1c.2a.3a.4e.5d.6b, 1c.2a.3a.4e.5d.6c,
1c.2a.3a.4e.5d.6d, 1c.2a.3a.4e.5d.6e, 1c.2a.3a.4e.5e.6a, 1c.2a.3a.4e.5e.6b,
1c.2a.3a.4e.5e.6c, 1c.2a.3a.4e.5e.6d, 1c.2a.3a.4e.5e.6e, 1c.2a.3b.4a.5a.6a,
1c.2a.3b.4a.5a.6b, 1c.2a.3b.4a.5a.6c, 1c.2a.3b.4a.5a.6d, 1c.2a.3b.4a.5a.6e,
1c.2a.3b.4a.5b.6a, 1c.2a.3b.4a.5b.6b, 1c.2a.3b.4a.5b.6c, 1c.2a.3b.4a.5b.6d,
1c.2a.3b.4a.5b.6e, 1c.2a.3b.4a.5c.6a, 1c.2a.3b.4a.5c.6b, 1c.2a.3b.4a.5c.6c,
1c.2a.3b.4a.5c.6d, 1c.2a.3b.4a.5c.6e, 1c.2a.3b.4a.5d.6a, 1c.2a.3b.4a.5d.6b,
1c.2a.3b.4a.5d.6c, 1c.2a.3b.4a.5d.6d, 1c.2a.3b.4a.5d.6e, 1c.2a.3b.4a.5e.6a,
1c.2a.3b.4a.5e.6b, 1c.2a.3b.4a.5e.6c, 1c.2a.3b.4a.5e.6d, 1c.2a.3b.4a.5e.6e,
1c.2a.3b.4b.5a.6a, 1c.2a.3b.4b.5a.6b, 1c.2a.3b.4b.5a.6c, 1c.2a.3b.4b.5a.6d,
1c.2a.3b.4b.5a.6e, 1c.2a.3b.4b.5b.6a, 1c.2a.3b.4b.5b.6b, 1c.2a.3b.4b.5b.6c,

TABLE 8-continued

List of Compounds of Formula (II)

1c.2a.3b.4b.5b.6d, 1c.2a.3b.4b.5b.6e, 1c.2a.3b.4b.5c.6a, 1c.2a.3b.4b.5c.6b,
1c.2a.3b.4b.5c.6c, 1c.2a.3b.4b.5c.6d, 1c.2a.3b.4b.5c.6e, 1c.2a.3b.4b.5d.6a,
1c.2a.3b.4b.5d.6b, 1c.2a.3b.4b.5d.6c, 1c.2a.3b.4b.5d.6d, 1c.2a.3b.4b.5d.6e,
1c.2a.3b.4b.5e.6a, 1c.2a.3b.4b.5e.6b, 1c.2a.3b.4b.5e.6c, 1c.2a.3b.4b.5e.6d,
1c.2a.3b.4b.5e.6e, 1c.2a.3b.4c.5a.6a, 1c.2a.3b.4c.5a.6b, 1c.2a.3b.4c.5a.6c,
1c.2a.3b.4c.5a.6d, 1c.2a.3b.4c.5a.6e, 1c.2a.3b.4c.5b.6a, 1c.2a.3b.4c.5b.6b,
1c.2a.3b.4c.5b.6c, 1c.2a.3b.4c.5b.6d, 1c.2a.3b.4c.5b.6e, 1c.2a.3b.4c.5c.6a,
1c.2a.3b.4c.5c.6b, 1c.2a.3b.4c.5c.6c, 1c.2a.3b.4c.5c.6d, 1c.2a.3b.4c.5c.6e,
1c.2a.3b.4c.5d.6a, 1c.2a.3b.4c.5d.6b, 1c.2a.3b.4c.5d.6c, 1c.2a.3b.4c.5d.6d,
1c.2a.3b.4c.5d.6e, 1c.2a.3b.4c.5e.6a, 1c.2a.3b.4c.5e.6b, 1c.2a.3b.4c.5e.6c,
1c.2a.3b.4c.5e.6d, 1c.2a.3b.4c.5e.6e, 1c.2a.3b.4d.5a.6a, 1c.2a.3b.4d.5a.6b,
1c.2a.3b.4d.5a.6c, 1c.2a.3b.4d.5a.6d, 1c.2a.3b.4d.5a.6e, 1c.2a.3b.4d.5b.6a,
1c.2a.3b.4d.5b.6b, 1c.2a.3b.4d.5b.6c, 1c.2a.3b.4d.5b.6d, 1c.2a.3b.4d.5b.6e,
1c.2a.3b.4d.5c.6a, 1c.2a.3b.4d.5c.6b, 1c.2a.3b.4d.5c.6c, 1c.2a.3b.4d.5c.6d,
1c.2a.3b.4d.5c.6e, 1c.2a.3b.4d.5d.6a, 1c.2a.3b.4d.5d.6b, 1c.2a.3b.4d.5d.6c,
1c.2a.3b.4d.5d.6d, 1c.2a.3b.4d.5d.6e, 1c.2a.3b.4d.5e.6a, 1c.2a.3b.4d.5e.6b,
1c.2a.3b.4d.5e.6c, 1c.2a.3b.4d.5e.6d, 1c.2a.3b.4d.5e.6e, 1c.2a.3b.4e.5a.6a,
1c.2a.3b.4e.5a.6b, 1c.2a.3b.4e.5a.6c, 1c.2a.3b.4e.5a.6d, 1c.2a.3b.4e.5a.6e,
1c.2a.3b.4e.5b.6a, 1c.2a.3b.4e.5b.6b, 1c.2a.3b.4e.5b.6c, 1c.2a.3b.4e.5b.6d,
1c.2a.3b.4e.5b.6e, 1c.2a.3b.4e.5c.6a, 1c.2a.3b.4e.5c.6b, 1c.2a.3b.4e.5c.6c,
1c.2a.3b.4e.5c.6d, 1c.2a.3b.4e.5c.6e, 1c.2a.3b.4e.5d.6a, 1c.2a.3b.4e.5d.6b,
1c.2a.3b.4e.5d.6c, 1c.2a.3b.4e.5d.6d, 1c.2a.3b.4e.5d.6e, 1c.2a.3b.4e.5e.6a,
1c.2a.3b.4e.5e.6b, 1c.2a.3b.4e.5e.6c, 1c.2a.3b.4e.5e.6d, 1c.2a.3b.4e.5e.6e,
1c.2a.3c.4a.5a.6a, 1c.2a.3c.4a.5a.6b, 1c.2a.3c.4a.5a.6c, 1c.2a.3c.4a.5a.6d,
1c.2a.3c.4a.5a.6e, 1c.2a.3c.4a.5b.6a, 1c.2a.3c.4a.5b.6b, 1c.2a.3c.4a.5b.6c,
1c.2a.3c.4a.5b.6d, 1c.2a.3c.4a.5b.6e, 1c.2a.3c.4a.5c.6a, 1c.2a.3c.4a.5c.6b,
1c.2a.3c.4a.5c.6c, 1c.2a.3c.4a.5c.6d, 1c.2a.3c.4a.5c.6e, 1c.2a.3c.4a.5d.6a,
1c.2a.3c.4a.5d.6b, 1c.2a.3c.4a.5d.6c, 1c.2a.3c.4a.5d.6d, 1c.2a.3c.4a.5d.6e,
1c.2a.3c.4a.5e.6a, 1c.2a.3c.4a.5e.6b, 1c.2a.3c.4a.5e.6c, 1c.2a.3c.4a.5e.6d,
1c.2a.3c.4a.5e.6e, 1c.2a.3c.4b.5a.6a, 1c.2a.3c.4b.5a.6b, 1c.2a.3c.4b.5a.6c,
1c.2a.3c.4b.5a.6d, 1c.2a.3c.4b.5a.6e, 1c.2a.3c.4b.5b.6a, 1c.2a.3c.4b.5b.6b,
1c.2a.3c.4b.5b.6c, 1c.2a.3c.4b.5b.6d, 1c.2a.3c.4b.5b.6e, 1c.2a.3c.4b.5c.6a,
1c.2a.3c.4b.5c.6b, 1c.2a.3c.4b.5c.6c, 1c.2a.3c.4b.5c.6d, 1c.2a.3c.4b.5c.6e,
1c.2a.3c.4b.5d.6a, 1c.2a.3c.4b.5d.6b, 1c.2a.3c.4b.5d.6c, 1c.2a.3c.4b.5d.6d,
1c.2a.3c.4b.5d.6e, 1c.2a.3c.4b.5e.6a, 1c.2a.3c.4b.5e.6b, 1c.2a.3c.4b.5e.6c,
1c.2a.3c.4b.5e.6d, 1c.2a.3c.4b.5e.6e, 1c.2a.3c.4c.5a.6a, 1c.2a.3c.4c.5a.6b,
1c.2a.3c.4c.5a.6c, 1c.2a.3c.4c.5a.6d, 1c.2a.3c.4c.5a.6e, 1c.2a.3c.4c.5b.6a,
1c.2a.3c.4c.5b.6b, 1c.2a.3c.4c.5b.6c, 1c.2a.3c.4c.5b.6d, 1c.2a.3c.4c.5b.6e,
1c.2a.3c.4c.5c.6a, 1c.2a.3c.4c.5c.6b, 1c.2a.3c.4c.5c.6c, 1c.2a.3c.4c.5c.6d,
1c.2a.3c.4c.5c.6e, 1c.2a.3c.4c.5d.6a, 1c.2a.3c.4c.5d.6b, 1c.2a.3c.4c.5d.6c,
1c.2a.3c.4c.5d.6d, 1c.2a.3c.4c.5d.6e, 1c.2a.3c.4c.5e.6a, 1c.2a.3c.4c.5e.6b,
1c.2a.3c.4c.5e.6c, 1c.2a.3c.4c.5e.6d, 1c.2a.3c.4c.5e.6e, 1c.2a.3c.4d.5a.6a,
1c.2a.3c.4d.5a.6b, 1c.2a.3c.4d.5a.6c, 1c.2a.3c.4d.5a.6d, 1c.2a.3c.4d.5a.6e,
1c.2a.3c.4d.5b.6a, 1c.2a.3c.4d.5b.6b, 1c.2a.3c.4d.5b.6c, 1c.2a.3c.4d.5b.6d,
1c.2a.3c.4d.5b.6e, 1c.2a.3c.4d.5c.6a, 1c.2a.3c.4d.5c.6b, 1c.2a.3c.4d.5c.6c,
1c.2a.3c.4d.5c.6d, 1c.2a.3c.4d.5c.6e, 1c.2a.3c.4d.5d.6a, 1c.2a.3c.4d.5d.6b,
1c.2a.3c.4d.5d.6c, 1c.2a.3c.4d.5d.6d, 1c.2a.3c.4d.5d.6e, 1c.2a.3c.4d.5e.6a,
1c.2a.3c.4d.5e.6b, 1c.2a.3c.4d.5e.6c, 1c.2a.3c.4d.5e.6d, 1c.2a.3c.4d.5e.6e,
1c.2a.3c.4e.5a.6a, 1c.2a.3c.4e.5a.6b, 1c.2a.3c.4e.5a.6c, 1c.2a.3c.4e.5a.6d,
1c.2a.3c.4e.5a.6e, 1c.2a.3c.4e.5b.6a, 1c.2a.3c.4e.5b.6b, 1c.2a.3c.4e.5b.6c,
1c.2a.3c.4e.5b.6d, 1c.2a.3c.4e.5b.6e, 1c.2a.3c.4e.5c.6a, 1c.2a.3c.4e.5c.6b,
1c.2a.3c.4e.5c.6c, 1c.2a.3c.4e.5c.6d, 1c.2a.3c.4e.5c.6e, 1c.2a.3c.4e.5d.6a,
1c.2a.3c.4e.5d.6b, 1c.2a.3c.4e.5d.6c, 1c.2a.3c.4e.5d.6d, 1c.2a.3c.4e.5d.6e,
1c.2a.3c.4e.5e.6a, 1c.2a.3c.4e.5e.6b, 1c.2a.3c.4e.5e.6c, 1c.2a.3c.4e.5e.6d,
1c.2a.3c.4e.5e.6e, 1c.2a.3d.4a.5a.6a, 1c.2a.3d.4a.5a.6b, 1c.2a.3d.4a.5a.6c,
1c.2a.3d.4a.5a.6d, 1c.2a.3d.4a.5a.6e, 1c.2a.3d.4a.5b.6a, 1c.2a.3d.4a.5b.6b,
1c.2a.3d.4a.5b.6c, 1c.2a.3d.4a.5b.6d, 1c.2a.3d.4a.5b.6e, 1c.2a.3d.4a.5c.6a,
1c.2a.3d.4a.5c.6b, 1c.2a.3d.4a.5c.6c, 1c.2a.3d.4a.5c.6d, 1c.2a.3d.4a.5c.6e,
1c.2a.3d.4a.5d.6a, 1c.2a.3d.4a.5d.6b, 1c.2a.3d.4a.5d.6c, 1c.2a.3d.4a.5d.6d,
1c.2a.3d.4a.5d.6e, 1c.2a.3d.4a.5e.6a, 1c.2a.3d.4a.5e.6b, 1c.2a.3d.4a.5e.6c,
1c.2a.3d.4a.5e.6d, 1c.2a.3d.4a.5e.6e, 1c.2a.3d.4b.5a.6a, 1c.2a.3d.4b.5a.6b,
1c.2a.3d.4b.5a.6c, 1c.2a.3d.4b.5a.6d, 1c.2a.3d.4b.5a.6e, 1c.2a.3d.4b.5b.6a,
1c.2a.3d.4b.5b.6b, 1c.2a.3d.4b.5b.6c, 1c.2a.3d.4b.5b.6d, 1c.2a.3d.4b.5b.6e,
1c.2a.3d.4b.5c.6a, 1c.2a.3d.4b.5c.6b, 1c.2a.3d.4b.5c.6c, 1c.2a.3d.4b.5c.6d,
1c.2a.3d.4b.5c.6e, 1c.2a.3d.4b.5d.6a, 1c.2a.3d.4b.5d.6b, 1c.2a.3d.4b.5d.6c,
1c.2a.3d.4b.5d.6d, 1c.2a.3d.4b.5d.6e, 1c.2a.3d.4b.5e.6a, 1c.2a.3d.4b.5e.6b,
1c.2a.3d.4b.5e.6c, 1c.2a.3d.4b.5e.6d, 1c.2a.3d.4b.5e.6e, 1c.2a.3d.4c.5a.6a,
1c.2a.3d.4c.5a.6b, 1c.2a.3d.4c.5a.6c, 1c.2a.3d.4c.5a.6d, 1c.2a.3d.4c.5a.6e,
1c.2a.3d.4c.5b.6a, 1c.2a.3d.4c.5b.6b, 1c.2a.3d.4c.5b.6c, 1c.2a.3d.4c.5b.6d,
1c.2a.3d.4c.5b.6e, 1c.2a.3d.4c.5c.6a, 1c.2a.3d.4c.5c.6b, 1c.2a.3d.4c.5c.6c,
1c.2a.3d.4c.5c.6d, 1c.2a.3d.4c.5c.6e, 1c.2a.3d.4c.5d.6a, 1c.2a.3d.4c.5d.6b,
1c.2a.3d.4c.5d.6c, 1c.2a.3d.4c.5d.6d, 1c.2a.3d.4c.5d.6e, 1c.2a.3d.4c.5e.6a,
1c.2a.3d.4c.5e.6b, 1c.2a.3d.4c.5e.6c, 1c.2a.3d.4c.5e.6d, 1c.2a.3d.4c.5e.6e,
1c.2a.3d.4d.5a.6a, 1c.2a.3d.4d.5a.6b, 1c.2a.3d.4d.5a.6c, 1c.2a.3d.4d.5a.6d,
1c.2a.3d.4d.5a.6e, 1c.2a.3d.4d.5b.6a, 1c.2a.3d.4d.5b.6b, 1c.2a.3d.4d.5b.6c,
1c.2a.3d.4d.5b.6d, 1c.2a.3d.4d.5b.6e, 1c.2a.3d.4d.5c.6a, 1c.2a.3d.4d.5c.6b,
1c.2a.3d.4d.5c.6c, 1c.2a.3d.4d.5c.6d, 1c.2a.3d.4d.5c.6e, 1c.2a.3d.4d.5d.6a,
1c.2a.3d.4d.5d.6b, 1c.2a.3d.4d.5d.6c, 1c.2a.3d.4d.5d.6d, 1c.2a.3d.4d.5d.6e,

TABLE 8-continued

List of Compounds of Formula (II)

1c.2a.3d.4d.5e.6a, 1c.2a.3d.4d.5e.6b, 1c.2a.3d.4d.5e.6c, 1c.2a.3d.4d.5e.6d,
1c.2a.3d.4d.5e.6e, 1c.2a.3d.4e.5a.6a, 1c.2a.3d.4e.5a.6b, 1c.2a.3d.4e.5a.6c,
1c.2a.3d.4e.5a.6d, 1c.2a.3d.4e.5a.6e, 1c.2a.3d.4e.5b.6a, 1c.2a.3d.4e.5b.6b,
1c.2a.3d.4e.5b.6c, 1c.2a.3d.4e.5b.6d, 1c.2a.3d.4e.5b.6e, 1c.2a.3d.4e.5c.6a,
1c.2a.3d.4e.5c.6b, 1c.2a.3d.4e.5c.6c, 1c.2a.3d.4e.5c.6d, 1c.2a.3d.4e.5c.6e,
1c.2a.3d.4e.5d.6a, 1c.2a.3d.4e.5d.6b, 1c.2a.3d.4e.5d.6c, 1c.2a.3d.4e.5d.6d,
1c.2a.3d.4e.5d.6e, 1c.2a.3d.4e.5e.6a, 1c.2a.3d.4e.5e.6b, 1c.2a.3d.4e.5e.6c,
1c.2a.3d.4e.5e.6d, 1c.2a.3d.4e.5e.6e, 1c.2a.3e.4a.5a.6a, 1c.2a.3e.4a.5a.6b,
1c.2a.3e.4a.5a.6c, 1c.2a.3e.4a.5a.6d, 1c.2a.3e.4a.5a.6e, 1c.2a.3e.4a.5b.6a,
1c.2a.3e.4a.5b.6b, 1c.2a.3e.4a.5b.6c, 1c.2a.3e.4a.5b.6d, 1c.2a.3e.4a.5b.6e,
1c.2a.3e.4a.5c.6a, 1c.2a.3e.4a.5c.6b, 1c.2a.3e.4a.5c.6c, 1c.2a.3e.4a.5c.6d,
1c.2a.3e.4a.5c.6e, 1c.2a.3e.4a.5d.6a, 1c.2a.3e.4a.5d.6b, 1c.2a.3e.4a.5d.6c,
1c.2a.3e.4a.5d.6d, 1c.2a.3e.4a.5d.6e, 1c.2a.3e.4a.5e.6a, 1c.2a.3e.4a.5e.6b,
1c.2a.3e.4a.5e.6c, 1c.2a.3e.4a.5e.6d, 1c.2a.3e.4a.5e.6e, 1c.2a.3e.4b.5a.6a,
1c.2a.3e.4b.5a.6b, 1c.2a.3e.4b.5a.6c, 1c.2a.3e.4b.5a.6d, 1c.2a.3e.4b.5a.6e,
1c.2a.3e.4b.5b.6a, 1c.2a.3e.4b.5b.6b, 1c.2a.3e.4b.5b.6c, 1c.2a.3e.4b.5b.6d,
1c.2a.3e.4b.5b.6e, 1c.2a.3e.4b.5c.6a, 1c.2a.3e.4b.5c.6b, 1c.2a.3e.4b.5c.6c,
1c.2a.3e.4b.5c.6d, 1c.2a.3e.4b.5c.6e, 1c.2a.3e.4b.5d.6a, 1c.2a.3e.4b.5d.6b,
1c.2a.3e.4b.5d.6c, 1c.2a.3e.4b.5d.6d, 1c.2a.3e.4b.5d.6e, 1c.2a.3e.4b.5e.6a,
1c.2a.3e.4b.5e.6b, 1c.2a.3e.4b.5e.6c, 1c.2a.3e.4b.5e.6d, 1c.2a.3e.4b.5e.6e,
1c.2a.3e.4c.5a.6a, 1c.2a.3e.4c.5a.6b, 1c.2a.3e.4c.5a.6c, 1c.2a.3e.4c.5a.6d,
1c.2a.3e.4c.5a.6e, 1c.2a.3e.4c.5b.6a, 1c.2a.3e.4c.5b.6b, 1c.2a.3e.4c.5b.6c,
1c.2a.3e.4c.5b.6d, 1c.2a.3e.4c.5b.6e, 1c.2a.3e.4c.5c.6a, 1c.2a.3e.4c.5c.6b,
1c.2a.3e.4c.5c.6c, 1c.2a.3e.4c.5c.6d, 1c.2a.3e.4c.5c.6e, 1c.2a.3e.4c.5d.6a,
1c.2a.3e.4c.5d.6b, 1c.2a.3e.4c.5d.6c, 1c.2a.3e.4c.5d.6d, 1c.2a.3e.4c.5d.6e,
1c.2a.3e.4c.5e.6a, 1c.2a.3e.4c.5e.6b, 1c.2a.3e.4c.5e.6c, 1c.2a.3e.4c.5e.6d,
1c.2a.3e.4c.5e.6e, 1c.2a.3e.4d.5a.6a, 1c.2a.3e.4d.5a.6b, 1c.2a.3e.4d.5a.6c,
1c.2a.3e.4d.5a.6d, 1c.2a.3e.4d.5a.6e, 1c.2a.3e.4d.5b.6a, 1c.2a.3e.4d.5b.6b,
1c.2a.3e.4d.5b.6c, 1c.2a.3e.4d.5b.6d, 1c.2a.3e.4d.5b.6e, 1c.2a.3e.4d.5c.6a,
1c.2a.3e.4d.5c.6b, 1c.2a.3e.4d.5c.6c, 1c.2a.3e.4d.5c.6d, 1c.2a.3e.4d.5c.6e,
1c.2a.3e.4d.5d.6a, 1c.2a.3e.4d.5d.6b, 1c.2a.3e.4d.5d.6c, 1c.2a.3e.4d.5d.6d,
1c.2a.3e.4d.5d.6e, 1c.2a.3e.4d.5e.6a, 1c.2a.3e.4d.5e.6b, 1c.2a.3e.4d.5e.6c,
1c.2a.3e.4d.5e.6d, 1c.2a.3e.4d.5e.6e, 1c.2a.3e.4e.5a.6a, 1c.2a.3e.4e.5a.6b,
1c.2a.3e.4e.5a.6c, 1c.2a.3e.4e.5a.6d, 1c.2a.3e.4e.5a.6e, 1c.2a.3e.4e.5b.6a,
1c.2a.3e.4e.5b.6b, 1c.2a.3e.4e.5b.6c, 1c.2a.3e.4e.5b.6d, 1c.2a.3e.4e.5b.6e,
1c.2a.3e.4e.5c.6a, 1c.2a.3e.4e.5c.6b, 1c.2a.3e.4e.5c.6c, 1c.2a.3e.4e.5c.6d,
1c.2a.3e.4e.5c.6e, 1c.2a.3e.4e.5d.6a, 1c.2a.3e.4e.5d.6b, 1c.2a.3e.4e.5d.6c,
1c.2a.3e.4e.5d.6d, 1c.2a.3e.4e.5d.6e, 1c.2a.3e.4e.5e.6a, 1c.2a.3e.4e.5e.6b,
1c.2a.3e.4e.5e.6c, 1c.2a.3e.4e.5e.6d, 1c.2a.3e.4e.5e.6e, 1c.2b.3a.4a.5a.6a,
1c.2b.3a.4a.5a.6b, 1c.2b.3a.4a.5a.6c, 1c.2b.3a.4a.5a.6d, 1c.2b.3a.4a.5a.6e,
1c.2b.3a.4a.5b.6a, 1c.2b.3a.4a.5b.6b, 1c.2b.3a.4a.5b.6c, 1c.2b.3a.4a.5b.6d,
1c.2b.3a.4a.5b.6e, 1c.2b.3a.4a.5c.6a, 1c.2b.3a.4a.5c.6b, 1c.2b.3a.4a.5c.6c,
1c.2b.3a.4a.5c.6d, 1c.2b.3a.4a.5c.6e, 1c.2b.3a.4a.5d.6a, 1c.2b.3a.4a.5d.6b,
1c.2b.3a.4a.5d.6c, 1c.2b.3a.4a.5d.6d, 1c.2b.3a.4a.5d.6e, 1c.2b.3a.4a.5e.6a,
1c.2b.3a.4a.5e.6b, 1c.2b.3a.4a.5e.6c, 1c.2b.3a.4a.5e.6d, 1c.2b.3a.4a.5e.6e,
1c.2b.3a.4b.5a.6a, 1c.2b.3a.4b.5a.6b, 1c.2b.3a.4b.5a.6c, 1c.2b.3a.4b.5a.6d,
1c.2b.3a.4b.5a.6e, 1c.2b.3a.4b.5b.6a, 1c.2b.3a.4b.5b.6b, 1c.2b.3a.4b.5b.6c,
1c.2b.3a.4b.5b.6d, 1c.2b.3a.4b.5b.6e, 1c.2b.3a.4b.5c.6a, 1c.2b.3a.4b.5c.6b,
1c.2b.3a.4b.5c.6c, 1c.2b.3a.4b.5c.6d, 1c.2b.3a.4b.5c.6e, 1c.2b.3a.4b.5d.6a,
1c.2b.3a.4b.5d.6b, 1c.2b.3a.4b.5d.6c, 1c.2b.3a.4b.5d.6d, 1c.2b.3a.4b.5d.6e,
1c.2b.3a.4b.5e.6a, 1c.2b.3a.4b.5e.6b, 1c.2b.3a.4b.5e.6c, 1c.2b.3a.4b.5e.6d,
1c.2b.3a.4b.5e.6e, 1c.2b.3a.4c.5a.6a, 1c.2b.3a.4c.5a.6b, 1c.2b.3a.4c.5a.6c,
1c.2b.3a.4c.5a.6d, 1c.2b.3a.4c.5a.6e, 1c.2b.3a.4c.5b.6a, 1c.2b.3a.4c.5b.6b,
1c.2b.3a.4c.5b.6c, 1c.2b.3a.4c.5b.6d, 1c.2b.3a.4c.5b.6e, 1c.2b.3a.4c.5c.6a,
1c.2b.3a.4c.5c.6b, 1c.2b.3a.4c.5c.6c, 1c.2b.3a.4c.5c.6d, 1c.2b.3a.4c.5c.6e,
1c.2b.3a.4c.5d.6a, 1c.2b.3a.4c.5d.6b, 1c.2b.3a.4c.5d.6c, 1c.2b.3a.4c.5d.6d,
1c.2b.3a.4c.5d.6e, 1c.2b.3a.4c.5e.6a, 1c.2b.3a.4c.5e.6b, 1c.2b.3a.4c.5e.6c,
1c.2b.3a.4c.5e.6d, 1c.2b.3a.4c.5e.6e, 1c.2b.3a.4d.5a.6a, 1c.2b.3a.4d.5a.6b,
1c.2b.3a.4d.5a.6c, 1c.2b.3a.4d.5a.6d, 1c.2b.3a.4d.5a.6e, 1c.2b.3a.4d.5b.6a,
1c.2b.3a.4d.5b.6b, 1c.2b.3a.4d.5b.6c, 1c.2b.3a.4d.5b.6d, 1c.2b.3a.4d.5b.6e,
1c.2b.3a.4d.5c.6a, 1c.2b.3a.4d.5c.6b, 1c.2b.3a.4d.5c.6c, 1c.2b.3a.4d.5c.6d,
1c.2b.3a.4d.5c.6e, 1c.2b.3a.4d.5d.6a, 1c.2b.3a.4d.5d.6b, 1c.2b.3a.4d.5d.6c,
1c.2b.3a.4d.5d.6d, 1c.2b.3a.4d.5d.6e, 1c.2b.3a.4d.5e.6a, 1c.2b.3a.4d.5e.6b,
1c.2b.3a.4d.5e.6c, 1c.2b.3a.4d.5e.6d, 1c.2b.3a.4d.5e.6e, 1c.2b.3a.4e.5a.6a,
1c.2b.3a.4e.5a.6b, 1c.2b.3a.4e.5a.6c, 1c.2b.3a.4e.5a.6d, 1c.2b.3a.4e.5a.6e,
1c.2b.3a.4e.5b.6a, 1c.2b.3a.4e.5b.6b, 1c.2b.3a.4e.5b.6c, 1c.2b.3a.4e.5b.6d,
1c.2b.3a.4e.5b.6e, 1c.2b.3a.4e.5c.6a, 1c.2b.3a.4e.5c.6b, 1c.2b.3a.4e.5c.6c,
1c.2b.3a.4e.5c.6d, 1c.2b.3a.4e.5c.6e, 1c.2b.3a.4e.5d.6a, 1c.2b.3a.4e.5d.6b,
1c.2b.3a.4e.5d.6c, 1c.2b.3a.4e.5d.6d, 1c.2b.3a.4e.5d.6e, 1c.2b.3a.4e.5e.6a,
1c.2b.3a.4e.5e.6b, 1c.2b.3a.4e.5e.6c, 1c.2b.3a.4e.5e.6d, 1c.2b.3a.4e.5e.6e,
1c.2b.3b.4a.5a.6a, 1c.2b.3b.4a.5a.6b, 1c.2b.3b.4a.5a.6c, 1c.2b.3b.4a.5a.6d,
1c.2b.3b.4a.5a.6e, 1c.2b.3b.4a.5b.6a, 1c.2b.3b.4a.5b.6b, 1c.2b.3b.4a.5b.6c,
1c.2b.3b.4a.5b.6d, 1c.2b.3b.4a.5b.6e, 1c.2b.3b.4a.5c.6a, 1c.2b.3b.4a.5c.6b,
1c.2b.3b.4a.5c.6c, 1c.2b.3b.4a.5c.6d, 1c.2b.3b.4a.5c.6e, 1c.2b.3b.4a.5d.6a,
1c.2b.3b.4a.5d.6b, 1c.2b.3b.4a.5d.6c, 1c.2b.3b.4a.5d.6d, 1c.2b.3b.4a.5d.6e,
1c.2b.3b.4a.5e.6a, 1c.2b.3b.4a.5e.6b, 1c.2b.3b.4a.5e.6c, 1c.2b.3b.4a.5e.6d,
1c.2b.3b.4a.5e.6e, 1c.2b.3b.4b.5a.6a, 1c.2b.3b.4b.5a.6b, 1c.2b.3b.4b.5a.6c,
1c.2b.3b.4b.5a.6d, 1c.2b.3b.4b.5a.6e, 1c.2b.3b.4b.5b.6a, 1c.2b.3b.4b.5b.6b,

TABLE 8-continued

List of Compounds of Formula (II)

1c.2b.3b.4b.5b.6c, 1c.2b.3b.4b.5b.6d, 1c.2b.3b.4b.5b.6e, 1c.2b.3b.4b.5c.6a,
1c.2b.3b.4b.5c.6b, 1c.2b.3b.4b.5c.6c, 1c.2b.3b.4b.5c.6d, 1c.2b.3b.4b.5c.6e,
1c.2b.3b.4b.5d.6a, 1c.2b.3b.4b.5d.6b, 1c.2b.3b.4b.5d.6c, 1c.2b.3b.4b.5d.6d,
1c.2b.3b.4b.5d.6e, 1c.2b.3b.4b.5e.6a, 1c.2b.3b.4b.5e.6b, 1c.2b.3b.4b.5e.6c,
1c.2b.3b.4b.5e.6d, 1c.2b.3b.4b.5e.6e, 1c.2b.3b.4c.5a.6a, 1c.2b.3b.4c.5a.6b,
1c.2b.3b.4c.5a.6c, 1c.2b.3b.4c.5a.6d, 1c.2b.3b.4c.5a.6e, 1c.2b.3b.4c.5b.6a,
1c.2b.3b.4c.5b.6b, 1c.2b.3b.4c.5b.6c, 1c.2b.3b.4c.5b.6d, 1c.2b.3b.4c.5b.6e,
1c.2b.3b.4c.5c.6a, 1c.2b.3b.4c.5c.6b, 1c.2b.3b.4c.5c.6c, 1c.2b.3b.4c.5c.6d,
1c.2b.3b.4c.5c.6e, 1c.2b.3b.4c.5d.6a, 1c.2b.3b.4c.5d.6b, 1c.2b.3b.4c.5d.6c,
1c.2b.3b.4c.5d.6d, 1c.2b.3b.4c.5d.6e, 1c.2b.3b.4c.5e.6a, 1c.2b.3b.4c.5e.6b,
1c.2b.3b.4c.5e.6c, 1c.2b.3b.4c.5e.6d, 1c.2b.3b.4c.5e.6e, 1c.2b.3b.4d.5a.6a,
1c.2b.3b.4d.5a.6b, 1c.2b.3b.4d.5a.6c, 1c.2b.3b.4d.5a.6d, 1c.2b.3b.4d.5a.6e,
1c.2b.3b.4d.5b.6a, 1c.2b.3b.4d.5b.6b, 1c.2b.3b.4d.5b.6c, 1c.2b.3b.4d.5b.6d,
1c.2b.3b.4d.5b.6e, 1c.2b.3b.4d.5c.6a, 1c.2b.3b.4d.5c.6b, 1c.2b.3b.4d.5c.6c,
1c.2b.3b.4d.5c.6d, 1c.2b.3b.4d.5c.6e, 1c.2b.3b.4d.5d.6a, 1c.2b.3b.4d.5d.6b,
1c.2b.3b.4d.5d.6c, 1c.2b.3b.4d.5d.6d, 1c.2b.3b.4d.5d.6e, 1c.2b.3b.4d.5e.6a,
1c.2b.3b.4d.5e.6b, 1c.2b.3b.4d.5e.6c, 1c.2b.3b.4d.5e.6d, 1c.2b.3b.4d.5e.6e,
1c.2b.3b.4e.5a.6a, 1c.2b.3b.4e.5a.6b, 1c.2b.3b.4e.5a.6c, 1c.2b.3b.4e.5a.6d,
1c.2b.3b.4e.5a.6e, 1c.2b.3b.4e.5b.6a, 1c.2b.3b.4e.5b.6b, 1c.2b.3b.4e.5b.6c,
1c.2b.3b.4e.5b.6d, 1c.2b.3b.4e.5b.6e, 1c.2b.3b.4e.5c.6a, 1c.2b.3b.4e.5c.6b,
1c.2b.3b.4e.5c.6c, 1c.2b.3b.4e.5c.6d, 1c.2b.3b.4e.5c.6e, 1c.2b.3b.4e.5d.6a,
1c.2b.3b.4e.5d.6b, 1c.2b.3b.4e.5d.6c, 1c.2b.3b.4e.5d.6d, 1c.2b.3b.4e.5d.6e,
1c.2b.3b.4e.5e.6a, 1c.2b.3b.4e.5e.6b, 1c.2b.3b.4e.5e.6c, 1c.2b.3b.4e.5e.6d,
1c.2b.3b.4e.5e.6e, 1c.2b.3c.4a.5a.6a, 1c.2b.3c.4a.5a.6b, 1c.2b.3c.4a.5a.6c,
1c.2b.3c.4a.5a.6d, 1c.2b.3c.4a.5a.6e, 1c.2b.3c.4a.5b.6a, 1c.2b.3c.4a.5b.6b,
1c.2b.3c.4a.5b.6c, 1c.2b.3c.4a.5b.6d, 1c.2b.3c.4a.5b.6e, 1c.2b.3c.4a.5c.6a,
1c.2b.3c.4a.5c.6b, 1c.2b.3c.4a.5c.6c, 1c.2b.3c.4a.5c.6d, 1c.2b.3c.4a.5c.6e,
1c.2b.3c.4a.5d.6a, 1c.2b.3c.4a.5d.6b, 1c.2b.3c.4a.5d.6c, 1c.2b.3c.4a.5d.6d,
1c.2b.3c.4a.5d.6e, 1c.2b.3c.4a.5e.6a, 1c.2b.3c.4a.5e.6b, 1c.2b.3c.4a.5e.6c,
1c.2b.3c.4a.5e.6d, 1c.2b.3c.4a.5e.6e, 1c.2b.3c.4b.5a.6a, 1c.2b.3c.4b.5a.6b,
1c.2b.3c.4b.5a.6c, 1c.2b.3c.4b.5a.6d, 1c.2b.3c.4b.5a.6e, 1c.2b.3c.4b.5b.6a,
1c.2b.3c.4b.5b.6b, 1c.2b.3c.4b.5b.6c, 1c.2b.3c.4b.5b.6d, 1c.2b.3c.4b.5b.6e,
1c.2b.3c.4b.5c.6a, 1c.2b.3c.4b.5c.6b, 1c.2b.3c.4b.5c.6c, 1c.2b.3c.4b.5c.6d,
1c.2b.3c.4b.5c.6e, 1c.2b.3c.4b.5d.6a, 1c.2b.3c.4b.5d.6b, 1c.2b.3c.4b.5d.6c,
1c.2b.3c.4b.5d.6d, 1c.2b.3c.4b.5d.6e, 1c.2b.3c.4b.5e.6a, 1c.2b.3c.4b.5e.6b,
1c.2b.3c.4b.5e.6c, 1c.2b.3c.4b.5e.6d, 1c.2b.3c.4b.5e.6e, 1c.2b.3c.4c.5a.6a,
1c.2b.3c.4c.5a.6b, 1c.2b.3c.4c.5a.6c, 1c.2b.3c.4c.5a.6d, 1c.2b.3c.4c.5a.6e,
1c.2b.3c.4c.5b.6a, 1c.2b.3c.4c.5b.6b, 1c.2b.3c.4c.5b.6c, 1c.2b.3c.4c.5b.6d,
1c.2b.3c.4c.5b.6e, 1c.2b.3c.4c.5c.6a, 1c.2b.3c.4c.5c.6b, 1c.2b.3c.4c.5c.6c,
1c.2b.3c.4c.5c.6d, 1c.2b.3c.4c.5c.6e, 1c.2b.3c.4c.5d.6a, 1c.2b.3c.4c.5d.6b,
1c.2b.3c.4c.5d.6c, 1c.2b.3c.4c.5d.6d, 1c.2b.3c.4c.5d.6e, 1c.2b.3c.4c.5e.6a,
1c.2b.3c.4c.5e.6b, 1c.2b.3c.4c.5e.6c, 1c.2b.3c.4c.5e.6d, 1c.2b.3c.4c.5e.6e,
1c.2b.3c.4d.5a.6a, 1c.2b.3c.4d.5a.6b, 1c.2b.3c.4d.5a.6c, 1c.2b.3c.4d.5a.6d,
1c.2b.3c.4d.5a.6e, 1c.2b.3c.4d.5b.6a, 1c.2b.3c.4d.5b.6b, 1c.2b.3c.4d.5b.6c,
1c.2b.3c.4d.5b.6d, 1c.2b.3c.4d.5b.6e, 1c.2b.3c.4d.5c.6a, 1c.2b.3c.4d.5c.6b,
1c.2b.3c.4d.5c.6c, 1c.2b.3c.4d.5c.6d, 1c.2b.3c.4d.5c.6e, 1c.2b.3c.4d.5d.6a,
1c.2b.3c.4d.5d.6b, 1c.2b.3c.4d.5d.6c, 1c.2b.3c.4d.5d.6d, 1c.2b.3c.4d.5d.6e,
1c.2b.3c.4d.5e.6a, 1c.2b.3c.4d.5e.6b, 1c.2b.3c.4d.5e.6c, 1c.2b.3c.4d.5e.6d,
1c.2b.3c.4d.5e.6e, 1c.2b.3c.4e.5a.6a, 1c.2b.3c.4e.5a.6b, 1c.2b.3c.4e.5a.6c,
1c.2b.3c.4e.5a.6d, 1c.2b.3c.4e.5a.6e, 1c.2b.3c.4e.5b.6a, 1c.2b.3c.4e.5b.6b,
1c.2b.3c.4e.5b.6c, 1c.2b.3c.4e.5b.6d, 1c.2b.3c.4e.5b.6e, 1c.2b.3c.4e.5c.6a,
1c.2b.3c.4e.5c.6b, 1c.2b.3c.4e.5c.6c, 1c.2b.3c.4e.5c.6d, 1c.2b.3c.4e.5c.6e,
1c.2b.3c.4e.5d.6a, 1c.2b.3c.4e.5d.6b, 1c.2b.3c.4e.5d.6c, 1c.2b.3c.4e.5d.6d,
1c.2b.3c.4e.5d.6e, 1c.2b.3c.4e.5e.6a, 1c.2b.3c.4e.5e.6b, 1c.2b.3c.4e.5e.6c,
1c.2b.3c.4e.5e.6d, 1c.2b.3c.4e.5e.6e, 1c.2b.3d.4a.5a.6a, 1c.2b.3d.4a.5a.6b,
1c.2b.3d.4a.5a.6c, 1c.2b.3d.4a.5a.6d, 1c.2b.3d.4a.5a.6e, 1c.2b.3d.4a.5b.6a,
1c.2b.3d.4a.5b.6b, 1c.2b.3d.4a.5b.6c, 1c.2b.3d.4a.5b.6d, 1c.2b.3d.4a.5b.6e,
1c.2b.3d.4a.5c.6a, 1c.2b.3d.4a.5c.6b, 1c.2b.3d.4a.5c.6c, 1c.2b.3d.4a.5c.6d,
1c.2b.3d.4a.5c.6e, 1c.2b.3d.4a.5d.6a, 1c.2b.3d.4a.5d.6b, 1c.2b.3d.4a.5d.6c,
1c.2b.3d.4a.5d.6d, 1c.2b.3d.4a.5d.6e, 1c.2b.3d.4a.5e.6a, 1c.2b.3d.4a.5e.6b,
1c.2b.3d.4a.5e.6c, 1c.2b.3d.4a.5e.6d, 1c.2b.3d.4a.5e.6e, 1c.2b.3d.4b.5a.6a,
1c.2b.3d.4b.5a.6b, 1c.2b.3d.4b.5a.6c, 1c.2b.3d.4b.5a.6d, 1c.2b.3d.4b.5a.6e,
1c.2b.3d.4b.5b.6a, 1c.2b.3d.4b.5b.6b, 1c.2b.3d.4b.5b.6c, 1c.2b.3d.4b.5b.6d,
1c.2b.3d.4b.5b.6e, 1c.2b.3d.4b.5c.6a, 1c.2b.3d.4b.5c.6b, 1c.2b.3d.4b.5c.6c,
1c.2b.3d.4b.5c.6d, 1c.2b.3d.4b.5c.6e, 1c.2b.3d.4b.5d.6a, 1c.2b.3d.4b.5d.6b,
1c.2b.3d.4b.5d.6c, 1c.2b.3d.4b.5d.6d, 1c.2b.3d.4b.5d.6e, 1c.2b.3d.4b.5e.6a,
1c.2b.3d.4b.5e.6b, 1c.2b.3d.4b.5e.6c, 1c.2b.3d.4b.5e.6d, 1c.2b.3d.4b.5e.6e,
1c.2b.3d.4c.5a.6a, 1c.2b.3d.4c.5a.6b, 1c.2b.3d.4c.5a.6c, 1c.2b.3d.4c.5a.6d,
1c.2b.3d.4c.5a.6e, 1c.2b.3d.4c.5b.6a, 1c.2b.3d.4c.5b.6b, 1c.2b.3d.4c.5b.6c,
1c.2b.3d.4c.5b.6d, 1c.2b.3d.4c.5b.6e, 1c.2b.3d.4c.5c.6a, 1c.2b.3d.4c.5c.6b,
1c.2b.3d.4c.5c.6c, 1c.2b.3d.4c.5c.6d, 1c.2b.3d.4c.5c.6e, 1c.2b.3d.4c.5d.6a,
1c.2b.3d.4c.5d.6b, 1c.2b.3d.4c.5d.6c, 1c.2b.3d.4c.5d.6d, 1c.2b.3d.4c.5d.6e,
1c.2b.3d.4c.5e.6a, 1c.2b.3d.4c.5e.6b, 1c.2b.3d.4c.5e.6c, 1c.2b.3d.4c.5e.6d,
1c.2b.3d.4c.5e.6e, 1c.2b.3d.4d.5a.6a, 1c.2b.3d.4d.5a.6b, 1c.2b.3d.4d.5a.6c,
1c.2b.3d.4d.5a.6d, 1c.2b.3d.4d.5a.6e, 1c.2b.3d.4d.5b.6a, 1c.2b.3d.4d.5b.6b,
1c.2b.3d.4d.5b.6c, 1c.2b.3d.4d.5b.6d, 1c.2b.3d.4d.5b.6e, 1c.2b.3d.4d.5c.6a,
1c.2b.3d.4d.5c.6b, 1c.2b.3d.4d.5c.6c, 1c.2b.3d.4d.5c.6d, 1c.2b.3d.4d.5c.6e,
1c.2b.3d.4d.5d.6a, 1c.2b.3d.4d.5d.6b, 1c.2b.3d.4d.5d.6c, 1c.2b.3d.4d.5d.6d,

TABLE 8-continued

List of Compounds of Formula (II)

1c.2b.3d.4d.5d.6e, 1c.2b.3d.4d.5e.6a, 1c.2b.3d.4d.5e.6b, 1c.2b.3d.4d.5e.6c,
1c.2b.3d.4d.5e.6d, 1c.2b.3d.4d.5e.6e, 1c.2b.3d.4e.5a.6a, 1c.2b.3d.4e.5a.6b,
1c.2b.3d.4e.5a.6c, 1c.2b.3d.4e.5a.6d, 1c.2b.3d.4e.5a.6e, 1c.2b.3d.4e.5b.6a,
1c.2b.3d.4e.5b.6b, 1c.2b.3d.4e.5b.6c, 1c.2b.3d.4e.5b.6d, 1c.2b.3d.4e.5b.6e,
1c.2b.3d.4e.5c.6a, 1c.2b.3d.4e.5c.6b, 1c.2b.3d.4e.5c.6c, 1c.2b.3d.4e.5c.6d,
1c.2b.3d.4e.5c.6e, 1c.2b.3d.4e.5d.6a, 1c.2b.3d.4e.5d.6b, 1c.2b.3d.4e.5d.6c,
1c.2b.3d.4e.5d.6d, 1c.2b.3d.4e.5d.6e, 1c.2b.3d.4e.5e.6a, 1c.2b.3d.4e.5e.6b,
1c.2b.3d.4e.5e.6c, 1c.2b.3d.4e.5e.6d, 1c.2b.3d.4e.5e.6e, 1c.2b.3e.4a.5a.6a,
1c.2b.3e.4a.5a.6b, 1c.2b.3e.4a.5a.6c, 1c.2b.3e.4a.5a.6d, 1c.2b.3e.4a.5a.6e,
1c.2b.3e.4a.5b.6a, 1c.2b.3e.4a.5b.6b, 1c.2b.3e.4a.5b.6c, 1c.2b.3e.4a.5b.6d,
1c.2b.3e.4a.5b.6e, 1c.2b.3e.4a.5c.6a, 1c.2b.3e.4a.5c.6b, 1c.2b.3e.4a.5c.6c,
1c.2b.3e.4a.5c.6d, 1c.2b.3e.4a.5c.6e, 1c.2b.3e.4a.5d.6a, 1c.2b.3e.4a.5d.6b,
1c.2b.3e.4a.5d.6c, 1c.2b.3e.4a.5d.6d, 1c.2b.3e.4a.5d.6e, 1c.2b.3e.4a.5e.6a,
1c.2b.3e.4a.5e.6b, 1c.2b.3e.4a.5e.6c, 1c.2b.3e.4a.5e.6d, 1c.2b.3e.4a.5e.6e,
1c.2b.3e.4b.5a.6a, 1c.2b.3e.4b.5a.6b, 1c.2b.3e.4b.5a.6c, 1c.2b.3e.4b.5a.6d,
1c.2b.3e.4b.5a.6e, 1c.2b.3e.4b.5b.6a, 1c.2b.3e.4b.5b.6b, 1c.2b.3e.4b.5b.6c,
1c.2b.3e.4b.5b.6d, 1c.2b.3e.4b.5b.6e, 1c.2b.3e.4b.5c.6a, 1c.2b.3e.4b.5c.6b,
1c.2b.3e.4b.5c.6c, 1c.2b.3e.4b.5c.6d, 1c.2b.3e.4b.5c.6e, 1c.2b.3e.4b.5d.6a,
1c.2b.3e.4b.5d.6b, 1c.2b.3e.4b.5d.6c, 1c.2b.3e.4b.5d.6d, 1c.2b.3e.4b.5d.6e,
1c.2b.3e.4b.5e.6a, 1c.2b.3e.4b.5e.6b, 1c.2b.3e.4b.5e.6c, 1c.2b.3e.4b.5e.6d,
1c.2b.3e.4b.5e.6e, 1c.2b.3e.4c.5a.6a, 1c.2b.3e.4c.5a.6b, 1c.2b.3e.4c.5a.6c,
1c.2b.3e.4c.5a.6d, 1c.2b.3e.4c.5a.6e, 1c.2b.3e.4c.5b.6a, 1c.2b.3e.4c.5b.6b,
1c.2b.3e.4c.5b.6c, 1c.2b.3e.4c.5b.6d, 1c.2b.3e.4c.5b.6e, 1c.2b.3e.4c.5c.6a,
1c.2b.3e.4c.5c.6b, 1c.2b.3e.4c.5c.6c, 1c.2b.3e.4c.5c.6d, 1c.2b.3e.4c.5c.6e,
1c.2b.3e.4c.5d.6a, 1c.2b.3e.4c.5d.6b, 1c.2b.3e.4c.5d.6c, 1c.2b.3e.4c.5d.6d,
1c.2b.3e.4c.5d.6e, 1c.2b.3e.4c.5e.6a, 1c.2b.3e.4c.5e.6b, 1c.2b.3e.4c.5e.6c,
1c.2b.3e.4c.5e.6d, 1c.2b.3e.4c.5e.6e, 1c.2b.3e.4d.5a.6a, 1c.2b.3e.4d.5a.6b,
1c.2b.3e.4d.5a.6c, 1c.2b.3e.4d.5a.6d, 1c.2b.3e.4d.5a.6e, 1c.2b.3e.4d.5b.6a,
1c.2b.3e.4d.5b.6b, 1c.2b.3e.4d.5b.6c, 1c.2b.3e.4d.5b.6d, 1c.2b.3e.4d.5b.6e,
1c.2b.3e.4d.5c.6a, 1c.2b.3e.4d.5c.6b, 1c.2b.3e.4d.5c.6c, 1c.2b.3e.4d.5c.6d,
1c.2b.3e.4d.5c.6e, 1c.2b.3e.4d.5d.6a, 1c.2b.3e.4d.5d.6b, 1c.2b.3e.4d.5d.6c,
1c.2b.3e.4d.5d.6d, 1c.2b.3e.4d.5d.6e, 1c.2b.3e.4d.5e.6a, 1c.2b.3e.4d.5e.6b,
1c.2b.3e.4d.5e.6c, 1c.2b.3e.4d.5e.6d, 1c.2b.3e.4d.5e.6e, 1c.2b.3e.4e.5a.6a,
1c.2b.3e.4e.5a.6b, 1c.2b.3e.4e.5a.6c, 1c.2b.3e.4e.5a.6d, 1c.2b.3e.4e.5a.6e,
1c.2b.3e.4e.5b.6a, 1c.2b.3e.4e.5b.6b, 1c.2b.3e.4e.5b.6c, 1c.2b.3e.4e.5b.6d,
1c.2b.3e.4e.5b.6e, 1c.2b.3e.4e.5c.6a, 1c.2b.3e.4e.5c.6b, 1c.2b.3e.4e.5c.6c,
1c.2b.3e.4e.5c.6d, 1c.2b.3e.4e.5c.6e, 1c.2b.3e.4e.5d.6a, 1c.2b.3e.4e.5d.6b,
1c.2b.3e.4e.5d.6c, 1c.2b.3e.4e.5d.6d, 1c.2b.3e.4e.5d.6e, 1c.2b.3e.4e.5e.6a,
1c.2b.3e.4e.5e.6b, 1c.2b.3e.4e.5e.6c, 1c.2b.3e.4e.5e.6d, 1c.2b.3e.4e.5e.6e,
1c.2c.3a.4a.5a.6a, 1c.2c.3a.4a.5a.6b, 1c.2c.3a.4a.5a.6c, 1c.2c.3a.4a.5a.6d,
1c.2c.3a.4a.5a.6e, 1c.2c.3a.4a.5b.6a, 1c.2c.3a.4a.5b.6b, 1c.2c.3a.4a.5b.6c,
1c.2c.3a.4a.5b.6d, 1c.2c.3a.4a.5b.6e, 1c.2c.3a.4a.5c.6a, 1c.2c.3a.4a.5c.6b,
1c.2c.3a.4a.5c.6c, 1c.2c.3a.4a.5c.6d, 1c.2c.3a.4a.5c.6e, 1c.2c.3a.4a.5d.6a,
1c.2c.3a.4a.5d.6b, 1c.2c.3a.4a.5d.6c, 1c.2c.3a.4a.5d.6d, 1c.2c.3a.4a.5d.6e,
1c.2c.3a.4a.5e.6a, 1c.2c.3a.4a.5e.6b, 1c.2c.3a.4a.5e.6c, 1c.2c.3a.4a.5e.6d,
1c.2c.3a.4a.5e.6e, 1c.2c.3a.4b.5a.6a, 1c.2c.3a.4b.5a.6b, 1c.2c.3a.4b.5a.6c,
1c.2c.3a.4b.5a.6d, 1c.2c.3a.4b.5a.6e, 1c.2c.3a.4b.5b.6a, 1c.2c.3a.4b.5b.6b,
1c.2c.3a.4b.5b.6c, 1c.2c.3a.4b.5b.6d, 1c.2c.3a.4b.5b.6e, 1c.2c.3a.4b.5c.6a,
1c.2c.3a.4b.5c.6b, 1c.2c.3a.4b.5c.6c, 1c.2c.3a.4b.5c.6d, 1c.2c.3a.4b.5c.6e,
1c.2c.3a.4b.5d.6a, 1c.2c.3a.4b.5d.6b, 1c.2c.3a.4b.5d.6c, 1c.2c.3a.4b.5d.6d,
1c.2c.3a.4b.5d.6e, 1c.2c.3a.4b.5e.6a, 1c.2c.3a.4b.5e.6b, 1c.2c.3a.4b.5e.6c,
1c.2c.3a.4b.5e.6d, 1c.2c.3a.4b.5e.6e, 1c.2c.3a.4c.5a.6a, 1c.2c.3a.4c.5a.6b,
1c.2c.3a.4c.5a.6c, 1c.2c.3a.4c.5a.6d, 1c.2c.3a.4c.5a.6e, 1c.2c.3a.4c.5b.6a,
1c.2c.3a.4c.5b.6b, 1c.2c.3a.4c.5b.6c, 1c.2c.3a.4c.5b.6d, 1c.2c.3a.4c.5b.6e,
1c.2c.3a.4c.5c.6a, 1c.2c.3a.4c.5c.6b, 1c.2c.3a.4c.5c.6c, 1c.2c.3a.4c.5c.6d,
1c.2c.3a.4c.5c.6e, 1c.2c.3a.4c.5d.6a, 1c.2c.3a.4c.5d.6b, 1c.2c.3a.4c.5d.6c,
1c.2c.3a.4c.5d.6d, 1c.2c.3a.4c.5d.6e, 1c.2c.3a.4c.5e.6a, 1c.2c.3a.4c.5e.6b,
1c.2c.3a.4c.5e.6c, 1c.2c.3a.4c.5e.6d, 1c.2c.3a.4c.5e.6e, 1c.2c.3a.4d.5a.6a,
1c.2c.3a.4d.5a.6b, 1c.2c.3a.4d.5a.6c, 1c.2c.3a.4d.5a.6d, 1c.2c.3a.4d.5a.6e,
1c.2c.3a.4d.5b.6a, 1c.2c.3a.4d.5b.6b, 1c.2c.3a.4d.5b.6c, 1c.2c.3a.4d.5b.6d,
1c.2c.3a.4d.5b.6e, 1c.2c.3a.4d.5c.6a, 1c.2c.3a.4d.5c.6b, 1c.2c.3a.4d.5c.6c,
1c.2c.3a.4d.5c.6d, 1c.2c.3a.4d.5c.6e, 1c.2c.3a.4d.5d.6a, 1c.2c.3a.4d.5d.6b,
1c.2c.3a.4d.5d.6c, 1c.2c.3a.4d.5d.6d, 1c.2c.3a.4d.5d.6e, 1c.2c.3a.4d.5e.6a,
1c.2c.3a.4d.5e.6b, 1c.2c.3a.4d.5e.6c, 1c.2c.3a.4d.5e.6d, 1c.2c.3a.4d.5e.6e,
1c.2c.3a.4e.5a.6a, 1c.2c.3a.4e.5a.6b, 1c.2c.3a.4e.5a.6c, 1c.2c.3a.4e.5a.6d,
1c.2c.3a.4e.5a.6e, 1c.2c.3a.4e.5b.6a, 1c.2c.3a.4e.5b.6b, 1c.2c.3a.4e.5b.6c,
1c.2c.3a.4e.5b.6d, 1c.2c.3a.4e.5b.6e, 1c.2c.3a.4e.5c.6a, 1c.2c.3a.4e.5c.6b,
1c.2c.3a.4e.5c.6c, 1c.2c.3a.4e.5c.6d, 1c.2c.3a.4e.5c.6e, 1c.2c.3a.4e.5d.6a,
1c.2c.3a.4e.5d.6b, 1c.2c.3a.4e.5d.6c, 1c.2c.3a.4e.5d.6d, 1c.2c.3a.4e.5d.6e,
1c.2c.3a.4e.5e.6a, 1c.2c.3a.4e.5e.6b, 1c.2c.3a.4e.5e.6c, 1c.2c.3a.4e.5e.6d,
1c.2c.3a.4e.5e.6e, 1c.2c.3b.4a.5a.6a, 1c.2c.3b.4a.5a.6b, 1c.2c.3b.4a.5a.6c,
1c.2c.3b.4a.5a.6d, 1c.2c.3b.4a.5a.6e, 1c.2c.3b.4a.5b.6a, 1c.2c.3b.4a.5b.6b,
1c.2c.3b.4a.5b.6c, 1c.2c.3b.4a.5b.6d, 1c.2c.3b.4a.5b.6e, 1c.2c.3b.4a.5c.6a,
1c.2c.3b.4a.5c.6b, 1c.2c.3b.4a.5c.6c, 1c.2c.3b.4a.5c.6d, 1c.2c.3b.4a.5c.6e,
1c.2c.3b.4a.5d.6a, 1c.2c.3b.4a.5d.6b, 1c.2c.3b.4a.5d.6c, 1c.2c.3b.4a.5d.6d,
1c.2c.3b.4a.5d.6e, 1c.2c.3b.4a.5e.6a, 1c.2c.3b.4a.5e.6b, 1c.2c.3b.4a.5e.6c,
1c.2c.3b.4a.5e.6d, 1c.2c.3b.4a.5e.6e, 1c.2c.3b.4b.5a.6a, 1c.2c.3b.4b.5a.6b,
1c.2c.3b.4b.5a.6c, 1c.2c.3b.4b.5a.6d, 1c.2c.3b.4b.5a.6e, 1c.2c.3b.4b.5b.6a,

TABLE 8-continued

List of Compounds of Formula (II)

1c.2c.3b.4b.5b.6b, 1c.2c.3b.4b.5b.6c, 1c.2c.3b.4b.5b.6d, 1c.2c.3b.4b.5b.6e,
1c.2c.3b.4b.5c.6a, 1c.2c.3b.4b.5c.6b, 1c.2c.3b.4b.5c.6c, 1c.2c.3b.4b.5c.6d,
1c.2c.3b.4b.5c.6e, 1c.2c.3b.4b.5d.6a, 1c.2c.3b.4b.5d.6b, 1c.2c.3b.4b.5d.6c,
1c.2c.3b.4b.5d.6d, 1c.2c.3b.4b.5d.6e, 1c.2c.3b.4b.5e.6a, 1c.2c.3b.4b.5e.6b,
1c.2c.3b.4b.5e.6c, 1c.2c.3b.4b.5e.6d, 1c.2c.3b.4b.5e.6e, 1c.2c.3b.4c.5a.6a,
1c.2c.3b.4c.5a.6b, 1c.2c.3b.4c.5a.6c, 1c.2c.3b.4c.5a.6d, 1c.2c.3b.4c.5a.6e,
1c.2c.3b.4c.5b.6a, 1c.2c.3b.4c.5b.6b, 1c.2c.3b.4c.5b.6c, 1c.2c.3b.4c.5b.6d,
1c.2c.3b.4c.5b.6e, 1c.2c.3b.4c.5c.6a, 1c.2c.3b.4c.5c.6b, 1c.2c.3b.4c.5c.6c,
1c.2c.3b.4c.5c.6d, 1c.2c.3b.4c.5c.6e, 1c.2c.3b.4c.5d.6a, 1c.2c.3b.4c.5d.6b,
1c.2c.3b.4c.5d.6c, 1c.2c.3b.4c.5d.6d, 1c.2c.3b.4c.5d.6e, 1c.2c.3b.4c.5e.6a,
1c.2c.3b.4c.5e.6b, 1c.2c.3b.4c.5e.6c, 1c.2c.3b.4c.5e.6d, 1c.2c.3b.4c.5e.6e,
1c.2c.3b.4d.5a.6a, 1c.2c.3b.4d.5a.6b, 1c.2c.3b.4d.5a.6c, 1c.2c.3b.4d.5a.6d,
1c.2c.3b.4d.5a.6e, 1c.2c.3b.4d.5b.6a, 1c.2c.3b.4d.5b.6b, 1c.2c.3b.4d.5b.6c,
1c.2c.3b.4d.5b.6d, 1c.2c.3b.4d.5b.6e, 1c.2c.3b.4d.5c.6a, 1c.2c.3b.4d.5c.6b,
1c.2c.3b.4d.5c.6c, 1c.2c.3b.4d.5c.6d, 1c.2c.3b.4d.5c.6e, 1c.2c.3b.4d.5d.6a,
1c.2c.3b.4d.5d.6b, 1c.2c.3b.4d.5d.6c, 1c.2c.3b.4d.5d.6d, 1c.2c.3b.4d.5d.6e,
1c.2c.3b.4d.5e.6a, 1c.2c.3b.4d.5e.6b, 1c.2c.3b.4d.5e.6c, 1c.2c.3b.4d.5e.6d,
1c.2c.3b.4d.5e.6e, 1c.2c.3b.4e.5a.6a, 1c.2c.3b.4e.5a.6b, 1c.2c.3b.4e.5a.6c,
1c.2c.3b.4e.5a.6d, 1c.2c.3b.4e.5a.6e, 1c.2c.3b.4e.5b.6a, 1c.2c.3b.4e.5b.6b,
1c.2c.3b.4e.5b.6c, 1c.2c.3b.4e.5b.6d, 1c.2c.3b.4e.5b.6e, 1c.2c.3b.4e.5c.6a,
1c.2c.3b.4e.5c.6b, 1c.2c.3b.4e.5c.6c, 1c.2c.3b.4e.5c.6d, 1c.2c.3b.4e.5c.6e,
1c.2c.3b.4e.5d.6a, 1c.2c.3b.4e.5d.6b, 1c.2c.3b.4e.5d.6c, 1c.2c.3b.4e.5d.6d,
1c.2c.3b.4e.5d.6e, 1c.2c.3b.4e.5e.6a, 1c.2c.3b.4e.5e.6b, 1c.2c.3b.4e.5e.6c,
1c.2c.3b.4e.5e.6d, 1c.2c.3b.4e.5e.6e, 1c.2c.3c.4a.5a.6a, 1c.2c.3c.4a.5a.6b,
1c.2c.3c.4a.5a.6c, 1c.2c.3c.4a.5a.6d, 1c.2c.3c.4a.5a.6e, 1c.2c.3c.4a.5b.6a,
1c.2c.3c.4a.5b.6b, 1c.2c.3c.4a.5b.6c, 1c.2c.3c.4a.5b.6d, 1c.2c.3c.4a.5b.6e,
1c.2c.3c.4a.5c.6a, 1c.2c.3c.4a.5c.6b, 1c.2c.3c.4a.5c.6c, 1c.2c.3c.4a.5c.6d,
1c.2c.3c.4a.5c.6e, 1c.2c.3c.4a.5d.6a, 1c.2c.3c.4a.5d.6b, 1c.2c.3c.4a.5d.6c,
1c.2c.3c.4a.5d.6d, 1c.2c.3c.4a.5d.6e, 1c.2c.3c.4a.5e.6a, 1c.2c.3c.4a.5e.6b,
1c.2c.3c.4a.5e.6c, 1c.2c.3c.4a.5e.6d, 1c.2c.3c.4a.5e.6e, 1c.2c.3c.4b.5a.6a,
1c.2c.3c.4b.5a.6b, 1c.2c.3c.4b.5a.6c, 1c.2c.3c.4b.5a.6d, 1c.2c.3c.4b.5a.6e,
1c.2c.3c.4b.5b.6a, 1c.2c.3c.4b.5b.6b, 1c.2c.3c.4b.5b.6c, 1c.2c.3c.4b.5b.6d,
1c.2c.3c.4b.5b.6e, 1c.2c.3c.4b.5c.6a, 1c.2c.3c.4b.5c.6b, 1c.2c.3c.4b.5c.6c,
1c.2c.3c.4b.5c.6d, 1c.2c.3c.4b.5c.6e, 1c.2c.3c.4b.5d.6a, 1c.2c.3c.4b.5d.6b,
1c.2c.3c.4b.5d.6c, 1c.2c.3c.4b.5d.6d, 1c.2c.3c.4b.5d.6e, 1c.2c.3c.4b.5e.6a,
1c.2c.3c.4b.5e.6b, 1c.2c.3c.4b.5e.6c, 1c.2c.3c.4b.5e.6d, 1c.2c.3c.4b.5e.6e,
1c.2c.3c.4c.5a.6a, 1c.2c.3c.4c.5a.6b, 1c.2c.3c.4c.5a.6c, 1c.2c.3c.4c.5a.6d,
1c.2c.3c.4c.5a.6e, 1c.2c.3c.4c.5b.6a, 1c.2c.3c.4c.5b.6b, 1c.2c.3c.4c.5b.6c,
1c.2c.3c.4c.5b.6d, 1c.2c.3c.4c.5b.6e, 1c.2c.3c.4c.5c.6a, 1c.2c.3c.4c.5c.6b,
1c.2c.3c.4c.5c.6c, 1c.2c.3c.4c.5c.6d, 1c.2c.3c.4c.5c.6e, 1c.2c.3c.4c.5d.6a,
1c.2c.3c.4c.5d.6b, 1c.2c.3c.4c.5d.6c, 1c.2c.3c.4c.5d.6d, 1c.2c.3c.4c.5d.6e,
1c.2c.3c.4c.5e.6a, 1c.2c.3c.4c.5e.6b, 1c.2c.3c.4c.5e.6c, 1c.2c.3c.4c.5e.6d,
1c.2c.3c.4c.5e.6e, 1c.2c.3c.4d.5a.6a, 1c.2c.3c.4d.5a.6b, 1c.2c.3c.4d.5a.6c,
1c.2c.3c.4d.5a.6d, 1c.2c.3c.4d.5a.6e, 1c.2c.3c.4d.5b.6a, 1c.2c.3c.4d.5b.6b,
1c.2c.3c.4d.5b.6c, 1c.2c.3c.4d.5b.6d, 1c.2c.3c.4d.5b.6e, 1c.2c.3c.4d.5c.6a,
1c.2c.3c.4d.5c.6b, 1c.2c.3c.4d.5c.6c, 1c.2c.3c.4d.5c.6d, 1c.2c.3c.4d.5c.6e,
1c.2c.3c.4d.5d.6a, 1c.2c.3c.4d.5d.6b, 1c.2c.3c.4d.5d.6c, 1c.2c.3c.4d.5d.6d,
1c.2c.3c.4d.5d.6e, 1c.2c.3c.4d.5e.6a, 1c.2c.3c.4d.5e.6b, 1c.2c.3c.4d.5e.6c,
1c.2c.3c.4d.5e.6d, 1c.2c.3c.4d.5e.6e, 1c.2c.3c.4e.5a.6a, 1c.2c.3c.4e.5a.6b,
1c.2c.3c.4e.5a.6c, 1c.2c.3c.4e.5a.6d, 1c.2c.3c.4e.5a.6e, 1c.2c.3c.4e.5b.6a,
1c.2c.3c.4e.5b.6b, 1c.2c.3c.4e.5b.6c, 1c.2c.3c.4e.5b.6d, 1c.2c.3c.4e.5b.6e,
1c.2c.3c.4e.5c.6a, 1c.2c.3c.4e.5c.6b, 1c.2c.3c.4e.5c.6c, 1c.2c.3c.4e.5c.6d,
1c.2c.3c.4e.5c.6e, 1c.2c.3c.4e.5d.6a, 1c.2c.3c.4e.5d.6b, 1c.2c.3c.4e.5d.6c,
1c.2c.3c.4e.5d.6d, 1c.2c.3c.4e.5d.6e, 1c.2c.3c.4e.5e.6a, 1c.2c.3c.4e.5e.6b,
1c.2c.3c.4e.5e.6c, 1c.2c.3c.4e.5e.6d, 1c.2c.3c.4e.5e.6e, 1c.2c.3d.4a.5a.6a,
1c.2c.3d.4a.5a.6b, 1c.2c.3d.4a.5a.6c, 1c.2c.3d.4a.5a.6d, 1c.2c.3d.4a.5a.6e,
1c.2c.3d.4a.5b.6a, 1c.2c.3d.4a.5b.6b, 1c.2c.3d.4a.5b.6c, 1c.2c.3d.4a.5b.6d,
1c.2c.3d.4a.5b.6e, 1c.2c.3d.4a.5c.6a, 1c.2c.3d.4a.5c.6b, 1c.2c.3d.4a.5c.6c,
1c.2c.3d.4a.5c.6d, 1c.2c.3d.4a.5c.6e, 1c.2c.3d.4a.5d.6a, 1c.2c.3d.4a.5d.6b,
1c.2c.3d.4a.5d.6c, 1c.2c.3d.4a.5d.6d, 1c.2c.3d.4a.5d.6e, 1c.2c.3d.4a.5e.6a,
1c.2c.3d.4a.5e.6b, 1c.2c.3d.4a.5e.6c, 1c.2c.3d.4a.5e.6d, 1c.2c.3d.4a.5e.6e,
1c.2c.3d.4b.5a.6a, 1c.2c.3d.4b.5a.6b, 1c.2c.3d.4b.5a.6c, 1c.2c.3d.4b.5a.6d,
1c.2c.3d.4b.5a.6e, 1c.2c.3d.4b.5b.6a, 1c.2c.3d.4b.5b.6b, 1c.2c.3d.4b.5b.6c,
1c.2c.3d.4b.5b.6d, 1c.2c.3d.4b.5b.6e, 1c.2c.3d.4b.5c.6a, 1c.2c.3d.4b.5c.6b,
1c.2c.3d.4b.5c.6c, 1c.2c.3d.4b.5c.6d, 1c.2c.3d.4b.5c.6e, 1c.2c.3d.4b.5d.6a,
1c.2c.3d.4b.5d.6b, 1c.2c.3d.4b.5d.6c, 1c.2c.3d.4b.5d.6d, 1c.2c.3d.4b.5d.6e,
1c.2c.3d.4b.5e.6a, 1c.2c.3d.4b.5e.6b, 1c.2c.3d.4b.5e.6c, 1c.2c.3d.4b.5e.6d,
1c.2c.3d.4b.5e.6e, 1c.2c.3d.4c.5a.6a, 1c.2c.3d.4c.5a.6b, 1c.2c.3d.4c.5a.6c,
1c.2c.3d.4c.5a.6d, 1c.2c.3d.4c.5a.6e, 1c.2c.3d.4c.5b.6a, 1c.2c.3d.4c.5b.6b,
1c.2c.3d.4c.5b.6c, 1c.2c.3d.4c.5b.6d, 1c.2c.3d.4c.5b.6e, 1c.2c.3d.4c.5c.6a,
1c.2c.3d.4c.5c.6b, 1c.2c.3d.4c.5c.6c, 1c.2c.3d.4c.5c.6d, 1c.2c.3d.4c.5c.6e,
1c.2c.3d.4c.5d.6a, 1c.2c.3d.4c.5d.6b, 1c.2c.3d.4c.5d.6c, 1c.2c.3d.4c.5d.6d,
1c.2c.3d.4c.5d.6e, 1c.2c.3d.4c.5e.6a, 1c.2c.3d.4c.5e.6b, 1c.2c.3d.4c.5e.6c,
1c.2c.3d.4c.5e.6d, 1c.2c.3d.4c.5e.6e, 1c.2c.3d.4d.5a.6a, 1c.2c.3d.4d.5a.6b,
1c.2c.3d.4d.5a.6c, 1c.2c.3d.4d.5a.6d, 1c.2c.3d.4d.5a.6e, 1c.2c.3d.4d.5b.6a,
1c.2c.3d.4d.5b.6b, 1c.2c.3d.4d.5b.6c, 1c.2c.3d.4d.5b.6d, 1c.2c.3d.4d.5b.6e,
1c.2c.3d.4d.5c.6a, 1c.2c.3d.4d.5c.6b, 1c.2c.3d.4d.5c.6c, 1c.2c.3d.4d.5c.6d,
1c.2c.3d.4d.5c.6e, 1c.2c.3d.4d.5d.6a, 1c.2c.3d.4d.5d.6b, 1c.2c.3d.4d.5d.6c,

TABLE 8-continued

List of Compounds of Formula (II)

1c.2c.3d.4d.5d.6d, 1c.2c.3d.4d.5d.6e, 1c.2c.3d.4d.5e.6a, 1c.2c.3d.4d.5e.6b,
1c.2c.3d.4d.5e.6c, 1c.2c.3d.4d.5e.6d, 1c.2c.3d.4d.5e.6e, 1c.2c.3d.4e.5a.6a,
1c.2c.3d.4e.5a.6b, 1c.2c.3d.4e.5a.6c, 1c.2c.3d.4e.5a.6d, 1c.2c.3d.4e.5a.6e,
1c.2c.3d.4e.5b.6a, 1c.2c.3d.4e.5b.6b, 1c.2c.3d.4e.5b.6c, 1c.2c.3d.4e.5b.6d,
1c.2c.3d.4e.5b.6e, 1c.2c.3d.4e.5c.6a, 1c.2c.3d.4e.5c.6b, 1c.2c.3d.4e.5c.6c,
1c.2c.3d.4e.5c.6d, 1c.2c.3d.4e.5c.6e, 1c.2c.3d.4e.5d.6a, 1c.2c.3d.4e.5d.6b,
1c.2c.3d.4e.5d.6c, 1c.2c.3d.4e.5d.6d, 1c.2c.3d.4e.5d.6e, 1c.2c.3d.4e.5e.6a,
1c.2c.3d.4e.5e.6b, 1c.2c.3d.4e.5e.6c, 1c.2c.3d.4e.5e.6d, 1c.2c.3d.4e.5e.6e,
1c.2c.3e.4a.5a.6a, 1c.2c.3e.4a.5a.6b, 1c.2c.3e.4a.5a.6c, 1c.2c.3e.4a.5a.6d,
1c.2c.3e.4a.5a.6e, 1c.2c.3e.4a.5b.6a, 1c.2c.3e.4a.5b.6b, 1c.2c.3e.4a.5b.6c,
1c.2c.3e.4a.5b.6d, 1c.2c.3e.4a.5b.6e, 1c.2c.3e.4a.5c.6a, 1c.2c.3e.4a.5c.6b,
1c.2c.3e.4a.5c.6c, 1c.2c.3e.4a.5c.6d, 1c.2c.3e.4a.5c.6e, 1c.2c.3e.4a.5d.6a,
1c.2c.3e.4a.5d.6b, 1c.2c.3e.4a.5d.6c, 1c.2c.3e.4a.5d.6d, 1c.2c.3e.4a.5d.6e,
1c.2c.3e.4a.5e.6a, 1c.2c.3e.4a.5e.6b, 1c.2c.3e.4a.5e.6c, 1c.2c.3e.4a.5e.6d,
1c.2c.3e.4a.5e.6e, 1c.2c.3e.4b.5a.6a, 1c.2c.3e.4b.5a.6b, 1c.2c.3e.4b.5a.6c,
1c.2c.3e.4b.5a.6d, 1c.2c.3e.4b.5a.6e, 1c.2c.3e.4b.5b.6a, 1c.2c.3e.4b.5b.6b,
1c.2c.3e.4b.5b.6c, 1c.2c.3e.4b.5b.6d, 1c.2c.3e.4b.5b.6e, 1c.2c.3e.4b.5c.6a,
1c.2c.3e.4b.5c.6b, 1c.2c.3e.4b.5c.6c, 1c.2c.3e.4b.5c.6d, 1c.2c.3e.4b.5c.6e,
1c.2c.3e.4b.5d.6a, 1c.2c.3e.4b.5d.6b, 1c.2c.3e.4b.5d.6c, 1c.2c.3e.4b.5d.6d,
1c.2c.3e.4b.5d.6e, 1c.2c.3e.4b.5e.6a, 1c.2c.3e.4b.5e.6b, 1c.2c.3e.4b.5e.6c,
1c.2c.3e.4b.5e.6d, 1c.2c.3e.4b.5e.6e, 1c.2c.3e.4c.5a.6a, 1c.2c.3e.4c.5a.6b,
1c.2c.3e.4c.5a.6c, 1c.2c.3e.4c.5a.6d, 1c.2c.3e.4c.5a.6e, 1c.2c.3e.4c.5b.6a,
1c.2c.3e.4c.5b.6b, 1c.2c.3e.4c.5b.6c, 1c.2c.3e.4c.5b.6d, 1c.2c.3e.4c.5b.6e,
1c.2c.3e.4c.5c.6a, 1c.2c.3e.4c.5c.6b, 1c.2c.3e.4c.5c.6c, 1c.2c.3e.4c.5c.6d,
1c.2c.3e.4c.5c.6e, 1c.2c.3e.4c.5d.6a, 1c.2c.3e.4c.5d.6b, 1c.2c.3e.4c.5d.6c,
1c.2c.3e.4c.5d.6d, 1c.2c.3e.4c.5d.6e, 1c.2c.3e.4c.5e.6a, 1c.2c.3e.4c.5e.6b,
1c.2c.3e.4c.5e.6c, 1c.2c.3e.4c.5e.6d, 1c.2c.3e.4c.5e.6e, 1c.2c.3e.4d.5a.6a,
1c.2c.3e.4d.5a.6b, 1c.2c.3e.4d.5a.6c, 1c.2c.3e.4d.5a.6d, 1c.2c.3e.4d.5a.6e,
1c.2c.3e.4d.5b.6a, 1c.2c.3e.4d.5b.6b, 1c.2c.3e.4d.5b.6c, 1c.2c.3e.4d.5b.6d,
1c.2c.3e.4d.5b.6e, 1c.2c.3e.4d.5c.6a, 1c.2c.3e.4d.5c.6b, 1c.2c.3e.4d.5c.6c,
1c.2c.3e.4d.5c.6d, 1c.2c.3e.4d.5c.6e, 1c.2c.3e.4d.5d.6a, 1c.2c.3e.4d.5d.6b,
1c.2c.3e.4d.5d.6c, 1c.2c.3e.4d.5d.6d, 1c.2c.3e.4d.5d.6e, 1c.2c.3e.4d.5e.6a,
1c.2c.3e.4d.5e.6b, 1c.2c.3e.4d.5e.6c, 1c.2c.3e.4d.5e.6d, 1c.2c.3e.4d.5e.6e,
1c.2c.3e.4e.5a.6a, 1c.2c.3e.4e.5a.6b, 1c.2c.3e.4e.5a.6c, 1c.2c.3e.4e.5a.6d,
1c.2c.3e.4e.5a.6e, 1c.2c.3e.4e.5b.6a, 1c.2c.3e.4e.5b.6b, 1c.2c.3e.4e.5b.6c,
1c.2c.3e.4e.5b.6d, 1c.2c.3e.4e.5b.6e, 1c.2c.3e.4e.5c.6a, 1c.2c.3e.4e.5c.6b,
1c.2c.3e.4e.5c.6c, 1c.2c.3e.4e.5c.6d, 1c.2c.3e.4e.5c.6e, 1c.2c.3e.4e.5d.6a,
1c.2c.3e.4e.5d.6b, 1c.2c.3e.4e.5d.6c, 1c.2c.3e.4e.5d.6d, 1c.2c.3e.4e.5d.6e,
1c.2c.3e.4e.5e.6a, 1c.2c.3e.4e.5e.6b, 1c.2c.3e.4e.5e.6c, 1c.2c.3e.4e.5e.6d,
1c.2c.3e.4e.5e.6e, 1c.2d.3a.4a.5a.6a, 1c.2d.3a.4a.5a.6b, 1c.2d.3a.4a.5a.6c,
1c.2d.3a.4a.5a.6d, 1c.2d.3a.4a.5a.6e, 1c.2d.3a.4a.5b.6a, 1c.2d.3a.4a.5b.6b,
1c.2d.3a.4a.5b.6c, 1c.2d.3a.4a.5b.6d, 1c.2d.3a.4a.5b.6e, 1c.2d.3a.4a.5c.6a,
1c.2d.3a.4a.5c.6b, 1c.2d.3a.4a.5c.6c, 1c.2d.3a.4a.5c.6d, 1c.2d.3a.4a.5c.6e,
1c.2d.3a.4a.5d.6a, 1c.2d.3a.4a.5d.6b, 1c.2d.3a.4a.5d.6c, 1c.2d.3a.4a.5d.6d,
1c.2d.3a.4a.5d.6e, 1c.2d.3a.4a.5e.6a, 1c.2d.3a.4a.5e.6b, 1c.2d.3a.4a.5e.6c,
1c.2d.3a.4a.5e.6d, 1c.2d.3a.4a.5e.6e, 1c.2d.3a.4b.5a.6a, 1c.2d.3a.4b.5a.6b,
1c.2d.3a.4b.5a.6c, 1c.2d.3a.4b.5a.6d, 1c.2d.3a.4b.5a.6e, 1c.2d.3a.4b.5b.6a,
1c.2d.3a.4b.5b.6b, 1c.2d.3a.4b.5b.6c, 1c.2d.3a.4b.5b.6d, 1c.2d.3a.4b.5b.6e,
1c.2d.3a.4b.5c.6a, 1c.2d.3a.4b.5c.6b, 1c.2d.3a.4b.5c.6c, 1c.2d.3a.4b.5c.6d,
1c.2d.3a.4b.5c.6e, 1c.2d.3a.4b.5d.6a, 1c.2d.3a.4b.5d.6b, 1c.2d.3a.4b.5d.6c,
1c.2d.3a.4b.5d.6d, 1c.2d.3a.4b.5d.6e, 1c.2d.3a.4b.5e.6a, 1c.2d.3a.4b.5e.6b,
1c.2d.3a.4b.5e.6c, 1c.2d.3a.4b.5e.6d, 1c.2d.3a.4b.5e.6e, 1c.2d.3a.4c.5a.6a,
1c.2d.3a.4c.5a.6b, 1c.2d.3a.4c.5a.6c, 1c.2d.3a.4c.5a.6d, 1c.2d.3a.4c.5a.6e,
1c.2d.3a.4c.5b.6a, 1c.2d.3a.4c.5b.6b, 1c.2d.3a.4c.5b.6c, 1c.2d.3a.4c.5b.6d,
1c.2d.3a.4c.5b.6e, 1c.2d.3a.4c.5c.6a, 1c.2d.3a.4c.5c.6b, 1c.2d.3a.4c.5c.6c,
1c.2d.3a.4c.5c.6d, 1c.2d.3a.4c.5c.6e, 1c.2d.3a.4c.5d.6a, 1c.2d.3a.4c.5d.6b,
1c.2d.3a.4c.5d.6c, 1c.2d.3a.4c.5d.6d, 1c.2d.3a.4c.5d.6e, 1c.2d.3a.4c.5e.6a,
1c.2d.3a.4c.5e.6b, 1c.2d.3a.4c.5e.6c, 1c.2d.3a.4c.5e.6d, 1c.2d.3a.4c.5e.6e,
1c.2d.3a.4d.5a.6a, 1c.2d.3a.4d.5a.6b, 1c.2d.3a.4d.5a.6c, 1c.2d.3a.4d.5a.6d,
1c.2d.3a.4d.5a.6e, 1c.2d.3a.4d.5b.6a, 1c.2d.3a.4d.5b.6b, 1c.2d.3a.4d.5b.6c,
1c.2d.3a.4d.5b.6d, 1c.2d.3a.4d.5b.6e, 1c.2d.3a.4d.5c.6a, 1c.2d.3a.4d.5c.6b,
1c.2d.3a.4d.5c.6c, 1c.2d.3a.4d.5c.6d, 1c.2d.3a.4d.5c.6e, 1c.2d.3a.4d.5d.6a,
1c.2d.3a.4d.5d.6b, 1c.2d.3a.4d.5d.6c, 1c.2d.3a.4d.5d.6d, 1c.2d.3a.4d.5d.6e,
1c.2d.3a.4d.5e.6a, 1c.2d.3a.4d.5e.6b, 1c.2d.3a.4d.5e.6c, 1c.2d.3a.4d.5e.6d,
1c.2d.3a.4d.5e.6e, 1c.2d.3a.4e.5a.6a, 1c.2d.3a.4e.5a.6b, 1c.2d.3a.4e.5a.6c,
1c.2d.3a.4e.5a.6d, 1c.2d.3a.4e.5a.6e, 1c.2d.3a.4e.5b.6a, 1c.2d.3a.4e.5b.6b,
1c.2d.3a.4e.5b.6c, 1c.2d.3a.4e.5b.6d, 1c.2d.3a.4e.5b.6e, 1c.2d.3a.4e.5c.6a,
1c.2d.3a.4e.5c.6b, 1c.2d.3a.4e.5c.6c, 1c.2d.3a.4e.5c.6d, 1c.2d.3a.4e.5c.6e,
1c.2d.3a.4e.5d.6a, 1c.2d.3a.4e.5d.6b, 1c.2d.3a.4e.5d.6c, 1c.2d.3a.4e.5d.6d,
1c.2d.3a.4e.5d.6e, 1c.2d.3a.4e.5e.6a, 1c.2d.3a.4e.5e.6b, 1c.2d.3a.4e.5e.6c,
1c.2d.3a.4e.5e.6d, 1c.2d.3a.4e.5e.6e, 1c.2d.3b.4a.5a.6a, 1c.2d.3b.4a.5a.6b,
1c.2d.3b.4a.5a.6c, 1c.2d.3b.4a.5a.6d, 1c.2d.3b.4a.5a.6e, 1c.2d.3b.4a.5b.6a,
1c.2d.3b.4a.5b.6b, 1c.2d.3b.4a.5b.6c, 1c.2d.3b.4a.5b.6d, 1c.2d.3b.4a.5b.6e,
1c.2d.3b.4a.5c.6a, 1c.2d.3b.4a.5c.6b, 1c.2d.3b.4a.5c.6c, 1c.2d.3b.4a.5c.6d,
1c.2d.3b.4a.5c.6e, 1c.2d.3b.4a.5d.6a, 1c.2d.3b.4a.5d.6b, 1c.2d.3b.4a.5d.6c,
1c.2d.3b.4a.5d.6d, 1c.2d.3b.4a.5d.6e, 1c.2d.3b.4a.5e.6a, 1c.2d.3b.4a.5e.6b,
1c.2d.3b.4a.5e.6c, 1c.2d.3b.4a.5e.6d, 1c.2d.3b.4a.5e.6e, 1c.2d.3b.4b.5a.6a,
1c.2d.3b.4b.5a.6b, 1c.2d.3b.4b.5a.6c, 1c.2d.3b.4b.5a.6d, 1c.2d.3b.4b.5a.6e,

TABLE 8-continued

List of Compounds of Formula (II)

1c.2d.3b.4b.5b.6a, 1c.2d.3b.4b.5b.6b, 1c.2d.3b.4b.5b.6c, 1c.2d.3b.4b.5b.6d,
1c.2d.3b.4b.5b.6e, 1c.2d.3b.4b.5c.6a, 1c.2d.3b.4b.5c.6b, 1c.2d.3b.4b.5c.6c,
1c.2d.3b.4b.5c.6d, 1c.2d.3b.4b.5c.6e, 1c.2d.3b.4b.5d.6a, 1c.2d.3b.4b.5d.6b,
1c.2d.3b.4b.5d.6c, 1c.2d.3b.4b.5d.6d, 1c.2d.3b.4b.5d.6e, 1c.2d.3b.4b.5e.6a,
1c.2d.3b.4b.5e.6b, 1c.2d.3b.4b.5e.6c, 1c.2d.3b.4b.5e.6d, 1c.2d.3b.4b.5e.6e,
1c.2d.3b.4c.5a.6a, 1c.2d.3b.4c.5a.6b, 1c.2d.3b.4c.5a.6c, 1c.2d.3b.4c.5a.6d,
1c.2d.3b.4c.5a.6e, 1c.2d.3b.4c.5b.6a, 1c.2d.3b.4c.5b.6b, 1c.2d.3b.4c.5b.6c,
1c.2d.3b.4c.5b.6d, 1c.2d.3b.4c.5b.6e, 1c.2d.3b.4c.5c.6a, 1c.2d.3b.4c.5c.6b,
1c.2d.3b.4c.5c.6c, 1c.2d.3b.4c.5c.6d, 1c.2d.3b.4c.5c.6e, 1c.2d.3b.4c.5d.6a,
1c.2d.3b.4c.5d.6b, 1c.2d.3b.4c.5d.6c, 1c.2d.3b.4c.5d.6d, 1c.2d.3b.4c.5d.6e,
1c.2d.3b.4c.5e.6a, 1c.2d.3b.4c.5e.6b, 1c.2d.3b.4c.5e.6c, 1c.2d.3b.4c.5e.6d,
1c.2d.3b.4c.5e.6e, 1c.2d.3b.4d.5a.6a, 1c.2d.3b.4d.5a.6b, 1c.2d.3b.4d.5a.6c,
1c.2d.3b.4d.5a.6d, 1c.2d.3b.4d.5a.6e, 1c.2d.3b.4d.5b.6a, 1c.2d.3b.4d.5b.6b,
1c.2d.3b.4d.5b.6c, 1c.2d.3b.4d.5b.6d, 1c.2d.3b.4d.5b.6e, 1c.2d.3b.4d.5c.6a,
1c.2d.3b.4d.5c.6b, 1c.2d.3b.4d.5c.6c, 1c.2d.3b.4d.5c.6d, 1c.2d.3b.4d.5c.6e,
1c.2d.3b.4d.5d.6a, 1c.2d.3b.4d.5d.6b, 1c.2d.3b.4d.5d.6c, 1c.2d.3b.4d.5d.6d,
1c.2d.3b.4d.5d.6e, 1c.2d.3b.4d.5e.6a, 1c.2d.3b.4d.5e.6b, 1c.2d.3b.4d.5e.6c,
1c.2d.3b.4d.5e.6d, 1c.2d.3b.4d.5e.6e, 1c.2d.3b.4e.5a.6a, 1c.2d.3b.4e.5a.6b,
1c.2d.3b.4e.5a.6c, 1c.2d.3b.4e.5a.6d, 1c.2d.3b.4e.5a.6e, 1c.2d.3b.4e.5b.6a,
1c.2d.3b.4e.5b.6b, 1c.2d.3b.4e.5b.6c, 1c.2d.3b.4e.5b.6d, 1c.2d.3b.4e.5b.6e,
1c.2d.3b.4e.5c.6a, 1c.2d.3b.4e.5c.6b, 1c.2d.3b.4e.5c.6c, 1c.2d.3b.4e.5c.6d,
1c.2d.3b.4e.5c.6e, 1c.2d.3b.4e.5d.6a, 1c.2d.3b.4e.5d.6b, 1c.2d.3b.4e.5d.6c,
1c.2d.3b.4e.5d.6d, 1c.2d.3b.4e.5d.6e, 1c.2d.3b.4e.5e.6a, 1c.2d.3b.4e.5e.6b,
1c.2d.3b.4e.5e.6c, 1c.2d.3b.4e.5e.6d, 1c.2d.3b.4e.5e.6e, 1c.2d.3c.4a.5a.6a,
1c.2d.3c.4a.5a.6b, 1c.2d.3c.4a.5a.6c, 1c.2d.3c.4a.5a.6d, 1c.2d.3c.4a.5a.6e,
1c.2d.3c.4a.5b.6a, 1c.2d.3c.4a.5b.6b, 1c.2d.3c.4a.5b.6c, 1c.2d.3c.4a.5b.6d,
1c.2d.3c.4a.5b.6e, 1c.2d.3c.4a.5c.6a, 1c.2d.3c.4a.5c.6b, 1c.2d.3c.4a.5c.6c,
1c.2d.3c.4a.5c.6d, 1c.2d.3c.4a.5c.6e, 1c.2d.3c.4a.5d.6a, 1c.2d.3c.4a.5d.6b,
1c.2d.3c.4a.5d.6c, 1c.2d.3c.4a.5d.6d, 1c.2d.3c.4a.5d.6e, 1c.2d.3c.4a.5e.6a,
1c.2d.3c.4a.5e.6b, 1c.2d.3c.4a.5e.6c, 1c.2d.3c.4a.5e.6d, 1c.2d.3c.4a.5e.6e,
1c.2d.3c.4b.5a.6a, 1c.2d.3c.4b.5a.6b, 1c.2d.3c.4b.5a.6c, 1c.2d.3c.4b.5a.6d,
1c.2d.3c.4b.5a.6e, 1c.2d.3c.4b.5b.6a, 1c.2d.3c.4b.5b.6b, 1c.2d.3c.4b.5b.6c,
1c.2d.3c.4b.5b.6d, 1c.2d.3c.4b.5b.6e, 1c.2d.3c.4b.5c.6a, 1c.2d.3c.4b.5c.6b,
1c.2d.3c.4b.5c.6c, 1c.2d.3c.4b.5c.6d, 1c.2d.3c.4b.5c.6e, 1c.2d.3c.4b.5d.6a,
1c.2d.3c.4b.5d.6b, 1c.2d.3c.4b.5d.6c, 1c.2d.3c.4b.5d.6d, 1c.2d.3c.4b.5d.6e,
1c.2d.3c.4b.5e.6a, 1c.2d.3c.4b.5e.6b, 1c.2d.3c.4b.5e.6c, 1c.2d.3c.4b.5e.6d,
1c.2d.3c.4b.5e.6e, 1c.2d.3c.4c.5a.6a, 1c.2d.3c.4c.5a.6b, 1c.2d.3c.4c.5a.6c,
1c.2d.3c.4c.5a.6d, 1c.2d.3c.4c.5a.6e, 1c.2d.3c.4c.5b.6a, 1c.2d.3c.4c.5b.6b,
1c.2d.3c.4c.5b.6c, 1c.2d.3c.4c.5b.6d, 1c.2d.3c.4c.5b.6e, 1c.2d.3c.4c.5c.6a,
1c.2d.3c.4c.5c.6b, 1c.2d.3c.4c.5c.6c, 1c.2d.3c.4c.5c.6d, 1c.2d.3c.4c.5c.6e,
1c.2d.3c.4c.5d.6a, 1c.2d.3c.4c.5d.6b, 1c.2d.3c.4c.5d.6c, 1c.2d.3c.4c.5d.6d,
1c.2d.3c.4c.5d.6e, 1c.2d.3c.4c.5e.6a, 1c.2d.3c.4c.5e.6b, 1c.2d.3c.4c.5e.6c,
1c.2d.3c.4c.5e.6d, 1c.2d.3c.4c.5e.6e, 1c.2d.3c.4d.5a.6a, 1c.2d.3c.4d.5a.6b,
1c.2d.3c.4d.5a.6c, 1c.2d.3c.4d.5a.6d, 1c.2d.3c.4d.5a.6e, 1c.2d.3c.4d.5b.6a,
1c.2d.3c.4d.5b.6b, 1c.2d.3c.4d.5b.6c, 1c.2d.3c.4d.5b.6d, 1c.2d.3c.4d.5b.6e,
1c.2d.3c.4d.5c.6a, 1c.2d.3c.4d.5c.6b, 1c.2d.3c.4d.5c.6c, 1c.2d.3c.4d.5c.6d,
1c.2d.3c.4d.5c.6e, 1c.2d.3c.4d.5d.6a, 1c.2d.3c.4d.5d.6b, 1c.2d.3c.4d.5d.6c,
1c.2d.3c.4d.5d.6d, 1c.2d.3c.4d.5d.6e, 1c.2d.3c.4d.5e.6a, 1c.2d.3c.4d.5e.6b,
1c.2d.3c.4d.5e.6c, 1c.2d.3c.4d.5e.6d, 1c.2d.3c.4d.5e.6e, 1c.2d.3c.4e.5a.6a,
1c.2d.3c.4e.5a.6b, 1c.2d.3c.4e.5a.6c, 1c.2d.3c.4e.5a.6d, 1c.2d.3c.4e.5a.6e,
1c.2d.3c.4e.5b.6a, 1c.2d.3c.4e.5b.6b, 1c.2d.3c.4e.5b.6c, 1c.2d.3c.4e.5b.6d,
1c.2d.3c.4e.5b.6e, 1c.2d.3c.4e.5c.6a, 1c.2d.3c.4e.5c.6b, 1c.2d.3c.4e.5c.6c,
1c.2d.3c.4e.5c.6d, 1c.2d.3c.4e.5c.6e, 1c.2d.3c.4e.5d.6a, 1c.2d.3c.4e.5d.6b,
1c.2d.3c.4e.5d.6c, 1c.2d.3c.4e.5d.6d, 1c.2d.3c.4e.5d.6e, 1c.2d.3c.4e.5e.6a,
1c.2d.3c.4e.5e.6b, 1c.2d.3c.4e.5e.6c, 1c.2d.3c.4e.5e.6d, 1c.2d.3c.4e.5e.6e,
1c.2d.3d.4a.5a.6a, 1c.2d.3d.4a.5a.6b, 1c.2d.3d.4a.5a.6c, 1c.2d.3d.4a.5a.6d,
1c.2d.3d.4a.5a.6e, 1c.2d.3d.4a.5b.6a, 1c.2d.3d.4a.5b.6b, 1c.2d.3d.4a.5b.6c,
1c.2d.3d.4a.5b.6d, 1c.2d.3d.4a.5b.6e, 1c.2d.3d.4a.5c.6a, 1c.2d.3d.4a.5c.6b,
1c.2d.3d.4a.5c.6c, 1c.2d.3d.4a.5c.6d, 1c.2d.3d.4a.5c.6e, 1c.2d.3d.4a.5d.6a,
1c.2d.3d.4a.5d.6b, 1c.2d.3d.4a.5d.6c, 1c.2d.3d.4a.5d.6d, 1c.2d.3d.4a.5d.6e,
1c.2d.3d.4a.5e.6a, 1c.2d.3d.4a.5e.6b, 1c.2d.3d.4a.5e.6c, 1c.2d.3d.4a.5e.6d,
1c.2d.3d.4a.5e.6e, 1c.2d.3d.4b.5a.6a, 1c.2d.3d.4b.5a.6b, 1c.2d.3d.4b.5a.6c,
1c.2d.3d.4b.5a.6d, 1c.2d.3d.4b.5a.6e, 1c.2d.3d.4b.5b.6a, 1c.2d.3d.4b.5b.6b,
1c.2d.3d.4b.5b.6c, 1c.2d.3d.4b.5b.6d, 1c.2d.3d.4b.5b.6e, 1c.2d.3d.4b.5c.6a,
1c.2d.3d.4b.5c.6b, 1c.2d.3d.4b.5c.6c, 1c.2d.3d.4b.5c.6d, 1c.2d.3d.4b.5c.6e,
1c.2d.3d.4b.5d.6a, 1c.2d.3d.4b.5d.6b, 1c.2d.3d.4b.5d.6c, 1c.2d.3d.4b.5d.6d,
1c.2d.3d.4b.5d.6e, 1c.2d.3d.4b.5e.6a, 1c.2d.3d.4b.5e.6b, 1c.2d.3d.4b.5e.6c,
1c.2d.3d.4b.5e.6d, 1c.2d.3d.4b.5e.6e, 1c.2d.3d.4c.5a.6a, 1c.2d.3d.4c.5a.6b,
1c.2d.3d.4c.5a.6c, 1c.2d.3d.4c.5a.6d, 1c.2d.3d.4c.5a.6e, 1c.2d.3d.4c.5b.6a,
1c.2d.3d.4c.5b.6b, 1c.2d.3d.4c.5b.6c, 1c.2d.3d.4c.5b.6d, 1c.2d.3d.4c.5b.6e,
1c.2d.3d.4c.5c.6a, 1c.2d.3d.4c.5c.6b, 1c.2d.3d.4c.5c.6c, 1c.2d.3d.4c.5c.6d,
1c.2d.3d.4c.5c.6e, 1c.2d.3d.4c.5d.6a, 1c.2d.3d.4c.5d.6b, 1c.2d.3d.4c.5d.6c,
1c.2d.3d.4c.5d.6d, 1c.2d.3d.4c.5d.6e, 1c.2d.3d.4c.5e.6a, 1c.2d.3d.4c.5e.6b,
1c.2d.3d.4c.5e.6c, 1c.2d.3d.4c.5e.6d, 1c.2d.3d.4c.5e.6e, 1c.2d.3d.4d.5a.6a,
1c.2d.3d.4d.5a.6b, 1c.2d.3d.4d.5a.6c, 1c.2d.3d.4d.5a.6d, 1c.2d.3d.4d.5a.6e,
1c.2d.3d.4d.5b.6a, 1c.2d.3d.4d.5b.6b, 1c.2d.3d.4d.5b.6c, 1c.2d.3d.4d.5b.6d,
1c.2d.3d.4d.5b.6e, 1c.2d.3d.4d.5c.6a, 1c.2d.3d.4d.5c.6b, 1c.2d.3d.4d.5c.6c,
1c.2d.3d.4d.5c.6d, 1c.2d.3d.4d.5c.6e, 1c.2d.3d.4d.5d.6a, 1c.2d.3d.4d.5d.6b,

TABLE 8-continued

List of Compounds of Formula (II)

1c.2d.3d.4d.5d.6c, 1c.2d.3d.4d.5d.6d, 1c.2d.3d.4d.5d.6e, 1c.2d.3d.4d.5e.6a,
1c.2d.3d.4d.5e.6b, 1c.2d.3d.4d.5e.6c, 1c.2d.3d.4d.5e.6d, 1c.2d.3d.4d.5e.6e,
1c.2d.3d.4e.5a.6a, 1c.2d.3d.4e.5a.6b, 1c.2d.3d.4e.5a.6c, 1c.2d.3d.4e.5a.6d,
1c.2d.3d.4e.5a.6e, 1c.2d.3d.4e.5b.6a, 1c.2d.3d.4e.5b.6b, 1c.2d.3d.4e.5b.6c,
1c.2d.3d.4e.5b.6d, 1c.2d.3d.4e.5b.6e, 1c.2d.3d.4e.5c.6a, 1c.2d.3d.4e.5c.6b,
1c.2d.3d.4e.5c.6c, 1c.2d.3d.4e.5c.6d, 1c.2d.3d.4e.5c.6e, 1c.2d.3d.4e.5d.6a,
1c.2d.3d.4e.5d.6b, 1c.2d.3d.4e.5d.6c, 1c.2d.3d.4e.5d.6d, 1c.2d.3d.4e.5d.6e,
1c.2d.3d.4e.5e.6a, 1c.2d.3d.4e.5e.6b, 1c.2d.3d.4e.5e.6c, 1c.2d.3d.4e.5e.6d,
1c.2d.3d.4e.5e.6e, 1c.2d.3e.4a.5a.6a, 1c.2d.3e.4a.5a.6b, 1c.2d.3e.4a.5a.6c,
1c.2d.3e.4a.5a.6d, 1c.2d.3e.4a.5a.6e, 1c.2d.3e.4a.5b.6a, 1c.2d.3e.4a.5b.6b,
1c.2d.3e.4a.5b.6c, 1c.2d.3e.4a.5b.6d, 1c.2d.3e.4a.5b.6e, 1c.2d.3e.4a.5c.6a,
1c.2d.3e.4a.5c.6b, 1c.2d.3e.4a.5c.6c, 1c.2d.3e.4a.5c.6d, 1c.2d.3e.4a.5c.6e,
1c.2d.3e.4a.5d.6a, 1c.2d.3e.4a.5d.6b, 1c.2d.3e.4a.5d.6c, 1c.2d.3e.4a.5d.6d,
1c.2d.3e.4a.5d.6e, 1c.2d.3e.4a.5e.6a, 1c.2d.3e.4a.5e.6b, 1c.2d.3e.4a.5e.6c,
1c.2d.3e.4a.5e.6d, 1c.2d.3e.4a.5e.6e, 1c.2d.3e.4b.5a.6a, 1c.2d.3e.4b.5a.6b,
1c.2d.3e.4b.5a.6c, 1c.2d.3e.4b.5a.6d, 1c.2d.3e.4b.5a.6e, 1c.2d.3e.4b.5b.6a,
1c.2d.3e.4b.5b.6b, 1c.2d.3e.4b.5b.6c, 1c.2d.3e.4b.5b.6d, 1c.2d.3e.4b.5b.6e,
1c.2d.3e.4b.5c.6a, 1c.2d.3e.4b.5c.6b, 1c.2d.3e.4b.5c.6c, 1c.2d.3e.4b.5c.6d,
1c.2d.3e.4b.5c.6e, 1c.2d.3e.4b.5d.6a, 1c.2d.3e.4b.5d.6b, 1c.2d.3e.4b.5d.6c,
1c.2d.3e.4b.5d.6d, 1c.2d.3e.4b.5d.6e, 1c.2d.3e.4b.5e.6a, 1c.2d.3e.4b.5e.6b,
1c.2d.3e.4b.5e.6c, 1c.2d.3e.4b.5e.6d, 1c.2d.3e.4b.5e.6e, 1c.2d.3e.4c.5a.6a,
1c.2d.3e.4c.5a.6b, 1c.2d.3e.4c.5a.6c, 1c.2d.3e.4c.5a.6d, 1c.2d.3e.4c.5a.6e,
1c.2d.3e.4c.5b.6a, 1c.2d.3e.4c.5b.6b, 1c.2d.3e.4c.5b.6c, 1c.2d.3e.4c.5b.6d,
1c.2d.3e.4c.5b.6e, 1c.2d.3e.4c.5c.6a, 1c.2d.3e.4c.5c.6b, 1c.2d.3e.4c.5c.6c,
1c.2d.3e.4c.5c.6d, 1c.2d.3e.4c.5c.6e, 1c.2d.3e.4c.5d.6a, 1c.2d.3e.4c.5d.6b,
1c.2d.3e.4c.5d.6c, 1c.2d.3e.4c.5d.6d, 1c.2d.3e.4c.5d.6e, 1c.2d.3e.4c.5e.6a,
1c.2d.3e.4c.5e.6b, 1c.2d.3e.4c.5e.6c, 1c.2d.3e.4c.5e.6d, 1c.2d.3e.4c.5e.6e,
1c.2d.3e.4d.5a.6a, 1c.2d.3e.4d.5a.6b, 1c.2d.3e.4d.5a.6c, 1c.2d.3e.4d.5a.6d,
1c.2d.3e.4d.5a.6e, 1c.2d.3e.4d.5b.6a, 1c.2d.3e.4d.5b.6b, 1c.2d.3e.4d.5b.6c,
1c.2d.3e.4d.5b.6d, 1c.2d.3e.4d.5b.6e, 1c.2d.3e.4d.5c.6a, 1c.2d.3e.4d.5c.6b,
1c.2d.3e.4d.5c.6c, 1c.2d.3e.4d.5c.6d, 1c.2d.3e.4d.5c.6e, 1c.2d.3e.4d.5d.6a,
1c.2d.3e.4d.5d.6b, 1c.2d.3e.4d.5d.6c, 1c.2d.3e.4d.5d.6d, 1c.2d.3e.4d.5d.6e,
1c.2d.3e.4d.5e.6a, 1c.2d.3e.4d.5e.6b, 1c.2d.3e.4d.5e.6c, 1c.2d.3e.4d.5e.6d,
1c.2d.3e.4d.5e.6e, 1c.2d.3e.4e.5a.6a, 1c.2d.3e.4e.5a.6b, 1c.2d.3e.4e.5a.6c,
1c.2d.3e.4e.5a.6d, 1c.2d.3e.4e.5a.6e, 1c.2d.3e.4e.5b.6a, 1c.2d.3e.4e.5b.6b,
1c.2d.3e.4e.5b.6c, 1c.2d.3e.4e.5b.6d, 1c.2d.3e.4e.5b.6e, 1c.2d.3e.4e.5c.6a,
1c.2d.3e.4e.5c.6b, 1c.2d.3e.4e.5c.6c, 1c.2d.3e.4e.5c.6d, 1c.2d.3e.4e.5c.6e,
1c.2d.3e.4e.5d.6a, 1c.2d.3e.4e.5d.6b, 1c.2d.3e.4e.5d.6c, 1c.2d.3e.4e.5d.6d,
1c.2d.3e.4e.5d.6e, 1c.2d.3e.4e.5e.6a, 1c.2d.3e.4e.5e.6b, 1c.2d.3e.4e.5e.6c,
1c.2d.3e.4e.5e.6d, 1c.2d.3e.4e.5e.6e, 1c.2e.3a.4a.5a.6a, 1c.2e.3a.4a.5a.6b,
1c.2e.3a.4a.5a.6c, 1c.2e.3a.4a.5a.6d, 1c.2e.3a.4a.5a.6e, 1c.2e.3a.4a.5b.6a,
1c.2e.3a.4a.5b.6b, 1c.2e.3a.4a.5b.6c, 1c.2e.3a.4a.5b.6d, 1c.2e.3a.4a.5b.6e,
1c.2e.3a.4a.5c.6a, 1c.2e.3a.4a.5c.6b, 1c.2e.3a.4a.5c.6c, 1c.2e.3a.4a.5c.6d,
1c.2e.3a.4a.5c.6e, 1c.2e.3a.4a.5d.6a, 1c.2e.3a.4a.5d.6b, 1c.2e.3a.4a.5d.6c,
1c.2e.3a.4a.5d.6d, 1c.2e.3a.4a.5d.6e, 1c.2e.3a.4a.5e.6a, 1c.2e.3a.4a.5e.6b,
1c.2e.3a.4a.5e.6c, 1c.2e.3a.4a.5e.6d, 1c.2e.3a.4a.5e.6e, 1c.2e.3a.4b.5a.6a,
1c.2e.3a.4b.5a.6b, 1c.2e.3a.4b.5a.6c, 1c.2e.3a.4b.5a.6d, 1c.2e.3a.4b.5a.6e,
1c.2e.3a.4b.5b.6a, 1c.2e.3a.4b.5b.6b, 1c.2e.3a.4b.5b.6c, 1c.2e.3a.4b.5b.6d,
1c.2e.3a.4b.5b.6e, 1c.2e.3a.4b.5c.6a, 1c.2e.3a.4b.5c.6b, 1c.2e.3a.4b.5c.6c,
1c.2e.3a.4b.5c.6d, 1c.2e.3a.4b.5c.6e, 1c.2e.3a.4b.5d.6a, 1c.2e.3a.4b.5d.6b,
1c.2e.3a.4b.5d.6c, 1c.2e.3a.4b.5d.6d, 1c.2e.3a.4b.5d.6e, 1c.2e.3a.4b.5e.6a,
1c.2e.3a.4b.5e.6b, 1c.2e.3a.4b.5e.6c, 1c.2e.3a.4b.5e.6d, 1c.2e.3a.4b.5e.6e,
1c.2e.3a.4c.5a.6a, 1c.2e.3a.4c.5a.6b, 1c.2e.3a.4c.5a.6c, 1c.2e.3a.4c.5a.6d,
1c.2e.3a.4c.5a.6e, 1c.2e.3a.4c.5b.6a, 1c.2e.3a.4c.5b.6b, 1c.2e.3a.4c.5b.6c,
1c.2e.3a.4c.5b.6d, 1c.2e.3a.4c.5b.6e, 1c.2e.3a.4c.5c.6a, 1c.2e.3a.4c.5c.6b,
1c.2e.3a.4c.5c.6c, 1c.2e.3a.4c.5c.6d, 1c.2e.3a.4c.5c.6e, 1c.2e.3a.4c.5d.6a,
1c.2e.3a.4c.5d.6b, 1c.2e.3a.4c.5d.6c, 1c.2e.3a.4c.5d.6d, 1c.2e.3a.4c.5d.6e,
1c.2e.3a.4c.5e.6a, 1c.2e.3a.4c.5e.6b, 1c.2e.3a.4c.5e.6c, 1c.2e.3a.4c.5e.6d,
1c.2e.3a.4c.5e.6e, 1c.2e.3a.4d.5a.6a, 1c.2e.3a.4d.5a.6b, 1c.2e.3a.4d.5a.6c,
1c.2e.3a.4d.5a.6d, 1c.2e.3a.4d.5a.6e, 1c.2e.3a.4d.5b.6a, 1c.2e.3a.4d.5b.6b,
1c.2e.3a.4d.5b.6c, 1c.2e.3a.4d.5b.6d, 1c.2e.3a.4d.5b.6e, 1c.2e.3a.4d.5c.6a,
1c.2e.3a.4d.5c.6b, 1c.2e.3a.4d.5c.6c, 1c.2e.3a.4d.5c.6d, 1c.2e.3a.4d.5c.6e,
1c.2e.3a.4d.5d.6a, 1c.2e.3a.4d.5d.6b, 1c.2e.3a.4d.5d.6c, 1c.2e.3a.4d.5d.6d,
1c.2e.3a.4d.5d.6e, 1c.2e.3a.4d.5e.6a, 1c.2e.3a.4d.5e.6b, 1c.2e.3a.4d.5e.6c,
1c.2e.3a.4d.5e.6d, 1c.2e.3a.4d.5e.6e, 1c.2e.3a.4e.5a.6a, 1c.2e.3a.4e.5a.6b,
1c.2e.3a.4e.5a.6c, 1c.2e.3a.4e.5a.6d, 1c.2e.3a.4e.5a.6e, 1c.2e.3a.4e.5b.6a,
1c.2e.3a.4e.5b.6b, 1c.2e.3a.4e.5b.6c, 1c.2e.3a.4e.5b.6d, 1c.2e.3a.4e.5b.6e,
1c.2e.3a.4e.5c.6a, 1c.2e.3a.4e.5c.6b, 1c.2e.3a.4e.5c.6c, 1c.2e.3a.4e.5c.6d,
1c.2e.3a.4e.5c.6e, 1c.2e.3a.4e.5d.6a, 1c.2e.3a.4e.5d.6b, 1c.2e.3a.4e.5d.6c,
1c.2e.3a.4e.5d.6d, 1c.2e.3a.4e.5d.6e, 1c.2e.3a.4e.5e.6a, 1c.2e.3a.4e.5e.6b,
1c.2e.3a.4e.5e.6c, 1c.2e.3a.4e.5e.6d, 1c.2e.3a.4e.5e.6e, 1c.2e.3b.4a.5a.6a,
1c.2e.3b.4a.5a.6b, 1c.2e.3b.4a.5a.6c, 1c.2e.3b.4a.5a.6d, 1c.2e.3b.4a.5a.6e,
1c.2e.3b.4a.5b.6a, 1c.2e.3b.4a.5b.6b, 1c.2e.3b.4a.5b.6c, 1c.2e.3b.4a.5b.6d,
1c.2e.3b.4a.5b.6e, 1c.2e.3b.4a.5c.6a, 1c.2e.3b.4a.5c.6b, 1c.2e.3b.4a.5c.6c,
1c.2e.3b.4a.5c.6d, 1c.2e.3b.4a.5c.6e, 1c.2e.3b.4a.5d.6a, 1c.2e.3b.4a.5d.6b,
1c.2e.3b.4a.5d.6c, 1c.2e.3b.4a.5d.6d, 1c.2e.3b.4a.5d.6e, 1c.2e.3b.4a.5e.6a,
1c.2e.3b.4a.5e.6b, 1c.2e.3b.4a.5e.6c, 1c.2e.3b.4a.5e.6d, 1c.2e.3b.4a.5e.6e,
1c.2e.3b.4b.5a.6a, 1c.2e.3b.4b.5a.6b, 1c.2e.3b.4b.5a.6c, 1c.2e.3b.4b.5a.6d,

TABLE 8-continued

List of Compounds of Formula (II)

1c.2e.3b.4b.5a.6e, 1c.2e.3b.4b.5b.6a, 1c.2e.3b.4b.5b.6b, 1c.2e.3b.4b.5b.6c,
1c.2e.3b.4b.5b.6d, 1c.2e.3b.4b.5b.6e, 1c.2e.3b.4b.5c.6a, 1c.2e.3b.4b.5c.6b,
1c.2e.3b.4b.5c.6c, 1c.2e.3b.4b.5c.6d, 1c.2e.3b.4b.5c.6e, 1c.2e.3b.4b.5d.6a,
1c.2e.3b.4b.5d.6b, 1c.2e.3b.4b.5d.6c, 1c.2e.3b.4b.5d.6d, 1c.2e.3b.4b.5d.6e,
1c.2e.3b.4b.5e.6a, 1c.2e.3b.4b.5e.6b, 1c.2e.3b.4b.5e.6c, 1c.2e.3b.4b.5e.6d,
1c.2e.3b.4b.5e.6e, 1c.2e.3b.4c.5a.6a, 1c.2e.3b.4c.5a.6b, 1c.2e.3b.4c.5a.6c,
1c.2e.3b.4c.5a.6d, 1c.2e.3b.4c.5a.6e, 1c.2e.3b.4c.5b.6a, 1c.2e.3b.4c.5b.6b,
1c.2e.3b.4c.5b.6c, 1c.2e.3b.4c.5b.6d, 1c.2e.3b.4c.5b.6e, 1c.2e.3b.4c.5c.6a,
1c.2e.3b.4c.5c.6b, 1c.2e.3b.4c.5c.6c, 1c.2e.3b.4c.5c.6d, 1c.2e.3b.4c.5c.6e,
1c.2e.3b.4c.5d.6a, 1c.2e.3b.4c.5d.6b, 1c.2e.3b.4c.5d.6c, 1c.2e.3b.4c.5d.6d,
1c.2e.3b.4c.5d.6e, 1c.2e.3b.4c.5e.6a, 1c.2e.3b.4c.5e.6b, 1c.2e.3b.4c.5e.6c,
1c.2e.3b.4c.5e.6d, 1c.2e.3b.4c.5e.6e, 1c.2e.3b.4d.5a.6a, 1c.2e.3b.4d.5a.6b,
1c.2e.3b.4d.5a.6c, 1c.2e.3b.4d.5a.6d, 1c.2e.3b.4d.5a.6e, 1c.2e.3b.4d.5b.6a,
1c.2e.3b.4d.5b.6b, 1c.2e.3b.4d.5b.6c, 1c.2e.3b.4d.5b.6d, 1c.2e.3b.4d.5b.6e,
1c.2e.3b.4d.5c.6a, 1c.2e.3b.4d.5c.6b, 1c.2e.3b.4d.5c.6c, 1c.2e.3b.4d.5c.6d,
1c.2e.3b.4d.5c.6e, 1c.2e.3b.4d.5d.6a, 1c.2e.3b.4d.5d.6b, 1c.2e.3b.4d.5d.6c,
1c.2e.3b.4d.5d.6d, 1c.2e.3b.4d.5d.6e, 1c.2e.3b.4d.5e.6a, 1c.2e.3b.4d.5e.6b,
1c.2e.3b.4d.5e.6c, 1c.2e.3b.4d.5e.6d, 1c.2e.3b.4d.5e.6e, 1c.2e.3b.4e.5a.6a,
1c.2e.3b.4e.5a.6b, 1c.2e.3b.4e.5a.6c, 1c.2e.3b.4e.5a.6d, 1c.2e.3b.4e.5a.6e,
1c.2e.3b.4e.5b.6a, 1c.2e.3b.4e.5b.6b, 1c.2e.3b.4e.5b.6c, 1c.2e.3b.4e.5b.6d,
1c.2e.3b.4e.5b.6e, 1c.2e.3b.4e.5c.6a, 1c.2e.3b.4e.5c.6b, 1c.2e.3b.4e.5c.6c,
1c.2e.3b.4e.5c.6d, 1c.2e.3b.4e.5c.6e, 1c.2e.3b.4e.5d.6a, 1c.2e.3b.4e.5d.6b,
1c.2e.3b.4e.5d.6c, 1c.2e.3b.4e.5d.6d, 1c.2e.3b.4e.5d.6e, 1c.2e.3b.4e.5e.6a,
1c.2e.3b.4e.5e.6b, 1c.2e.3b.4e.5e.6c, 1c.2e.3b.4e.5e.6d, 1c.2e.3b.4e.5e.6e,
1c.2e.3c.4a.5a.6a, 1c.2e.3c.4a.5a.6b, 1c.2e.3c.4a.5a.6c, 1c.2e.3c.4a.5a.6d,
1c.2e.3c.4a.5a.6e, 1c.2e.3c.4a.5b.6a, 1c.2e.3c.4a.5b.6b, 1c.2e.3c.4a.5b.6c,
1c.2e.3c.4a.5b.6d, 1c.2e.3c.4a.5b.6e, 1c.2e.3c.4a.5c.6a, 1c.2e.3c.4a.5c.6b,
1c.2e.3c.4a.5c.6c, 1c.2e.3c.4a.5c.6d, 1c.2e.3c.4a.5c.6e, 1c.2e.3c.4a.5d.6a,
1c.2e.3c.4a.5d.6b, 1c.2e.3c.4a.5d.6c, 1c.2e.3c.4a.5d.6d, 1c.2e.3c.4a.5d.6e,
1c.2e.3c.4a.5e.6a, 1c.2e.3c.4a.5e.6b, 1c.2e.3c.4a.5e.6c, 1c.2e.3c.4a.5e.6d,
1c.2e.3c.4a.5e.6e, 1c.2e.3c.4b.5a.6a, 1c.2e.3c.4b.5a.6b, 1c.2e.3c.4b.5a.6c,
1c.2e.3c.4b.5a.6d, 1c.2e.3c.4b.5a.6e, 1c.2e.3c.4b.5b.6a, 1c.2e.3c.4b.5b.6b,
1c.2e.3c.4b.5b.6c, 1c.2e.3c.4b.5b.6d, 1c.2e.3c.4b.5b.6e, 1c.2e.3c.4b.5c.6a,
1c.2e.3c.4b.5c.6b, 1c.2e.3c.4b.5c.6c, 1c.2e.3c.4b.5c.6d, 1c.2e.3c.4b.5c.6e,
1c.2e.3c.4b.5d.6a, 1c.2e.3c.4b.5d.6b, 1c.2e.3c.4b.5d.6c, 1c.2e.3c.4b.5d.6d,
1c.2e.3c.4b.5d.6e, 1c.2e.3c.4b.5e.6a, 1c.2e.3c.4b.5e.6b, 1c.2e.3c.4b.5e.6c,
1c.2e.3c.4b.5e.6d, 1c.2e.3c.4b.5e.6e, 1c.2e.3c.4c.5a.6a, 1c.2e.3c.4c.5a.6b,
1c.2e.3c.4c.5a.6c, 1c.2e.3c.4c.5a.6d, 1c.2e.3c.4c.5a.6e, 1c.2e.3c.4c.5b.6a,
1c.2e.3c.4c.5b.6b, 1c.2e.3c.4c.5b.6c, 1c.2e.3c.4c.5b.6d, 1c.2e.3c.4c.5b.6e,
1c.2e.3c.4c.5c.6a, 1c.2e.3c.4c.5c.6b, 1c.2e.3c.4c.5c.6c, 1c.2e.3c.4c.5c.6d,
1c.2e.3c.4c.5c.6e, 1c.2e.3c.4c.5d.6a, 1c.2e.3c.4c.5d.6b, 1c.2e.3c.4c.5d.6c,
1c.2e.3c.4c.5d.6d, 1c.2e.3c.4c.5d.6e, 1c.2e.3c.4c.5e.6a, 1c.2e.3c.4c.5e.6b,
1c.2e.3c.4c.5e.6c, 1c.2e.3c.4c.5e.6d, 1c.2e.3c.4c.5e.6e, 1c.2e.3c.4d.5a.6a,
1c.2e.3c.4d.5a.6b, 1c.2e.3c.4d.5a.6c, 1c.2e.3c.4d.5a.6d, 1c.2e.3c.4d.5a.6e,
1c.2e.3c.4d.5b.6a, 1c.2e.3c.4d.5b.6b, 1c.2e.3c.4d.5b.6c, 1c.2e.3c.4d.5b.6d,
1c.2e.3c.4d.5b.6e, 1c.2e.3c.4d.5c.6a, 1c.2e.3c.4d.5c.6b, 1c.2e.3c.4d.5c.6c,
1c.2e.3c.4d.5c.6d, 1c.2e.3c.4d.5c.6e, 1c.2e.3c.4d.5d.6a, 1c.2e.3c.4d.5d.6b,
1c.2e.3c.4d.5d.6c, 1c.2e.3c.4d.5d.6d, 1c.2e.3c.4d.5d.6e, 1c.2e.3c.4d.5e.6a,
1c.2e.3c.4d.5e.6b, 1c.2e.3c.4d.5e.6c, 1c.2e.3c.4d.5e.6d, 1c.2e.3c.4d.5e.6e,
1c.2e.3c.4e.5a.6a, 1c.2e.3c.4e.5a.6b, 1c.2e.3c.4e.5a.6c, 1c.2e.3c.4e.5a.6d,
1c.2e.3c.4e.5a.6e, 1c.2e.3c.4e.5b.6a, 1c.2e.3c.4e.5b.6b, 1c.2e.3c.4e.5b.6c,
1c.2e.3c.4e.5b.6d, 1c.2e.3c.4e.5b.6e, 1c.2e.3c.4e.5c.6a, 1c.2e.3c.4e.5c.6b,
1c.2e.3c.4e.5c.6c, 1c.2e.3c.4e.5c.6d, 1c.2e.3c.4e.5c.6e, 1c.2e.3c.4e.5d.6a,
1c.2e.3c.4e.5d.6b, 1c.2e.3c.4e.5d.6c, 1c.2e.3c.4e.5d.6d, 1c.2e.3c.4e.5d.6e,
1c.2e.3c.4e.5e.6a, 1c.2e.3c.4e.5e.6b, 1c.2e.3c.4e.5e.6c, 1c.2e.3c.4e.5e.6d,
1c.2e.3c.4e.5e.6e, 1c.2e.3d.4a.5a.6a, 1c.2e.3d.4a.5a.6b, 1c.2e.3d.4a.5a.6c,
1c.2e.3d.4a.5a.6d, 1c.2e.3d.4a.5a.6e, 1c.2e.3d.4a.5b.6a, 1c.2e.3d.4a.5b.6b,
1c.2e.3d.4a.5b.6c, 1c.2e.3d.4a.5b.6d, 1c.2e.3d.4a.5b.6e, 1c.2e.3d.4a.5c.6a,
1c.2e.3d.4a.5c.6b, 1c.2e.3d.4a.5c.6c, 1c.2e.3d.4a.5c.6d, 1c.2e.3d.4a.5c.6e,
1c.2e.3d.4a.5d.6a, 1c.2e.3d.4a.5d.6b, 1c.2e.3d.4a.5d.6c, 1c.2e.3d.4a.5d.6d,
1c.2e.3d.4a.5d.6e, 1c.2e.3d.4a.5e.6a, 1c.2e.3d.4a.5e.6b, 1c.2e.3d.4a.5e.6c,
1c.2e.3d.4a.5e.6d, 1c.2e.3d.4a.5e.6e, 1c.2e.3d.4b.5a.6a, 1c.2e.3d.4b.5a.6b,
1c.2e.3d.4b.5a.6c, 1c.2e.3d.4b.5a.6d, 1c.2e.3d.4b.5a.6e, 1c.2e.3d.4b.5b.6a,
1c.2e.3d.4b.5b.6b, 1c.2e.3d.4b.5b.6c, 1c.2e.3d.4b.5b.6d, 1c.2e.3d.4b.5b.6e,
1c.2e.3d.4b.5c.6a, 1c.2e.3d.4b.5c.6b, 1c.2e.3d.4b.5c.6c, 1c.2e.3d.4b.5c.6d,
1c.2e.3d.4b.5c.6e, 1c.2e.3d.4b.5d.6a, 1c.2e.3d.4b.5d.6b, 1c.2e.3d.4b.5d.6c,
1c.2e.3d.4b.5d.6d, 1c.2e.3d.4b.5d.6e, 1c.2e.3d.4b.5e.6a, 1c.2e.3d.4b.5e.6b,
1c.2e.3d.4b.5e.6c, 1c.2e.3d.4b.5e.6d, 1c.2e.3d.4b.5e.6e, 1c.2e.3d.4c.5a.6a,
1c.2e.3d.4c.5a.6b, 1c.2e.3d.4c.5a.6c, 1c.2e.3d.4c.5a.6d, 1c.2e.3d.4c.5a.6e,
1c.2e.3d.4c.5b.6a, 1c.2e.3d.4c.5b.6b, 1c.2e.3d.4c.5b.6c, 1c.2e.3d.4c.5b.6d,
1c.2e.3d.4c.5b.6e, 1c.2e.3d.4c.5c.6a, 1c.2e.3d.4c.5c.6b, 1c.2e.3d.4c.5c.6c,
1c.2e.3d.4c.5c.6d, 1c.2e.3d.4c.5c.6e, 1c.2e.3d.4c.5d.6a, 1c.2e.3d.4c.5d.6b,
1c.2e.3d.4c.5d.6c, 1c.2e.3d.4c.5d.6d, 1c.2e.3d.4c.5d.6e, 1c.2e.3d.4c.5e.6a,
1c.2e.3d.4c.5e.6b, 1c.2e.3d.4c.5e.6c, 1c.2e.3d.4c.5e.6d, 1c.2e.3d.4c.5e.6e,
1c.2e.3d.4d.5a.6a, 1c.2e.3d.4d.5a.6b, 1c.2e.3d.4d.5a.6c, 1c.2e.3d.4d.5a.6d,
1c.2e.3d.4d.5a.6e, 1c.2e.3d.4d.5b.6a, 1c.2e.3d.4d.5b.6b, 1c.2e.3d.4d.5b.6c,
1c.2e.3d.4d.5b.6d, 1c.2e.3d.4d.5b.6e, 1c.2e.3d.4d.5c.6a, 1c.2e.3d.4d.5c.6b,
1c.2e.3d.4d.5c.6c, 1c.2e.3d.4d.5c.6d, 1c.2e.3d.4d.5c.6e, 1c.2e.3d.4d.5d.6a,

TABLE 8-continued

List of Compounds of Formula (II)

1c.2e.3d.4d.5d.6b, 1c.2e.3d.4d.5d.6c, 1c.2e.3d.4d.5d.6d, 1c.2e.3d.4d.5d.6e,
1c.2e.3d.4d.5e.6a, 1c.2e.3d.4d.5e.6b, 1c.2e.3d.4d.5e.6c, 1c.2e.3d.4d.5e.6d,
1c.2e.3d.4d.5e.6e, 1c.2e.3d.4e.5a.6a, 1c.2e.3d.4e.5a.6b, 1c.2e.3d.4e.5a.6c,
1c.2e.3d.4e.5a.6d, 1c.2e.3d.4e.5a.6e, 1c.2e.3d.4e.5b.6a, 1c.2e.3d.4e.5b.6b,
1c.2e.3d.4e.5b.6c, 1c.2e.3d.4e.5b.6d, 1c.2e.3d.4e.5b.6e, 1c.2e.3d.4e.5c.6a,
1c.2e.3d.4e.5c.6b, 1c.2e.3d.4e.5c.6c, 1c.2e.3d.4e.5c.6d, 1c.2e.3d.4e.5c.6e,
1c.2e.3d.4e.5d.6a, 1c.2e.3d.4e.5d.6b, 1c.2e.3d.4e.5d.6c, 1c.2e.3d.4e.5d.6d,
1c.2e.3d.4e.5d.6e, 1c.2e.3d.4e.5e.6a, 1c.2e.3d.4e.5e.6b, 1c.2e.3d.4e.5e.6c,
1c.2e.3d.4e.5e.6d, 1c.2e.3d.4e.5e.6e, 1c.2e.3e.4a.5a.6a, 1c.2e.3e.4a.5a.6b,
1c.2e.3e.4a.5a.6c, 1c.2e.3e.4a.5a.6d, 1c.2e.3e.4a.5a.6e, 1c.2e.3e.4a.5b.6a,
1c.2e.3e.4a.5b.6b, 1c.2e.3e.4a.5b.6c, 1c.2e.3e.4a.5b.6d, 1c.2e.3e.4a.5b.6e,
1c.2e.3e.4a.5c.6a, 1c.2e.3e.4a.5c.6b, 1c.2e.3e.4a.5c.6c, 1c.2e.3e.4a.5c.6d,
1c.2e.3e.4a.5c.6e, 1c.2e.3e.4a.5d.6a, 1c.2e.3e.4a.5d.6b, 1c.2e.3e.4a.5d.6c,
1c.2e.3e.4a.5d.6d, 1c.2e.3e.4a.5d.6e, 1c.2e.3e.4a.5e.6a, 1c.2e.3e.4a.5e.6b,
1c.2e.3e.4a.5e.6c, 1c.2e.3e.4a.5e.6d, 1c.2e.3e.4a.5e.6e, 1c.2e.3e.4b.5a.6a,
1c.2e.3e.4b.5a.6b, 1c.2e.3e.4b.5a.6c, 1c.2e.3e.4b.5a.6d, 1c.2e.3e.4b.5a.6e,
1c.2e.3e.4b.5b.6a, 1c.2e.3e.4b.5b.6b, 1c.2e.3e.4b.5b.6c, 1c.2e.3e.4b.5b.6d,
1c.2e.3e.4b.5b.6e, 1c.2e.3e.4b.5c.6a, 1c.2e.3e.4b.5c.6b, 1c.2e.3e.4b.5c.6c,
1c.2e.3e.4b.5c.6d, 1c.2e.3e.4b.5c.6e, 1c.2e.3e.4b.5d.6a, 1c.2e.3e.4b.5d.6b,
1c.2e.3e.4b.5d.6c, 1c.2e.3e.4b.5d.6d, 1c.2e.3e.4b.5d.6e, 1c.2e.3e.4b.5e.6a,
1c.2e.3e.4b.5e.6b, 1c.2e.3e.4b.5e.6c, 1c.2e.3e.4b.5e.6d, 1c.2e.3e.4b.5e.6e,
1c.2e.3e.4c.5a.6a, 1c.2e.3e.4c.5a.6b, 1c.2e.3e.4c.5a.6c, 1c.2e.3e.4c.5a.6d,
1c.2e.3e.4c.5a.6e, 1c.2e.3e.4c.5b.6a, 1c.2e.3e.4c.5b.6b, 1c.2e.3e.4c.5b.6c,
1c.2e.3e.4c.5b.6d, 1c.2e.3e.4c.5b.6e, 1c.2e.3e.4c.5c.6a, 1c.2e.3e.4c.5c.6b,
1c.2e.3e.4c.5c.6c, 1c.2e.3e.4c.5c.6d, 1c.2e.3e.4c.5c.6e, 1c.2e.3e.4c.5d.6a,
1c.2e.3e.4c.5d.6b, 1c.2e.3e.4c.5d.6c, 1c.2e.3e.4c.5d.6d, 1c.2e.3e.4c.5d.6e,
1c.2e.3e.4c.5e.6a, 1c.2e.3e.4c.5e.6b, 1c.2e.3e.4c.5e.6c, 1c.2e.3e.4c.5e.6d,
1c.2e.3e.4c.5e.6e, 1c.2e.3e.4d.5a.6a, 1c.2e.3e.4d.5a.6b, 1c.2e.3e.4d.5a.6c,
1c.2e.3e.4d.5a.6d, 1c.2e.3e.4d.5a.6e, 1c.2e.3e.4d.5b.6a, 1c.2e.3e.4d.5b.6b,
1c.2e.3e.4d.5b.6c, 1c.2e.3e.4d.5b.6d, 1c.2e.3e.4d.5b.6e, 1c.2e.3e.4d.5c.6a,
1c.2e.3e.4d.5c.6b, 1c.2e.3e.4d.5c.6c, 1c.2e.3e.4d.5c.6d, 1c.2e.3e.4d.5c.6e,
1c.2e.3e.4d.5d.6a, 1c.2e.3e.4d.5d.6b, 1c.2e.3e.4d.5d.6c, 1c.2e.3e.4d.5d.6d,
1c.2e.3e.4d.5d.6e, 1c.2e.3e.4d.5e.6a, 1c.2e.3e.4d.5e.6b, 1c.2e.3e.4d.5e.6c,
1c.2e.3e.4d.5e.6d, 1c.2e.3e.4d.5e.6e, 1c.2e.3e.4e.5a.6a, 1c.2e.3e.4e.5a.6b,
1c.2e.3e.4e.5a.6c, 1c.2e.3e.4e.5a.6d, 1c.2e.3e.4e.5a.6e, 1c.2e.3e.4e.5b.6a,
1c.2e.3e.4e.5b.6b, 1c.2e.3e.4e.5b.6c, 1c.2e.3e.4e.5b.6d, 1c.2e.3e.4e.5b.6e,
1c.2e.3e.4e.5c.6a, 1c.2e.3e.4e.5c.6b, 1c.2e.3e.4e.5c.6c, 1c.2e.3e.4e.5c.6d,
1c.2e.3e.4e.5c.6e, 1c.2e.3e.4e.5d.6a, 1c.2e.3e.4e.5d.6b, 1c.2e.3e.4e.5d.6c,
1c.2e.3e.4e.5d.6d, 1c.2e.3e.4e.5d.6e, 1c.2e.3e.4e.5e.6a, 1c.2e.3e.4e.5e.6b,
1c.2e.3e.4e.5e.6c, 1c.2e.3e.4e.5e.6d, 1c.2e.3e.4e.5e.6e, 1d.2a.3a.4a.5a.6a,
1d.2a.3a.4a.5a.6b, 1d.2a.3a.4a.5a.6c, 1d.2a.3a.4a.5a.6d, 1d.2a.3a.4a.5a.6e,
1d.2a.3a.4a.5b.6a, 1d.2a.3a.4a.5b.6b, 1d.2a.3a.4a.5b.6c, 1d.2a.3a.4a.5b.6d,
1d.2a.3a.4a.5b.6e, 1d.2a.3a.4a.5c.6a, 1d.2a.3a.4a.5c.6b, 1d.2a.3a.4a.5c.6c,
1d.2a.3a.4a.5c.6d, 1d.2a.3a.4a.5c.6e, 1d.2a.3a.4a.5d.6a, 1d.2a.3a.4a.5d.6b,
1d.2a.3a.4a.5d.6c, 1d.2a.3a.4a.5d.6d, 1d.2a.3a.4a.5d.6e, 1d.2a.3a.4a.5e.6a,
1d.2a.3a.4a.5e.6b, 1d.2a.3a.4a.5e.6c, 1d.2a.3a.4a.5e.6d, 1d.2a.3a.4a.5e.6e,
1d.2a.3a.4b.5a.6a, 1d.2a.3a.4b.5a.6b, 1d.2a.3a.4b.5a.6c, 1d.2a.3a.4b.5a.6d,
1d.2a.3a.4b.5a.6e, 1d.2a.3a.4b.5b.6a, 1d.2a.3a.4b.5b.6b, 1d.2a.3a.4b.5b.6c,
1d.2a.3a.4b.5b.6d, 1d.2a.3a.4b.5b.6e, 1d.2a.3a.4b.5c.6a, 1d.2a.3a.4b.5c.6b,
1d.2a.3a.4b.5c.6c, 1d.2a.3a.4b.5c.6d, 1d.2a.3a.4b.5c.6e, 1d.2a.3a.4b.5d.6a,
1d.2a.3a.4b.5d.6b, 1d.2a.3a.4b.5d.6c, 1d.2a.3a.4b.5d.6d, 1d.2a.3a.4b.5d.6e,
1d.2a.3a.4b.5e.6a, 1d.2a.3a.4b.5e.6b, 1d.2a.3a.4b.5e.6c, 1d.2a.3a.4b.5e.6d,
1d.2a.3a.4b.5e.6e, 1d.2a.3a.4c.5a.6a, 1d.2a.3a.4c.5a.6b, 1d.2a.3a.4c.5a.6c,
1d.2a.3a.4c.5a.6d, 1d.2a.3a.4c.5a.6e, 1d.2a.3a.4c.5b.6a, 1d.2a.3a.4c.5b.6b,
1d.2a.3a.4c.5b.6c, 1d.2a.3a.4c.5b.6d, 1d.2a.3a.4c.5b.6e, 1d.2a.3a.4c.5c.6a,
1d.2a.3a.4c.5c.6b, 1d.2a.3a.4c.5c.6c, 1d.2a.3a.4c.5c.6d, 1d.2a.3a.4c.5c.6e,
1d.2a.3a.4c.5d.6a, 1d.2a.3a.4c.5d.6b, 1d.2a.3a.4c.5d.6c, 1d.2a.3a.4c.5d.6d,
1d.2a.3a.4c.5d.6e, 1d.2a.3a.4c.5e.6a, 1d.2a.3a.4c.5e.6b, 1d.2a.3a.4c.5e.6c,
1d.2a.3a.4c.5e.6d, 1d.2a.3a.4c.5e.6e, 1d.2a.3a.4d.5a.6a, 1d.2a.3a.4d.5a.6b,
1d.2a.3a.4d.5a.6c, 1d.2a.3a.4d.5a.6d, 1d.2a.3a.4d.5a.6e, 1d.2a.3a.4d.5b.6a,
1d.2a.3a.4d.5b.6b, 1d.2a.3a.4d.5b.6c, 1d.2a.3a.4d.5b.6d, 1d.2a.3a.4d.5b.6e,
1d.2a.3a.4d.5c.6a, 1d.2a.3a.4d.5c.6b, 1d.2a.3a.4d.5c.6c, 1d.2a.3a.4d.5c.6d,
1d.2a.3a.4d.5c.6e, 1d.2a.3a.4d.5d.6a, 1d.2a.3a.4d.5d.6b, 1d.2a.3a.4d.5d.6c,
1d.2a.3a.4d.5d.6d, 1d.2a.3a.4d.5d.6e, 1d.2a.3a.4d.5e.6a, 1d.2a.3a.4d.5e.6b,
1d.2a.3a.4d.5e.6c, 1d.2a.3a.4d.5e.6d, 1d.2a.3a.4d.5e.6e, 1d.2a.3a.4e.5a.6a,
1d.2a.3a.4e.5a.6b, 1d.2a.3a.4e.5a.6c, 1d.2a.3a.4e.5a.6d, 1d.2a.3a.4e.5a.6e,
1d.2a.3a.4e.5b.6a, 1d.2a.3a.4e.5b.6b, 1d.2a.3a.4e.5b.6c, 1d.2a.3a.4e.5b.6d,
1d.2a.3a.4e.5b.6e, 1d.2a.3a.4e.5c.6a, 1d.2a.3a.4e.5c.6b, 1d.2a.3a.4e.5c.6c,
1d.2a.3a.4e.5c.6d, 1d.2a.3a.4e.5c.6e, 1d.2a.3a.4e.5d.6a, 1d.2a.3a.4e.5d.6b,
1d.2a.3a.4e.5d.6c, 1d.2a.3a.4e.5d.6d, 1d.2a.3a.4e.5d.6e, 1d.2a.3a.4e.5e.6a,
1d.2a.3a.4e.5e.6b, 1d.2a.3a.4e.5e.6c, 1d.2a.3a.4e.5e.6d, 1d.2a.3a.4e.5e.6e,
1d.2a.3b.4a.5a.6a, 1d.2a.3b.4a.5a.6b, 1d.2a.3b.4a.5a.6c, 1d.2a.3b.4a.5a.6d,
1d.2a.3b.4a.5a.6e, 1d.2a.3b.4a.5b.6a, 1d.2a.3b.4a.5b.6b, 1d.2a.3b.4a.5b.6c,
1d.2a.3b.4a.5b.6d, 1d.2a.3b.4a.5b.6e, 1d.2a.3b.4a.5c.6a, 1d.2a.3b.4a.5c.6b,
1d.2a.3b.4a.5c.6c, 1d.2a.3b.4a.5c.6d, 1d.2a.3b.4a.5c.6e, 1d.2a.3b.4a.5d.6a,
1d.2a.3b.4a.5d.6b, 1d.2a.3b.4a.5d.6c, 1d.2a.3b.4a.5d.6d, 1d.2a.3b.4a.5d.6e,
1d.2a.3b.4a.5e.6a, 1d.2a.3b.4a.5e.6b, 1d.2a.3b.4a.5e.6c, 1d.2a.3b.4a.5e.6d,
1d.2a.3b.4a.5e.6e, 1d.2a.3b.4b.5a.6a, 1d.2a.3b.4b.5a.6b, 1d.2a.3b.4b.5a.6c,

TABLE 8-continued

List of Compounds of Formula (II)

1d.2a.3b.4b.5a.6d, 1d.2a.3b.4b.5a.6e, 1d.2a.3b.4b.5b.6a, 1d.2a.3b.4b.5b.6b,
1d.2a.3b.4b.5b.6c, 1d.2a.3b.4b.5b.6d, 1d.2a.3b.4b.5b.6e, 1d.2a.3b.4b.5c.6a,
1d.2a.3b.4b.5c.6b, 1d.2a.3b.4b.5c.6c, 1d.2a.3b.4b.5c.6d, 1d.2a.3b.4b.5c.6e,
1d.2a.3b.4b.5d.6a, 1d.2a.3b.4b.5d.6b, 1d.2a.3b.4b.5d.6c, 1d.2a.3b.4b.5d.6d,
1d.2a.3b.4b.5d.6e, 1d.2a.3b.4b.5e.6a, 1d.2a.3b.4b.5e.6b, 1d.2a.3b.4b.5e.6c,
1d.2a.3b.4b.5e.6d, 1d.2a.3b.4b.5e.6e, 1d.2a.3b.4c.5a.6a, 1d.2a.3b.4c.5a.6b,
1d.2a.3b.4c.5a.6c, 1d.2a.3b.4c.5a.6d, 1d.2a.3b.4c.5a.6e, 1d.2a.3b.4c.5b.6a,
1d.2a.3b.4c.5b.6b, 1d.2a.3b.4c.5b.6c, 1d.2a.3b.4c.5b.6d, 1d.2a.3b.4c.5b.6e,
1d.2a.3b.4c.5c.6a, 1d.2a.3b.4c.5c.6b, 1d.2a.3b.4c.5c.6c, 1d.2a.3b.4c.5c.6d,
1d.2a.3b.4c.5c.6e, 1d.2a.3b.4c.5d.6a, 1d.2a.3b.4c.5d.6b, 1d.2a.3b.4c.5d.6c,
1d.2a.3b.4c.5d.6d, 1d.2a.3b.4c.5d.6e, 1d.2a.3b.4c.5e.6a, 1d.2a.3b.4c.5e.6b,
1d.2a.3b.4c.5e.6c, 1d.2a.3b.4c.5e.6d, 1d.2a.3b.4c.5e.6e, 1d.2a.3b.4d.5a.6a,
1d.2a.3b.4d.5a.6b, 1d.2a.3b.4d.5a.6c, 1d.2a.3b.4d.5a.6d, 1d.2a.3b.4d.5a.6e,
1d.2a.3b.4d.5b.6a, 1d.2a.3b.4d.5b.6b, 1d.2a.3b.4d.5b.6c, 1d.2a.3b.4d.5b.6d,
1d.2a.3b.4d.5b.6e, 1d.2a.3b.4d.5c.6a, 1d.2a.3b.4d.5c.6b, 1d.2a.3b.4d.5c.6c,
1d.2a.3b.4d.5c.6d, 1d.2a.3b.4d.5c.6e, 1d.2a.3b.4d.5d.6a, 1d.2a.3b.4d.5d.6b,
1d.2a.3b.4d.5d.6c, 1d.2a.3b.4d.5d.6d, 1d.2a.3b.4d.5d.6e, 1d.2a.3b.4d.5e.6a,
1d.2a.3b.4d.5e.6b, 1d.2a.3b.4d.5e.6c, 1d.2a.3b.4d.5e.6d, 1d.2a.3b.4d.5e.6e,
1d.2a.3b.4e.5a.6a, 1d.2a.3b.4e.5a.6b, 1d.2a.3b.4e.5a.6c, 1d.2a.3b.4e.5a.6d,
1d.2a.3b.4e.5a.6e, 1d.2a.3b.4e.5b.6a, 1d.2a.3b.4e.5b.6b, 1d.2a.3b.4e.5b.6c,
1d.2a.3b.4e.5b.6d, 1d.2a.3b.4e.5b.6e, 1d.2a.3b.4e.5c.6a, 1d.2a.3b.4e.5c.6b,
1d.2a.3b.4e.5c.6c, 1d.2a.3b.4e.5c.6d, 1d.2a.3b.4e.5c.6e, 1d.2a.3b.4e.5d.6a,
1d.2a.3b.4e.5d.6b, 1d.2a.3b.4e.5d.6c, 1d.2a.3b.4e.5d.6d, 1d.2a.3b.4e.5d.6e,
1d.2a.3b.4e.5e.6a, 1d.2a.3b.4e.5e.6b, 1d.2a.3b.4e.5e.6c, 1d.2a.3b.4e.5e.6d,
1d.2a.3b.4e.5e.6e, 1d.2a.3c.4a.5a.6a, 1d.2a.3c.4a.5a.6b, 1d.2a.3c.4a.5a.6c,
1d.2a.3c.4a.5a.6d, 1d.2a.3c.4a.5a.6e, 1d.2a.3c.4a.5b.6a, 1d.2a.3c.4a.5b.6b,
1d.2a.3c.4a.5b.6c, 1d.2a.3c.4a.5b.6d, 1d.2a.3c.4a.5b.6e, 1d.2a.3c.4a.5c.6a,
1d.2a.3c.4a.5c.6b, 1d.2a.3c.4a.5c.6c, 1d.2a.3c.4a.5c.6d, 1d.2a.3c.4a.5c.6e,
1d.2a.3c.4a.5d.6a, 1d.2a.3c.4a.5d.6b, 1d.2a.3c.4a.5d.6c, 1d.2a.3c.4a.5d.6d,
1d.2a.3c.4a.5d.6e, 1d.2a.3c.4a.5e.6a, 1d.2a.3c.4a.5e.6b, 1d.2a.3c.4a.5e.6c,
1d.2a.3c.4a.5e.6d, 1d.2a.3c.4a.5e.6e, 1d.2a.3c.4b.5a.6a, 1d.2a.3c.4b.5a.6b,
1d.2a.3c.4b.5a.6c, 1d.2a.3c.4b.5a.6d, 1d.2a.3c.4b.5a.6e, 1d.2a.3c.4b.5b.6a,
1d.2a.3c.4b.5b.6b, 1d.2a.3c.4b.5b.6c, 1d.2a.3c.4b.5b.6d, 1d.2a.3c.4b.5b.6e,
1d.2a.3c.4b.5c.6a, 1d.2a.3c.4b.5c.6b, 1d.2a.3c.4b.5c.6c, 1d.2a.3c.4b.5c.6d,
1d.2a.3c.4b.5c.6e, 1d.2a.3c.4b.5d.6a, 1d.2a.3c.4b.5d.6b, 1d.2a.3c.4b.5d.6c,
1d.2a.3c.4b.5d.6d, 1d.2a.3c.4b.5d.6e, 1d.2a.3c.4b.5e.6a, 1d.2a.3c.4b.5e.6b,
1d.2a.3c.4b.5e.6c, 1d.2a.3c.4b.5e.6d, 1d.2a.3c.4b.5e.6e, 1d.2a.3c.4c.5a.6a,
1d.2a.3c.4c.5a.6b, 1d.2a.3c.4c.5a.6c, 1d.2a.3c.4c.5a.6d, 1d.2a.3c.4c.5a.6e,
1d.2a.3c.4c.5b.6a, 1d.2a.3c.4c.5b.6b, 1d.2a.3c.4c.5b.6c, 1d.2a.3c.4c.5b.6d,
1d.2a.3c.4c.5b.6e, 1d.2a.3c.4c.5c.6a, 1d.2a.3c.4c.5c.6b, 1d.2a.3c.4c.5c.6c,
1d.2a.3c.4c.5c.6d, 1d.2a.3c.4c.5c.6e, 1d.2a.3c.4c.5d.6a, 1d.2a.3c.4c.5d.6b,
1d.2a.3c.4c.5d.6c, 1d.2a.3c.4c.5d.6d, 1d.2a.3c.4c.5d.6e, 1d.2a.3c.4c.5e.6a,
1d.2a.3c.4c.5e.6b, 1d.2a.3c.4c.5e.6c, 1d.2a.3c.4c.5e.6d, 1d.2a.3c.4c.5e.6e,
1d.2a.3c.4d.5a.6a, 1d.2a.3c.4d.5a.6b, 1d.2a.3c.4d.5a.6c, 1d.2a.3c.4d.5a.6d,
1d.2a.3c.4d.5a.6e, 1d.2a.3c.4d.5b.6a, 1d.2a.3c.4d.5b.6b, 1d.2a.3c.4d.5b.6c,
1d.2a.3c.4d.5b.6d, 1d.2a.3c.4d.5b.6e, 1d.2a.3c.4d.5c.6a, 1d.2a.3c.4d.5c.6b,
1d.2a.3c.4d.5c.6c, 1d.2a.3c.4d.5c.6d, 1d.2a.3c.4d.5c.6e, 1d.2a.3c.4d.5d.6a,
1d.2a.3c.4d.5d.6b, 1d.2a.3c.4d.5d.6c, 1d.2a.3c.4d.5d.6d, 1d.2a.3c.4d.5d.6e,
1d.2a.3c.4d.5e.6a, 1d.2a.3c.4d.5e.6b, 1d.2a.3c.4d.5e.6c, 1d.2a.3c.4d.5e.6d,
1d.2a.3c.4d.5e.6e, 1d.2a.3c.4e.5a.6a, 1d.2a.3c.4e.5a.6b, 1d.2a.3c.4e.5a.6c,
1d.2a.3c.4e.5a.6d, 1d.2a.3c.4e.5a.6e, 1d.2a.3c.4e.5b.6a, 1d.2a.3c.4e.5b.6b,
1d.2a.3c.4e.5b.6c, 1d.2a.3c.4e.5b.6d, 1d.2a.3c.4e.5b.6e, 1d.2a.3c.4e.5c.6a,
1d.2a.3c.4e.5c.6b, 1d.2a.3c.4e.5c.6c, 1d.2a.3c.4e.5c.6d, 1d.2a.3c.4e.5c.6e,
1d.2a.3c.4e.5d.6a, 1d.2a.3c.4e.5d.6b, 1d.2a.3c.4e.5d.6c, 1d.2a.3c.4e.5d.6d,
1d.2a.3c.4e.5d.6e, 1d.2a.3c.4e.5e.6a, 1d.2a.3c.4e.5e.6b, 1d.2a.3c.4e.5e.6c,
1d.2a.3c.4e.5e.6d, 1d.2a.3c.4e.5e.6e, 1d.2a.3d.4a.5a.6a, 1d.2a.3d.4a.5a.6b,
1d.2a.3d.4a.5a.6c, 1d.2a.3d.4a.5a.6d, 1d.2a.3d.4a.5a.6e, 1d.2a.3d.4a.5b.6a,
1d.2a.3d.4a.5b.6b, 1d.2a.3d.4a.5b.6c, 1d.2a.3d.4a.5b.6d, 1d.2a.3d.4a.5b.6e,
1d.2a.3d.4a.5c.6a, 1d.2a.3d.4a.5c.6b, 1d.2a.3d.4a.5c.6c, 1d.2a.3d.4a.5c.6d,
1d.2a.3d.4a.5c.6e, 1d.2a.3d.4a.5d.6a, 1d.2a.3d.4a.5d.6b, 1d.2a.3d.4a.5d.6c,
1d.2a.3d.4a.5d.6d, 1d.2a.3d.4a.5d.6e, 1d.2a.3d.4a.5e.6a, 1d.2a.3d.4a.5e.6b,
1d.2a.3d.4a.5e.6c, 1d.2a.3d.4a.5e.6d, 1d.2a.3d.4a.5e.6e, 1d.2a.3d.4b.5a.6a,
1d.2a.3d.4b.5a.6b, 1d.2a.3d.4b.5a.6c, 1d.2a.3d.4b.5a.6d, 1d.2a.3d.4b.5a.6e,
1d.2a.3d.4b.5b.6a, 1d.2a.3d.4b.5b.6b, 1d.2a.3d.4b.5b.6c, 1d.2a.3d.4b.5b.6d,
1d.2a.3d.4b.5b.6e, 1d.2a.3d.4b.5c.6a, 1d.2a.3d.4b.5c.6b, 1d.2a.3d.4b.5c.6c,
1d.2a.3d.4b.5c.6d, 1d.2a.3d.4b.5c.6e, 1d.2a.3d.4b.5d.6a, 1d.2a.3d.4b.5d.6b,
1d.2a.3d.4b.5d.6c, 1d.2a.3d.4b.5d.6d, 1d.2a.3d.4b.5d.6e, 1d.2a.3d.4b.5e.6a,
1d.2a.3d.4b.5e.6b, 1d.2a.3d.4b.5e.6c, 1d.2a.3d.4b.5e.6d, 1d.2a.3d.4b.5e.6e,
1d.2a.3d.4c.5a.6a, 1d.2a.3d.4c.5a.6b, 1d.2a.3d.4c.5a.6c, 1d.2a.3d.4c.5a.6d,
1d.2a.3d.4c.5a.6e, 1d.2a.3d.4c.5b.6a, 1d.2a.3d.4c.5b.6b, 1d.2a.3d.4c.5b.6c,
1d.2a.3d.4c.5b.6d, 1d.2a.3d.4c.5b.6e, 1d.2a.3d.4c.5c.6a, 1d.2a.3d.4c.5c.6b,
1d.2a.3d.4c.5c.6c, 1d.2a.3d.4c.5c.6d, 1d.2a.3d.4c.5c.6e, 1d.2a.3d.4c.5d.6a,
1d.2a.3d.4c.5d.6b, 1d.2a.3d.4c.5d.6c, 1d.2a.3d.4c.5d.6d, 1d.2a.3d.4c.5d.6e,
1d.2a.3d.4c.5e.6a, 1d.2a.3d.4c.5e.6b, 1d.2a.3d.4c.5e.6c, 1d.2a.3d.4c.5e.6d,
1d.2a.3d.4c.5e.6e, 1d.2a.3d.4d.5a.6a, 1d.2a.3d.4d.5a.6b, 1d.2a.3d.4d.5a.6c,
1d.2a.3d.4d.5a.6d, 1d.2a.3d.4d.5a.6e, 1d.2a.3d.4d.5b.6a, 1d.2a.3d.4d.5b.6b,
1d.2a.3d.4d.5b.6c, 1d.2a.3d.4d.5b.6d, 1d.2a.3d.4d.5b.6e, 1d.2a.3d.4d.5c.6a,
1d.2a.3d.4d.5c.6b, 1d.2a.3d.4d.5c.6c, 1d.2a.3d.4d.5c.6d, 1d.2a.3d.4d.5c.6e,

TABLE 8-continued

List of Compounds of Formula (II)

1d.2a.3d.4d.5d.6a, 1d.2a.3d.4d.5d.6b, 1d.2a.3d.4d.5d.6c, 1d.2a.3d.4d.5d.6d,
1d.2a.3d.4d.5d.6e, 1d.2a.3d.4d.5e.6a, 1d.2a.3d.4d.5e.6b, 1d.2a.3d.4d.5e.6c,
1d.2a.3d.4d.5e.6d, 1d.2a.3d.4d.5e.6e, 1d.2a.3d.4e.5a.6a, 1d.2a.3d.4e.5a.6b,
1d.2a.3d.4e.5a.6c, 1d.2a.3d.4e.5a.6d, 1d.2a.3d.4e.5a.6e, 1d.2a.3d.4e.5b.6a,
1d.2a.3d.4e.5b.6b, 1d.2a.3d.4e.5b.6c, 1d.2a.3d.4e.5b.6d, 1d.2a.3d.4e.5b.6e,
1d.2a.3d.4e.5c.6a, 1d.2a.3d.4e.5c.6b, 1d.2a.3d.4e.5c.6c, 1d.2a.3d.4e.5c.6d,
1d.2a.3d.4e.5c.6e, 1d.2a.3d.4e.5d.6a, 1d.2a.3d.4e.5d.6b, 1d.2a.3d.4e.5d.6c,
1d.2a.3d.4e.5d.6d, 1d.2a.3d.4e.5d.6e, 1d.2a.3d.4e.5e.6a, 1d.2a.3d.4e.5e.6b,
1d.2a.3d.4e.5e.6c, 1d.2a.3d.4e.5e.6d, 1d.2a.3d.4e.5e.6e, 1d.2a.3e.4a.5a.6a,
1d.2a.3e.4a.5a.6b, 1d.2a.3e.4a.5a.6c, 1d.2a.3e.4a.5a.6d, 1d.2a.3e.4a.5a.6e,
1d.2a.3e.4a.5b.6a, 1d.2a.3e.4a.5b.6b, 1d.2a.3e.4a.5b.6c, 1d.2a.3e.4a.5b.6d,
1d.2a.3e.4a.5b.6e, 1d.2a.3e.4a.5c.6a, 1d.2a.3e.4a.5c.6b, 1d.2a.3e.4a.5c.6c,
1d.2a.3e.4a.5c.6d, 1d.2a.3e.4a.5c.6e, 1d.2a.3e.4a.5d.6a, 1d.2a.3e.4a.5d.6b,
1d.2a.3e.4a.5d.6c, 1d.2a.3e.4a.5d.6d, 1d.2a.3e.4a.5d.6e, 1d.2a.3e.4a.5e.6a,
1d.2a.3e.4a.5e.6b, 1d.2a.3e.4a.5e.6c, 1d.2a.3e.4a.5e.6d, 1d.2a.3e.4a.5e.6e,
1d.2a.3e.4b.5a.6a, 1d.2a.3e.4b.5a.6b, 1d.2a.3e.4b.5a.6c, 1d.2a.3e.4b.5a.6d,
1d.2a.3e.4b.5a.6e, 1d.2a.3e.4b.5b.6a, 1d.2a.3e.4b.5b.6b, 1d.2a.3e.4b.5b.6c,
1d.2a.3e.4b.5b.6d, 1d.2a.3e.4b.5b.6e, 1d.2a.3e.4b.5c.6a, 1d.2a.3e.4b.5c.6b,
1d.2a.3e.4b.5c.6c, 1d.2a.3e.4b.5c.6d, 1d.2a.3e.4b.5c.6e, 1d.2a.3e.4b.5d.6a,
1d.2a.3e.4b.5d.6b, 1d.2a.3e.4b.5d.6c, 1d.2a.3e.4b.5d.6d, 1d.2a.3e.4b.5d.6e,
1d.2a.3e.4b.5e.6a, 1d.2a.3e.4b.5e.6b, 1d.2a.3e.4b.5e.6c, 1d.2a.3e.4b.5e.6d,
1d.2a.3e.4b.5e.6e, 1d.2a.3e.4c.5a.6a, 1d.2a.3e.4c.5a.6b, 1d.2a.3e.4c.5a.6c,
1d.2a.3e.4c.5a.6d, 1d.2a.3e.4c.5a.6e, 1d.2a.3e.4c.5b.6a, 1d.2a.3e.4c.5b.6b,
1d.2a.3e.4c.5b.6c, 1d.2a.3e.4c.5b.6d, 1d.2a.3e.4c.5b.6e, 1d.2a.3e.4c.5c.6a,
1d.2a.3e.4c.5c.6b, 1d.2a.3e.4c.5c.6c, 1d.2a.3e.4c.5c.6d, 1d.2a.3e.4c.5c.6e,
1d.2a.3e.4c.5d.6a, 1d.2a.3e.4c.5d.6b, 1d.2a.3e.4c.5d.6c, 1d.2a.3e.4c.5d.6d,
1d.2a.3e.4c.5d.6e, 1d.2a.3e.4c.5e.6a, 1d.2a.3e.4c.5e.6b, 1d.2a.3e.4c.5e.6c,
1d.2a.3e.4c.5e.6d, 1d.2a.3e.4c.5e.6e, 1d.2a.3e.4d.5a.6a, 1d.2a.3e.4d.5a.6b,
1d.2a.3e.4d.5a.6c, 1d.2a.3e.4d.5a.6d, 1d.2a.3e.4d.5a.6e, 1d.2a.3e.4d.5b.6a,
1d.2a.3e.4d.5b.6b, 1d.2a.3e.4d.5b.6c, 1d.2a.3e.4d.5b.6d, 1d.2a.3e.4d.5b.6e,
1d.2a.3e.4d.5c.6a, 1d.2a.3e.4d.5c.6b, 1d.2a.3e.4d.5c.6c, 1d.2a.3e.4d.5c.6d,
1d.2a.3e.4d.5c.6e, 1d.2a.3e.4d.5d.6a, 1d.2a.3e.4d.5d.6b, 1d.2a.3e.4d.5d.6c,
1d.2a.3e.4d.5d.6d, 1d.2a.3e.4d.5d.6e, 1d.2a.3e.4d.5e.6a, 1d.2a.3e.4d.5e.6b,
1d.2a.3e.4d.5e.6c, 1d.2a.3e.4d.5e.6d, 1d.2a.3e.4d.5e.6e, 1d.2a.3e.4e.5a.6a,
1d.2a.3e.4e.5a.6b, 1d.2a.3e.4e.5a.6c, 1d.2a.3e.4e.5a.6d, 1d.2a.3e.4e.5a.6e,
1d.2a.3e.4e.5b.6a, 1d.2a.3e.4e.5b.6b, 1d.2a.3e.4e.5b.6c, 1d.2a.3e.4e.5b.6d,
1d.2a.3e.4e.5b.6e, 1d.2a.3e.4e.5c.6a, 1d.2a.3e.4e.5c.6b, 1d.2a.3e.4e.5c.6c,
1d.2a.3e.4e.5c.6d, 1d.2a.3e.4e.5c.6e, 1d.2a.3e.4e.5d.6a, 1d.2a.3e.4e.5d.6b,
1d.2a.3e.4e.5d.6c, 1d.2a.3e.4e.5d.6d, 1d.2a.3e.4e.5d.6e, 1d.2a.3e.4e.5e.6a,
1d.2a.3e.4e.5e.6b, 1d.2a.3e.4e.5e.6c, 1d.2a.3e.4e.5e.6d, 1d.2a.3e.4e.5e.6e,
1d.2b.3a.4a.5a.6a, 1d.2b.3a.4a.5a.6b, 1d.2b.3a.4a.5a.6c, 1d.2b.3a.4a.5a.6d,
1d.2b.3a.4a.5a.6e, 1d.2b.3a.4a.5b.6a, 1d.2b.3a.4a.5b.6b, 1d.2b.3a.4a.5b.6c,
1d.2b.3a.4a.5b.6d, 1d.2b.3a.4a.5b.6e, 1d.2b.3a.4a.5c.6a, 1d.2b.3a.4a.5c.6b,
1d.2b.3a.4a.5c.6c, 1d.2b.3a.4a.5c.6d, 1d.2b.3a.4a.5c.6e, 1d.2b.3a.4a.5d.6a,
1d.2b.3a.4a.5d.6b, 1d.2b.3a.4a.5d.6c, 1d.2b.3a.4a.5d.6d, 1d.2b.3a.4a.5d.6e,
1d.2b.3a.4a.5e.6a, 1d.2b.3a.4a.5e.6b, 1d.2b.3a.4a.5e.6c, 1d.2b.3a.4a.5e.6d,
1d.2b.3a.4a.5e.6e, 1d.2b.3a.4b.5a.6a, 1d.2b.3a.4b.5a.6b, 1d.2b.3a.4b.5a.6c,
1d.2b.3a.4b.5a.6d, 1d.2b.3a.4b.5a.6e, 1d.2b.3a.4b.5b.6a, 1d.2b.3a.4b.5b.6b,
1d.2b.3a.4b.5b.6c, 1d.2b.3a.4b.5b.6d, 1d.2b.3a.4b.5b.6e, 1d.2b.3a.4b.5c.6a,
1d.2b.3a.4b.5c.6b, 1d.2b.3a.4b.5c.6c, 1d.2b.3a.4b.5c.6d, 1d.2b.3a.4b.5c.6e,
1d.2b.3a.4b.5d.6a, 1d.2b.3a.4b.5d.6b, 1d.2b.3a.4b.5d.6c, 1d.2b.3a.4b.5d.6d,
1d.2b.3a.4b.5d.6e, 1d.2b.3a.4b.5e.6a, 1d.2b.3a.4b.5e.6b, 1d.2b.3a.4b.5e.6c,
1d.2b.3a.4b.5e.6d, 1d.2b.3a.4b.5e.6e, 1d.2b.3a.4c.5a.6a, 1d.2b.3a.4c.5a.6b,
1d.2b.3a.4c.5a.6c, 1d.2b.3a.4c.5a.6d, 1d.2b.3a.4c.5a.6e, 1d.2b.3a.4c.5b.6a,
1d.2b.3a.4c.5b.6b, 1d.2b.3a.4c.5b.6c, 1d.2b.3a.4c.5b.6d, 1d.2b.3a.4c.5b.6e,
1d.2b.3a.4c.5c.6a, 1d.2b.3a.4c.5c.6b, 1d.2b.3a.4c.5c.6c, 1d.2b.3a.4c.5c.6d,
1d.2b.3a.4c.5c.6e, 1d.2b.3a.4c.5d.6a, 1d.2b.3a.4c.5d.6b, 1d.2b.3a.4c.5d.6c,
1d.2b.3a.4c.5d.6d, 1d.2b.3a.4c.5d.6e, 1d.2b.3a.4c.5e.6a, 1d.2b.3a.4c.5e.6b,
1d.2b.3a.4c.5e.6c, 1d.2b.3a.4c.5e.6d, 1d.2b.3a.4c.5e.6e, 1d.2b.3a.4d.5a.6a,
1d.2b.3a.4d.5a.6b, 1d.2b.3a.4d.5a.6c, 1d.2b.3a.4d.5a.6d, 1d.2b.3a.4d.5a.6e,
1d.2b.3a.4d.5b.6a, 1d.2b.3a.4d.5b.6b, 1d.2b.3a.4d.5b.6c, 1d.2b.3a.4d.5b.6d,
1d.2b.3a.4d.5b.6e, 1d.2b.3a.4d.5c.6a, 1d.2b.3a.4d.5c.6b, 1d.2b.3a.4d.5c.6c,
1d.2b.3a.4d.5c.6d, 1d.2b.3a.4d.5c.6e, 1d.2b.3a.4d.5d.6a, 1d.2b.3a.4d.5d.6b,
1d.2b.3a.4d.5d.6c, 1d.2b.3a.4d.5d.6d, 1d.2b.3a.4d.5d.6e, 1d.2b.3a.4d.5e.6a,
1d.2b.3a.4d.5e.6b, 1d.2b.3a.4d.5e.6c, 1d.2b.3a.4d.5e.6d, 1d.2b.3a.4d.5e.6e,
1d.2b.3a.4e.5a.6a, 1d.2b.3a.4e.5a.6b, 1d.2b.3a.4e.5a.6c, 1d.2b.3a.4e.5a.6d,
1d.2b.3a.4e.5a.6e, 1d.2b.3a.4e.5b.6a, 1d.2b.3a.4e.5b.6b, 1d.2b.3a.4e.5b.6c,
1d.2b.3a.4e.5b.6d, 1d.2b.3a.4e.5b.6e, 1d.2b.3a.4e.5c.6a, 1d.2b.3a.4e.5c.6b,
1d.2b.3a.4e.5c.6c, 1d.2b.3a.4e.5c.6d, 1d.2b.3a.4e.5c.6e, 1d.2b.3a.4e.5d.6a,
1d.2b.3a.4e.5d.6b, 1d.2b.3a.4e.5d.6c, 1d.2b.3a.4e.5d.6d, 1d.2b.3a.4e.5d.6e,
1d.2b.3a.4e.5e.6a, 1d.2b.3a.4e.5e.6b, 1d.2b.3a.4e.5e.6c, 1d.2b.3a.4e.5e.6d,
1d.2b.3a.4e.5e.6e, 1d.2b.3b.4a.5a.6a, 1d.2b.3b.4a.5a.6b, 1d.2b.3b.4a.5a.6c,
1d.2b.3b.4a.5a.6d, 1d.2b.3b.4a.5a.6e, 1d.2b.3b.4a.5b.6a, 1d.2b.3b.4a.5b.6b,
1d.2b.3b.4a.5b.6c, 1d.2b.3b.4a.5b.6d, 1d.2b.3b.4a.5b.6e, 1d.2b.3b.4a.5c.6a,
1d.2b.3b.4a.5c.6b, 1d.2b.3b.4a.5c.6c, 1d.2b.3b.4a.5c.6d, 1d.2b.3b.4a.5c.6e,
1d.2b.3b.4a.5d.6a, 1d.2b.3b.4a.5d.6b, 1d.2b.3b.4a.5d.6c, 1d.2b.3b.4a.5d.6d,
1d.2b.3b.4a.5d.6e, 1d.2b.3b.4a.5e.6a, 1d.2b.3b.4a.5e.6b, 1d.2b.3b.4a.5e.6c,
1d.2b.3b.4a.5e.6d, 1d.2b.3b.4a.5e.6e, 1d.2b.3b.4b.5a.6a, 1d.2b.3b.4b.5a.6b,

TABLE 8-continued

List of Compounds of Formula (II)

1d.2b.3b.4b.5a.6c, 1d.2b.3b.4b.5a.6d, 1d.2b.3b.4b.5a.6e, 1d.2b.3b.4b.5b.6a,
1d.2b.3b.4b.5b.6b, 1d.2b.3b.4b.5b.6c, 1d.2b.3b.4b.5b.6d, 1d.2b.3b.4b.5b.6e,
1d.2b.3b.4b.5c.6a, 1d.2b.3b.4b.5c.6b, 1d.2b.3b.4b.5c.6c, 1d.2b.3b.4b.5c.6d,
1d.2b.3b.4b.5c.6e, 1d.2b.3b.4b.5d.6a, 1d.2b.3b.4b.5d.6b, 1d.2b.3b.4b.5d.6c,
1d.2b.3b.4b.5d.6d, 1d.2b.3b.4b.5d.6e, 1d.2b.3b.4b.5e.6a, 1d.2b.3b.4b.5e.6b,
1d.2b.3b.4b.5e.6c, 1d.2b.3b.4b.5e.6d, 1d.2b.3b.4b.5e.6e, 1d.2b.3b.4c.5a.6a,
1d.2b.3b.4c.5a.6b, 1d.2b.3b.4c.5a.6c, 1d.2b.3b.4c.5a.6d, 1d.2b.3b.4c.5a.6e,
1d.2b.3b.4c.5b.6a, 1d.2b.3b.4c.5b.6b, 1d.2b.3b.4c.5b.6c, 1d.2b.3b.4c.5b.6d,
1d.2b.3b.4c.5b.6e, 1d.2b.3b.4c.5c.6a, 1d.2b.3b.4c.5c.6b, 1d.2b.3b.4c.5c.6c,
1d.2b.3b.4c.5c.6d, 1d.2b.3b.4c.5c.6e, 1d.2b.3b.4c.5d.6a, 1d.2b.3b.4c.5d.6b,
1d.2b.3b.4c.5d.6c, 1d.2b.3b.4c.5d.6d, 1d.2b.3b.4c.5d.6e, 1d.2b.3b.4c.5e.6a,
1d.2b.3b.4c.5e.6b, 1d.2b.3b.4c.5e.6c, 1d.2b.3b.4c.5e.6d, 1d.2b.3b.4c.5e.6e,
1d.2b.3b.4d.5a.6a, 1d.2b.3b.4d.5a.6b, 1d.2b.3b.4d.5a.6c, 1d.2b.3b.4d.5a.6d,
1d.2b.3b.4d.5a.6e, 1d.2b.3b.4d.5b.6a, 1d.2b.3b.4d.5b.6b, 1d.2b.3b.4d.5b.6c,
1d.2b.3b.4d.5b.6d, 1d.2b.3b.4d.5b.6e, 1d.2b.3b.4d.5c.6a, 1d.2b.3b.4d.5c.6b,
1d.2b.3b.4d.5c.6c, 1d.2b.3b.4d.5c.6d, 1d.2b.3b.4d.5c.6e, 1d.2b.3b.4d.5d.6a,
1d.2b.3b.4d.5d.6b, 1d.2b.3b.4d.5d.6c, 1d.2b.3b.4d.5d.6d, 1d.2b.3b.4d.5d.6e,
1d.2b.3b.4d.5e.6a, 1d.2b.3b.4d.5e.6b, 1d.2b.3b.4d.5e.6c, 1d.2b.3b.4d.5e.6d,
1d.2b.3b.4d.5e.6e, 1d.2b.3b.4e.5a.6a, 1d.2b.3b.4e.5a.6b, 1d.2b.3b.4e.5a.6c,
1d.2b.3b.4e.5a.6d, 1d.2b.3b.4e.5a.6e, 1d.2b.3b.4e.5b.6a, 1d.2b.3b.4e.5b.6b,
1d.2b.3b.4e.5b.6c, 1d.2b.3b.4e.5b.6d, 1d.2b.3b.4e.5b.6e, 1d.2b.3b.4e.5c.6a,
1d.2b.3b.4e.5c.6b, 1d.2b.3b.4e.5c.6c, 1d.2b.3b.4e.5c.6d, 1d.2b.3b.4e.5c.6e,
1d.2b.3b.4e.5d.6a, 1d.2b.3b.4e.5d.6b, 1d.2b.3b.4e.5d.6c, 1d.2b.3b.4e.5d.6d,
1d.2b.3b.4e.5d.6e, 1d.2b.3b.4e.5e.6a, 1d.2b.3b.4e.5e.6b, 1d.2b.3b.4e.5e.6c,
1d.2b.3b.4e.5e.6d, 1d.2b.3b.4e.5e.6e, 1d.2b.3c.4a.5a.6a, 1d.2b.3c.4a.5a.6b,
1d.2b.3c.4a.5a.6c, 1d.2b.3c.4a.5a.6d, 1d.2b.3c.4a.5a.6e, 1d.2b.3c.4a.5b.6a,
1d.2b.3c.4a.5b.6b, 1d.2b.3c.4a.5b.6c, 1d.2b.3c.4a.5b.6d, 1d.2b.3c.4a.5b.6e,
1d.2b.3c.4a.5c.6a, 1d.2b.3c.4a.5c.6b, 1d.2b.3c.4a.5c.6c, 1d.2b.3c.4a.5c.6d,
1d.2b.3c.4a.5c.6e, 1d.2b.3c.4a.5d.6a, 1d.2b.3c.4a.5d.6b, 1d.2b.3c.4a.5d.6c,
1d.2b.3c.4a.5d.6d, 1d.2b.3c.4a.5d.6e, 1d.2b.3c.4a.5e.6a, 1d.2b.3c.4a.5e.6b,
1d.2b.3c.4a.5e.6c, 1d.2b.3c.4a.5e.6d, 1d.2b.3c.4a.5e.6e, 1d.2b.3c.4b.5a.6a,
1d.2b.3c.4b.5a.6b, 1d.2b.3c.4b.5a.6c, 1d.2b.3c.4b.5a.6d, 1d.2b.3c.4b.5a.6e,
1d.2b.3c.4b.5b.6a, 1d.2b.3c.4b.5b.6b, 1d.2b.3c.4b.5b.6c, 1d.2b.3c.4b.5b.6d,
1d.2b.3c.4b.5b.6e, 1d.2b.3c.4b.5c.6a, 1d.2b.3c.4b.5c.6b, 1d.2b.3c.4b.5c.6c,
1d.2b.3c.4b.5c.6d, 1d.2b.3c.4b.5c.6e, 1d.2b.3c.4b.5d.6a, 1d.2b.3c.4b.5d.6b,
1d.2b.3c.4b.5d.6c, 1d.2b.3c.4b.5d.6d, 1d.2b.3c.4b.5d.6e, 1d.2b.3c.4b.5e.6a,
1d.2b.3c.4b.5e.6b, 1d.2b.3c.4b.5e.6c, 1d.2b.3c.4b.5e.6d, 1d.2b.3c.4b.5e.6e,
1d.2b.3c.4c.5a.6a, 1d.2b.3c.4c.5a.6b, 1d.2b.3c.4c.5a.6c, 1d.2b.3c.4c.5a.6d,
1d.2b.3c.4c.5a.6e, 1d.2b.3c.4c.5b.6a, 1d.2b.3c.4c.5b.6b, 1d.2b.3c.4c.5b.6c,
1d.2b.3c.4c.5b.6d, 1d.2b.3c.4c.5b.6e, 1d.2b.3c.4c.5c.6a, 1d.2b.3c.4c.5c.6b,
1d.2b.3c.4c.5c.6c, 1d.2b.3c.4c.5c.6d, 1d.2b.3c.4c.5c.6e, 1d.2b.3c.4c.5d.6a,
1d.2b.3c.4c.5d.6b, 1d.2b.3c.4c.5d.6c, 1d.2b.3c.4c.5d.6d, 1d.2b.3c.4c.5d.6e,
1d.2b.3c.4c.5e.6a, 1d.2b.3c.4c.5e.6b, 1d.2b.3c.4c.5e.6c, 1d.2b.3c.4c.5e.6d,
1d.2b.3c.4c.5e.6e, 1d.2b.3c.4d.5a.6a, 1d.2b.3c.4d.5a.6b, 1d.2b.3c.4d.5a.6c,
1d.2b.3c.4d.5a.6d, 1d.2b.3c.4d.5a.6e, 1d.2b.3c.4d.5b.6a, 1d.2b.3c.4d.5b.6b,
1d.2b.3c.4d.5b.6c, 1d.2b.3c.4d.5b.6d, 1d.2b.3c.4d.5b.6e, 1d.2b.3c.4d.5c.6a,
1d.2b.3c.4d.5c.6b, 1d.2b.3c.4d.5c.6c, 1d.2b.3c.4d.5c.6d, 1d.2b.3c.4d.5c.6e,
1d.2b.3c.4d.5d.6a, 1d.2b.3c.4d.5d.6b, 1d.2b.3c.4d.5d.6c, 1d.2b.3c.4d.5d.6d,
1d.2b.3c.4d.5d.6e, 1d.2b.3c.4d.5e.6a, 1d.2b.3c.4d.5e.6b, 1d.2b.3c.4d.5e.6c,
1d.2b.3c.4d.5e.6d, 1d.2b.3c.4d.5e.6e, 1d.2b.3c.4e.5a.6a, 1d.2b.3c.4e.5a.6b,
1d.2b.3c.4e.5a.6c, 1d.2b.3c.4e.5a.6d, 1d.2b.3c.4e.5a.6e, 1d.2b.3c.4e.5b.6a,
1d.2b.3c.4e.5b.6b, 1d.2b.3c.4e.5b.6c, 1d.2b.3c.4e.5b.6d, 1d.2b.3c.4e.5b.6e,
1d.2b.3c.4e.5c.6a, 1d.2b.3c.4e.5c.6b, 1d.2b.3c.4e.5c.6c, 1d.2b.3c.4e.5c.6d,
1d.2b.3c.4e.5c.6e, 1d.2b.3c.4e.5d.6a, 1d.2b.3c.4e.5d.6b, 1d.2b.3c.4e.5d.6c,
1d.2b.3c.4e.5d.6d, 1d.2b.3c.4e.5d.6e, 1d.2b.3c.4e.5e.6a, 1d.2b.3c.4e.5e.6b,
1d.2b.3c.4e.5e.6c, 1d.2b.3c.4e.5e.6d, 1d.2b.3c.4e.5e.6e, 1d.2b.3d.4a.5a.6a,
1d.2b.3d.4a.5a.6b, 1d.2b.3d.4a.5a.6c, 1d.2b.3d.4a.5a.6d, 1d.2b.3d.4a.5a.6e,
1d.2b.3d.4a.5b.6a, 1d.2b.3d.4a.5b.6b, 1d.2b.3d.4a.5b.6c, 1d.2b.3d.4a.5b.6d,
1d.2b.3d.4a.5b.6e, 1d.2b.3d.4a.5c.6a, 1d.2b.3d.4a.5c.6b, 1d.2b.3d.4a.5c.6c,
1d.2b.3d.4a.5c.6d, 1d.2b.3d.4a.5c.6e, 1d.2b.3d.4a.5d.6a, 1d.2b.3d.4a.5d.6b,
1d.2b.3d.4a.5d.6c, 1d.2b.3d.4a.5d.6d, 1d.2b.3d.4a.5d.6e, 1d.2b.3d.4a.5e.6a,
1d.2b.3d.4a.5e.6b, 1d.2b.3d.4a.5e.6c, 1d.2b.3d.4a.5e.6d, 1d.2b.3d.4a.5e.6e,
1d.2b.3d.4b.5a.6a, 1d.2b.3d.4b.5a.6b, 1d.2b.3d.4b.5a.6c, 1d.2b.3d.4b.5a.6d,
1d.2b.3d.4b.5a.6e, 1d.2b.3d.4b.5b.6a, 1d.2b.3d.4b.5b.6b, 1d.2b.3d.4b.5b.6c,
1d.2b.3d.4b.5b.6d, 1d.2b.3d.4b.5b.6e, 1d.2b.3d.4b.5c.6a, 1d.2b.3d.4b.5c.6b,
1d.2b.3d.4b.5c.6c, 1d.2b.3d.4b.5c.6d, 1d.2b.3d.4b.5c.6e, 1d.2b.3d.4b.5d.6a,
1d.2b.3d.4b.5d.6b, 1d.2b.3d.4b.5d.6c, 1d.2b.3d.4b.5d.6d, 1d.2b.3d.4b.5d.6e,
1d.2b.3d.4b.5e.6a, 1d.2b.3d.4b.5e.6b, 1d.2b.3d.4b.5e.6c, 1d.2b.3d.4b.5e.6d,
1d.2b.3d.4b.5e.6e, 1d.2b.3d.4c.5a.6a, 1d.2b.3d.4c.5a.6b, 1d.2b.3d.4c.5a.6c,
1d.2b.3d.4c.5a.6d, 1d.2b.3d.4c.5a.6e, 1d.2b.3d.4c.5b.6a, 1d.2b.3d.4c.5b.6b,
1d.2b.3d.4c.5b.6c, 1d.2b.3d.4c.5b.6d, 1d.2b.3d.4c.5b.6e, 1d.2b.3d.4c.5c.6a,
1d.2b.3d.4c.5c.6b, 1d.2b.3d.4c.5c.6c, 1d.2b.3d.4c.5c.6d, 1d.2b.3d.4c.5c.6e,
1d.2b.3d.4c.5d.6a, 1d.2b.3d.4c.5d.6b, 1d.2b.3d.4c.5d.6c, 1d.2b.3d.4c.5d.6d,
1d.2b.3d.4c.5d.6e, 1d.2b.3d.4c.5e.6a, 1d.2b.3d.4c.5e.6b, 1d.2b.3d.4c.5e.6c,
1d.2b.3d.4c.5e.6d, 1d.2b.3d.4c.5e.6e, 1d.2b.3d.4d.5a.6a, 1d.2b.3d.4d.5a.6b,
1d.2b.3d.4d.5a.6c, 1d.2b.3d.4d.5a.6d, 1d.2b.3d.4d.5a.6e, 1d.2b.3d.4d.5b.6a,
1d.2b.3d.4d.5b.6b, 1d.2b.3d.4d.5b.6c, 1d.2b.3d.4d.5b.6d, 1d.2b.3d.4d.5b.6e,
1d.2b.3d.4d.5c.6a, 1d.2b.3d.4d.5c.6b, 1d.2b.3d.4d.5c.6c, 1d.2b.3d.4d.5c.6d,

TABLE 8-continued

List of Compounds of Formula (II)

1d.2b.3d.4d.5c.6e, 1d.2b.3d.4d.5d.6a, 1d.2b.3d.4d.5d.6b, 1d.2b.3d.4d.5d.6c,
1d.2b.3d.4d.5d.6d, 1d.2b.3d.4d.5d.6e, 1d.2b.3d.4d.5e.6a, 1d.2b.3d.4d.5e.6b,
1d.2b.3d.4d.5e.6c, 1d.2b.3d.4d.5e.6d, 1d.2b.3d.4d.5e.6e, 1d.2b.3d.4e.5a.6a,
1d.2b.3d.4e.5a.6b, 1d.2b.3d.4e.5a.6c, 1d.2b.3d.4e.5a.6d, 1d.2b.3d.4e.5a.6e,
1d.2b.3d.4e.5b.6a, 1d.2b.3d.4e.5b.6b, 1d.2b.3d.4e.5b.6c, 1d.2b.3d.4e.5b.6d,
1d.2b.3d.4e.5b.6e, 1d.2b.3d.4e.5c.6a, 1d.2b.3d.4e.5c.6b, 1d.2b.3d.4e.5c.6c,
1d.2b.3d.4e.5c.6d, 1d.2b.3d.4e.5c.6e, 1d.2b.3d.4e.5d.6a, 1d.2b.3d.4e.5d.6b,
1d.2b.3d.4e.5d.6c, 1d.2b.3d.4e.5d.6d, 1d.2b.3d.4e.5d.6e, 1d.2b.3d.4e.5e.6a,
1d.2b.3d.4e.5e.6b, 1d.2b.3d.4e.5e.6c, 1d.2b.3d.4e.5e.6d, 1d.2b.3d.4e.5e.6e,
1d.2b.3e.4a.5a.6a, 1d.2b.3e.4a.5a.6b, 1d.2b.3e.4a.5a.6c, 1d.2b.3e.4a.5a.6d,
1d.2b.3e.4a.5a.6e, 1d.2b.3e.4a.5b.6a, 1d.2b.3e.4a.5b.6b, 1d.2b.3e.4a.5b.6c,
1d.2b.3e.4a.5b.6d, 1d.2b.3e.4a.5b.6e, 1d.2b.3e.4a.5c.6a, 1d.2b.3e.4a.5c.6b,
1d.2b.3e.4a.5c.6c, 1d.2b.3e.4a.5c.6d, 1d.2b.3e.4a.5c.6e, 1d.2b.3e.4a.5d.6a,
1d.2b.3e.4a.5d.6b, 1d.2b.3e.4a.5d.6c, 1d.2b.3e.4a.5d.6d, 1d.2b.3e.4a.5d.6e,
1d.2b.3e.4a.5e.6a, 1d.2b.3e.4a.5e.6b, 1d.2b.3e.4a.5e.6c, 1d.2b.3e.4a.5e.6d,
1d.2b.3e.4a.5e.6e, 1d.2b.3e.4b.5a.6a, 1d.2b.3e.4b.5a.6b, 1d.2b.3e.4b.5a.6c,
1d.2b.3e.4b.5a.6d, 1d.2b.3e.4b.5a.6e, 1d.2b.3e.4b.5b.6a, 1d.2b.3e.4b.5b.6b,
1d.2b.3e.4b.5b.6c, 1d.2b.3e.4b.5b.6d, 1d.2b.3e.4b.5b.6e, 1d.2b.3e.4b.5c.6a,
1d.2b.3e.4b.5c.6b, 1d.2b.3e.4b.5c.6c, 1d.2b.3e.4b.5c.6d, 1d.2b.3e.4b.5c.6e,
1d.2b.3e.4b.5d.6a, 1d.2b.3e.4b.5d.6b, 1d.2b.3e.4b.5d.6c, 1d.2b.3e.4b.5d.6d,
1d.2b.3e.4b.5d.6e, 1d.2b.3e.4b.5e.6a, 1d.2b.3e.4b.5e.6b, 1d.2b.3e.4b.5e.6c,
1d.2b.3e.4b.5e.6d, 1d.2b.3e.4b.5e.6e, 1d.2b.3e.4c.5a.6a, 1d.2b.3e.4c.5a.6b,
1d.2b.3e.4c.5a.6c, 1d.2b.3e.4c.5a.6d, 1d.2b.3e.4c.5a.6e, 1d.2b.3e.4c.5b.6a,
1d.2b.3e.4c.5b.6b, 1d.2b.3e.4c.5b.6c, 1d.2b.3e.4c.5b.6d, 1d.2b.3e.4c.5b.6e,
1d.2b.3e.4c.5c.6a, 1d.2b.3e.4c.5c.6b, 1d.2b.3e.4c.5c.6c, 1d.2b.3e.4c.5c.6d,
1d.2b.3e.4c.5c.6e, 1d.2b.3e.4c.5d.6a, 1d.2b.3e.4c.5d.6b, 1d.2b.3e.4c.5d.6c,
1d.2b.3e.4c.5d.6d, 1d.2b.3e.4c.5d.6e, 1d.2b.3e.4c.5e.6a, 1d.2b.3e.4c.5e.6b,
1d.2b.3e.4c.5e.6c, 1d.2b.3e.4c.5e.6d, 1d.2b.3e.4c.5e.6e, 1d.2b.3e.4d.5a.6a,
1d.2b.3e.4d.5a.6b, 1d.2b.3e.4d.5a.6c, 1d.2b.3e.4d.5a.6d, 1d.2b.3e.4d.5a.6e,
1d.2b.3e.4d.5b.6a, 1d.2b.3e.4d.5b.6b, 1d.2b.3e.4d.5b.6c, 1d.2b.3e.4d.5b.6d,
1d.2b.3e.4d.5b.6e, 1d.2b.3e.4d.5c.6a, 1d.2b.3e.4d.5c.6b, 1d.2b.3e.4d.5c.6c,
1d.2b.3e.4d.5c.6d, 1d.2b.3e.4d.5c.6e, 1d.2b.3e.4d.5d.6a, 1d.2b.3e.4d.5d.6b,
1d.2b.3e.4d.5d.6c, 1d.2b.3e.4d.5d.6d, 1d.2b.3e.4d.5d.6e, 1d.2b.3e.4d.5e.6a,
1d.2b.3e.4d.5e.6b, 1d.2b.3e.4d.5e.6c, 1d.2b.3e.4d.5e.6d, 1d.2b.3e.4d.5e.6e,
1d.2b.3e.4e.5a.6a, 1d.2b.3e.4e.5a.6b, 1d.2b.3e.4e.5a.6c, 1d.2b.3e.4e.5a.6d,
1d.2b.3e.4e.5a.6e, 1d.2b.3e.4e.5b.6a, 1d.2b.3e.4e.5b.6b, 1d.2b.3e.4e.5b.6c,
1d.2b.3e.4e.5b.6d, 1d.2b.3e.4e.5b.6e, 1d.2b.3e.4e.5c.6a, 1d.2b.3e.4e.5c.6b,
1d.2b.3e.4e.5c.6c, 1d.2b.3e.4e.5c.6d, 1d.2b.3e.4e.5c.6e, 1d.2b.3e.4e.5d.6a,
1d.2b.3e.4e.5d.6b, 1d.2b.3e.4e.5d.6c, 1d.2b.3e.4e.5d.6d, 1d.2b.3e.4e.5d.6e,
1d.2b.3e.4e.5e.6a, 1d.2b.3e.4e.5e.6b, 1d.2b.3e.4e.5e.6c, 1d.2b.3e.4e.5e.6d,
1d.2b.3e.4e.5e.6e, 1d.2c.3a.4a.5a.6a, 1d.2c.3a.4a.5a.6b, 1d.2c.3a.4a.5a.6c,
1d.2c.3a.4a.5a.6d, 1d.2c.3a.4a.5a.6e, 1d.2c.3a.4a.5b.6a, 1d.2c.3a.4a.5b.6b,
1d.2c.3a.4a.5b.6c, 1d.2c.3a.4a.5b.6d, 1d.2c.3a.4a.5b.6e, 1d.2c.3a.4a.5c.6a,
1d.2c.3a.4a.5c.6b, 1d.2c.3a.4a.5c.6c, 1d.2c.3a.4a.5c.6d, 1d.2c.3a.4a.5c.6e,
1d.2c.3a.4a.5d.6a, 1d.2c.3a.4a.5d.6b, 1d.2c.3a.4a.5d.6c, 1d.2c.3a.4a.5d.6d,
1d.2c.3a.4a.5d.6e, 1d.2c.3a.4a.5e.6a, 1d.2c.3a.4a.5e.6b, 1d.2c.3a.4a.5e.6c,
1d.2c.3a.4a.5e.6d, 1d.2c.3a.4a.5e.6e, 1d.2c.3a.4b.5a.6a, 1d.2c.3a.4b.5a.6b,
1d.2c.3a.4b.5a.6c, 1d.2c.3a.4b.5a.6d, 1d.2c.3a.4b.5a.6e, 1d.2c.3a.4b.5b.6a,
1d.2c.3a.4b.5b.6b, 1d.2c.3a.4b.5b.6c, 1d.2c.3a.4b.5b.6d, 1d.2c.3a.4b.5b.6e,
1d.2c.3a.4b.5c.6a, 1d.2c.3a.4b.5c.6b, 1d.2c.3a.4b.5c.6c, 1d.2c.3a.4b.5c.6d,
1d.2c.3a.4b.5c.6e, 1d.2c.3a.4b.5d.6a, 1d.2c.3a.4b.5d.6b, 1d.2c.3a.4b.5d.6c,
1d.2c.3a.4b.5d.6d, 1d.2c.3a.4b.5d.6e, 1d.2c.3a.4b.5e.6a, 1d.2c.3a.4b.5e.6b,
1d.2c.3a.4b.5e.6c, 1d.2c.3a.4b.5e.6d, 1d.2c.3a.4b.5e.6e, 1d.2c.3a.4c.5a.6a,
1d.2c.3a.4c.5a.6b, 1d.2c.3a.4c.5a.6c, 1d.2c.3a.4c.5a.6d, 1d.2c.3a.4c.5a.6e,
1d.2c.3a.4c.5b.6a, 1d.2c.3a.4c.5b.6b, 1d.2c.3a.4c.5b.6c, 1d.2c.3a.4c.5b.6d,
1d.2c.3a.4c.5b.6e, 1d.2c.3a.4c.5c.6a, 1d.2c.3a.4c.5c.6b, 1d.2c.3a.4c.5c.6c,
1d.2c.3a.4c.5c.6d, 1d.2c.3a.4c.5c.6e, 1d.2c.3a.4c.5d.6a, 1d.2c.3a.4c.5d.6b,
1d.2c.3a.4c.5d.6c, 1d.2c.3a.4c.5d.6d, 1d.2c.3a.4c.5d.6e, 1d.2c.3a.4c.5e.6a,
1d.2c.3a.4c.5e.6b, 1d.2c.3a.4c.5e.6c, 1d.2c.3a.4c.5e.6d, 1d.2c.3a.4c.5e.6e,
1d.2c.3a.4d.5a.6a, 1d.2c.3a.4d.5a.6b, 1d.2c.3a.4d.5a.6c, 1d.2c.3a.4d.5a.6d,
1d.2c.3a.4d.5a.6e, 1d.2c.3a.4d.5b.6a, 1d.2c.3a.4d.5b.6b, 1d.2c.3a.4d.5b.6c,
1d.2c.3a.4d.5b.6d, 1d.2c.3a.4d.5b.6e, 1d.2c.3a.4d.5c.6a, 1d.2c.3a.4d.5c.6b,
1d.2c.3a.4d.5c.6c, 1d.2c.3a.4d.5c.6d, 1d.2c.3a.4d.5c.6e, 1d.2c.3a.4d.5d.6a,
1d.2c.3a.4d.5d.6b, 1d.2c.3a.4d.5d.6c, 1d.2c.3a.4d.5d.6d, 1d.2c.3a.4d.5d.6e,
1d.2c.3a.4d.5e.6a, 1d.2c.3a.4d.5e.6b, 1d.2c.3a.4d.5e.6c, 1d.2c.3a.4d.5e.6d,
1d.2c.3a.4d.5e.6e, 1d.2c.3a.4e.5a.6a, 1d.2c.3a.4e.5a.6b, 1d.2c.3a.4e.5a.6c,
1d.2c.3a.4e.5a.6d, 1d.2c.3a.4e.5a.6e, 1d.2c.3a.4e.5b.6a, 1d.2c.3a.4e.5b.6b,
1d.2c.3a.4e.5b.6c, 1d.2c.3a.4e.5b.6d, 1d.2c.3a.4e.5b.6e, 1d.2c.3a.4e.5c.6a,
1d.2c.3a.4e.5c.6b, 1d.2c.3a.4e.5c.6c, 1d.2c.3a.4e.5c.6d, 1d.2c.3a.4e.5c.6e,
1d.2c.3a.4e.5d.6a, 1d.2c.3a.4e.5d.6b, 1d.2c.3a.4e.5d.6c, 1d.2c.3a.4e.5d.6d,
1d.2c.3a.4e.5d.6e, 1d.2c.3a.4e.5e.6a, 1d.2c.3a.4e.5e.6b, 1d.2c.3a.4e.5e.6c,
1d.2c.3a.4e.5e.6d, 1d.2c.3a.4e.5e.6e, 1d.2c.3b.4a.5a.6a, 1d.2c.3b.4a.5a.6b,
1d.2c.3b.4a.5a.6c, 1d.2c.3b.4a.5a.6d, 1d.2c.3b.4a.5a.6e, 1d.2c.3b.4a.5b.6a,
1d.2c.3b.4a.5b.6b, 1d.2c.3b.4a.5b.6c, 1d.2c.3b.4a.5b.6d, 1d.2c.3b.4a.5b.6e,
1d.2c.3b.4a.5c.6a, 1d.2c.3b.4a.5c.6b, 1d.2c.3b.4a.5c.6c, 1d.2c.3b.4a.5c.6d,
1d.2c.3b.4a.5c.6e, 1d.2c.3b.4a.5d.6a, 1d.2c.3b.4a.5d.6b, 1d.2c.3b.4a.5d.6c,
1d.2c.3b.4a.5d.6d, 1d.2c.3b.4a.5d.6e, 1d.2c.3b.4a.5e.6a, 1d.2c.3b.4a.5e.6b,
1d.2c.3b.4a.5e.6c, 1d.2c.3b.4a.5e.6d, 1d.2c.3b.4a.5e.6e, 1d.2c.3b.4b.5a.6a,

TABLE 8-continued

List of Compounds of Formula (II)

1d.2c.3b.4b.5a.6b, 1d.2c.3b.4b.5a.6c, 1d.2c.3b.4b.5a.6d, 1d.2c.3b.4b.5a.6e,
1d.2c.3b.4b.5b.6a, 1d.2c.3b.4b.5b.6b, 1d.2c.3b.4b.5b.6c, 1d.2c.3b.4b.5b.6d,
1d.2c.3b.4b.5b.6e, 1d.2c.3b.4b.5c.6a, 1d.2c.3b.4b.5c.6b, 1d.2c.3b.4b.5c.6c,
1d.2c.3b.4b.5c.6d, 1d.2c.3b.4b.5c.6e, 1d.2c.3b.4b.5d.6a, 1d.2c.3b.4b.5d.6b,
1d.2c.3b.4b.5d.6c, 1d.2c.3b.4b.5d.6d, 1d.2c.3b.4b.5d.6e, 1d.2c.3b.4b.5e.6a,
1d.2c.3b.4b.5e.6b, 1d.2c.3b.4b.5e.6c, 1d.2c.3b.4b.5e.6d, 1d.2c.3b.4b.5e.6e,
1d.2c.3b.4c.5a.6a, 1d.2c.3b.4c.5a.6b, 1d.2c.3b.4c.5a.6c, 1d.2c.3b.4c.5a.6d,
1d.2c.3b.4c.5a.6e, 1d.2c.3b.4c.5b.6a, 1d.2c.3b.4c.5b.6b, 1d.2c.3b.4c.5b.6c,
1d.2c.3b.4c.5b.6d, 1d.2c.3b.4c.5b.6e, 1d.2c.3b.4c.5c.6a, 1d.2c.3b.4c.5c.6b,
1d.2c.3b.4c.5c.6c, 1d.2c.3b.4c.5c.6d, 1d.2c.3b.4c.5c.6e, 1d.2c.3b.4c.5d.6a,
1d.2c.3b.4c.5d.6b, 1d.2c.3b.4c.5d.6c, 1d.2c.3b.4c.5d.6d, 1d.2c.3b.4c.5d.6e,
1d.2c.3b.4c.5e.6a, 1d.2c.3b.4c.5e.6b, 1d.2c.3b.4c.5e.6c, 1d.2c.3b.4c.5e.6d,
1d.2c.3b.4c.5e.6e, 1d.2c.3b.4d.5a.6a, 1d.2c.3b.4d.5a.6b, 1d.2c.3b.4d.5a.6c,
1d.2c.3b.4d.5a.6d, 1d.2c.3b.4d.5a.6e, 1d.2c.3b.4d.5b.6a, 1d.2c.3b.4d.5b.6b,
1d.2c.3b.4d.5b.6c, 1d.2c.3b.4d.5b.6d, 1d.2c.3b.4d.5b.6e, 1d.2c.3b.4d.5c.6a,
1d.2c.3b.4d.5c.6b, 1d.2c.3b.4d.5c.6c, 1d.2c.3b.4d.5c.6d, 1d.2c.3b.4d.5c.6e,
1d.2c.3b.4d.5d.6a, 1d.2c.3b.4d.5d.6b, 1d.2c.3b.4d.5d.6c, 1d.2c.3b.4d.5d.6d,
1d.2c.3b.4d.5d.6e, 1d.2c.3b.4d.5e.6a, 1d.2c.3b.4d.5e.6b, 1d.2c.3b.4d.5e.6c,
1d.2c.3b.4d.5e.6d, 1d.2c.3b.4d.5e.6e, 1d.2c.3b.4e.5a.6a, 1d.2c.3b.4e.5a.6b,
1d.2c.3b.4e.5a.6c, 1d.2c.3b.4e.5a.6d, 1d.2c.3b.4e.5a.6e, 1d.2c.3b.4e.5b.6a,
1d.2c.3b.4e.5b.6b, 1d.2c.3b.4e.5b.6c, 1d.2c.3b.4e.5b.6d, 1d.2c.3b.4e.5b.6e,
1d.2c.3b.4e.5c.6a, 1d.2c.3b.4e.5c.6b, 1d.2c.3b.4e.5c.6c, 1d.2c.3b.4e.5c.6d,
1d.2c.3b.4e.5c.6e, 1d.2c.3b.4e.5d.6a, 1d.2c.3b.4e.5d.6b, 1d.2c.3b.4e.5d.6c,
1d.2c.3b.4e.5d.6d, 1d.2c.3b.4e.5d.6e, 1d.2c.3b.4e.5e.6a, 1d.2c.3b.4e.5e.6b,
1d.2c.3b.4e.5e.6c, 1d.2c.3b.4e.5e.6d, 1d.2c.3b.4e.5e.6e, 1d.2c.3c.4a.5a.6a,
1d.2c.3c.4a.5a.6b, 1d.2c.3c.4a.5a.6c, 1d.2c.3c.4a.5a.6d, 1d.2c.3c.4a.5a.6e,
1d.2c.3c.4a.5b.6a, 1d.2c.3c.4a.5b.6b, 1d.2c.3c.4a.5b.6c, 1d.2c.3c.4a.5b.6d,
1d.2c.3c.4a.5b.6e, 1d.2c.3c.4a.5c.6a, 1d.2c.3c.4a.5c.6b, 1d.2c.3c.4a.5c.6c,
1d.2c.3c.4a.5c.6d, 1d.2c.3c.4a.5c.6e, 1d.2c.3c.4a.5d.6a, 1d.2c.3c.4a.5d.6b,
1d.2c.3c.4a.5d.6c, 1d.2c.3c.4a.5d.6d, 1d.2c.3c.4a.5d.6e, 1d.2c.3c.4a.5e.6a,
1d.2c.3c.4a.5e.6b, 1d.2c.3c.4a.5e.6c, 1d.2c.3c.4a.5e.6d, 1d.2c.3c.4a.5e.6e,
1d.2c.3c.4b.5a.6a, 1d.2c.3c.4b.5a.6b, 1d.2c.3c.4b.5a.6c, 1d.2c.3c.4b.5a.6d,
1d.2c.3c.4b.5a.6e, 1d.2c.3c.4b.5b.6a, 1d.2c.3c.4b.5b.6b, 1d.2c.3c.4b.5b.6c,
1d.2c.3c.4b.5b.6d, 1d.2c.3c.4b.5b.6e, 1d.2c.3c.4b.5c.6a, 1d.2c.3c.4b.5c.6b,
1d.2c.3c.4b.5c.6c, 1d.2c.3c.4b.5c.6d, 1d.2c.3c.4b.5c.6e, 1d.2c.3c.4b.5d.6a,
1d.2c.3c.4b.5d.6b, 1d.2c.3c.4b.5d.6c, 1d.2c.3c.4b.5d.6d, 1d.2c.3c.4b.5d.6e,
1d.2c.3c.4b.5e.6a, 1d.2c.3c.4b.5e.6b, 1d.2c.3c.4b.5e.6c, 1d.2c.3c.4b.5e.6d,
1d.2c.3c.4b.5e.6e, 1d.2c.3c.4c.5a.6a, 1d.2c.3c.4c.5a.6b, 1d.2c.3c.4c.5a.6c,
1d.2c.3c.4c.5a.6d, 1d.2c.3c.4c.5a.6e, 1d.2c.3c.4c.5b.6a, 1d.2c.3c.4c.5b.6b,
1d.2c.3c.4c.5b.6c, 1d.2c.3c.4c.5b.6d, 1d.2c.3c.4c.5b.6e, 1d.2c.3c.4c.5c.6a,
1d.2c.3c.4c.5c.6b, 1d.2c.3c.4c.5c.6c, 1d.2c.3c.4c.5c.6d, 1d.2c.3c.4c.5c.6e,
1d.2c.3c.4c.5d.6a, 1d.2c.3c.4c.5d.6b, 1d.2c.3c.4c.5d.6c, 1d.2c.3c.4c.5d.6d,
1d.2c.3c.4c.5d.6e, 1d.2c.3c.4c.5e.6a, 1d.2c.3c.4c.5e.6b, 1d.2c.3c.4c.5e.6c,
1d.2c.3c.4c.5e.6d, 1d.2c.3c.4c.5e.6e, 1d.2c.3c.4d.5a.6a, 1d.2c.3c.4d.5a.6b,
1d.2c.3c.4d.5a.6c, 1d.2c.3c.4d.5a.6d, 1d.2c.3c.4d.5a.6e, 1d.2c.3c.4d.5b.6a,
1d.2c.3c.4d.5b.6b, 1d.2c.3c.4d.5b.6c, 1d.2c.3c.4d.5b.6d, 1d.2c.3c.4d.5b.6e,
1d.2c.3c.4d.5c.6a, 1d.2c.3c.4d.5c.6b, 1d.2c.3c.4d.5c.6c, 1d.2c.3c.4d.5c.6d,
1d.2c.3c.4d.5c.6e, 1d.2c.3c.4d.5d.6a, 1d.2c.3c.4d.5d.6b, 1d.2c.3c.4d.5d.6c,
1d.2c.3c.4d.5d.6d, 1d.2c.3c.4d.5d.6e, 1d.2c.3c.4d.5e.6a, 1d.2c.3c.4d.5e.6b,
1d.2c.3c.4d.5e.6c, 1d.2c.3c.4d.5e.6d, 1d.2c.3c.4d.5e.6e, 1d.2c.3c.4e.5a.6a,
1d.2c.3c.4e.5a.6b, 1d.2c.3c.4e.5a.6c, 1d.2c.3c.4e.5a.6d, 1d.2c.3c.4e.5a.6e,
1d.2c.3c.4e.5b.6a, 1d.2c.3c.4e.5b.6b, 1d.2c.3c.4e.5b.6c, 1d.2c.3c.4e.5b.6d,
1d.2c.3c.4e.5b.6e, 1d.2c.3c.4e.5c.6a, 1d.2c.3c.4e.5c.6b, 1d.2c.3c.4e.5c.6c,
1d.2c.3c.4e.5c.6d, 1d.2c.3c.4e.5c.6e, 1d.2c.3c.4e.5d.6a, 1d.2c.3c.4e.5d.6b,
1d.2c.3c.4e.5d.6c, 1d.2c.3c.4e.5d.6d, 1d.2c.3c.4e.5d.6e, 1d.2c.3c.4e.5e.6a,
1d.2c.3c.4e.5e.6b, 1d.2c.3c.4e.5e.6c, 1d.2c.3c.4e.5e.6d, 1d.2c.3c.4e.5e.6e,
1d.2c.3d.4a.5a.6a, 1d.2c.3d.4a.5a.6b, 1d.2c.3d.4a.5a.6c, 1d.2c.3d.4a.5a.6d,
1d.2c.3d.4a.5a.6e, 1d.2c.3d.4a.5b.6a, 1d.2c.3d.4a.5b.6b, 1d.2c.3d.4a.5b.6c,
1d.2c.3d.4a.5b.6d, 1d.2c.3d.4a.5b.6e, 1d.2c.3d.4a.5c.6a, 1d.2c.3d.4a.5c.6b,
1d.2c.3d.4a.5c.6c, 1d.2c.3d.4a.5c.6d, 1d.2c.3d.4a.5c.6e, 1d.2c.3d.4a.5d.6a,
1d.2c.3d.4a.5d.6b, 1d.2c.3d.4a.5d.6c, 1d.2c.3d.4a.5d.6d, 1d.2c.3d.4a.5d.6e,
1d.2c.3d.4a.5e.6a, 1d.2c.3d.4a.5e.6b, 1d.2c.3d.4a.5e.6c, 1d.2c.3d.4a.5e.6d,
1d.2c.3d.4a.5e.6e, 1d.2c.3d.4b.5a.6a, 1d.2c.3d.4b.5a.6b, 1d.2c.3d.4b.5a.6c,
1d.2c.3d.4b.5a.6d, 1d.2c.3d.4b.5a.6e, 1d.2c.3d.4b.5b.6a, 1d.2c.3d.4b.5b.6b,
1d.2c.3d.4b.5b.6c, 1d.2c.3d.4b.5b.6d, 1d.2c.3d.4b.5b.6e, 1d.2c.3d.4b.5c.6a,
1d.2c.3d.4b.5c.6b, 1d.2c.3d.4b.5c.6c, 1d.2c.3d.4b.5c.6d, 1d.2c.3d.4b.5c.6e,
1d.2c.3d.4b.5d.6a, 1d.2c.3d.4b.5d.6b, 1d.2c.3d.4b.5d.6c, 1d.2c.3d.4b.5d.6d,
1d.2c.3d.4b.5d.6e, 1d.2c.3d.4b.5e.6a, 1d.2c.3d.4b.5e.6b, 1d.2c.3d.4b.5e.6c,
1d.2c.3d.4b.5e.6d, 1d.2c.3d.4b.5e.6e, 1d.2c.3d.4c.5a.6a, 1d.2c.3d.4c.5a.6b,
1d.2c.3d.4c.5a.6c, 1d.2c.3d.4c.5a.6d, 1d.2c.3d.4c.5a.6e, 1d.2c.3d.4c.5b.6a,
1d.2c.3d.4c.5b.6b, 1d.2c.3d.4c.5b.6c, 1d.2c.3d.4c.5b.6d, 1d.2c.3d.4c.5b.6e,
1d.2c.3d.4c.5c.6a, 1d.2c.3d.4c.5c.6b, 1d.2c.3d.4c.5c.6c, 1d.2c.3d.4c.5c.6d,
1d.2c.3d.4c.5c.6e, 1d.2c.3d.4c.5d.6a, 1d.2c.3d.4c.5d.6b, 1d.2c.3d.4c.5d.6c,
1d.2c.3d.4c.5d.6d, 1d.2c.3d.4c.5d.6e, 1d.2c.3d.4c.5e.6a, 1d.2c.3d.4c.5e.6b,
1d.2c.3d.4c.5e.6c, 1d.2c.3d.4c.5e.6d, 1d.2c.3d.4c.5e.6e, 1d.2c.3d.4d.5a.6a,
1d.2c.3d.4d.5a.6b, 1d.2c.3d.4d.5a.6c, 1d.2c.3d.4d.5a.6d, 1d.2c.3d.4d.5a.6e,
1d.2c.3d.4d.5b.6a, 1d.2c.3d.4d.5b.6b, 1d.2c.3d.4d.5b.6c, 1d.2c.3d.4d.5b.6d,
1d.2c.3d.4d.5b.6e, 1d.2c.3d.4d.5c.6a, 1d.2c.3d.4d.5c.6b, 1d.2c.3d.4d.5c.6c,

TABLE 8-continued

List of Compounds of Formula (II)

1d.2c.3d.4d.5c.6d, 1d.2c.3d.4d.5c.6e, 1d.2c.3d.4d.5d.6a, 1d.2c.3d.4d.5d.6b,
1d.2c.3d.4d.5d.6c, 1d.2c.3d.4d.5d.6d, 1d.2c.3d.4d.5d.6e, 1d.2c.3d.4d.5e.6a,
1d.2c.3d.4d.5e.6b, 1d.2c.3d.4d.5e.6c, 1d.2c.3d.4d.5e.6d, 1d.2c.3d.4d.5e.6e,
1d.2c.3d.4e.5a.6a, 1d.2c.3d.4e.5a.6b, 1d.2c.3d.4e.5a.6c, 1d.2c.3d.4e.5a.6d,
1d.2c.3d.4e.5a.6e, 1d.2c.3d.4e.5b.6a, 1d.2c.3d.4e.5b.6b, 1d.2c.3d.4e.5b.6c,
1d.2c.3d.4e.5b.6d, 1d.2c.3d.4e.5b.6e, 1d.2c.3d.4e.5c.6a, 1d.2c.3d.4e.5c.6b,
1d.2c.3d.4e.5c.6c, 1d.2c.3d.4e.5c.6d, 1d.2c.3d.4e.5c.6e, 1d.2c.3d.4e.5d.6a,
1d.2c.3d.4e.5d.6b, 1d.2c.3d.4e.5d.6c, 1d.2c.3d.4e.5d.6d, 1d.2c.3d.4e.5d.6e,
1d.2c.3d.4e.5e.6a, 1d.2c.3d.4e.5e.6b, 1d.2c.3d.4e.5e.6c, 1d.2c.3d.4e.5e.6d,
1d.2c.3d.4e.5e.6e, 1d.2c.3e.4a.5a.6a, 1d.2c.3e.4a.5a.6b, 1d.2c.3e.4a.5a.6c,
1d.2c.3e.4a.5a.6d, 1d.2c.3e.4a.5a.6e, 1d.2c.3e.4a.5b.6a, 1d.2c.3e.4a.5b.6b,
1d.2c.3e.4a.5b.6c, 1d.2c.3e.4a.5b.6d, 1d.2c.3e.4a.5b.6e, 1d.2c.3e.4a.5c.6a,
1d.2c.3e.4a.5c.6b, 1d.2c.3e.4a.5c.6c, 1d.2c.3e.4a.5c.6d, 1d.2c.3e.4a.5c.6e,
1d.2c.3e.4a.5d.6a, 1d.2c.3e.4a.5d.6b, 1d.2c.3e.4a.5d.6c, 1d.2c.3e.4a.5d.6d,
1d.2c.3e.4a.5d.6e, 1d.2c.3e.4a.5e.6a, 1d.2c.3e.4a.5e.6b, 1d.2c.3e.4a.5e.6c,
1d.2c.3e.4a.5e.6d, 1d.2c.3e.4a.5e.6e, 1d.2c.3e.4b.5a.6a, 1d.2c.3e.4b.5a.6b,
1d.2c.3e.4b.5a.6c, 1d.2c.3e.4b.5a.6d, 1d.2c.3e.4b.5a.6e, 1d.2c.3e.4b.5b.6a,
1d.2c.3e.4b.5b.6b, 1d.2c.3e.4b.5b.6c, 1d.2c.3e.4b.5b.6d, 1d.2c.3e.4b.5b.6e,
1d.2c.3e.4b.5c.6a, 1d.2c.3e.4b.5c.6b, 1d.2c.3e.4b.5c.6c, 1d.2c.3e.4b.5c.6d,
1d.2c.3e.4b.5c.6e, 1d.2c.3e.4b.5d.6a, 1d.2c.3e.4b.5d.6b, 1d.2c.3e.4b.5d.6c,
1d.2c.3e.4b.5d.6d, 1d.2c.3e.4b.5d.6e, 1d.2c.3e.4b.5e.6a, 1d.2c.3e.4b.5e.6b,
1d.2c.3e.4b.5e.6c, 1d.2c.3e.4b.5e.6d, 1d.2c.3e.4b.5e.6e, 1d.2c.3e.4c.5a.6a,
1d.2c.3e.4c.5a.6b, 1d.2c.3e.4c.5a.6c, 1d.2c.3e.4c.5a.6d, 1d.2c.3e.4c.5a.6e,
1d.2c.3e.4c.5b.6a, 1d.2c.3e.4c.5b.6b, 1d.2c.3e.4c.5b.6c, 1d.2c.3e.4c.5b.6d,
1d.2c.3e.4c.5b.6e, 1d.2c.3e.4c.5c.6a, 1d.2c.3e.4c.5c.6b, 1d.2c.3e.4c.5c.6c,
1d.2c.3e.4c.5c.6d, 1d.2c.3e.4c.5c.6e, 1d.2c.3e.4c.5d.6a, 1d.2c.3e.4c.5d.6b,
1d.2c.3e.4c.5d.6c, 1d.2c.3e.4c.5d.6d, 1d.2c.3e.4c.5d.6e, 1d.2c.3e.4c.5e.6a,
1d.2c.3e.4c.5e.6b, 1d.2c.3e.4c.5e.6c, 1d.2c.3e.4c.5e.6d, 1d.2c.3e.4c.5e.6e,
1d.2c.3e.4d.5a.6a, 1d.2c.3e.4d.5a.6b, 1d.2c.3e.4d.5a.6c, 1d.2c.3e.4d.5a.6d,
1d.2c.3e.4d.5a.6e, 1d.2c.3e.4d.5b.6a, 1d.2c.3e.4d.5b.6b, 1d.2c.3e.4d.5b.6c,
1d.2c.3e.4d.5b.6d, 1d.2c.3e.4d.5b.6e, 1d.2c.3e.4d.5c.6a, 1d.2c.3e.4d.5c.6b,
1d.2c.3e.4d.5c.6c, 1d.2c.3e.4d.5c.6d, 1d.2c.3e.4d.5c.6e, 1d.2c.3e.4d.5d.6a,
1d.2c.3e.4d.5d.6b, 1d.2c.3e.4d.5d.6c, 1d.2c.3e.4d.5d.6d, 1d.2c.3e.4d.5d.6e,
1d.2c.3e.4d.5e.6a, 1d.2c.3e.4d.5e.6b, 1d.2c.3e.4d.5e.6c, 1d.2c.3e.4d.5e.6d,
1d.2c.3e.4d.5e.6e, 1d.2c.3e.4e.5a.6a, 1d.2c.3e.4e.5a.6b, 1d.2c.3e.4e.5a.6c,
1d.2c.3e.4e.5a.6d, 1d.2c.3e.4e.5a.6e, 1d.2c.3e.4e.5b.6a, 1d.2c.3e.4e.5b.6b,
1d.2c.3e.4e.5b.6c, 1d.2c.3e.4e.5b.6d, 1d.2c.3e.4e.5b.6e, 1d.2c.3e.4e.5c.6a,
1d.2c.3e.4e.5c.6b, 1d.2c.3e.4e.5c.6c, 1d.2c.3e.4e.5c.6d, 1d.2c.3e.4e.5c.6e,
1d.2c.3e.4e.5d.6a, 1d.2c.3e.4e.5d.6b, 1d.2c.3e.4e.5d.6c, 1d.2c.3e.4e.5d.6d,
1d.2c.3e.4e.5d.6e, 1d.2c.3e.4e.5e.6a, 1d.2c.3e.4e.5e.6b, 1d.2c.3e.4e.5e.6c,
1d.2c.3e.4e.5e.6d, 1d.2c.3e.4e.5e.6e, 1d.2d.3a.4a.5a.6a, 1d.2d.3a.4a.5a.6b,
1d.2d.3a.4a.5a.6c, 1d.2d.3a.4a.5a.6d, 1d.2d.3a.4a.5a.6e, 1d.2d.3a.4a.5b.6a,
1d.2d.3a.4a.5b.6b, 1d.2d.3a.4a.5b.6c, 1d.2d.3a.4a.5b.6d, 1d.2d.3a.4a.5b.6e,
1d.2d.3a.4a.5c.6a, 1d.2d.3a.4a.5c.6b, 1d.2d.3a.4a.5c.6c, 1d.2d.3a.4a.5c.6d,
1d.2d.3a.4a.5c.6e, 1d.2d.3a.4a.5d.6a, 1d.2d.3a.4a.5d.6b, 1d.2d.3a.4a.5d.6c,
1d.2d.3a.4a.5d.6d, 1d.2d.3a.4a.5d.6e, 1d.2d.3a.4a.5e.6a, 1d.2d.3a.4a.5e.6b,
1d.2d.3a.4a.5e.6c, 1d.2d.3a.4a.5e.6d, 1d.2d.3a.4a.5e.6e, 1d.2d.3a.4b.5a.6a,
1d.2d.3a.4b.5a.6b, 1d.2d.3a.4b.5a.6c, 1d.2d.3a.4b.5a.6d, 1d.2d.3a.4b.5a.6e,
1d.2d.3a.4b.5b.6a, 1d.2d.3a.4b.5b.6b, 1d.2d.3a.4b.5b.6c, 1d.2d.3a.4b.5b.6d,
1d.2d.3a.4b.5b.6e, 1d.2d.3a.4b.5c.6a, 1d.2d.3a.4b.5c.6b, 1d.2d.3a.4b.5c.6c,
1d.2d.3a.4b.5c.6d, 1d.2d.3a.4b.5c.6e, 1d.2d.3a.4b.5d.6a, 1d.2d.3a.4b.5d.6b,
1d.2d.3a.4b.5d.6c, 1d.2d.3a.4b.5d.6d, 1d.2d.3a.4b.5d.6e, 1d.2d.3a.4b.5e.6a,
1d.2d.3a.4b.5e.6b, 1d.2d.3a.4b.5e.6c, 1d.2d.3a.4b.5e.6d, 1d.2d.3a.4b.5e.6e,
1d.2d.3a.4c.5a.6a, 1d.2d.3a.4c.5a.6b, 1d.2d.3a.4c.5a.6c, 1d.2d.3a.4c.5a.6d,
1d.2d.3a.4c.5a.6e, 1d.2d.3a.4c.5b.6a, 1d.2d.3a.4c.5b.6b, 1d.2d.3a.4c.5b.6c,
1d.2d.3a.4c.5b.6d, 1d.2d.3a.4c.5b.6e, 1d.2d.3a.4c.5c.6a, 1d.2d.3a.4c.5c.6b,
1d.2d.3a.4c.5c.6c, 1d.2d.3a.4c.5c.6d, 1d.2d.3a.4c.5c.6e, 1d.2d.3a.4c.5d.6a,
1d.2d.3a.4c.5d.6b, 1d.2d.3a.4c.5d.6c, 1d.2d.3a.4c.5d.6d, 1d.2d.3a.4c.5d.6e,
1d.2d.3a.4c.5e.6a, 1d.2d.3a.4c.5e.6b, 1d.2d.3a.4c.5e.6c, 1d.2d.3a.4c.5e.6d,
1d.2d.3a.4c.5e.6e, 1d.2d.3a.4d.5a.6a, 1d.2d.3a.4d.5a.6b, 1d.2d.3a.4d.5a.6c,
1d.2d.3a.4d.5a.6d, 1d.2d.3a.4d.5a.6e, 1d.2d.3a.4d.5b.6a, 1d.2d.3a.4d.5b.6b,
1d.2d.3a.4d.5b.6c, 1d.2d.3a.4d.5b.6d, 1d.2d.3a.4d.5b.6e, 1d.2d.3a.4d.5c.6a,
1d.2d.3a.4d.5c.6b, 1d.2d.3a.4d.5c.6c, 1d.2d.3a.4d.5c.6d, 1d.2d.3a.4d.5c.6e,
1d.2d.3a.4d.5d.6a, 1d.2d.3a.4d.5d.6b, 1d.2d.3a.4d.5d.6c, 1d.2d.3a.4d.5d.6d,
1d.2d.3a.4d.5d.6e, 1d.2d.3a.4d.5e.6a, 1d.2d.3a.4d.5e.6b, 1d.2d.3a.4d.5e.6c,
1d.2d.3a.4d.5e.6d, 1d.2d.3a.4d.5e.6e, 1d.2d.3a.4e.5a.6a, 1d.2d.3a.4e.5a.6b,
1d.2d.3a.4e.5a.6c, 1d.2d.3a.4e.5a.6d, 1d.2d.3a.4e.5a.6e, 1d.2d.3a.4e.5b.6a,
1d.2d.3a.4e.5b.6b, 1d.2d.3a.4e.5b.6c, 1d.2d.3a.4e.5b.6d, 1d.2d.3a.4e.5b.6e,
1d.2d.3a.4e.5c.6a, 1d.2d.3a.4e.5c.6b, 1d.2d.3a.4e.5c.6c, 1d.2d.3a.4e.5c.6d,
1d.2d.3a.4e.5c.6e, 1d.2d.3a.4e.5d.6a, 1d.2d.3a.4e.5d.6b, 1d.2d.3a.4e.5d.6c,
1d.2d.3a.4e.5d.6d, 1d.2d.3a.4e.5d.6e, 1d.2d.3a.4e.5e.6a, 1d.2d.3a.4e.5e.6b,
1d.2d.3a.4e.5e.6c, 1d.2d.3a.4e.5e.6d, 1d.2d.3a.4e.5e.6e, 1d.2d.3b.4a.5a.6a,
1d.2d.3b.4a.5a.6b, 1d.2d.3b.4a.5a.6c, 1d.2d.3b.4a.5a.6d, 1d.2d.3b.4a.5a.6e,
1d.2d.3b.4a.5b.6a, 1d.2d.3b.4a.5b.6b, 1d.2d.3b.4a.5b.6c, 1d.2d.3b.4a.5b.6d,
1d.2d.3b.4a.5b.6e, 1d.2d.3b.4a.5c.6a, 1d.2d.3b.4a.5c.6b, 1d.2d.3b.4a.5c.6c,
1d.2d.3b.4a.5c.6d, 1d.2d.3b.4a.5c.6e, 1d.2d.3b.4a.5d.6a, 1d.2d.3b.4a.5d.6b,
1d.2d.3b.4a.5d.6c, 1d.2d.3b.4a.5d.6d, 1d.2d.3b.4a.5d.6e, 1d.2d.3b.4a.5e.6a,
1d.2d.3b.4a.5e.6b, 1d.2d.3b.4a.5e.6c, 1d.2d.3b.4a.5e.6d, 1d.2d.3b.4a.5e.6e,

TABLE 8-continued

List of Compounds of Formula (II)

1d.2d.3b.4b.5a.6a, 1d.2d.3b.4b.5a.6b, 1d.2d.3b.4b.5a.6c, 1d.2d.3b.4b.5a.6d,
1d.2d.3b.4b.5a.6e, 1d.2d.3b.4b.5b.6a, 1d.2d.3b.4b.5b.6b, 1d.2d.3b.4b.5b.6c,
1d.2d.3b.4b.5b.6d, 1d.2d.3b.4b.5b.6e, 1d.2d.3b.4b.5c.6a, 1d.2d.3b.4b.5c.6b,
1d.2d.3b.4b.5c.6c, 1d.2d.3b.4b.5c.6d, 1d.2d.3b.4b.5c.6e, 1d.2d.3b.4b.5d.6a,
1d.2d.3b.4b.5d.6b, 1d.2d.3b.4b.5d.6c, 1d.2d.3b.4b.5d.6d, 1d.2d.3b.4b.5d.6e,
1d.2d.3b.4b.5e.6a, 1d.2d.3b.4b.5e.6b, 1d.2d.3b.4b.5e.6c, 1d.2d.3b.4b.5e.6d,
1d.2d.3b.4b.5e.6e, 1d.2d.3b.4c.5a.6a, 1d.2d.3b.4c.5a.6b, 1d.2d.3b.4c.5a.6c,
1d.2d.3b.4c.5a.6d, 1d.2d.3b.4c.5a.6e, 1d.2d.3b.4c.5b.6a, 1d.2d.3b.4c.5b.6b,
1d.2d.3b.4c.5b.6c, 1d.2d.3b.4c.5b.6d, 1d.2d.3b.4c.5b.6e, 1d.2d.3b.4c.5c.6a,
1d.2d.3b.4c.5c.6b, 1d.2d.3b.4c.5c.6c, 1d.2d.3b.4c.5c.6d, 1d.2d.3b.4c.5c.6e,
1d.2d.3b.4c.5d.6a, 1d.2d.3b.4c.5d.6b, 1d.2d.3b.4c.5d.6c, 1d.2d.3b.4c.5d.6d,
1d.2d.3b.4c.5d.6e, 1d.2d.3b.4c.5e.6a, 1d.2d.3b.4c.5e.6b, 1d.2d.3b.4c.5e.6c,
1d.2d.3b.4c.5e.6d, 1d.2d.3b.4c.5e.6e, 1d.2d.3b.4d.5a.6a, 1d.2d.3b.4d.5a.6b,
1d.2d.3b.4d.5a.6c, 1d.2d.3b.4d.5a.6d, 1d.2d.3b.4d.5a.6e, 1d.2d.3b.4d.5b.6a,
1d.2d.3b.4d.5b.6b, 1d.2d.3b.4d.5b.6c, 1d.2d.3b.4d.5b.6d, 1d.2d.3b.4d.5b.6e,
1d.2d.3b.4d.5c.6a, 1d.2d.3b.4d.5c.6b, 1d.2d.3b.4d.5c.6c, 1d.2d.3b.4d.5c.6d,
1d.2d.3b.4d.5c.6e, 1d.2d.3b.4d.5d.6a, 1d.2d.3b.4d.5d.6b, 1d.2d.3b.4d.5d.6c,
1d.2d.3b.4d.5d.6d, 1d.2d.3b.4d.5d.6e, 1d.2d.3b.4d.5e.6a, 1d.2d.3b.4d.5e.6b,
1d.2d.3b.4d.5e.6c, 1d.2d.3b.4d.5e.6d, 1d.2d.3b.4d.5e.6e, 1d.2d.3b.4e.5a.6a,
1d.2d.3b.4e.5a.6b, 1d.2d.3b.4e.5a.6c, 1d.2d.3b.4e.5a.6d, 1d.2d.3b.4e.5a.6e,
1d.2d.3b.4e.5b.6a, 1d.2d.3b.4e.5b.6b, 1d.2d.3b.4e.5b.6c, 1d.2d.3b.4e.5b.6d,
1d.2d.3b.4e.5b.6e, 1d.2d.3b.4e.5c.6a, 1d.2d.3b.4e.5c.6b, 1d.2d.3b.4e.5c.6c,
1d.2d.3b.4e.5c.6d, 1d.2d.3b.4e.5c.6e, 1d.2d.3b.4e.5d.6a, 1d.2d.3b.4e.5d.6b,
1d.2d.3b.4e.5d.6c, 1d.2d.3b.4e.5d.6d, 1d.2d.3b.4e.5d.6e, 1d.2d.3b.4e.5e.6a,
1d.2d.3b.4e.5e.6b, 1d.2d.3b.4e.5e.6c, 1d.2d.3b.4e.5e.6d, 1d.2d.3b.4e.5e.6e,
1d.2d.3c.4a.5a.6a, 1d.2d.3c.4a.5a.6b, 1d.2d.3c.4a.5a.6c, 1d.2d.3c.4a.5a.6d,
1d.2d.3c.4a.5a.6e, 1d.2d.3c.4a.5b.6a, 1d.2d.3c.4a.5b.6b, 1d.2d.3c.4a.5b.6c,
1d.2d.3c.4a.5b.6d, 1d.2d.3c.4a.5b.6e, 1d.2d.3c.4a.5c.6a, 1d.2d.3c.4a.5c.6b,
1d.2d.3c.4a.5c.6c, 1d.2d.3c.4a.5c.6d, 1d.2d.3c.4a.5c.6e, 1d.2d.3c.4a.5d.6a,
1d.2d.3c.4a.5d.6b, 1d.2d.3c.4a.5d.6c, 1d.2d.3c.4a.5d.6d, 1d.2d.3c.4a.5d.6e,
1d.2d.3c.4a.5e.6a, 1d.2d.3c.4a.5e.6b, 1d.2d.3c.4a.5e.6c, 1d.2d.3c.4a.5e.6d,
1d.2d.3c.4a.5e.6e, 1d.2d.3c.4b.5a.6a, 1d.2d.3c.4b.5a.6b, 1d.2d.3c.4b.5a.6c,
1d.2d.3c.4b.5a.6d, 1d.2d.3c.4b.5a.6e, 1d.2d.3c.4b.5b.6a, 1d.2d.3c.4b.5b.6b,
1d.2d.3c.4b.5b.6c, 1d.2d.3c.4b.5b.6d, 1d.2d.3c.4b.5b.6e, 1d.2d.3c.4b.5c.6a,
1d.2d.3c.4b.5c.6b, 1d.2d.3c.4b.5c.6c, 1d.2d.3c.4b.5c.6d, 1d.2d.3c.4b.5c.6e,
1d.2d.3c.4b.5d.6a, 1d.2d.3c.4b.5d.6b, 1d.2d.3c.4b.5d.6c, 1d.2d.3c.4b.5d.6d,
1d.2d.3c.4b.5d.6e, 1d.2d.3c.4b.5e.6a, 1d.2d.3c.4b.5e.6b, 1d.2d.3c.4b.5e.6c,
1d.2d.3c.4b.5e.6d, 1d.2d.3c.4b.5e.6e, 1d.2d.3c.4c.5a.6a, 1d.2d.3c.4c.5a.6b,
1d.2d.3c.4c.5a.6c, 1d.2d.3c.4c.5a.6d, 1d.2d.3c.4c.5a.6e, 1d.2d.3c.4c.5b.6a,
1d.2d.3c.4c.5b.6b, 1d.2d.3c.4c.5b.6c, 1d.2d.3c.4c.5b.6d, 1d.2d.3c.4c.5b.6e,
1d.2d.3c.4c.5c.6a, 1d.2d.3c.4c.5c.6b, 1d.2d.3c.4c.5c.6c, 1d.2d.3c.4c.5c.6d,
1d.2d.3c.4c.5c.6e, 1d.2d.3c.4c.5d.6a, 1d.2d.3c.4c.5d.6b, 1d.2d.3c.4c.5d.6c,
1d.2d.3c.4c.5d.6d, 1d.2d.3c.4c.5d.6e, 1d.2d.3c.4c.5e.6a, 1d.2d.3c.4c.5e.6b,
1d.2d.3c.4c.5e.6c, 1d.2d.3c.4c.5e.6d, 1d.2d.3c.4c.5e.6e, 1d.2d.3c.4d.5a.6a,
1d.2d.3c.4d.5a.6b, 1d.2d.3c.4d.5a.6c, 1d.2d.3c.4d.5a.6d, 1d.2d.3c.4d.5a.6e,
1d.2d.3c.4d.5b.6a, 1d.2d.3c.4d.5b.6b, 1d.2d.3c.4d.5b.6c, 1d.2d.3c.4d.5b.6d,
1d.2d.3c.4d.5b.6e, 1d.2d.3c.4d.5c.6a, 1d.2d.3c.4d.5c.6b, 1d.2d.3c.4d.5c.6c,
1d.2d.3c.4d.5c.6d, 1d.2d.3c.4d.5c.6e, 1d.2d.3c.4d.5d.6a, 1d.2d.3c.4d.5d.6b,
1d.2d.3c.4d.5d.6c, 1d.2d.3c.4d.5d.6d, 1d.2d.3c.4d.5d.6e, 1d.2d.3c.4d.5e.6a,
1d.2d.3c.4d.5e.6b, 1d.2d.3c.4d.5e.6c, 1d.2d.3c.4d.5e.6d, 1d.2d.3c.4d.5e.6e,
1d.2d.3c.4e.5a.6a, 1d.2d.3c.4e.5a.6b, 1d.2d.3c.4e.5a.6c, 1d.2d.3c.4e.5a.6d,
1d.2d.3c.4e.5a.6e, 1d.2d.3c.4e.5b.6a, 1d.2d.3c.4e.5b.6b, 1d.2d.3c.4e.5b.6c,
1d.2d.3c.4e.5b.6d, 1d.2d.3c.4e.5b.6e, 1d.2d.3c.4e.5c.6a, 1d.2d.3c.4e.5c.6b,
1d.2d.3c.4e.5c.6c, 1d.2d.3c.4e.5c.6d, 1d.2d.3c.4e.5c.6e, 1d.2d.3c.4e.5d.6a,
1d.2d.3c.4e.5d.6b, 1d.2d.3c.4e.5d.6c, 1d.2d.3c.4e.5d.6d, 1d.2d.3c.4e.5d.6e,
1d.2d.3c.4e.5e.6a, 1d.2d.3c.4e.5e.6b, 1d.2d.3c.4e.5e.6c, 1d.2d.3c.4e.5e.6d,
1d.2d.3c.4e.5e.6e, 1d.2d.3d.4a.5a.6a, 1d.2d.3d.4a.5a.6b, 1d.2d.3d.4a.5a.6c,
1d.2d.3d.4a.5a.6d, 1d.2d.3d.4a.5a.6e, 1d.2d.3d.4a.5b.6a, 1d.2d.3d.4a.5b.6b,
1d.2d.3d.4a.5b.6c, 1d.2d.3d.4a.5b.6d, 1d.2d.3d.4a.5b.6e, 1d.2d.3d.4a.5c.6a,
1d.2d.3d.4a.5c.6b, 1d.2d.3d.4a.5c.6c, 1d.2d.3d.4a.5c.6d, 1d.2d.3d.4a.5c.6e,
1d.2d.3d.4a.5d.6a, 1d.2d.3d.4a.5d.6b, 1d.2d.3d.4a.5d.6c, 1d.2d.3d.4a.5d.6d,
1d.2d.3d.4a.5d.6e, 1d.2d.3d.4a.5e.6a, 1d.2d.3d.4a.5e.6b, 1d.2d.3d.4a.5e.6c,
1d.2d.3d.4a.5e.6d, 1d.2d.3d.4a.5e.6e, 1d.2d.3d.4b.5a.6a, 1d.2d.3d.4b.5a.6b,
1d.2d.3d.4b.5a.6c, 1d.2d.3d.4b.5a.6d, 1d.2d.3d.4b.5a.6e, 1d.2d.3d.4b.5b.6a,
1d.2d.3d.4b.5b.6b, 1d.2d.3d.4b.5b.6c, 1d.2d.3d.4b.5b.6d, 1d.2d.3d.4b.5b.6e,
1d.2d.3d.4b.5c.6a, 1d.2d.3d.4b.5c.6b, 1d.2d.3d.4b.5c.6c, 1d.2d.3d.4b.5c.6d,
1d.2d.3d.4b.5c.6e, 1d.2d.3d.4b.5d.6a, 1d.2d.3d.4b.5d.6b, 1d.2d.3d.4b.5d.6c,
1d.2d.3d.4b.5d.6d, 1d.2d.3d.4b.5d.6e, 1d.2d.3d.4b.5e.6a, 1d.2d.3d.4b.5e.6b,
1d.2d.3d.4b.5e.6c, 1d.2d.3d.4b.5e.6d, 1d.2d.3d.4b.5e.6e, 1d.2d.3d.4c.5a.6a,
1d.2d.3d.4c.5a.6b, 1d.2d.3d.4c.5a.6c, 1d.2d.3d.4c.5a.6d, 1d.2d.3d.4c.5a.6e,
1d.2d.3d.4c.5b.6a, 1d.2d.3d.4c.5b.6b, 1d.2d.3d.4c.5b.6c, 1d.2d.3d.4c.5b.6d,
1d.2d.3d.4c.5b.6e, 1d.2d.3d.4c.5c.6a, 1d.2d.3d.4c.5c.6b, 1d.2d.3d.4c.5c.6c,
1d.2d.3d.4c.5c.6d, 1d.2d.3d.4c.5c.6e, 1d.2d.3d.4c.5d.6a, 1d.2d.3d.4c.5d.6b,
1d.2d.3d.4c.5d.6c, 1d.2d.3d.4c.5d.6d, 1d.2d.3d.4c.5d.6e, 1d.2d.3d.4c.5e.6a,
1d.2d.3d.4c.5e.6b, 1d.2d.3d.4c.5e.6c, 1d.2d.3d.4c.5e.6d, 1d.2d.3d.4c.5e.6e,
1d.2d.3d.4d.5a.6a, 1d.2d.3d.4d.5a.6b, 1d.2d.3d.4d.5a.6c, 1d.2d.3d.4d.5a.6d,
1d.2d.3d.4d.5a.6e, 1d.2d.3d.4d.5b.6a, 1d.2d.3d.4d.5b.6b, 1d.2d.3d.4d.5b.6c,
1d.2d.3d.4d.5b.6d, 1d.2d.3d.4d.5b.6e, 1d.2d.3d.4d.5c.6a, 1d.2d.3d.4d.5c.6b,

TABLE 8-continued

List of Compounds of Formula (II)

1d.2d.3d.4d.5c.6c, 1d.2d.3d.4d.5c.6d, 1d.2d.3d.4d.5c.6e, 1d.2d.3d.4d.5d.6a,
1d.2d.3d.4d.5d.6b, 1d.2d.3d.4d.5d.6c, 1d.2d.3d.4d.5d.6d, 1d.2d.3d.4d.5d.6e,
1d.2d.3d.4d.5e.6a, 1d.2d.3d.4d.5e.6b, 1d.2d.3d.4d.5e.6c, 1d.2d.3d.4d.5e.6d,
1d.2d.3d.4d.5e.6e, 1d.2d.3d.4e.5a.6a, 1d.2d.3d.4e.5a.6b, 1d.2d.3d.4e.5a.6c,
1d.2d.3d.4e.5a.6d, 1d.2d.3d.4e.5a.6e, 1d.2d.3d.4e.5b.6a, 1d.2d.3d.4e.5b.6b,
1d.2d.3d.4e.5b.6c, 1d.2d.3d.4e.5b.6d, 1d.2d.3d.4e.5b.6e, 1d.2d.3d.4e.5c.6a,
1d.2d.3d.4e.5c.6b, 1d.2d.3d.4e.5c.6c, 1d.2d.3d.4e.5c.6d, 1d.2d.3d.4e.5c.6e,
1d.2d.3d.4e.5d.6a, 1d.2d.3d.4e.5d.6b, 1d.2d.3d.4e.5d.6c, 1d.2d.3d.4e.5d.6d,
1d.2d.3d.4e.5d.6e, 1d.2d.3d.4e.5e.6a, 1d.2d.3d.4e.5e.6b, 1d.2d.3d.4e.5e.6c,
1d.2d.3d.4e.5e.6d, 1d.2d.3d.4e.5e.6e, 1d.2d.3e.4a.5a.6a, 1d.2d.3e.4a.5a.6b,
1d.2d.3e.4a.5a.6c, 1d.2d.3e.4a.5a.6d, 1d.2d.3e.4a.5a.6e, 1d.2d.3e.4a.5b.6a,
1d.2d.3e.4a.5b.6b, 1d.2d.3e.4a.5b.6c, 1d.2d.3e.4a.5b.6d, 1d.2d.3e.4a.5b.6e,
1d.2d.3e.4a.5c.6a, 1d.2d.3e.4a.5c.6b, 1d.2d.3e.4a.5c.6c, 1d.2d.3e.4a.5c.6d,
1d.2d.3e.4a.5c.6e, 1d.2d.3e.4a.5d.6a, 1d.2d.3e.4a.5d.6b, 1d.2d.3e.4a.5d.6c,
1d.2d.3e.4a.5d.6d, 1d.2d.3e.4a.5d.6e, 1d.2d.3e.4a.5e.6a, 1d.2d.3e.4a.5e.6b,
1d.2d.3e.4a.5e.6c, 1d.2d.3e.4a.5e.6d, 1d.2d.3e.4a.5e.6e, 1d.2d.3e.4b.5a.6a,
1d.2d.3e.4b.5a.6b, 1d.2d.3e.4b.5a.6c, 1d.2d.3e.4b.5a.6d, 1d.2d.3e.4b.5a.6e,
1d.2d.3e.4b.5b.6a, 1d.2d.3e.4b.5b.6b, 1d.2d.3e.4b.5b.6c, 1d.2d.3e.4b.5b.6d,
1d.2d.3e.4b.5b.6e, 1d.2d.3e.4b.5c.6a, 1d.2d.3e.4b.5c.6b, 1d.2d.3e.4b.5c.6c,
1d.2d.3e.4b.5c.6d, 1d.2d.3e.4b.5c.6e, 1d.2d.3e.4b.5d.6a, 1d.2d.3e.4b.5d.6b,
1d.2d.3e.4b.5d.6c, 1d.2d.3e.4b.5d.6d, 1d.2d.3e.4b.5d.6e, 1d.2d.3e.4b.5e.6a,
1d.2d.3e.4b.5e.6b, 1d.2d.3e.4b.5e.6c, 1d.2d.3e.4b.5e.6d, 1d.2d.3e.4b.5e.6e,
1d.2d.3e.4c.5a.6a, 1d.2d.3e.4c.5a.6b, 1d.2d.3e.4c.5a.6c, 1d.2d.3e.4c.5a.6d,
1d.2d.3e.4c.5a.6e, 1d.2d.3e.4c.5b.6a, 1d.2d.3e.4c.5b.6b, 1d.2d.3e.4c.5b.6c,
1d.2d.3e.4c.5b.6d, 1d.2d.3e.4c.5b.6e, 1d.2d.3e.4c.5c.6a, 1d.2d.3e.4c.5c.6b,
1d.2d.3e.4c.5c.6c, 1d.2d.3e.4c.5c.6d, 1d.2d.3e.4c.5c.6e, 1d.2d.3e.4c.5d.6a,
1d.2d.3e.4c.5d.6b, 1d.2d.3e.4c.5d.6c, 1d.2d.3e.4c.5d.6d, 1d.2d.3e.4c.5d.6e,
1d.2d.3e.4c.5e.6a, 1d.2d.3e.4c.5e.6b, 1d.2d.3e.4c.5e.6c, 1d.2d.3e.4c.5e.6d,
1d.2d.3e.4c.5e.6e, 1d.2d.3e.4d.5a.6a, 1d.2d.3e.4d.5a.6b, 1d.2d.3e.4d.5a.6c,
1d.2d.3e.4d.5a.6d, 1d.2d.3e.4d.5a.6e, 1d.2d.3e.4d.5b.6a, 1d.2d.3e.4d.5b.6b,
1d.2d.3e.4d.5b.6c, 1d.2d.3e.4d.5b.6d, 1d.2d.3e.4d.5b.6e, 1d.2d.3e.4d.5c.6a,
1d.2d.3e.4d.5c.6b, 1d.2d.3e.4d.5c.6c, 1d.2d.3e.4d.5c.6d, 1d.2d.3e.4d.5c.6e,
1d.2d.3e.4d.5d.6a, 1d.2d.3e.4d.5d.6b, 1d.2d.3e.4d.5d.6c, 1d.2d.3e.4d.5d.6d,
1d.2d.3e.4d.5d.6e, 1d.2d.3e.4d.5e.6a, 1d.2d.3e.4d.5e.6b, 1d.2d.3e.4d.5e.6c,
1d.2d.3e.4d.5e.6d, 1d.2d.3e.4d.5e.6e, 1d.2d.3e.4e.5a.6a, 1d.2d.3e.4e.5a.6b,
1d.2d.3e.4e.5a.6c, 1d.2d.3e.4e.5a.6d, 1d.2d.3e.4e.5a.6e, 1d.2d.3e.4e.5b.6a,
1d.2d.3e.4e.5b.6b, 1d.2d.3e.4e.5b.6c, 1d.2d.3e.4e.5b.6d, 1d.2d.3e.4e.5b.6e,
1d.2d.3e.4e.5c.6a, 1d.2d.3e.4e.5c.6b, 1d.2d.3e.4e.5c.6c, 1d.2d.3e.4e.5c.6d,
1d.2d.3e.4e.5c.6e, 1d.2d.3e.4e.5d.6a, 1d.2d.3e.4e.5d.6b, 1d.2d.3e.4e.5d.6c,
1d.2d.3e.4e.5d.6d, 1d.2d.3e.4e.5d.6e, 1d.2d.3e.4e.5e.6a, 1d.2d.3e.4e.5e.6b,
1d.2d.3e.4e.5e.6c, 1d.2d.3e.4e.5e.6d, 1d.2d.3e.4e.5e.6e, 1d.2e.3a.4a.5a.6a,
1d.2e.3a.4a.5a.6b, 1d.2e.3a.4a.5a.6c, 1d.2e.3a.4a.5a.6d, 1d.2e.3a.4a.5a.6e,
1d.2e.3a.4a.5b.6a, 1d.2e.3a.4a.5b.6b, 1d.2e.3a.4a.5b.6c, 1d.2e.3a.4a.5b.6d,
1d.2e.3a.4a.5b.6e, 1d.2e.3a.4a.5c.6a, 1d.2e.3a.4a.5c.6b, 1d.2e.3a.4a.5c.6c,
1d.2e.3a.4a.5c.6d, 1d.2e.3a.4a.5c.6e, 1d.2e.3a.4a.5d.6a, 1d.2e.3a.4a.5d.6b,
1d.2e.3a.4a.5d.6c, 1d.2e.3a.4a.5d.6d, 1d.2e.3a.4a.5d.6e, 1d.2e.3a.4a.5e.6a,
1d.2e.3a.4a.5e.6b, 1d.2e.3a.4a.5e.6c, 1d.2e.3a.4a.5e.6d, 1d.2e.3a.4a.5e.6e,
1d.2e.3a.4b.5a.6a, 1d.2e.3a.4b.5a.6b, 1d.2e.3a.4b.5a.6c, 1d.2e.3a.4b.5a.6d,
1d.2e.3a.4b.5a.6e, 1d.2e.3a.4b.5b.6a, 1d.2e.3a.4b.5b.6b, 1d.2e.3a.4b.5b.6c,
1d.2e.3a.4b.5b.6d, 1d.2e.3a.4b.5b.6e, 1d.2e.3a.4b.5c.6a, 1d.2e.3a.4b.5c.6b,
1d.2e.3a.4b.5c.6c, 1d.2e.3a.4b.5c.6d, 1d.2e.3a.4b.5c.6e, 1d.2e.3a.4b.5d.6a,
1d.2e.3a.4b.5d.6b, 1d.2e.3a.4b.5d.6c, 1d.2e.3a.4b.5d.6d, 1d.2e.3a.4b.5d.6e,
1d.2e.3a.4b.5e.6a, 1d.2e.3a.4b.5e.6b, 1d.2e.3a.4b.5e.6c, 1d.2e.3a.4b.5e.6d,
1d.2e.3a.4b.5e.6e, 1d.2e.3a.4c.5a.6a, 1d.2e.3a.4c.5a.6b, 1d.2e.3a.4c.5a.6c,
1d.2e.3a.4c.5a.6d, 1d.2e.3a.4c.5a.6e, 1d.2e.3a.4c.5b.6a, 1d.2e.3a.4c.5b.6b,
1d.2e.3a.4c.5b.6c, 1d.2e.3a.4c.5b.6d, 1d.2e.3a.4c.5b.6e, 1d.2e.3a.4c.5c.6a,
1d.2e.3a.4c.5c.6b, 1d.2e.3a.4c.5c.6c, 1d.2e.3a.4c.5c.6d, 1d.2e.3a.4c.5c.6e,
1d.2e.3a.4c.5d.6a, 1d.2e.3a.4c.5d.6b, 1d.2e.3a.4c.5d.6c, 1d.2e.3a.4c.5d.6d,
1d.2e.3a.4c.5d.6e, 1d.2e.3a.4c.5e.6a, 1d.2e.3a.4c.5e.6b, 1d.2e.3a.4c.5e.6c,
1d.2e.3a.4c.5e.6d, 1d.2e.3a.4c.5e.6e, 1d.2e.3a.4d.5a.6a, 1d.2e.3a.4d.5a.6b,
1d.2e.3a.4d.5a.6c, 1d.2e.3a.4d.5a.6d, 1d.2e.3a.4d.5a.6e, 1d.2e.3a.4d.5b.6a,
1d.2e.3a.4d.5b.6b, 1d.2e.3a.4d.5b.6c, 1d.2e.3a.4d.5b.6d, 1d.2e.3a.4d.5b.6e,
1d.2e.2a.4d.5c.6a, 1d.2e.3a.4d.5c.6b, 1d.2e.3a.4d.5c.6c, 1d.2e.3a.4d.5c.6d,
1d.2e.3a.4d.5c.6e, 1d.2e.3a.4d.5d.6a, 1d.2e.3a.4d.5d.6b, 1d.2e.3a.4d.5d.6c,
1d.2e.3a.4d.5d.6d, 1d.2e.3a.4d.5d.6e, 1d.2e.3a.4d.5e.6a, 1d.2e.3a.4d.5e.6b,
1d.2e.3a.4d.5e.6c, 1d.2e.3a.4d.5e.6d, 1d.2e.3a.4d.5e.6e, 1d.2e.3a.4e.5a.6a,
1d.2e.3a.4e.5a.6b, 1d.2e.3a.4e.5a.6c, 1d.2e.3a.4e.5a.6d, 1d.2e.3a.4e.5a.6e,
1d.2e.3a.4e.5b.6a, 1d.2e.3a.4e.5b.6b, 1d.2e.3a.4e.5b.6c, 1d.2e.3a.4e.5b.6d,
1d.2e.3a.4e.5b.6e, 1d.2e.3a.4e.5c.6a, 1d.2e.3a.4e.5c.6b, 1d.2e.3a.4e.5c.6c,
1d.2e.3a.4e.5c.6d, 1d.2e.3a.4e.5c.6e, 1d.2e.3a.4e.5d.6a, 1d.2e.3a.4e.5d.6b,
1d.2e.3a.4e.5d.6c, 1d.2e.3a.4e.5d.6d, 1d.2e.3a.4e.5d.6e, 1d.2e.3a.4e.5e.6a,
1d.2e.3a.4e.5e.6b, 1d.2e.3a.4e.5e.6c, 1d.2e.3a.4e.5e.6d, 1d.2e.3a.4e.5e.6e,
1d.2e.3b.4a.5a.6a, 1d.2e.3b.4a.5a.6b, 1d.2e.3b.4a.5a.6c, 1d.2e.3b.4a.5a.6d,
1d.2e.3b.4a.5a.6e, 1d.2e.3b.4a.5b.6a, 1d.2e.3b.4a.5b.6b, 1d.2e.3b.4a.5b.6c,
1d.2e.3b.4a.5b.6d, 1d.2e.3b.4a.5b.6e, 1d.2e.3b.4a.5c.6a, 1d.2e.3b.4a.5c.6b,
1d.2e.3b.4a.5c.6c, 1d.2e.3b.4a.5c.6d, 1d.2e.3b.4a.5c.6e, 1d.2e.3b.4a.5d.6a,
1d.2e.3b.4a.5d.6b, 1d.2e.3b.4a.5d.6c, 1d.2e.3b.4a.5d.6d, 1d.2e.3b.4a.5d.6e,
1d.2e.3b.4a.5e.6a, 1d.2e.3b.4a.5e.6b, 1d.2e.3b.4a.5e.6c, 1d.2e.3b.4a.5e.6d,

TABLE 8-continued

List of Compounds of Formula (II)

1d.2e.3b.4a.5e.6e, 1d.2e.3b.4b.5a.6a, 1d.2e.3b.4b.5a.6b, 1d.2e.3b.4b.5a.6c,
1d.2e.3b.4b.5a.6d, 1d.2e.3b.4b.5a.6e, 1d.2e.3b.4b.5b.6a, 1d.2e.3b.4b.5b.6b,
1d.2e.3b.4b.5b.6c, 1d.2e.3b.4b.5b.6d, 1d.2e.3b.4b.5b.6e, 1d.2e.3b.4b.5c.6a,
1d.2e.3b.4b.5c.6b, 1d.2e.3b.4b.5c.6c, 1d.2e.3b.4b.5c.6d, 1d.2e.3b.4b.5c.6e,
1d.2e.3b.4b.5d.6a, 1d.2e.3b.4b.5d.6b, 1d.2e.3b.4b.5d.6c, 1d.2e.3b.4b.5d.6d,
1d.2e.3b.4b.5d.6e, 1d.2e.3b.4b.5e.6a, 1d.2e.3b.4b.5e.6b, 1d.2e.3b.4b.5e.6c,
1d.2e.3b.4b.5e.6d, 1d.2e.3b.4b.5e.6e, 1d.2e.3b.4c.5a.6a, 1d.2e.3b.4c.5a.6b,
1d.2e.3b.4c.5a.6c, 1d.2e.3b.4c.5a.6d, 1d.2e.3b.4c.5a.6e, 1d.2e.3b.4c.5b.6a,
1d.2e.3b.4c.5b.6b, 1d.2e.3b.4c.5b.6c, 1d.2e.3b.4c.5b.6d, 1d.2e.3b.4c.5b.6e,
1d.2e.3b.4c.5c.6a, 1d.2e.3b.4c.5c.6b, 1d.2e.3b.4c.5c.6c, 1d.2e.3b.4c.5c.6d,
1d.2e.3b.4c.5c.6e, 1d.2e.3b.4c.5d.6a, 1d.2e.3b.4c.5d.6b, 1d.2e.3b.4c.5d.6c,
1d.2e.3b.4c.5d.6d, 1d.2e.3b.4c.5d.6e, 1d.2e.3b.4c.5e.6a, 1d.2e.3b.4c.5e.6b,
1d.2e.3b.4c.5e.6c, 1d.2e.3b.4c.5e.6d, 1d.2e.3b.4c.5e.6e, 1d.2e.3b.4d.5a.6a,
1d.2e.3b.4d.5a.6b, 1d.2e.3b.4d.5a.6c, 1d.2e.3b.4d.5a.6d, 1d.2e.3b.4d.5a.6e,
1d.2e.3b.4d.5b.6a, 1d.2e.3b.4d.5b.6b, 1d.2e.3b.4d.5b.6c, 1d.2e.3b.4d.5b.6d,
1d.2e.3b.4d.5b.6e, 1d.2e.3b.4d.5c.6a, 1d.2e.3b.4d.5c.6b, 1d.2e.3b.4d.5c.6c,
1d.2e.3b.4d.5c.6d, 1d.2e.3b.4d.5c.6e, 1d.2e.3b.4d.5d.6a, 1d.2e.3b.4d.5d.6b,
1d.2e.3b.4d.5d.6c, 1d.2e.3b.4d.5d.6d, 1d.2e.3b.4d.5d.6e, 1d.2e.3b.4d.5e.6a,
1d.2e.3b.4d.5e.6b, 1d.2e.3b.4d.5e.6c, 1d.2e.3b.4d.5e.6d, 1d.2e.3b.4d.5e.6e,
1d.2e.3b.4e.5a.6a, 1d.2e.3b.4e.5a.6b, 1d.2e.3b.4e.5a.6c, 1d.2e.3b.4e.5a.6d,
1d.2e.3b.4e.5a.6e, 1d.2e.3b.4e.5b.6a, 1d.2e.3b.4e.5b.6b, 1d.2e.3b.4e.5b.6c,
1d.2e.3b.4e.5b.6d, 1d.2e.3b.4e.5b.6e, 1d.2e.3b.4e.5c.6a, 1d.2e.3b.4e.5c.6b,
1d.2e.3b.4e.5c.6c, 1d.2e.3b.4e.5c.6d, 1d.2e.3b.4e.5c.6e, 1d.2e.3b.4e.5d.6a,
1d.2e.3b.4e.5d.6b, 1d.2e.3b.4e.5d.6c, 1d.2e.3b.4e.5d.6d, 1d.2e.3b.4e.5d.6e,
1d.2e.3b.4e.5e.6a, 1d.2e.3b.4e.5e.6b, 1d.2e.3b.4e.5e.6c, 1d.2e.3b.4e.5e.6d,
1d.2e.3b.4e.5e.6e, 1d.2e.3c.4a.5a.6a, 1d.2e.3c.4a.5a.6b, 1d.2e.3c.4a.5a.6c,
1d.2e.3c.4a.5a.6d, 1d.2e.3c.4a.5a.6e, 1d.2e.3c.4a.5b.6a, 1d.2e.3c.4a.5b.6b,
1d.2e.3c.4a.5b.6c, 1d.2e.3c.4a.5b.6d, 1d.2e.3c.4a.5b.6e, 1d.2e.3c.4a.5c.6a,
1d.2e.3c.4a.5c.6b, 1d.2e.3c.4a.5c.6c, 1d.2e.3c.4a.5c.6d, 1d.2e.3c.4a.5c.6e,
1d.2e.3c.4a.5d.6a, 1d.2e.3c.4a.5d.6b, 1d.2e.3c.4a.5d.6c, 1d.2e.3c.4a.5d.6d,
1d.2e.3c.4a.5d.6e, 1d.2e.3c.4a.5e.6a, 1d.2e.3c.4a.5e.6b, 1d.2e.3c.4a.5e.6c,
1d.2e.3c.4a.5e.6d, 1d.2e.3c.4a.5e.6e, 1d.2e.3c.4b.5a.6a, 1d.2e.3c.4b.5a.6b,
1d.2e.3c.4b.5a.6c, 1d.2e.3c.4b.5a.6d, 1d.2e.3c.4b.5a.6e, 1d.2e.3c.4b.5b.6a,
1d.2e.3c.4b.5b.6b, 1d.2e.3c.4b.5b.6c, 1d.2e.3c.4b.5b.6d, 1d.2e.3c.4b.5b.6e,
1d.2e.3c.4b.5c.6a, 1d.2e.3c.4b.5c.6b, 1d.2e.3c.4b.5c.6c, 1d.2e.3c.4b.5c.6d,
1d.2e.3c.4b.5c.6e, 1d.2e.3c.4b.5d.6a, 1d.2e.3c.4b.5d.6b, 1d.2e.3c.4b.5d.6c,
1d.2e.3c.4b.5d.6d, 1d.2e.3c.4b.5d.6e, 1d.2e.3c.4b.5e.6a, 1d.2e.3c.4b.5e.6b,
1d.2e.3c.4b.5e.6c, 1d.2e.3c.4b.5e.6d, 1d.2e.3c.4b.5e.6e, 1d.2e.3c.4c.5a.6a,
1d.2e.3c.4c.5a.6b, 1d.2e.3c.4c.5a.6c, 1d.2e.3c.4c.5a.6d, 1d.2e.3c.4c.5a.6e,
1d.2e.3c.4c.5b.6a, 1d.2e.3c.4c.5b.6b, 1d.2e.3c.4c.5b.6c, 1d.2e.3c.4c.5b.6d,
1d.2e.3c.4c.5b.6e, 1d.2e.3c.4c.5c.6a, 1d.2e.3c.4c.5c.6b, 1d.2e.3c.4c.5c.6c,
1d.2e.3c.4c.5c.6d, 1d.2e.3c.4c.5c.6e, 1d.2e.3c.4c.5d.6a, 1d.2e.3c.4c.5d.6b,
1d.2e.3c.4c.5d.6c, 1d.2e.3c.4c.5d.6d, 1d.2e.3c.4c.5d.6e, 1d.2e.3c.4c.5e.6a,
1d.2e.3c.4c.5e.6b, 1d.2e.3c.4c.5e.6c, 1d.2e.3c.4c.5e.6d, 1d.2e.3c.4c.5e.6e,
1d.2e.3c.4d.5a.6a, 1d.2e.3c.4d.5a.6b, 1d.2e.3c.4d.5a.6c, 1d.2e.3c.4d.5a.6d,
1d.2e.3c.4d.5a.6e, 1d.2e.3c.4d.5b.6a, 1d.2e.3c.4d.5b.6b, 1d.2e.3c.4d.5b.6c,
1d.2e.3c.4d.5b.6d, 1d.2e.3c.4d.5b.6e, 1d.2e.3c.4d.5c.6a, 1d.2e.3c.4d.5c.6b,
1d.2e.3c.4d.5c.6c, 1d.2e.3c.4d.5c.6d, 1d.2e.3c.4d.5c.6e, 1d.2e.3c.4d.5d.6a,
1d.2e.3c.4d.5d.6b, 1d.2e.3c.4d.5d.6c, 1d.2e.3c.4d.5d.6d, 1d.2e.3c.4d.5d.6e,
1d.2e.3c.4d.5e.6a, 1d.2e.3c.4d.5e.6b, 1d.2e.3c.4d.5e.6c, 1d.2e.3c.4d.5e.6d,
1d.2e.3c.4d.5e.6e, 1d.2e.3c.4e.5a.6a, 1d.2e.3c.4e.5a.6b, 1d.2e.3c.4e.5a.6c,
1d.2e.3c.4e.5a.6d, 1d.2e.3c.4e.5a.6e, 1d.2e.3c.4e.5b.6a, 1d.2e.3c.4e.5b.6b,
1d.2e.3c.4e.5b.6c, 1d.2e.3c.4e.5b.6d, 1d.2e.3c.4e.5b.6e, 1d.2e.3c.4e.5c.6a,
1d.2e.3c.4e.5c.6b, 1d.2e.3c.4e.5c.6c, 1d.2e.3c.4e.5c.6d, 1d.2e.3c.4e.5c.6e,
1d.2e.3c.4e.5d.6a, 1d.2e.3c.4e.5d.6b, 1d.2e.3c.4e.5d.6c, 1d.2e.3c.4e.5d.6d,
1d.2e.3c.4e.5d.6e, 1d.2e.3c.4e.5e.6a, 1d.2e.3c.4e.5e.6b, 1d.2e.3c.4e.5e.6c,
1d.2e.3c.4e.5e.6d, 1d.2e.3c.4e.5e.6e, 1d.2e.3d.4a.5a.6a, 1d.2e.3d.4a.5a.6b,
1d.2e.3d.4a.5a.6c, 1d.2e.3d.4a.5a.6d, 1d.2e.3d.4a.5a.6e, 1d.2e.3d.4a.5b.6a,
1d.2e.3d.4a.5b.6b, 1d.2e.3d.4a.5b.6c, 1d.2e.3d.4a.5b.6d, 1d.2e.3d.4a.5b.6e,
1d.2e.3d.4a.5c.6a, 1d.2e.3d.4a.5c.6b, 1d.2e.3d.4a.5c.6c, 1d.2e.3d.4a.5c.6d,
1d.2e.3d.4a.5c.6e, 1d.2e.3d.4a.5d.6a, 1d.2e.3d.4a.5d.6b, 1d.2e.3d.4a.5d.6c,
1d.2e.3d.4a.5d.6d, 1d.2e.3d.4a.5d.6e, 1d.2e.3d.4a.5e.6a, 1d.2e.3d.4a.5e.6b,
1d.2e.3d.4a.5e.6c, 1d.2e.3d.4a.5e.6d, 1d.2e.3d.4a.5e.6e, 1d.2e.3d.4b.5a.6a,
1d.2e.3d.4b.5a.6b, 1d.2e.3d.4b.5a.6c, 1d.2e.3d.4b.5a.6d, 1d.2e.3d.4b.5a.6e,
1d.2e.3d.4b.5b.6a, 1d.2e.3d.4b.5b.6b, 1d.2e.3d.4b.5b.6c, 1d.2e.3d.4b.5b.6d,
1d.2e.3d.4b.5b.6e, 1d.2e.3d.4b.5c.6a, 1d.2e.3d.4b.5c.6b, 1d.2e.3d.4b.5c.6c,
1d.2e.3d.4b.5c.6d, 1d.2e.3d.4b.5c.6e, 1d.2e.3d.4b.5d.6a, 1d.2e.3d.4b.5d.6b,
1d.2e.3d.4b.5d.6c, 1d.2e.3d.4b.5d.6d, 1d.2e.3d.4b.5d.6e, 1d.2e.3d.4b.5e.6a,
1d.2e.3d.4b.5e.6b, 1d.2e.3d.4b.5e.6c, 1d.2e.3d.4b.5e.6d, 1d.2e.3d.4b.5e.6e,
1d.2e.3d.4c.5a.6a, 1d.2e.3d.4c.5a.6b, 1d.2e.3d.4c.5a.6c, 1d.2e.3d.4c.5a.6d,
1d.2e.3d.4c.5a.6e, 1d.2e.3d.4c.5b.6a, 1d.2e.3d.4c.5b.6b, 1d.2e.3d.4c.5b.6c,
1d.2e.3d.4c.5b.6d, 1d.2e.3d.4c.5b.6e, 1d.2e.3d.4c.5c.6a, 1d.2e.3d.4c.5c.6b,
1d.2e.3d.4c.5c.6c, 1d.2e.3d.4c.5c.6d, 1d.2e.3d.4c.5c.6e, 1d.2e.3d.4c.5d.6a,
1d.2e.3d.4c.5d.6b, 1d.2e.3d.4c.5d.6c, 1d.2e.3d.4c.5d.6d, 1d.2e.3d.4c.5d.6e,
1d.2e.3d.4c.5e.6a, 1d.2e.3d.4c.5e.6b, 1d.2e.3d.4c.5e.6c, 1d.2e.3d.4c.5e.6d,
1d.2e.3d.4c.5e.6e, 1d.2e.3d.4d.5a.6a, 1d.2e.3d.4d.5a.6b, 1d.2e.3d.4d.5a.6c,
1d.2e.3d.4d.5a.6d, 1d.2e.3d.4d.5a.6e, 1d.2e.3d.4d.5b.6a, 1d.2e.3d.4d.5b.6b,
1d.2e.3d.4d.5b.6c, 1d.2e.3d.4d.5b.6d, 1d.2e.3d.4d.5b.6e, 1d.2e.3d.4d.5c.6a,

TABLE 8-continued

List of Compounds of Formula (II)

1d.2e.3d.4d.5c.6b, 1d.2e.3d.4d.5c.6c, 1d.2e.3d.4d.5c.6d, 1d.2e.3d.4d.5c.6e,
1d.2e.3d.4d.5d.6a, 1d.2e.3d.4d.5d.6b, 1d.2e.3d.4d.5d.6c, 1d.2e.3d.4d.5d.6d,
1d.2e.3d.4d.5d.6e, 1d.2e.3d.4d.5e.6a, 1d.2e.3d.4d.5e.6b, 1d.2e.3d.4d.5e.6c,
1d.2e.3d.4d.5e.6d, 1d.2e.3d.4d.5e.6e, 1d.2e.3d.4e.5a.6a, 1d.2e.3d.4e.5a.6b,
1d.2e.3d.4e.5a.6c, 1d.2e.3d.4e.5a.6d, 1d.2e.3d.4e.5a.6e, 1d.2e.3d.4e.5b.6a,
1d.2e.3d.4e.5b.6b, 1d.2e.3d.4e.5b.6c, 1d.2e.3d.4e.5b.6d, 1d.2e.3d.4e.5b.6e,
1d.2e.3d.4e.5c.6a, 1d.2e.3d.4e.5c.6b, 1d.2e.3d.4e.5c.6c, 1d.2e.3d.4e.5c.6d,
1d.2e.3d.4e.5c.6e, 1d.2e.3d.4e.5d.6a, 1d.2e.3d.4e.5d.6b, 1d.2e.3d.4e.5d.6c,
1d.2e.3d.4e.5d.6d, 1d.2e.3d.4e.5d.6e, 1d.2e.3d.4e.5e.6a, 1d.2e.3d.4e.5e.6b,
1d.2e.3d.4e.5e.6c, 1d.2e.3d.4e.5e.6d, 1d.2e.3d.4e.5e.6e, 1d.2e.3e.4a.5a.6a,
1d.2e.3e.4a.5a.6b, 1d.2e.3e.4a.5a.6c, 1d.2e.3e.4a.5a.6d, 1d.2e.3e.4a.5a.6e,
1d.2e.3e.4a.5b.6a, 1d.2e.3e.4a.5b.6b, 1d.2e.3e.4a.5b.6c, 1d.2e.3e.4a.5b.6d,
1d.2e.3e.4a.5b.6e, 1d.2e.3e.4a.5c.6a, 1d.2e.3e.4a.5c.6b, 1d.2e.3e.4a.5c.6c,
1d.2e.3e.4a.5c.6d, 1d.2e.3e.4a.5c.6e, 1d.2e.3e.4a.5d.6a, 1d.2e.3e.4a.5d.6b,
1d.2e.3e.4a.5d.6c, 1d.2e.3e.4a.5d.6d, 1d.2e.3e.4a.5d.6e, 1d.2e.3e.4a.5e.6a,
1d.2e.3e.4a.5e.6b, 1d.2e.3e.4a.5e.6c, 1d.2e.3e.4a.5e.6d, 1d.2e.3e.4a.5e.6e,
1d.2e.3e.4b.5a.6a, 1d.2e.3e.4b.5a.6b, 1d.2e.3e.4b.5a.6c, 1d.2e.3e.4b.5a.6d,
1d.2e.3e.4b.5a.6e, 1d.2e.3e.4b.5b.6a, 1d.2e.3e.4b.5b.6b, 1d.2e.3e.4b.5b.6c,
1d.2e.3e.4b.5b.6d, 1d.2e.3e.4b.5b.6e, 1d.2e.3e.4b.5c.6a, 1d.2e.3e.4b.5c.6b,
1d.2e.3e.4b.5c.6c, 1d.2e.3e.4b.5c.6d, 1d.2e.3e.4b.5c.6e, 1d.2e.3e.4b.5d.6a,
1d.2e.3e.4b.5d.6b, 1d.2e.3e.4b.5d.6c, 1d.2e.3e.4b.5d.6d, 1d.2e.3e.4b.5d.6e,
1d.2e.3e.4b.5e.6a, 1d.2e.3e.4b.5e.6b, 1d.2e.3e.4b.5e.6c, 1d.2e.3e.4b.5e.6d,
1d.2e.3e.4b.5e.6e, 1d.2e.3e.4c.5a.6a, 1d.2e.3e.4c.5a.6b, 1d.2e.3e.4c.5a.6c,
1d.2e.3e.4c.5a.6d, 1d.2e.3e.4c.5a.6e, 1d.2e.3e.4c.5b.6a, 1d.2e.3e.4c.5b.6b,
1d.2e.3e.4c.5b.6c, 1d.2e.3e.4c.5b.6d, 1d.2e.3e.4c.5b.6e, 1d.2e.3e.4c.5c.6a,
1d.2e.3e.4c.5c.6b, 1d.2e.3e.4c.5c.6c, 1d.2e.3e.4c.5c.6d, 1d.2e.3e.4c.5c.6e,
1d.2e.3e.4c.5d.6a, 1d.2e.3e.4c.5d.6b, 1d.2e.3e.4c.5d.6c, 1d.2e.3e.4c.5d.6d,
1d.2e.3e.4c.5d.6e, 1d.2e.3e.4c.5e.6a, 1d.2e.3e.4c.5e.6b, 1d.2e.3e.4c.5e.6c,
1d.2e.3e.4c.5e.6d, 1d.2e.3e.4c.5e.6e, 1d.2e.3e.4d.5a.6a, 1d.2e.3e.4d.5a.6b,
1d.2e.3e.4d.5a.6c, 1d.2e.3e.4d.5a.6d, 1d.2e.3e.4d.5a.6e, 1d.2e.3e.4d.5b.6a,
1d.2e.3e.4d.5b.6b, 1d.2e.3e.4d.5b.6c, 1d.2e.3e.4d.5b.6d, 1d.2e.3e.4d.5b.6e,
1d.2e.3e.4d.5c.6a, 1d.2e.3e.4d.5c.6b, 1d.2e.3e.4d.5c.6c, 1d.2e.3e.4d.5c.6d,
1d.2e.3e.4d.5c.6e, 1d.2e.3e.4d.5d.6a, 1d.2e.3e.4d.5d.6b, 1d.2e.3e.4d.5d.6c,
1d.2e.3e.4d.5d.6d, 1d.2e.3e.4d.5d.6e, 1d.2e.3e.4d.5e.6a, 1d.2e.3e.4d.5e.6b,
1d.2e.3e.4d.5e.6c, 1d.2e.3e.4d.5e.6d, 1d.2e.3e.4d.5e.6e, 1d.2e.3e.4e.5a.6a,
1d.2e.3e.4e.5a.6b, 1d.2e.3e.4e.5a.6c, 1d.2e.3e.4e.5a.6d, 1d.2e.3e.4e.5a.6e,
1d.2e.3e.4e.5b.6a, 1d.2e.3e.4e.5b.6b, 1d.2e.3e.4e.5b.6c, 1d.2e.3e.4e.5b.6d,
1d.2e.3e.4e.5b.6e, 1d.2e.3e.4e.5c.6a, 1d.2e.3e.4e.5c.6b, 1d.2e.3e.4e.5c.6c,
1d.2e.3e.4e.5c.6d, 1d.2e.3e.4e.5c.6e, 1d.2e.3e.4e.5d.6a, 1d.2e.3e.4e.5d.6b,
1d.2e.3e.4e.5d.6c, 1d.2e.3e.4e.5d.6d, 1d.2e.3e.4e.5d.6e, 1d.2e.3e.4e.5e.6a,
1d.2e.3e.4e.5e.6b, 1d.2e.3e.4e.5e.6c, 1d.2e.3e.4e.5e.6d, 1d.2e.3e.4e.5e.6e.

EXAMPLES

Example A

Scheme 1

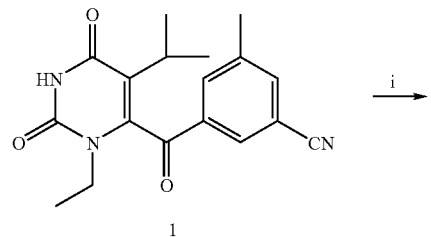

1

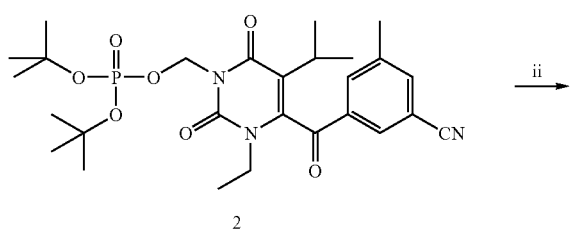

2

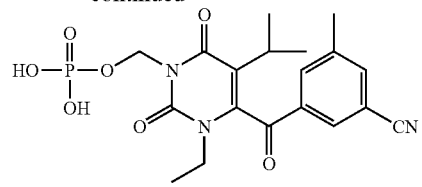

A

Reagents and Conditions: i. di-tert-butylchloromethyl phosphate, potassium carbonate, DMF; ii. TFA, $CH_2Cl_2$.

Synthesis of Phosphoric acid di-tert-butyl ester 4-(3-cyano-5-methyl-benzoyl)-3-ethyl-5-isopropyl-2,6-dioxo-3,6-dihydro-2H-pyrimidin-1-ylmethyl ester (2)

To a mixture of cesium carbonate (53.1 mg, 0.163 mmol), 3-(3-ethyl-5-isopropyl-2,6-dioxo-1,2,3,6-tetrahydro-pyrimidine-4-carbonyl)-5-methyl-benzonitrile (1) (44.2 mg, 0.136 mmol) in DMF (0.7 mL) was added phosphoric acid di-tert-butyl chloromethyl phosphate (42.2, 0.163 mmol, prepared according to Mantyla et al. *Tet. Lett.* 2002, 43, 3793-3794) and the reaction mixture was stirred for 72 h at 50° C. The reaction mixture was partioned between ethyl acetate and brine. The organic layer was removed, dried ($MgSO_4$), concentrated and purified by reverse phase HPLC (Phenomenex Synergi® column, 5 to 100% acetonitrile/H$_2$O) to give a colorless film after concentration (45.1 mg, 61%). $^1$H NMR (300 MHz, CDCl$_3$): 8.11 (s, 1H), 7.99 (s, 1H), 7.80 (s, 1H), 5.9-5.7 (m, 2H), 3.95-3.85 (m, 1H), 3.2-3.1 (m, 1H), 2.54 (s, 3H), 2.3-2.1 (m, 1H), 1.54 (s, 18H), 1.3-1.0 (m, 9H). Mass spectrum: 570.0 (M+Na).

Synthesis of Example A

To a solution of phosphoric acid di-tert-butyl ester 4-(3-cyano-5-methyl-benzoyl)-3-ethyl-5-isopropyl-2,6-dioxo-3,6-dihydro-2H-pyrimidin-1-ylmethyl ester (2) (45.1 mg, 0.0823 mmol) in dichloromethane (0.5 mL) at 0° C. was added TFA (0.5 mL). After 30 min, the reaction mixture was concentrated and purified by reverse phase HPLC (Phenomenex Synergi® column, 5 to 100% acetonitrile/H$_2$O) to give a white powder after lyophilization (22.5 mg, 64%). $^1$H NMR (300 MHz, CD$_3$OD): 8.29 (s, 1H), 8.21 (s, 1H), 7.99 (s, 1H), 5.86 (d, J=7.5 Hz, 2H), 4.0-3.8 (m, 1H), 3.4-3.2 (m, 1H), 2.52 (s, 3H), 2.3-2.1 (m, 1H), 1.19 (d, J=6.6 Hz, 3H), 1.3-1.0 (m, 6H). Mass spectrum: 435.9 (M+H).

Example B

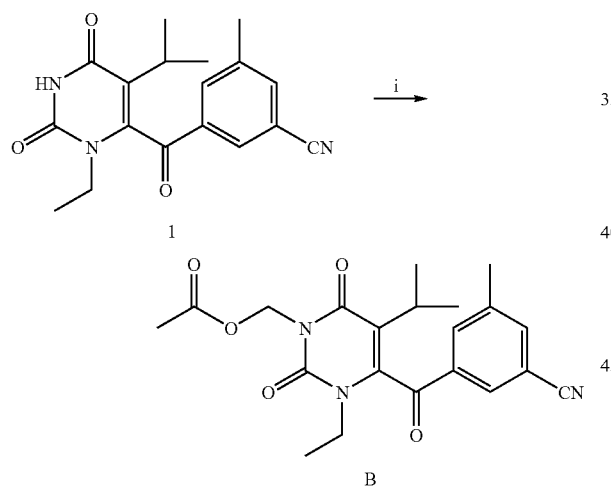

Reagents and Conditions: i. acetic acid bromomethyl ester, potassium carbonate, DMF

Synthesis of Example B

To a mixture of potassium carbonate (96 mg, 0.695 mmol), 3-(3-ethyl-5-isopropyl-2,6-dioxo-1,2,3,6-tetrahydro-pyrimidine-4-carbonyl)-5-methyl-benzonitrile (1) (226 mg, 0.695 mmol) in DMF (7 mL) was added acetic acid bromomethyl ester (68 uL, 0.695 mmol). The reaction mixture was stirred at room temperature overnight. Ethyl acetate was added to the reaction mixture and washed with brine. The organic layer was concentrated and purified by silica column (ethyl acetate/hexane) to give a white solid (176 mg, 64%). $^1$H NMR (300 MHz, CDCl$_3$): 8.06 (s, 1H), 7.99 (s, 1H), 7.81 (s, 1H), 6.02 (s, 2H), 3.91 (m, 1H), 3.20 (m, 1H), 2.54 (s, 3H), 2.24 (m, 1H), 2.15 (s, 3H), 1.3-1.1 (m, 6H). Mass spectrum: 397.9 (M+1).

Example C

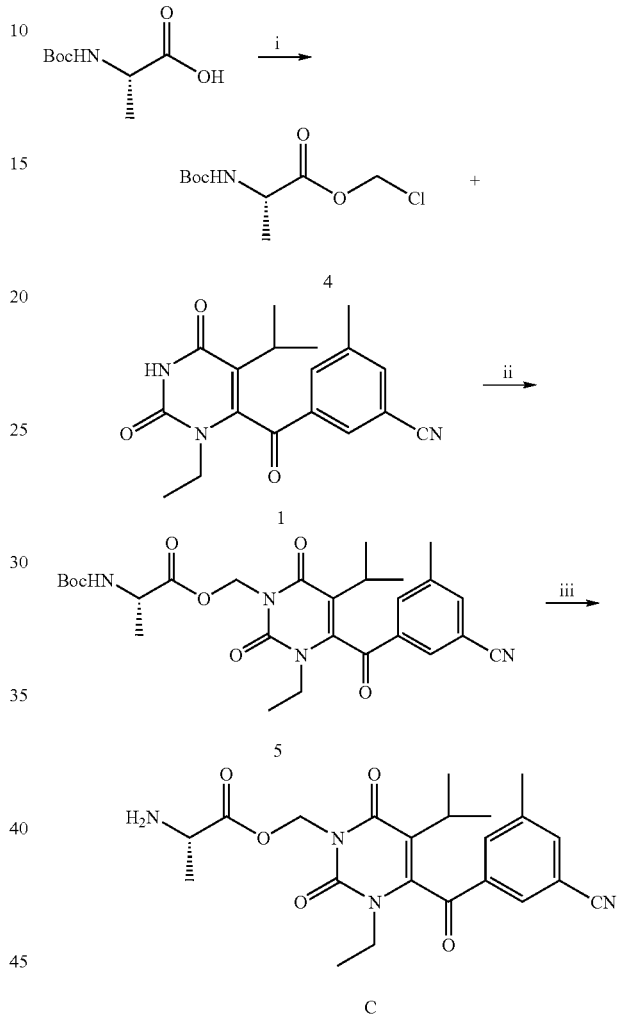

Reagents and conditions: i. Chloromethyl chlorosulfate, NaHCO3, tetrabutylammonium hydrogen sulfate, H2O/CH2Cl2, 97%; ii. K2CO3, tetrabutylammonium iodide, DMF, 71%; iii. 4N HCl, dioxane.

Synthesis of 2-tert-Butoxycarbonylamino-propionic acid chloromethyl ester (4)

To a solution of 2-tert-butoxycarbonylamino-propionic acid (0.507 g, 2.68 mol), sodium bicarbonate (1.13 g, 13.4 mmol) and tetrabutylammonium hydrogen sulfate (0.090 g, 0.268 mmol) in H$_2$O (21 mL) at 0° C. was added dichloromethane (12 mL) and the mixture was stirred vigorously. Chloromethyl chlorosulfate (0.326 mL, 3.22 mmol) in dichloromethane (7 mL) was added and the mixture was warmed to rt overnight. The reaction mixture was diluted with ethyl acetate, washed with brine, dried (MgSO$_4$) and concentrated. The resulting oil was purified by flash column chromatography (silica gel, 0 to 30% ethyl acetate/hexane) to give a colorless oil (4) (0.6207 g, 97%). $^1$H NMR (300 MHz, CDCl₃): 5.75 (d, J=5.4 Hz, 1H), 5.57 (d, J=5.4 Hz, 1H), 5.04 (br s, 1H), 4.28 (m, 1H), 1.37 (s, 9H), 1.32 (s, 3H).

Synthesis of 2-tert-Butoxycarbonylamino-propionic acid 4-(3-cyano-5-methyl-benzoyl)-3-ethyl-5-isopropyl-2,6-dioxo-3,6-dihydro-2H-pyrimidin-1-ylmethyl ester (5)

To a solution of 2-tert-butoxycarbonylamino-propionic acid chloromethyl ester (4) (0.6207 g, 2.61 mmol) and 3-(3-ethyl-5-isopropyl-2,6-dioxo-1,2,3,6-tetrahydro-pyrimidine-4-carbonyl)-5-methyl-benzonitrile (0.780 g, 2.40 mmol) in DMF (10 mL) was added K₂CO₃ and tetrabutylammonium iodide (0.193 g, 0.522 mmol), and the reaction mixture stirred for 48 h. The reaction mixture was concentrated, diluted with ethyl acetate and washed with H₂O (2×), brine, dried (MgSO₄) and concentrated. The residue was purified by flash column chromatography (silica gel, 0 to 50% ethyl acetate/hexane) to give a yellow foam (5) (0.9028 g, 71%). ¹H NMR (300 MHz, CDCl₃): 8.01 (s, 1H), 7.94 (s, 1H), 7.77 (s, 1H), 6.1-5.9 (m, 2H), 5.05 (br s, 1H), 4.32 (br s, 1H), 3.9-3.8 (m, 1H), 3.2-3.1 (m, 1H), 2.49 (s, 3H), 2.2-2.1 (m, 1H), 1.39 (s, 9H), 1.37 (s, 3H), 1.2-1.1 (m, 9H). Mass spectrum: 549.1 (M+Na).

Synthesis of Example C

A solution of 2-tert-butoxycarbonylamino-propionic acid 4-(3-cyano-5-methyl-benzoyl)-3-ethyl-5-isopropyl-2,6-dioxo-3,6-dihydro-2H-pyrimidin-1-ylmethyl ester (5) (0.9033 g, 1.71 mmol) in 4N HCl in dioxane (9.5 mL) was stirred at 0° C. for 4 h, then concentrated. The residue was purified by reverse phase HPLC (Phenomenex Synergi® column, 5 to 100% acetonitrile/H₂O+0.1% HCl) to give a white powder (C) (0.559 g, 71%). ¹H NMR (300 MHz, CD₃OD): 8.2 (s, 1H), 8.14 (s, 1H), 7.90 (s, 1H), 6.04 (s, 2H), 4.09 (br s, 1H), 3.82 (br s, 1H), 3.12 (br s, 1H), 2.44 (s, 3H), 2.17 (br s, 1H), 1.48 (br s, 3H), 1.1-1.0 (m, 9H), 1.39 (s, 9H). Mass spectrum: 427.0 (M+H).

Example D

Scheme 4

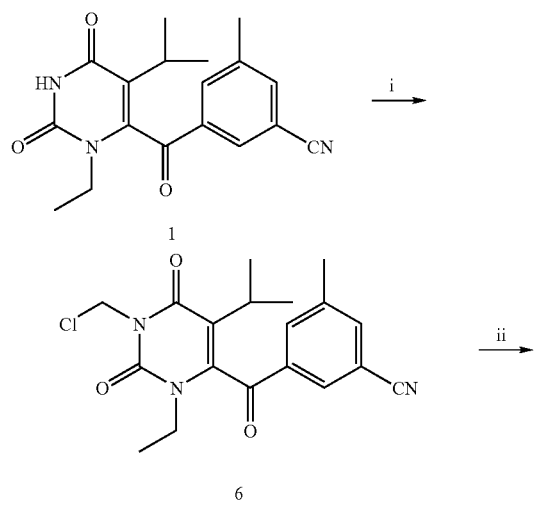

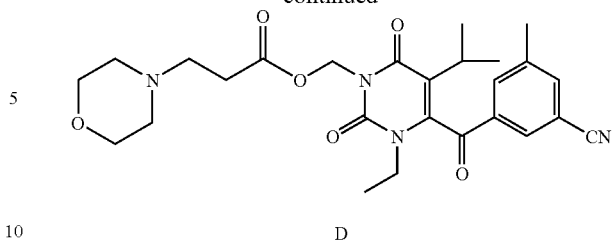

D

Reagents and conditions: i. bromo-iodo-methane, potassium carbonate, DMF; ii. 3-morpholin-4-yl-propionic acid HCl salt, cesium carbonate, DMF.

Synthesis of 3-(1-Chloromethyl-3-ethyl-5-isopropyl-2,6-dioxo-1,2,3,6-tetrahydro-pyrimidine-4-carbonyl)-5-methyl-benzonitrile (6)

To a mixture of potassium carbonate (1.52 g, 11.05 mmol, 3 eq.), 3-(3-ethyl-5-isopropyl-2,6-dioxo-1,2,3,6-tetrahydro-pyrimidine-4-carbonyl)-5-methyl-benzonitrile (1) (1199 mg, 3.68 mmol, 1 eq.) in DMF (15 mL) was added bromo-iodo-methane (9.8 mL, 40 eq.). The reaction mixture was stirred at room temperature overnight. Ethyl acetate was added to the reaction mixture and washed with brine. The organic layer was concentrated and purified by silica column (ethyl acetate/hexane) to give a white solid (6) (590 mg, 43%). ¹H NMR (300 MHz, CDCl₃): 8.04 (s, 1H), 7.96 (s, 1H), 7.80 (s, 1H), 5.80 (s, 2H), 3.91 (m, 1H), 3.20 (m, 1H), 2.54 (s, 3H), 2.24 (m, 1H), 1.3-1.1 (m, 9H). Mass spectrum: 374.7 (M+1).

Synthesis of Example D

To a mixture of cesium carbonate (1.18 g, 3.63 mmol, 2.3 eq.), 3-(1-chloromethyl-3-ethyl-5-isopropyl-2,6-dioxo-1,2,3,6-tetrahydro-pyrimidine-4-carbonyl)-5-methyl-benzonitrile (6) (590 mg, 1.58 mmol, 1 eq.) in DMF (15 mL) was added 3-morpholin-4-yl-propionic acid HCl salt (370 mg, 1.89 mmol, 1.2 eq.). The reaction mixture was stirred at room temperature overnight. Ethyl acetate was added to the reaction mixture and washed with brine. The organic layer was concentrated and purified by silica column (ethyl acetate/hexane) to give a light yellow solid (D) (624 mg, 68%). ¹H NMR (300 MHz, CDCl₃): 8.37 (s, 1H), 8.23 (s, 1H), 8.01 (s, 1H), 6.00 (m, 2H), 3.91 (m, 1H), 3.63 (m, 4H), 3.28 (m, 1H), 2.70 (m, 2H), 2.59 (m, 2H), 2.58 (s, 3H), 2.49 (m, 4H), 2.28 (m, 1H), 1.2-1.1 (m, 9H). Mass spectrum: 497.2 (M+1).

Example E

Scheme 5

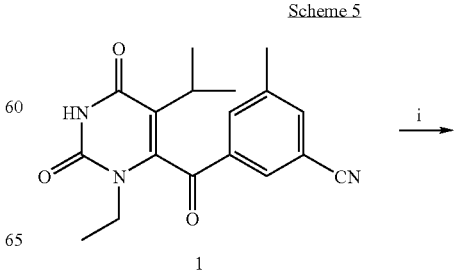

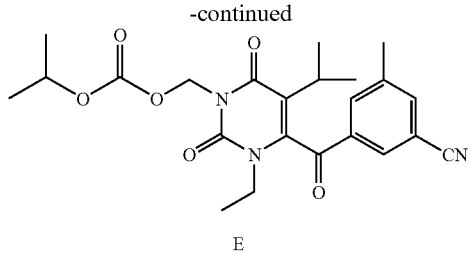

Reagents and conditions: i. Carbonic acid chloromethyl ester isopropyl ester, NaH, DMF.

Synthesis of Example E

Sodium hydride (60% in mineral oil, 424 mg, 10.6 mmol, 1.15 eq.) was added to 3-(3-ethyl-5-isopropyl-2,6-dioxo-1,2, 3,6-tetrahydro-pyrimidine-4-carbonyl)-5-methyl-benzonitrile (1) (3 g, 9.22 mmol, 1 eq.) in DMF (19 mL) at 0° C. Carbonic acid chloromethyl ester isopropyl ester (1.54 g, 10.14 mmol, 1.1 eq.) was added to the reaction mixture. The reaction mixture was stirred and warmed up to room temperature overnight. Ethyl acetate was added to the reaction mixture and washed with brine. The organic layer was concentrated and purified by silica column (ethyl acetate/hexane) to give a white solid (E) (3.73 g, 92%). The product was recrystallized using isopropanol: water (23 mL:20 mL) at 90° C. then cooled down to room temperature to give crystal material 3.33 g (84%). The melting point of the crystal is 153-155° C.
$^1$H NMR (300 MHz, CDCl$_3$): 8.10 (s, 1 H), 7.98 (s, 1H), 7.81 (s, 1H), 6.06 (m, 2H), 4.98 (m, 1H), 3.91 (m, 1H), 3.19 (m, 1H), 2.54 (s, 3H), 2.22 (m, 1H), 1.37 (d, 6H), 1.2-1.1 (m, 9H).
Mass spectrum: 441.9 (M+1)

Preparation of Compound 1

Scheme 3

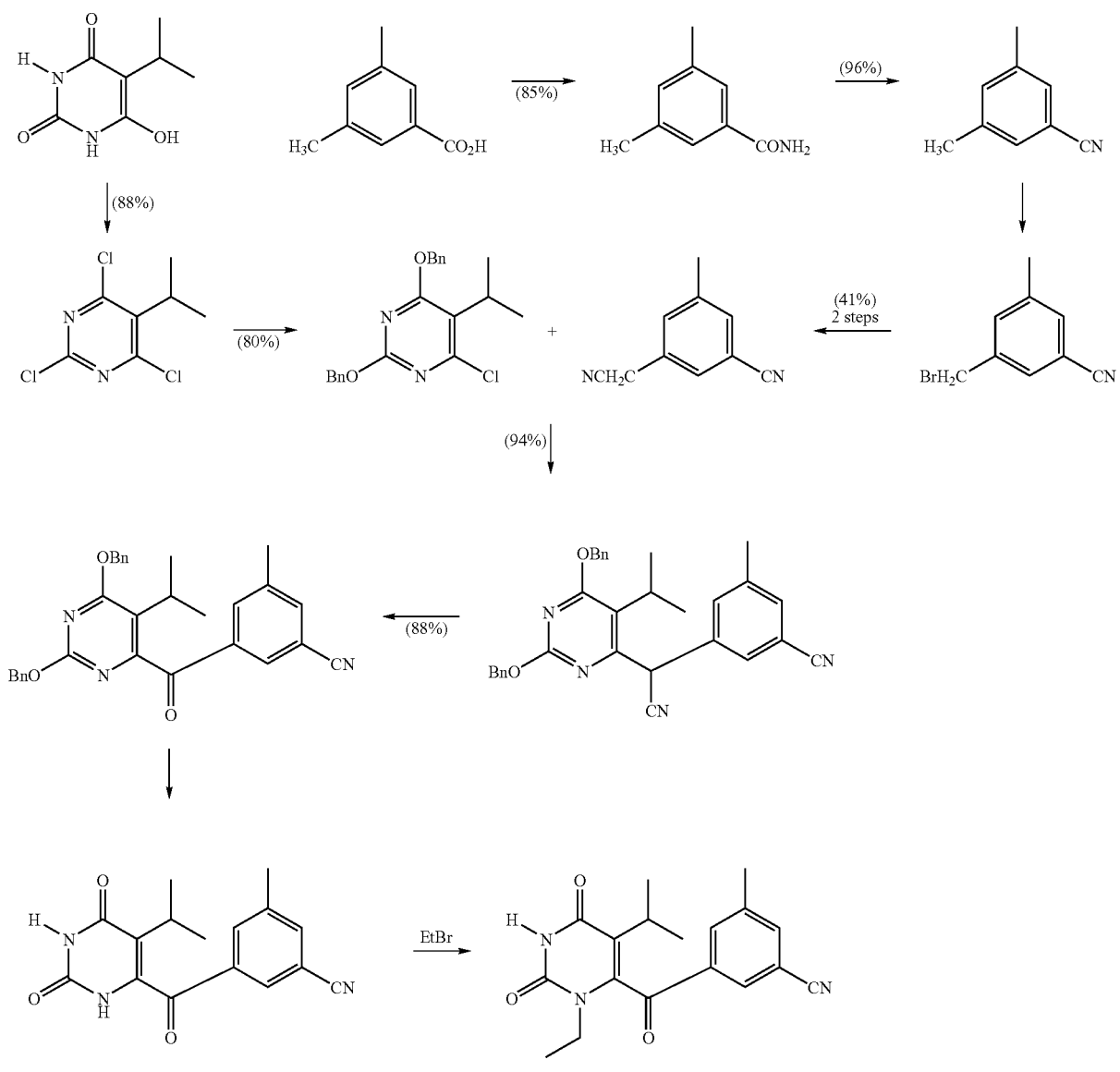

2,4,6-trichloro-5-isopropylpyrimidine

With vigorous stirring, 5-isopropyl barbtric acid (Lancaster, 75 g, 0.44M) was added to phosphorus oxychloride (250 mL). N,N-diethylaniline (72 mL, 0.44M) was then added and the reaction mixture was refluxed in an oil bath (ca. 140° C.) for overnight. After cooling to room temperature, the excess phosphorus oxychloride was evaporated in vacuo and the residue was poured into crushed ice (exothermic reaction). An earth-like precipitate was formed immediately.

After stirring at room temperature for ca. 4 hr., the precipitate was filtered and washed with water several times. The precipitate was then dissolved in hexane (or ether), washed with sat. aqueous sodium bicarbonate solution, dried with anhydrous magnesium sulfate, filtered and evaporated in vacuo to afford the crude product as a yellow solid.

The yellow solid was dissolved in ether (100 mL) and methanol (100 mL) was added. The mixture was then concentrated and recrystallized to give a white precipitate. The precipitate was filtered, washed with methanol, and dried in vacuo to afford 87 g (88%) of 2,4,6-trichloro-5-isopropylpyrimidine as a white solid, after repeating this procedure 3 times. m.p. 70-71° C. $^1$H NMR (200 MHz, CDCl$_3$) δ 1.44 (6H, d, J=7.2 Hz), 3.76 (1H, m). $^{13}$C NMR (50 MHz, CDCl$_3$) δ 18.69, 29.49, 135.19, 155.99, 162.20, m/z (EI) 225 (M$^+$).

2,4-bis(benzyloxy)-6-chloro-5-isopropylpyrimidine

To a stirred solution of benzyl alcohol (600 mL) in water bath, was added sodium metal (12.24 g, 0.532 M) under nitrogen atmosphere.

After complete reaction of sodium metal, the mixture was cooled in an ice bath and 2,4,6-trichloro-5-isopropylpyrimidine (63 g, 0.28 M) was added portionwise. After stirring for ca. 1 hr. in an ice bath, the reaction mixture was stirred at room temperature for overnight. Excess benzyl alcohol was evaporated in vacuo (water bath temp. ca. 80° C.), and the residue was dissolved in ether, washed with water, dried with anhydrous magnesium sulfate, filtered, and evaporated in vacuo to give a light yellow oil. The yellow oil was then recrystallized from ether/hexane to afford 41 g of 2,4-bis(benzyloxy)-6-chloro-5-isopropylpyrimidine as a white solid. The mother liquor was evaporated in vacuo and the residue was purified by silica gel column chromatography (eluent, ether:hexane (3:97)) to give 37 g of 2,4-bis(benzyloxy)-6-chloro-5-isopropylpyrimidine as a white solid. The combined yield was 78 g (80%). m.p. 77-78° C. $^1$H NMR (200 MHz, CDCl$_3$) 1.26 (6H, d, J=7.0 Hz), 3.45 (1H, m), 5.37 (2H, s), 5.42 (2H, s), 7.30-7.40 (10H, m). $^{13}$C NMR (50 MHz, CDCl$_3$) δ 19.80, 27.54, 69.11, 69.41, 117.69, 127.86, 128.07, 128.50, 135.86, 136.10, 159.19, 161.18, 169.59, m/z (EI) 368 (M$^+$).

3,5-dimethylbenzamide 3,5-Dimethylbenzoic acid (50 g, 0.33 M, Aldrich) was suspended in thionyl chloride (150 mL) and DMF (0.5 mL) was added. The mixture was then refluxed for 2.5 hr. Excess thionyl chloride was evaporated in vacuo and the residue was added dropwise to ammonium hydroxide solution (ACS, 250 mL) cooled in an ice bath. The mixture was stirred for further 30 min. The white precipitate was then filtered, washed with water several times, and dried by standing on air. The crude product was dissolved in MC, washed with water, dried with anhydrous magnesium sulfate, filtered, and evaporated in vacuo to afford 42 g (85%) of 3,5-dimethylbenzamide as a white solid. m.p. 148-149° C. $^1$H NMR (200 MHz, CDCl$_3$) δ 2.35 (6H, s), 6.01 (2H, br. s), 7.15 (1H, s), 7.42 (2H, s).

3,5-dimethylbenzonitrile 3,5-dimethylbenzamide (50 g, 0.3356 M) was suspended in benzene (400 mL). Thionyl chloride (49 mL, 0.671 M) and DMF (2 mL) were added and the mixture was refluxed for 2 hr. After cooling to room temperature, the mixture was poured into a crushed ice. After 1 hr., the solution was neutralized by the addition of 6 N sodium hydroxide solution. The product was then extracted with ether, dried with anhydrous magnesium sulfate, filtered, and evaporated in vacuo to give a yellow solid. The crude product was then purified by silica gel column chromatography (eluent, EA:hexane (1:4)) to afford 42 g (95%) of 3,5-dimethylbenzonitrile as a yellow solid. m.p. 51-52° C. $^1$H NMR (300 MHz, CDCl$_3$) δ 2.34 (6H, s), 7.21 (1H, s), 7.26 (2H, s).

3-(bromomethyl)-5-methylbenzonitrile

To a stirred solution of carbon tetrachloride (270 mL), was added 3,5-dimethylbenzonitrile (37 g, 0.282 M), N-bromo succinimide (NBS) (50 g, 0.282 M), and benzoyl peroxide (3.4 g, 14 mmol). The mixture was then refluxed for 3 hr. under a 500 W tungsten lamp. After cooling to room temperature, the mixture was filtered, evaporated, and the residue was purified by silica gel column chromatography (eluent, ether:hexane (1:10)) to give 48 g (81%) of 3-(bromomethyl)-5-methylbenzonitrile as a white solid. m.p. 80-81° C. $^1$H NMR (200 MHz, CDCl$_3$) δ 2.39 (3H, s), 4.43 (2H, s), 7.39 (1H, s), 7.43 (1H, s), 7.48 (1H, s).

3-(cyanomethyl)-5-methylbenzonitrile

To a stirred ethanol (150 mL), was added 3-(bromomethyl)-5-methylbenzonitrile (48 g, 0.228 M), potassium cyanide (27 g, 0.42 M), and distilled water (77 mL). The mixture was then refluxed for 3 hr. After cooling to room temperature, the reaction mixture was evaporated in vacuo and the residue was partitioned between ether and water. The ether layer was taken, dried with anhydrous magnesium sulfate, filtered, evaporated in vacuo and the residue was purified by silica gel column chromatography (eluent, ether:hexane (1:1)) to afford 18.3 g (51%) of 3-(cyanomethyl)-5-methylbenzonitrile as a pale yellow solid. m.p. 63-64° C. $^1$H NMR (300 MHz, CDCl$_3$) δ 2.42 (3H, s), 3.77 (2H, s), 7.42 (2H, s), 7.45 (1H, s).

3-((2,6-bis(benzyloxy)-5-isopropylpyrimidin-4-yl)(cyano)methyl)-5-methylbenzonitrile 2,4-bis(benzyloxy)-6-chloro-5-isopropylpyrimidine (45.4 g, 0.123 M) and 3-(cyanomethyl)-5-methylbenzonitrile (18.3 g, 0.117 M) were dissolved in anhydrous DMF (200 mL). After cooling the mixture in an ice bath under nitrogen atmosphere, 60% sodium hydride (9.38 g, 0.235 M) was added portionwise (addition time ca. 1.5 hr.). The mixture was stirred for further 1 hr. in an ice bath and stirred for ca. 20 hr. at room temperature. The reaction mixture was then cooled in an ice bath and sat. aqueous ammonium chloride solution was added thoroughly. The crude product was extracted with ether, washed with water twice, dried with magnesium sulfate, filtered, and evaporated in vacuo to give a light brown syrup, which was purified by silica gel column chromatography (eluent, ethyl acetate:hexane (1:9)) to afford 53.46 g (94%) of 3-((2,6-bis(benzyloxy)-5-isopropylpyrimidin-4-yl)

(cyano)methyl)-5-methylbenzonitrile as a light brown syrup. $\lambda_{max}$ (film) 2236 (nitrile) cm$^{-1}$, $^1$H NMR (200 MHz, CDCl$_3$) δ 1.10 (3H, d, J=6.9 Hz), 1.12 (3H, d, J=6.9 Hz), 2.36 (3H, s), 2.96 (1H, m), 5.37 (1H, s), 5.44 (4H, s), 7.32-7.55 (13H, m).

3-(2,6-bis(benzyloxy)-5-isopropylpyrimidine-4-carbonyl)-5-methylbenzonitrile

To a stirred solution of 3-((2,6-bis(benzyloxy)-5-isopropylpyrimidin-4-yl)(cyano)methyl)-5-methylbenzonitrile (53.46 g, 0.0195 M) in anhydrous DMF (400 mL) in a water bath under nitrogen atmosphere, was added 60% sodium hydride (4.87 g, 0.1205 M) portionwise. After 30 min., oxygen gas was bubbled into the reaction mixture using oxygen balloon. After 3 hr., sat. aqueous ammonium chloride solution was added and the product was extracted with ether. Ether layer was washed with water twice, dried with anhydrous magnesium sulfate, filtered, and evaporated in vacuo to give a crude product as a light yellow solid. The crude product was purified by silica gel column chromatography (eluent, ethyl acetate:hexane (1:9)) to afford 45.7 g (88%) of 3-(2,6-bis(benzyloxy)-5-isopropylpyrimidine-4-carbonyl)-5-methylbenzonitrile as a light yellow solid. m.p. 129-130° C. $^1$H NMR (300 MHz, CDCl$_3$) δ 1.20 (3H, d, J=7.0 Hz), 1.22 (3H, d, J=7.0 Hz), 2.43 (3H, s), 2.84 (1H, m), 5.34 (2H, s), 5.51 (2H, s), 7.29-7.46 (10H, m), 7.66 (1H, s), 7.83 (1H, s), 7.90 (1H, s).

Compound 3

3-(2,6-bis(benzyloxy)-5-isopropylpyrimidine-4-carbonyl)-5-methylbenzonitrile (22 g, 46 mmol), anhydrous ethanol (150 mL), 10 drops of glacial acetic acid, and 10% palladium on carbon (3 g) was placed into a 500 mL bottle. The mixture was then hydrogenated using Parr Hydrogenator under hydrogen atmosphere (20 psi) for ca. 1 hr. The mixture was then filtered through celite pad and the pad was washed with chloroform and ethanol. The combined filtrate was evaporated in vacuo to give a crude product as a yellow solid.

The crude product was filtered through short silica gel column (eluent, methanol:chloroform (1:5)) to give a product contaminated with side product (more polar than product). To get rid of the side product, the mixture was dissolved in methanol (225 mL) and ethanol (200 mL). The solution was then concentrated as much as possible and the precipitate was filtered, washed with ethanol, and dried in high vacuo to afford a pure product (3). After repeating this process 3 times, 10.5 g (76.6%) of compound was obtained as a white solid (3). m.p. 262-263° C., $\lambda_{max}$ (film) 2236 (nitrile, weak) cm$^{-1}$, $^1$H NMR (200 MHz, CD$_3$OD/CDCl$_3$) δ 1.16 (6H, d, J=6.9 Hz), 2.41 (1H, m), 2.52 (3H, s), 7.79 (1H, s), 7.94 (1H, s), 8.04 (1H, s). $^{13}$C NMR (50 MHz, DMSO-d$_6$) δ 20.11, 20.28, 27.35, 112.50, 114.11, 117.78, 130.92, 133.87, 135.13, 138.65, 140.95, 144.00, 150.44, 163.61, 189.47. m/z (EI) 308 (M$^+$).

Compound 1: To a mixture of potassium carbonate (0.67 g, 4.85 mmol), Compound 3 (1.44 g, 4.85 mmol, 1.0 eq.) in DMF (23 mL) at 0° C. was added iodoethane (0.326 mL, 4.04 mmol). Reaction mixture was warmed to room temperature overnight, then concentrated. The residue was partioned between ethyl acetate and saturated ammonium chloride solution. The organic layer was removed, dried (MgSO$_4$), concentrated and purified by flash column chromatography (20 to 50% ethyl acetate/hexane) to give Compound 1 (0.900 g, 68%); $^1$H NMR (300 MHz, CDCl$_3$): δ 8.69 (br, 1H), 8.02 (s, 1H), 7.92 (s, 1H), 7.76 (s, 1H), 3.9-3.8 (m, 1H), 3.2-3.1 (m, 1H), 2.49 (s, 3H), 2.3-2.1 (m, 1H), 1.17 (d, J=6.9 Hz, 3H), 1.1-1.0 (m, 6H); Mass spectrum: 326.2 (M+H), 324.0 (M−H).

Biological Assay

The compounds of the present invention were tested for antiviral activity by utilizing MT-2 cells, 50 µl of 2× test concentration of 5-fold serially diluted compound in culture medium with 10% FBS was added to each well of a 96-well plate (9 concentrations) in triplicate. MT-2 cells were infected with HIV-IIIb at a multiplicity of infection (m.o.i) of 0.01 for 3 hours. Fifty microliters of infected cell suspension in culture medium with 10% FBS (~1.5×10$^4$ cells) was then added to each well containing 50 µl of diluted compound. The plates were then incubated at 37° C. for 5 days. For the antiviral assay utilizing MT-4 cells, 20 µl of 2× test concentration of 5-fold serially diluted compound in culture medium with 10% FBS was added to each well of a 384-well plate (7 concentrations) in triplicate. MT-4 cells were next mixed with HIV-IIIb at an m.o.i. of 0.1 and 20 µl of virus/cell mixture (~2000 cells) was immediately added to each well containing 20 µl of diluted compound. The plates were then incubated at 37° C. for 5 days. After 5 days of incubation, 100 µl of CellTiter-Glo™ Reagent (catalog #G7571, Promega Biosciences, Inc., Madison, Wis.) was added to each well containing MT-2 cells and 40 µl to each well containing MT-4 cells. Cell lysis was carried out by incubation at room temperature for 10 min and chemiluminescence was read.

For compound cytotoxicity assessment in MT-2 cells, the protocol was identical to that of the antiviral assay in MT-2 cells, except that uninfected cells and a 3-fold serial dilution of compounds were used. For cytotoxicity assessment in MT-4 cells, the protocol is identical to that of the antiviral assay in MT-2 cells, except that no virus was added.

The compounds of the present invention have shown antiviral EC50 values (nM) in the range of about 0.1 to about 1000, or about 0.1 to about 500, or about 0.1 to about 300, or about 0.1 to about 200, or about 0.1 to about 100, or about 0.1 to about 50, or less than about 500, or less than about 400, or less than about 300, or less than about 200, or less than about 100, or less than about 50, or less than about 20, or less than about 10.

We claim:

1. A compound of Formula (I):

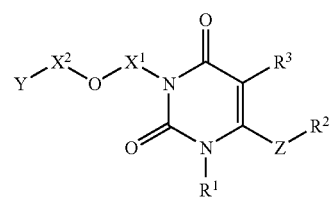

or a pharmaceutically acceptable tautomer, salt, and/or ester thereof, wherein:

$R^1$ and $R^3$ are each independently H, alkyl, or substituted alkyl;

$R^2$ is carbocyclyl, substituted carbocyclyl, aryl, or substituted aryl;

$X^1$ is alkylene or substituted alkylene;

$X^2$ is a covalent bond;

Z is —C(O)— or —NR$^3$—C(O)—;

Y is:

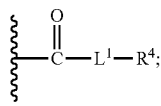

$L^1$ is a covalent bond or —O—;

$R^4$ is H, alkyl, substituted alkyl, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, substituted heterocyclylalkyl, -alkylene-C(O)—O—$R^7$, -(substituted alkylene)-C(O)—O—$R^7$, -alkylene-O—C(O)—O—$R^7$, or -(substituted alkylene)-O—C(O)—O—$R^7$; and $R^7$ is H, alkyl, substituted alkyl, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, or substituted heterocyclylalkyl; and provided that:

when $L^1$ is a covalent bond, then $R^4$ is not H.

2. The compound of claim 1, wherein:
$R^1$ and $R^3$ are each independently alkyl or substituted alkyl.

3. The compound of claim 1, wherein:
$R^2$ is aryl or substituted aryl.

4. The compound of claim 3, wherein:
$R^2$ is phenyl or substituted phenyl.

5. The compound of claim 3, wherein:
$R^2$ is substituted phenyl having one or more substituents selected from the group consisting of alkyl, alkenyl, alkynyl, halo, cyano, nitro, hydroxyl, amino, alkoxy, N-alkyl amino, N,N-dialkyl amino, and combinations thereof.

6. The compound of claim 1, wherein:
$X^1$ is —$CH_2$— or —$CH_2CH_2$—.

7. The compound of claim 1, wherein:
$R^4$ is alkyl, substituted alkyl, heterocyclylalkyl, or substituted heterocyclylalkyl.

8. The compound of claim 1, wherein:
—$X^1$—O—$X^2$—Y is —$CH_2$—O—C(O)—$CH_3$.

9. A compound selected from the group consisting of:

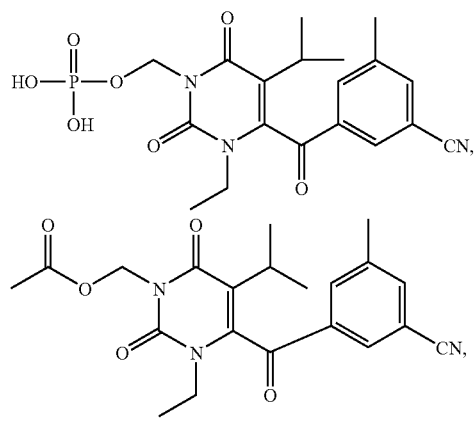

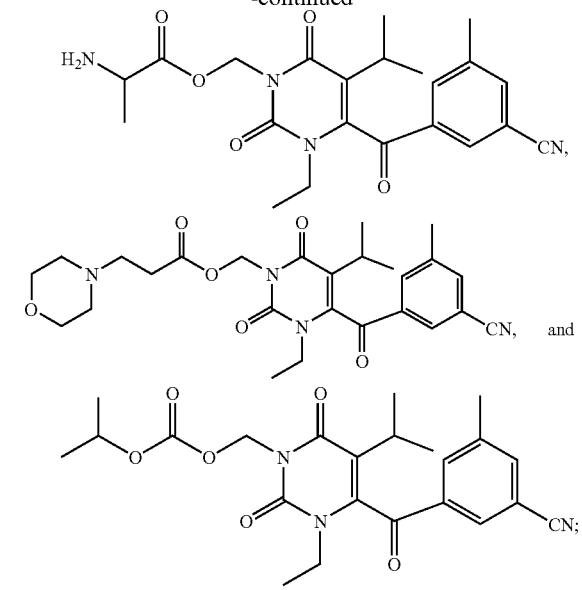

or a pharmaceutically acceptable tautomer, salt, and/or ester thereof.

10. A pharmaceutical composition comprising:
a therapeutically effective amount of at least one compound of claim 1, or a pharmaceutically acceptable salt, and/or ester thereof;
and a pharmaceutically acceptable carrier or excipient.

11. The pharmaceutical composition of claim 10, further comprising
at least one additional active agent selected from the group consisting of HIV protease inhibitors, HIV non-nucleoside inhibitors of reverse transcriptase, HIV nucleoside inhibitors of reverse transcriptase, HIV nucleotide inhibitors of reverse transcriptase, and HIV integrase inhibitors, and mixtures thereof.

12. The pharmaceutical composition of claim 11, wherein:
(1) said HIV protease inhibitors are selected from the group consisting of amprenavir (Agenerase), atazanavir (Reyataz), fosamprenavir (Lexiva), indinavir (Crixivan), lopinavir, ritonavir (norvir), nelfinavir (Viracept), saquinavir (Invirase), tipranavir (Aptivus), brecanavir, darunavir (Prezista), TMC-126, TMC-114, mozenavir (DMP-450), JE-2147 (AG1776), L-756423, RO0334649, KNI-272, DPC-681, DPC-684, DG17, GS-8374, MK-8122 (PPL-100), DG35, and AG 1859, SPI-256, TMC 52390, PL-337, SM-322377, SM-309515, GRL-02031, CRS-074, CRS-075, KB-98, and A-790742;
(2) said HIV non-nucleoside inhibitors of reverse transcriptase are selected from the group consisting of capravirine, emivirine, delaviridine (Rescriptor), efavirenz (Sustiva), nevirapine (Viramune), (+)-calanolide A, calanolide B, etravirine (Intelence), GW5634, DPC-083, DPC-961, DPC-963, MIV-150, MIV-160, MIV-170, dapivirine (TMC-120), rilpivirine (TMC-278), BILR 355 BS, VRX 840773, UK-453061, and RDEA806, RDEA 427, RDEA 640, IDX 899, ANX-201 (Thiovir), R-1206, LOC-dd, IQP-0410 (SJ-3366), YM-215389, YM-228855, CMX-052, and CMX-182;
(3) said HIV nucleoside inhibitors of reverse transcriptase are selected from the group consisting of zidovudine (Retrovir), emtricitabine (Emtriva), didanosine (Videx), stavudine (Zerit), zalcitabine (Hivid), lamivudine (Epivir), abacavir (Ziagen), amdoxovir, elvucitabine (ACH 126443), alovudine (MIV-310), MIV-210, racivir (racemic FTC, PSI-5004), D-d4FC, phosphazide, fozivudine tidoxil, apricitibine (AVX754, SPD-754), GS-7340, KP-1461, AVX756, OBP-601, dioxolane thymine, TMC-254072, INK-20, PPI-801, PPI-802, MIV-410, 4'-Ed4T, B-108, and fosalvudine tidoxil (HDP 99.0003);

(4) said HIV nucleotide inhibitors of reverse transcriptase are selected from the group consisting of tenofovir disoproxil fumarate (Viread), and adefovir dipivoxil;

(5) said HIV integrase inhibitors are selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, raltegravir (Isentress, MK-0518), elvitegravir (GS-9137), BMS-538158, GSK364735C, BMS-707035, MK-2048, GSK-349572 (S-349572), GSK-265744 (S-265744), GSK-247303 (S-247303), S-1360 (GW810871), 1,5-DCQA, INH-001, INT-349, V-165, RIN-25, BFX-1001, BFX-1002, BFX-1003, RSC-1838, BCH-33040, and BA 011.

13. A combination pharmaceutical agent comprising:
a) a first pharmaceutical composition comprising at least one compound of claim 1, or a pharmaceutically acceptable salt, and/or ester thereof; and
b) a second pharmaceutical composition comprising at least one additional active agent selected from the group consisting of HIV protease inhibitors, HIV non-nucleoside inhibitors of reverse transcriptase, HIV nucleoside inhibitors of reverse transcriptase, HIV nucleotide inhibitors of reverse transcriptase, and HIV integrase inhibitors, and mixtures thereof.

14. The compound of claim 1, wherein:
Z is —C(O)—.

* * * * *